(12) United States Patent
Adams et al.

(10) Patent No.: US 9,242,963 B2
(45) Date of Patent: Jan. 26, 2016

(54) ORGANIC COMPOUNDS

(71) Applicants: Christopher Michael Adams, Somerville, MA (US); Qi-Ying Hu, Needham, MA (US); Leslie Wighton McQuire, Warren, NJ (US); Julien Papillon, Somerville, MA (US)

(72) Inventors: Christopher Michael Adams, Somerville, MA (US); Qi-Ying Hu, Needham, MA (US); Leslie Wighton McQuire, Warren, NJ (US); Julien Papillon, Somerville, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/677,260

(22) Filed: Apr. 2, 2015

(65) Prior Publication Data

US 2015/0210672 A1  Jul. 30, 2015

Related U.S. Application Data

(63) Continuation of application No. 14/288,699, filed on May 28, 2014, now abandoned, which is a continuation of application No. 12/492,383, filed on Jun. 26, 2009, now Pat. No. 8,030,334.

(60) Provisional application No. 61/076,452, filed on Jun. 27, 2008.

(51) Int. Cl.

| C07D 401/04 | (2006.01) |
| A61K 31/4439 | (2006.01) |
| A61K 45/06 | (2006.01) |
| C07D 401/14 | (2006.01) |
| C07D 213/61 | (2006.01) |
| C07D 401/06 | (2006.01) |
| C07D 401/12 | (2006.01) |

(52) U.S. Cl.
CPC .......... *C07D 401/14* (2013.01); *A61K 31/4439* (2013.01); *A61K 45/06* (2013.01); *C07D 213/61* (2013.01); *C07D 401/04* (2013.01); *C07D 401/06* (2013.01); *C07D 401/12* (2013.01)

(58) Field of Classification Search
None
See application file for complete search history.

(56) References Cited

U.S. PATENT DOCUMENTS

| 3,370,063 A | 2/1968 | Suh |
| 3,381,006 A | 4/1968 | Suh |
| 3,409,626 A | 11/1968 | Cavalito |
| 3,454,586 A | 7/1969 | Suh |
| 3,467,670 A | 9/1969 | Suh |
| 3,468,894 A | 9/1969 | Pfenninger |
| 3,491,114 A | 1/1970 | Suh |
| 3,492,123 A | 1/1970 | Mee |
| 3,501,484 A | 3/1970 | Schut et al. |
| 3,505,070 A | 4/1970 | Litzerman et al. |
| 4,226,868 A | 10/1980 | Zigman et al. |
| 4,232,121 A | 11/1980 | Gilman et al. |
| 4,460,777 A | 7/1984 | Renfroe |
| 4,478,842 A | 10/1984 | Renfroe |
| 4,511,573 A | 4/1985 | Renfroe |
| 4,843,091 A | 6/1989 | Rosentreter et al. |
| 4,874,756 A | 10/1989 | Mertens et al. |
| 4,950,680 A | 8/1990 | Taylor et al. |
| 4,981,864 A | 1/1991 | Von der Saal et al. |
| 5,021,448 A | 6/1991 | Piraino et al. |
| 5,629,325 A | 5/1997 | Lin et al. |
| 5,952,355 A | 9/1999 | Ikeda et al. |
| 6,127,386 A | 10/2000 | Lin et al. |
| 6,184,238 B1 | 2/2001 | Takano et al. |
| 6,437,138 B1 | 8/2002 | Lin et al. |
| 6,630,493 B1 | 10/2003 | Lubisch et al. |
| 6,673,797 B1 * | 1/2004 | Matsuoka et al. ... C07D 401/04 514/249 |
| 6,770,666 B2 | 8/2004 | Hashimoto et al. |
| 7,285,551 B2 | 10/2007 | Hashimoto et al. |
| 7,462,638 B2 | 12/2008 | Michaelis et al. |
| 7,511,069 B2 | 3/2009 | Miyoshi et al. |
| 8,030,334 B2 | 10/2011 | Adams et al. |
| 8,791,141 B2 | 7/2014 | Adams et al. |
| 2001/0039286 A1 | 11/2001 | Dinnell et al. |
| 2004/0009976 A1 | 1/2004 | Takeuchi et al. |
| 2004/0082798 A1 | 4/2004 | Alonso-Alija et al. |
| 2004/0209917 A1 | 10/2004 | Hartz et al. |
| 2005/0209465 A1 | 9/2005 | Li et al. |
| 2005/0245517 A1 | 11/2005 | Skolnick et al. |
| 2006/0089496 A1 | 4/2006 | Lam et al. |

(Continued)

FOREIGN PATENT DOCUMENTS

| CA | 2052125 A1 | 3/1992 |
| DE | 102004034380 A1 | 2/2006 |

(Continued)

OTHER PUBLICATIONS

Horig, H., Pullman, W. From bench to clinic and back: Perspective on the 1st IQPC Translational Research Conference. Journal of Translational Medicine. Dec. 2, 2004, 44.*

(Continued)

*Primary Examiner* — Alicia L Otton
(74) *Attorney, Agent, or Firm* — Sophie Binet Cross

(57) ABSTRACT

The present invention provides novel organic compounds of Formula (I): methods of use, and pharmaceutical compositions thereof.

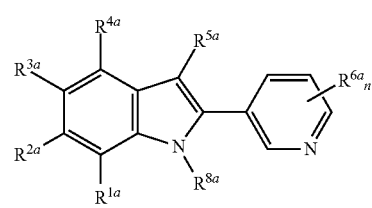

11 Claims, No Drawings

(56) References Cited

U.S. PATENT DOCUMENTS

| | | |
|---|---|---|
| 2006/0205751 A1 | 9/2006 | Lee et al. |
| 2007/0140960 A1 | 6/2007 | Siclovan et al. |
| 2007/0287708 A1 | 12/2007 | Cole et al. |
| 2008/0096877 A1 | 4/2008 | Yasuma et al. |
| 2008/0096903 A1 | 4/2008 | Chen et al. |
| 2014/0288126 A1 | 9/2014 | Adams et al. |

FOREIGN PATENT DOCUMENTS

| | | |
|---|---|---|
| EP | 0057933 B1 | 2/1982 |
| EP | 0266979 A2 | 5/1988 |
| EP | 0266980 B1 | 5/1988 |
| EP | 0296873 B1 | 6/1988 |
| EP | 0300675 A2 | 1/1989 |
| EP | 0406734 A2 | 7/1989 |
| EP | 0553682 A1 | 8/1993 |
| EP | 0680950 A1 | 11/1995 |
| EP | 1086950 A1 | 3/2001 |
| EP | 1156045 A1 | 11/2001 |
| EP | 0628559 B1 | 4/2002 |
| EP | 1243268 A1 | 9/2002 |
| EP | 0924209 B1 | 5/2003 |
| FR | 2679561 A1 | 1/1993 |
| GB | 1224530 | 3/1971 |
| JP | 55151505 A | 11/1980 |
| JP | 61282834 A | 12/1986 |
| JP | 02085251 A | 3/1990 |
| JP | 11344787 A | 12/1999 |
| JP | 2003342276 A | 12/2003 |
| JP | 2006290791 A | 10/2006 |
| SU | 703527 A1 | 3/1978 |
| WO | 8903691 A1 | 5/1989 |
| WO | 9113872 A1 | 9/1991 |
| WO | 9318030 A1 | 9/1993 |
| WO | 9319067 A1 | 9/1993 |
| WO | 9603400 A1 | 2/1996 |
| WO | 98/33496 A1 | 8/1998 |
| WO | 9857937 A1 | 12/1998 |
| WO | 99/33822 A1 | 7/1999 |
| WO | 9943651 A1 | 11/1999 |
| WO | 9955697 A1 | 11/1999 |
| WO | 0015645 A1 | 3/2000 |
| WO | 0035886 A2 | 6/2000 |
| WO | 0039108 A1 | 7/2000 |
| WO | 0059902 A1 | 10/2000 |
| WO | 0132167 A1 | 5/2001 |
| WO | 0147883 A1 | 7/2001 |
| WO | 0189519 A1 | 11/2001 |
| WO | 0200646 A1 | 1/2002 |
| WO | 0200651 A2 | 1/2002 |
| WO | 0210146 A1 | 2/2002 |
| WO | 0228831 A1 | 4/2002 |
| WO | 0230358 A2 | 4/2002 |
| WO | 02072549 A1 | 9/2002 |
| WO | 03000254 A1 | 1/2003 |
| WO | 03035620 A1 | 5/2003 |
| WO | 03042184 A1 | 5/2003 |
| WO | 0304752 A2 | 6/2003 |
| WO | 2004003010 A1 | 12/2003 |
| WO | 2004022057 A1 | 3/2004 |
| WO | 2004069394 A2 | 8/2004 |
| WO | 2004083174 A2 | 9/2004 |
| WO | 2004083177 A2 | 9/2004 |
| WO | 2004087714 A1 | 10/2004 |
| WO | 2005014543 A1 | 2/2005 |
| WO | 2005016862 A1 | 2/2005 |
| WO | 2005030203 A1 | 2/2005 |
| WO | 2005028444 A1 | 3/2005 |
| WO | 2005030130 A2 | 4/2005 |
| WO | 2005030191 A1 | 4/2005 |
| WO | 2005030192 A1 | 4/2005 |
| WO | 2005034941 A1 | 4/2005 |
| WO | 2005080388 A1 | 9/2005 |
| WO | 2005084439 A1 | 9/2005 |
| WO | 2005092855 A1 | 10/2005 |
| WO | 2005121132 A1 | 12/2005 |
| WO | 2006008133 A2 | 1/2006 |
| WO | 2006010637 A2 | 2/2006 |
| WO | 2006020049 A2 | 2/2006 |
| WO | 2006046914 A1 | 5/2006 |
| WO | 2006092430 A1 | 9/2006 |
| WO | 2006092430 A1 | 9/2006 |
| WO | 2006102645 A1 | 9/2006 |
| WO | 2006050109 A2 | 11/2006 |
| WO | 2006123257 A2 | 11/2006 |
| WO | 2006138347 A2 | 12/2006 |
| WO | 2007/002458 A2 | 1/2007 |
| WO | 2007039146 A1 | 4/2007 |
| WO | 2007/050655 A2 | 5/2007 |
| WO | 2007/061676 A2 | 5/2007 |
| WO | 2007/061763 A2 | 5/2007 |
| WO | 2007/065892 A1 | 6/2007 |
| WO | 2007/093600 A1 | 8/2007 |
| WO | 2007/093827 A1 | 8/2007 |
| WO | 2007/115231 A2 | 10/2007 |
| WO | 2007/115287 A2 | 10/2007 |
| WO | 2007/115306 A1 | 10/2007 |
| WO | 2007/117715 A2 | 10/2007 |
| WO | 2007/134864 A1 | 11/2007 |
| WO | 2007/147874 A1 | 12/2007 |
| WO | 20071147874 A1 | 12/2007 |
| WO | 2008/076862 A2 | 6/2008 |
| WO | 2008/082487 A2 | 7/2008 |
| WO | 2008082487 A2 | 7/2008 |
| WO | 2008/108729 A1 | 9/2008 |
| WO | 2008108729 A1 | 9/2008 |
| WO | 2008/133867 A1 | 11/2008 |
| WO | 2009/013010 A2 | 1/2009 |
| WO | 2009/042092 A1 | 4/2009 |
| WO | 2009/062319 A1 | 5/2009 |
| WO | 2009/117335 A2 | 9/2009 |

OTHER PUBLICATIONS

Schafer, S., Kolkhof, P. Failure is an option: learning from unsuccessful proof-of-concept trials. Drug Discovery Today. Nov. 13, 2008, 913-916.*
"Stroke," Google Health, Accessed Nov. 6, 2010 <https://health.google.com/health/ref/Stroke#Treatment>.*
Saris et al.; Clinical Pharmacology & Therapeutics (St. Louis, MO, United States) (1993),54(1),65-9.
Saxena, Jagdeesh P.; Indian Journal of Chemistry (1967),5(2),73-6.
Schut et al.; Journal of Medicinal Chemistry (1970), 13(3),394-7.
Shukri et al.; Journal of the Indian Chemical Society (1970), 47(2), 123-4.
Smeesters et al.; Transplantation Proceedings (1988), 20(2, Suppl. 2), 663-9.
Smeesters et al.; Transplantation Proceedings (1988),20(3, Suppl. 3), 658-64.
Somei et al.; Heterocycles (1988),27(7),1585-7.
Sugasawa et al.; Chemical & Pharmaceutical Bulletin (1958), 6,111-12.
Sugasawa et al.; Pharmaceutical Bulletin (1956), 4,16-19.
Sufh, John T.; Puma, Barbara M.; Journal of Organic Chemistry (1965),30(7),2253-9.
Tang et al.; International Journal of Cancer (1993),54(2),338-47.
Thompson et al.; Journal of the American Pharmaceutical Association (1912-1977) (1953), 42, 647-52.
Tiwari et al.; Die Pharmazie (1980), 35(12), 742-3.
Wacker et al.; Tetrahedron Letters (2002), 43(29), 5189-5191.
Wadhwani et al.; Diabetes (1989), 38(11), 1469-77.
Wu et al.; Journal of Organic Chemistry (1998), 63(12), 4055-4061.
Zakurdaev et al.; Russian Chemical Bulletin (2005), 54(5), 1219-1228.
Zhao et al.; Organic Leiters (2005), 7(13), 2523-2526.
Zhao et al.; Organic Leiters (2006), 8(18), 4173.
Zigman et al.; Science (Washington, DC. United States) (1980),208(4440),188-91.
Zymalkowski, Felix; Arch. Pharm. (1958), 291,436-42.
Voets, et al.; J. Med. Chem. 2006, 49, 2222-2231.

(56) References Cited

OTHER PUBLICATIONS

Penner, Thomas et al., Photographic Science and Engineering (1975), 19(2):102-14.
Registry No. 157427-58-2 and Registry No. 23768-17-4 "The Stille Reaction" Organic Reactions (Hoboken, NJ, United States (1997), 50 No pp given. 2008:1383562 (see full references on Scifinder report).
Do Khac Manh et al., "Syntheses d'analogues de !'ibogaine," Bulletin de la societe chimique de France 11:4154-4159 (1969).
Opatz et al., "Preparation of Indoles from alpha-Aminonitriles: A Short Synthesis of FGIN-1-27," Organic Letters 8 (20):4473-4475 (2006).
Schut et al., "2-Tetrahydropyridylindoles as Histamine and Serotonin Antagonists," Journal of Medicinal Chemistry 13 (3):394 (1970).
Johnson et al., "Palladium (0)-Catalysed Arylations using Pyrrole and Indole 2-Boronic Acids," Synlett 1025-1027 (Sep. 1998).
Li et al., "Molecular Hologram QSAR Study of 3-Pyridyl Ether Analogues," Huaxue Xuebao 63(11):1018-1022 (2005).
Ishikura et al., "Novel Aspects on the Reaction ofTrialkyl-(1-methylindo1-2-y1)borates," J. Chern. Soc. Chern. Commun. 2:135-136 (1989).
Wahed et al., "Effects of Eplerenone, a Selective Aldosterone Blocker, on the Progression of Left Ventricular Dysfunction and Remodeling in Rates with Dilated Cardiomyopathy," Pharmacology 73:81-88 (2005).
Weber, Karl, "Aldosterone in Congestive Heart Failure," N Engl J Med 345(23):1689-1696 (Dec. 6, 2001).
Mottram et al., "Effect of Aldosterone Antagonism on Myocardial Dysfunction in Hypertensive Patients with Diastolic Heart Failure," Circulation 110:558-565 (2004).
Freel and Connell, "Mechanisms of Hypertension: The Expanding Role of Aldosterone," J Am Soc Nephrol 15 (8):1993-2001 (Aug. 2004).
Connell et al., "A Lifetime of Aldosterone Excess: Long-Term Consequences of Altered Regulation of Aldosterone Production for Cardiovascular Function," Endocrine Reviews 29(2):133-154 (2008).
Wei et al., "The Effect of Aldosterone Antagonists for Ventricular Arrhythmia: A Meta-Analysis," Clin. Cardiol. 33 (9):572-577 (2010).
Zannad et al., "Treatment of Congestive Heart Failure: Interfering the Aldosterone-Cardiac Extracellular Matrix Relationship," Hypertension 38:1227-1232 (2001).
Kosmala et al., "A Randomized Study of the Beneficial Effects of Aldosterone Antagonism on LV Function, Structure, and Fibrosis Markers in Metabolic Syndrome," Cardiovascular Imaging 4(12):1239-1249 (Dec. 2011).
Nishioka et al., "Eplerenone Attenuates Myocardial Fibrosis in the Angiotensin II-Induced Hypertensive Mouse: Involvement of Tenascin-C Induced by Aldosterone-Mediated Inflammation," J Cardiovasc Pharmacol 49(5):261-268 (May 2007).
Sun et al., "Fibrosis of atria and great vessels in response to angiotensin II or aldosterone infusion," Cardiovascular Research 35:138-147 (1997).
Duprez et al., "Aldosterone and Vascular Damage," Current Hypertension Reports 2:327-334 (2000).
Hatakeyama et al., "Vascular Aldosterone," The Journal of Biological Chemistry 269(39):24316-24320 (Sep. 30, 1994).
Beygui et al., "High Plasma Aldosterone Levels on Admission Are Associated with Death in Patients Presenting with Acute ST-Elevation Myocardial Infarction," Circulation 114:2604-2610 (2006).
Rocha et al., "Aldosterone: A Mediator of Myocardial Necrosis and Renal Arteriopathy," Endocrinology 141 (10):3871-3878 (2000).
Xavier et al., "Aldosterone induces endothelial dysfunction in resistance arteries from normotensive and hypertensive rats by increasing thromboxane A2 and prostacyclin," British Journal of Pharmacology 154:1225-1235 (2008).
Blanco-Rivero et al., "Participation of Prostacyclin in Endothelial Dysfunction Induced by Aldosterone in Normotensive and Hypertensive Rats," Hypertension 46:107-112 (2005).

Milliez et al., "Evidence for an Increased Rate of Cardiovascular Events in Patients with Primary Aldosteronism," Journal of the American College of Cardiology 45(8):1243-8 (2005).
Rocha et al., "Mineralocorticoid Blockade Reduces Vascular Injury in Stroke-Prone Hypertensive Rats," Hypertension 31:451-458 (1998).
Dinh et al., "Aldosterone and the mineralocorticoid receptor in the cerebral circulation and stroke," Experimental and Translational Stroke Medicine 4:21 (2012).
Del Vecchio et al., "Mechanisms of Disease: the role of aldosterone in kidney damage and clinical benefits of its blockade," Nature Clinical Practice Nephrology 3(1):42-48 (Jan. 2007).
Colussi et al., "Insulin Resistance and Hyperinsulinemia Are Related to Plasma Aldosterone Levels in Hypertensive Patients," Diabetes Care 30(9):2349-2354 (Sep. 2007).
Kidambi et al., "Association of Adrenal Steriods with Hypertension and the Metabolic Syndrome in Blacks," Hypertension 49:704-711 (2007).
Catena et al., "Insulin Sensitivity in Patients with Primary Aldosteronisms: A Follow-Up Study," J Clin Endocrinol Metab 91:3457-3463 (2006).
Monahan et al., "Aldosterone Impairs Baroreflex Sensitivity in Healthy Adults," Am J Physiol Heart Circ Physiol 292: H190-H197 (2007).
Ortlepp et al., "Genetic polymorphisms in the renin-angiotensin-aldosterone system associated with expression of left ventricular hypertrophy in hypertrophic cardiomyopathy . . ." Heart 87:270-275 (2002).
Tsybouleva et al., "Aldosterone, Through Novel Signaling Proteins, Is a Fundamental Molecular Bridge Between the Genetic Defect and the Cardiac Phenotype of Hypertrophic Cardiomyopathy," Circulation 109:1284-1291 (2004).
Pitt et al., "Effects of Eplerenome, Enalapril, and Eplerenone/Enalapril in Patients with Essential Hypertension and Left Ventricular Hypertrophy: The 4E-Left Ventricular Hypertrophy Study," Circulation 108:1831-1838 (2003).
Okoshi et al., "Aldosterone Directly Stimulates Cardiac Myocyte Hypertrophy," Journal of Cardiac Failure 10 (6):511-517 (2004).
Gradman et al,. Current Opinion in Pharmacology, 2008, 8: 120-126.
Al-Azavve, Subhi; Sarkis, George Y; Journal of Chemical and Engineering Data (1973), 18(1), 109-11.
Ambler et al.; British Journal of Pharmacology (1985),86(2),497-504 0.
Anderson et al.; Transplantation Proceedings (1989),21(1, Book 1),1161-4.
Arcadi et al.; Tetrahedron Letters (1989),30(19),2581-4.
Attia et al.; Die Pharmazie (1995),50(7),455-9.
Baradarani et al.; Journal of the Chemical Society, Perkin Transactions 1: Organic and Bio-Organic Chemistry (1972-1999) (1985), (7), 1503-8.
Barrett et al.; Thrombosis and Haemostasis (1986), 56(3), 311-17.
Bearn et al.; International Journal of Experimental Pathology (1993), 74(1),1-8.
Bitterman et al.; Proceedings of the Society for Experimental Biology and Medicine (1987), 185(3), 262-6.
Boi Do et al.; Journal of Heterocyclic Chemistry (1998), 35(4), 853-858.
Buchmann et al.; Die Pharmazie (1968),23(10),557-60.
Butler et al.; Thrombosis Research (1987), 45(6), 751-61.
Cacchi et al.; Journal of Organometallic Chemistry (1994), 475(1-2), 289-96.
Chu et al.; Tetrahedron Letters (1997), 38(22), 3871-3874.
Costa, L. F.; Gilman, P. B., Jr; Photographic Science and Engineering (1975), 19(4), 207-11.
Dinnell et al.; Bioorganic & Medicinal Chemistry Letters (2001),11 (9),1237-1240.
Dohle et al.; Chemistry—A European Journal (2003), 9(21), 5323-5331.
Duc, Do Khac Mann; Fetizon, Marcel; Bulletin de la Societe Chimique de France (1966), (2), 771-2.
Duc, Do Khac Mann; Fetizon, Marcel; Bulletin de la Societe Chimique de France (1969), (11),4154-9.

(56) References Cited

OTHER PUBLICATIONS

El-Desoky et al.; Journal of Heterocyclic Chemistry (1999), 36(1),153-160.
Gallagher, P. T.; Science of Synthesis (2000), 10, 693-744.
Gilman et al.; Photographic Science and Engineering (1984), 28(6),238-45.
Gilman. P. B., Jr.; Photographic Science and Engineering (1974),18(5),475-85.
Grauer et al.; American Journal of Veterinary Research (1992), 53(5), 808-13.
Grauer et al.; American Journal of Veterinary Research (1992), 53(9), 1631-5.
Gray et al.; Journal of the American Chemical Society (1957), 79, 3554-9.
Gri Eve et al.; Biochemical Pharmacology (1990), 40(10), 2323-9.
Gri Eve et al.; Biochemical Pharmacology (1993), 45(6), 1351-4.
Grieve et al.; Nephrotoxicity (1991),193-8. Editor(s): Bach, Peter H. Publisher: Dekker, New York, N.Y.
Hailstone, R. K.; Journal of Photographic Science (1984),32(1),25-36.
Haines et al.; Journal of the American Chemical Society (1945), 67, 1258-62.
Herbich et al.; Journal of Physical Chemistry A (2002),106(10),2158-2163.
Hock et al.; Research Communications in Chemical Pathology and Pharmacology (1986), 52(3), 285-94.
Huffman, John W; Journal of Organic Chemistry (1962),27,503-6.
Ishikura et al.; Journal of the Chemical Society, Chemical Communications (1989), (2), 135-6.
Jennings et al.; Bioorganic & Medicinal Chemistry (2004),12(19),5115-5131.
Jennings et al.; Bioorganic & Medicinal Chemistry (2005), 13(20), 5884.
Johnson et al.; Synlett (1998), (9), 1025-1027.
Kakimoto et al.; Pharmaceutical Bulletin (1956), 4, 4-6.
Keith et al.; American Journal of Obstetrics and Gynecology (1989),161 (5),1305-13.
Kennedy et al.; Bioorganic & Medicinal Chemistry Letters (2000),10(15),1751-1754.
Kenyon, J.; Thaker, Kumar; Journal of the Chemical Society (1957) 2531-6.
Kitzen et al.; Pharmacology (1988). 37(3), 171-86.
Kost et al.; Doklady Akademii Nauk SSSR (1979),244(1),103-5 [Chem.].
Ksander et al.; Journal of Medicinal Chemistry (1994),37(12),1823-32.
Kudo et al.; Angewandle Chemie, International Edition (2006), 45(8), 1282-1284.
Kyrychenko et al.; Journal of the American Chemical Society (2000),122(12),2818-2827.
Labadie et al.; Journal of Organic Chemistry (1994), 59(15), 4250-4.
Laforge, F. B.; Journal of the American Chemical Society (1928), 50,2477-83.
Lane et al.; Organic Letters (2004), 6(17), 2897-2900.
L'Azou et al.; Toxicology in Vitro (1993), 7(4), 417-20.
Len Hard, J.; Journal of Imaging Science (1986), 30(1), 27-35.
Levens et al.; Hypertension (1989), 13(1), 51-62.
Levens et al.; Journal of Pharmacology and Experimental Therapeutics (1991), 259(1), 219-27.
Li et al.; Huaxue Xuebao(2005), 63(11), 1018-1022.
Lin et al.; Bioorganic & Medicinal Chemistry Letters (2001), 11(5), 631-633.
Longhofer et al.; American Journal of Veterinary Research (1990), 51(11), 1746-50.
Longhofer et al.; American Journal of Veterinary Research (1991), 52(3), 480-7.
Loutfy, R. O.; Sharp, J. H.; Photographic Science and Engineering (1976), 20(4), 165-74.
Mangino et al.; Journal of Pharmacology and Experimental Therapeutics (1989), 248(1), 23-8.
Martin et al.; Clinical Pharmacology & Therapeutics (St. Louis, MO, United States) (1991), 49(4), 433-41.
Mertens et al.; Journal of Medicinal Chemistry (1990),33(10),2870-5.
Murray, Margaret M.; Bull. World Health Organization (1953), 9, 211-16.
Nanji et al.; Gastroenterology (1997), 112(1), 200-207.
Nonami et al.; Rapid Communications in Mass Spectrometry (2001), 15(23), 2354-2373.
Olson et al.; European Journal of Pharmacology (1987).133(3),265-73.
Olson et al.; European Journal of Pharmacology (1993), 236(1), 75-87.
Opatz et al.; Organic Letters (2006), 8(20), 4473-4475.
Pena et al.; Journal of Organic Chemistry (2007),72(4),1271-1275.
Sakamoto et al.; J. Chem. Soc., Perkin Trans. 1, (1996),1927-1934.
Psychoyos et al.; Agents and Actions (1989), 26(3-4), 372-7.

* cited by examiner

ORGANIC COMPOUNDS

This application is a continuation application of U.S. patent application Ser. No. 14/288,699 filed on May 28, 2014, which is a continuation application of U.S. patent application Ser. No. 12/996,904 filed on Dec. 8, 2010, which is the U.S. national Phase filing of International Serial No. PCT/EP2009/057947 filed Jun. 25, 2009, and claims priority to U.S. provisional application No. 61/076,452 filed Jun. 27, 2008, the contents of which are incorporated herein by reference in their entirety.

The mineralocorticoid hormone aldosterone is produced by the adrenal gland and acts on the distal tubules and collecting ducts of the kidney to increase reabsorption of ions and water in the kidney. Aldosterone causes conservation of sodium, secretion of potassium, increased water retention, and increased blood pressure.

Aldosterone has been implicated in the pathogenesis of cardiovascular diseases such as hypertension and heart failure. In clinical trials, treatment with the nonselective mineralocorticoid receptor antagonist (MRA) spironolactone or the selective MRA eplerenone significantly reduced morbidity and mortality among patients with heart failure or myocardial infarction already taking an angiotensin-converting enzyme inhibitor or a β-blocker. However, significant side effects such as gynecomastia and impotence were observed in male patients receiving spironolactone while hyperkalemia was seen in patients taking either drug.

The invention pertains to the compounds and methods for using them as described herein. Examples of compounds of the invention include the compounds of Formulae I-IV, and the compounds of the examples.

In another embodiment, the invention pertains, at least in part, to a method for treating an aldosterone synthase-mediated disorder or disease in a subject by administering to the subject a therapeutically effective amount of a compound of Formulae I-IV, such that the aldosterone synthase-mediated disorder or disease in the subject is treated.

In yet another embodiment, the invention pertains, at least in part, to a method for treating a subject for hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, comprising administering to the subject a therapeutically effective amount of a compound of Formulae I-IV, such that the subject is treated.

In yet another embodiment, the invention pertains, at least in part, to pharmaceutical compositions, comprising an effective amount of a compound of Formulae 1, II, III or IV, wherein said effective amount is effective to treat an aldosterone synthase associated state.

An alternative approach to ameliorate the deleterious effects of aldosterone is to suppress its production by inhibitors of aldosterone synthase, an enzyme responsible for the final steps of the biosynthesis of aldosterone from deoxycorticosterone, via conversion of corticosterone to form 18-OH-corticosterone, which is then converted to aldosterone.

The invention pertains, at least in part, to compounds, pharmaceutical compositions containing the compound and methods of use thereof. The present invention also relates to novel compounds which may be used, for example, as modulators of aldosterone synthase, or inhibitors of aldosterone synthesis.

The compounds of the present invention may, for example, be used to treat various aldosterone synthase associated states such as hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, and fibrinoid necrosis of coronary arteries.

Compounds of the Invention

The present invention pertains, at least in part, to compounds of Formula I:

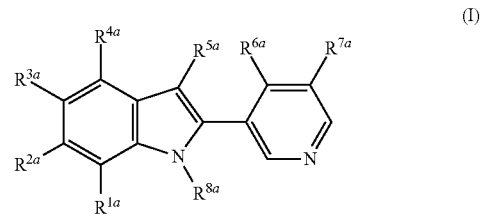

(I)

wherein:

$R^{1a}$, $R^{2a}$, $R^{3a}$, and $R^{4a}$ are each independently hydrogen, halogen, cyano, hydroxy, alkoxy, alkyl, alkenyl, or alkoxycarbonyl;

$R^{5a}$ is hydrogen halogen, cyano, alkyl, alkenyl, arylalkyl, heteroarylalkyl, aminocarbonyl, alkylaminocarbonyl, carboxylate, alkoxycarbonyl, heterocyclylcarbonyl, aryl, or heteroaryl;

$R^{6a}$ and $R^{7a}$ are each independently hydrogen, halogen, hydroxy, alkoxy, amino, alkyl, sulfonyl, —O-sulfonyl, alkylamino, heterocyclyl, aminocarbonyl, carboxylate, or alkoxycarbonyl;

$R^{8a}$ is hydrogen, alkyl, arylalkyl, heteroarylalkyl, alkoxycarbonyl, sulfonyl, aroyl, aryl, or heteroaryl; and pharmaceutically acceptable salts, polymorphs, rotamers, prodrugs, enantiomers, hydrates, and solvates thereof;

with the proviso that at least one of $R^{1a}$-$R^{8a}$ is other than hydrogen; and when $R^{1a}$ is lower alkyl or halogen, then at least one of $R^{1a}$, $R^{2a}$ and $R^{4a}$-$R^{8a}$ is other than hydrogen; and when $R^{5a}$ is cyano or lower alkyl optionally substituted with cyano, —C(O)-piperidine, amino, alkylamino, dialkylamino, carboxylate, alkoxycarbonyl, aminocarbonyl, or heterocyclyl, then at least one of $R^{1a}$-$R^{4a}$ and $R^{6a}$-$R^{8a}$ is other than hydrogen; and when $R^{7a}$ is imidazolyl, then at least one of $R^{1a}$-$R^{6a}$ and $R^{8a}$ is other than hydrogen; and when $R^{8a}$ is lower alkyl, arylalkyl or alkoxycarbonyl, then at least one of $R^{1a}$-$R^{7a}$ is other than hydrogen; and when $R^{5a}$ is lower alkyl and $R^{8a}$ is alkyl substituted with carboxylate or $PO_3R^{21}R^{22}$ wherein $R^{21}$ and $R^{22}$ are each independently hydrogen or lower alkyl, then at least one of $R^{1a}$-$R^{4a}$ and $R^{6a}$ and $R^{7a}$ is other than hydrogen; and when $R^{7a}$ is halogen and $R^{5a}$ and $R^{8a}$ are independently lower alkyl optionally substituted with carboxylate, alkoxycarbonyl, or —C(O)-piperidine, then at least one of $R^{1a}$, $R^{2a}$, $R^{4a}$, $R^{6a}$ and $R^{7a}$ is other than hydrogen; and when $R^{5a}$ is lower alkenyl substituted with heteroaryl and $R^{8a}$ is lower alkyl, then at least one of $R^{1a}$-$R^{4a}$, $R^{6a}$ and $R^{7a}$ is other than hydrogen; and when $R^{3a}$ is halogen or lower alkyl and $R^{5a}$ is lower alkyl substituted with dialkylamino, dialkylaminocarbonyl, carboxylate, alkoxycarbonyl or aminocarbonyl, then at least one of $R^{1a}$, $R^{2a}$, $R^{4a}$, and $R^{6a}$-$R^{8a}$ is other than hydrogen; and when $R^{3a}$ is —O-benzyl and $R^{5a}$ is alkyl-$NH_2$, then at least one of $R^{1a}$, $R^{2a}$, $R^{4a}$, and $R^{6a}$-$R^{8a}$ is other than hydrogen; and when $R^{2a}$ and $R^{3a}$ are each alkoxy and $R^{5a}$ is cyano, then at least one of $R^{1a}$, $R^{4a}$ and $R^{6a}$-$R^{8a}$ is other than hydrogen; and when $R^{1a}$ and $R^{3a}$ are each halogen and $R^{5a}$ is alkyl-$NH_2$, then at least one of $R^{2a}$, $R^{4a}$, and $R^{6a}$-$R^{8a}$ is other than hydrogen; and when $R^{2a}$ is alkoxycarbonyl and $R^{4a}$ is halogen, then at least one of $R^{1a}$, $R^{3a}$, $R^{5a}$ and $R^{6a}$-$R^{8a}$ is other than hydrogen; and when $R^{5a}$ is alkyl and $R^{7a}$ is —$OCH_2$—(N-methyl pyrrolidine), then at least one of $R^{1a}$-$R^{4a}$, $R^{6a}$ and $R^{8a}$ is other than hydrogen; and when $R^{3a}$ is cycloalkyl and $R^{5a}$ is alkyl-$NH_2$, then at least one of $R^{1a}$, $R^{2a}$, $R^{4a}$, and $R^{6a}$-$R^{8a}$ is other than hydrogen; and when $R^{3a}$ is alkyl substituted with aroyl, and $R^5$ and $R^8$ are each independently hydrogen or lower alkyl, then at least one of $R^{1a}$, $R^{2a}$, and $R^{4a}$ is other than hydrogen.

Examples of $R^{1a}$ include hydrogen, halogen (e.g., chlorine or fluorine), hydroxy, and alkoxy (e.g., methoxy).

In a further embodiment, $R^{1a}$ is optionally substituted alkyl (e.g., methyl, ethyl, or propyl), which may be substituted with groups such as carboxylate, hydroxy, alkylamino (e.g., ethylamino) which may be further substituted with hydroxy, and aryl (e.g., phenyl) which may be further substituted with carboxylate.

In yet a further embodiment, $R^{1a}$ is optionally substituted alkenyl (e.g., alkenyl is ethenyl or propenyl), which may be substituted with groups such as hydroxy, alkoxycarbonyl (e.g., butoxycarbonyl), and aryl (e.g., phenyl) which may be further substituted with alkoxycarbonyl (e.g., methoxycarbonyl).

In one embodiment, $R^{2a}$ includes hydrogen, halogen (e.g., chlorine or fluorine), hydroxy, alkyl (e.g., methyl), and alkoxy (e.g., methoxy).

Examples of $R^{3a}$ include, hydrogen, halogen (e.g., chlorine or fluorine), alkoxy (e.g., methoxy), cyano, and alkoxycarbonyl (e.g., methoxycarbonyl).

In a further embodiment, $R^{3a}$ is optionally substituted alkyl (e.g., methyl or ethyl), which may be substituted with groups such as carboxylate, alkoxycarbonyl (e.g., ethoxycarbonyl), hydroxy, and halogen. This optionally substituted alkyl may be, for example trifluoromethyl.

Examples of $R^{4a}$ include, hydrogen, halogen (e.g., fluorine), and cyano.

In one embodiment, $R^{5a}$ includes hydrogen, halogen (e.g., bromine), alkenyl (e.g., propenyl), cyano, —C(O)$NH_2$, carboxylate, alkoxycarbonyl (e.g., methoxycarbonyl or isopropoxycarbonyl), arylalkyl (e.g., benzyl), heteroarylalkyl (e.g., imidazolylmethyl), heterocyclylcarbonyl (e.g., pyrrolidinylcarbonyl), alkylaminocarbonyl (e.g., ethylaminocarbonyl), and aryl (e.g., phenyl).

In another embodiment, $R^{5a}$ includes optionally substituted alkyl (e.g., methyl, ethyl, propyl or butyl), which may be substituted with groups such as hydroxy, alkoxy (e.g., ethoxy), and carboxylate.

In yet another embodiment, $R^{5a}$ includes optionally substituted heteroaryl (e.g., 1,2,4-oxadiazolyl), which may be substituted with groups such as alkyl (e.g., methyl).

Examples of $R^{6a}$ and $R^{7a}$ include alkoxy (e.g., methoxy, ethoxy, or benzyloxy), which may be substituted with hydroxy or aryl (e.g., phenyl); halogen (e.g., chlorine or fluorine); hydroxy; sulfonyl, which may be substituted with aryl (e.g., phenylsulfonyl) or alkyl (e.g., butylsulfonyl); alkylamino (e.g., ethylamino); carboxylate; alkoxycarbonyl (e.g., ethoxycarbonyl); aminocarbonyl; and amino (e.g., —NH(S(O)$_2$($CH_3$)$_2$, NR'S(O)$_2$-alkyl, —NR'—C(O)-alkyl, —NR'—C(O)—NR'-alkyl, and —NR'—C(O)—O-alkyl, wherein each R' is independently hydrogen, $C_1$-$C_4$-alkyl, or $C_3$-$C_6$-cycloalkyl). In another embodiment, $R^{6a}$ is —NH—S(O)$_2$—$CH_3$.

In one embodiment, $R^{6a}$ and $R^{7a}$ includes optionally substituted heterocyclyl (e.g., piperazinyl), which may be substituted with groups such as alkyl (e.g., methyl).

In another embodiment, $R^{6a}$ and $R^{7a}$ includes optionally substituted alkyl (e.g., methyl or ethyl), which may be substituted with groups such as heterocyclyl (e.g., morpholinyl, piperazinyl, pyrrolidinyl, or thiomorpholinyl dioxide), which may itself be substituted with alkyl (e.g., methyl) or —$NH_2$; hydroxy; alkoxy (e.g., methoxy); or halogen. This optionally substituted alkyl may be, for example, trifluoromethyl.

In another embodiment, $R^{6a}$ and $R^{7a}$ includes optionally substituted alkyl (e.g., methyl or ethyl), which may be substituted with amino (e.g., —$NR^{30b}R^{31b}$). Examples of $R^{30b}$ include hydrogen and methyl. Examples of $R^{31b}$ include alkoxycarbonyl (e.g., ethoxycarbonyl); alkylaminocarbonyl (e.g., ethylaminocarbonyl); heterocyclylcarbonyl (e.g., morpholinyl); acyl (e.g., —C(O)($CH_2$)$_2CH_3$); alkyl (e.g., ethyl), which may optionally be substituted with hydroxy; sulfonyl, which may be substituted with benzyl; dialkylamino (e.g., diethylaminosulfonyl); alkyl (e.g., methylsulfonyl, ethylsulfonyl, propylsulfonyl, butylsulfonyl, or trifluoromethylsulfonyl); or aryl (e.g., phenylsulfonyl). This phenylsulfonyl may be, for example, further substituted with halogen (e.g., fluorine).

In another embodiment, $R^{6a}$ and $R^{7a}$ includes optionally substituted —O-sulfonyl, which may be substituted with groups such as alkyl (e.g., methyl); amino (e.g., dimethylamino, diethylamino, or —N(Et)(benzyl)); or heterocyclyl (e.g., morpholinyl, piperazinyl, N-methyl piperazinyl, or pyrrolidinyl).

In one embodiment, $R^{8a}$ includes hydrogen, heteroaryl (e.g., 3-pyridinyl), and alkoxycarbonyl (e.g., isopropoxycarbonyl or butoxycarbonyl).

In another embodiment, $R^{8a}$ includes optionally substituted arylalkyl (e.g., benzyl), which may be substituted with groups at the para position and/or at the meta position. Examples of such groups include alkoxycarbonyl (e.g., methoxycarbonyl); carboxylate; alkyl (e.g., methyl); cyano; alkoxy (e.g., methoxy); halogen (e.g., fluorine); sulfonyl, which is optionally substituted with alkyl (e.g., methylsulfonyl); heteroaryl (e.g., tetrazolyl); alkoxy (e.g., methoxy or benzyloxy); or combinations thereof.

In yet another embodiment, $R^{8a}$ includes optionally substituted heteroarylalkyl (e.g., benzoimidizolyl methyl, 1,2,3- triazolylmethyl, or isoxazolyl methyl), which may be substituted with alkyl (e.g., methyl), which may optionally be further substituted with aryl (e.g., phenyl) such that $R^{8a}$ is heteroarylalkyl substituted with benzyl.

In another embodiment, $R^{8a}$ includes optionally substituted aroyl (e.g., benzoyl), which may be substituted with groups at the para position and/or at the meta position. Examples of such groups include cyano, alkyl (e.g., methyl or ethyl), alkoxy (e.g., methoxy or dimethoxy), alkoxycarbonyl (e.g., butoxycarbonyl), carboxylate, or combinations thereof.

In another embodiment, $R^{8a}$ includes optionally substituted alkyl (e.g., methyl, ethyl, propyl, isopropyl or butyl), which may be substituted with groups such as —NHC(O)$R^{20a}$ and —OC(O)$R^{20a}$, wherein $R^{20a}$ is alkyl (e.g., butyl).

In yet another embodiment, $R^{8a}$ includes optionally substituted alkyl (e.g., methyl, ethyl, propyl, isopropyl or butyl), which may be substituted with groups such as cycloalkyl (e.g., cyclohexyl); carboxylate; hydroxy; alkoxycarbonyl (e.g., butoxycarbonyl); and sulfonyl, which is optionally substituted with aryl (e.g., phenylsulfonyl).

In still another embodiment, $R^{8a}$ includes optionally substituted alkyl (e.g., methyl, ethyl, propyl, isopropyl or butyl), which may be substituted with groups such as heterocyclyl (e.g., piperazinyl or azetidyl), which may itself be substituted with groups such as alkyl, dialkyl (e.g., dimethyl), and =O.

In yet another embodiment, $R^{8a}$ includes optionally substituted alkyl (e.g., methyl, ethyl, propyl, isopropyl or butyl), which may be substituted with groups such as heterocyclylcarbonyl (e.g., piperazinylcarbonyl), which may itself be substituted with groups such as alkyl or dialkyl (e.g., dimethyl); aryl (e.g., phenyl), which may itself be substituted with groups such as carboxylate; and alkoxy (e.g., methoxy, ethoxy, propoxy, butoxy, pentoxy, or phenoxy), which may itself be substituted with groups such as alkoxycarbonyl (e.g., methoxycarbonyl or ethoxycarbonyl), carboxylate, and hydroxy.

In one embodiment, $R^{8a}$ is phenoxy substituted alkyl (e.g., methyl, ethyl, propyl, isopropyl or butyl), and this phenoxy is optionally substituted at the para position and/or at the meta position with groups such as alkoxycarbonyl (e.g., methoxycarbonyl or ethoxycarbonyl), carboxylate, and hydroxy.

Another example of $R^{8a}$ includes optionally substituted aryl (e.g., phenyl), which may be substituted at the para position and/or at the meta position with groups such as cyano, alkoxy (e.g., methoxy), or combinations thereof.

Another example of $R^{8a}$ includes optionally substituted sulfonyl, which may be substituted with groups such as aryl (e.g., phenyl), which may itself be substituted with groups such as alkyl (e.g., methyl), carboxylate, or combinations thereof.

In one embodiment of the present invention $R^{5a}$ is hydrogen, methyl, ethyl, cyano, carboxylate, or alkoxycarbonyl.

In another embodiment of the present invention $R^{8a}$ is hydrogen, methyl, ethyl, benzyl-$CO_2H$, or benzyl-$CO_2Me$.

In yet another embodiment, $R^{8a}$ is:

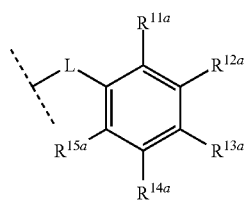

L is alkyl, carbonyl, sulfonyl, or —$(CH_2)_2$—O—; and $R^{11a}$, $R^{12a}$, $R^{13a}$, $R^{14a}$, and $R^{15a}$ are each independently hydrogen, alkyl, cyano, halogen, alkoxy, alkoxycarbonyl, carboxylate, heteroaryl, or sulfonyl.

Each of the aforementioned groups $R^{1a}$, $R^{2a}$, $R^{3a}$, $R^{4a}$, $R^{5a}$, $R^{6a}$ and $R^{8a}$ may be optionally substituted.

Another embodiment of Formula (I), wherein:

$R^{1a}$ is hydrogen, halogen, hydroxy, alkoxy, alkyl, or alkenyl;

$R^{2a}$ is hydrogen, halogen, alkyl, hydroxy, or alkoxy;

$R^{3a}$ is hydrogen, halogen, cyano, alkoxy, alkyl, or alkoxycarbonyl;

$R^{4a}$ is hydrogen, halogen, or cyano;

$R^{5a}$ is hydrogen, halogen, cyano, alkyl, alkenyl, arylalkyl, heteroarylalkyl, aminocarbonyl, alkylaminocarbonyl, carboxylate, alkoxycarbonyl, heterocyclylcarbonyl, aryl, or heteroaryl;

$R^{6a}$ and $R^{7a}$ are each independently hydrogen, halogen, hydroxy, alkoxy, amino, alkyl, sulfonyl, —O-sulfonyl, alkylamino, heterocyclyl, aminocarbonyl, carboxylate, or alkoxycarbonyl; and $R^{8a}$ is hydrogen, alkyl, arylalkyl, heteroarylalkyl, alkoxycarbonyl, sulfonyl, aroyl, aryl, or heteroaryl.

Another embodiment of Formula (I), wherein:

$R^{5a}$ is hydrogen, cyano, methyl, ethyl, carboxylate, or methoxycarbonyl.

Another embodiment of Formula (I), wherein:

$R^{8a}$ is hydrogen, methyl, ethyl, benzyl-$CO_2H$, or benzyl-$CO_2Me$.

Another embodiment of Formula (I), wherein:

$R^{1a}$ is hydrogen;

$R^{2a}$ is hydrogen, halogen, or hydroxy;

$R^{3a}$ is hydrogen, halogen, cyano, or alkoxy;

$R^{4a}$ is hydrogen or halogen;

$R^{5a}$ is hydrogen or alkyl;

$R^{6a}$ and $R^{7a}$ are hydrogen;

$R^{8a}$ is:

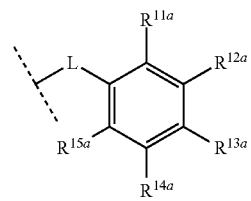

L is alkyl, carbonyl, sulfonyl, or —$(CH_2)_2$—O—; and $R^{11a}$, $R^{12a}$, $R^{13a}$, $R^{14a}$, and $R^{15a}$ are each independently hydrogen, alkyl, cyano, halogen, alkoxy, alkoxycarbonyl, carboxylate, heteroaryl, or sulfonyl.

Another embodiment of Formula (I) wherein:

$R^{11a}$ and $R^{15a}$ are each independently hydrogen, alkyl, cyano, halogen, or alkoxy;

$R^{12a}$ and $R^{14a}$ are each independently hydrogen, alkyl, cyano, halogen, alkoxy, alkoxycarbonyl, carboxylate, heteroaryl, or sulfonyl; and $R^{13a}$ is hydrogen, alkyl, cyano, alkoxy, alkoxycarbonyl, carboxylate, heteroaryl, or sulfonyl.

In yet another embodiment, the invention pertains, at least in part, to compounds of Formula II:

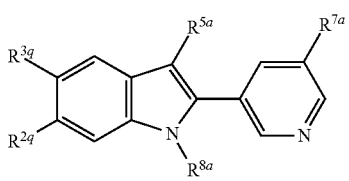

(II)

wherein:
R$^{2a}$ is hydrogen or halogen;
R$^{3a}$ is hydrogen, halogen, or cyano;
R$^{5a}$ is hydrogen, alkyl, or cyano;
R$^{7a}$ is hydrogen, halogen, alkoxy, —OSO$_2$-heterocyclyl, —O-arylalkyl, —NR'—SO$_2$-alkyl, —NR'—C(O)-alkyl, —NR'—C(O)—NR'-alkyl, —NR'—C(O)—O-alkyl, haloalkyl, or alkyl optionally substituted with heterocyclyl, —NR'—SO$_2$-alkyl, —NR'—SO$_2$-haloalkyl, NR'—C(O)-alkyl, NR'—C(O)-heterocyclyl, —NR'—C(O)—NR'-alkyl, or —NR'—C(O)—O-alkyl;
R$^{8a}$ is hydrogen, alkyl, hydroxyalkyl, -alkyl-OC(O)-alkyl, carboxylate, alkoxycarbonyl, or arylalkyl substituted with alkyl, or aroyl substituted with cyano and/or alkyl, or -alkyl-O-aryl substituted with alkoxycarbonyl;
each R' is independently hydrogen, C$_1$-C$_4$-alkyl, or C$_3$-C$_6$-cycloalkyl; and pharmaceutically acceptable salts, polymorphs, rotamers, prodrugs, enantiomers, hydrates, and solvates thereof,
with the proviso that at least one of R$^{2a}$, R$^{3a}$, R$^{5a}$, R$^{7a}$ and R$^{8a}$ is other than hydrogen; and when R$^{8a}$ is lower alkyl or alkoxycarbonyl, then at least one of R$^{2a}$, R$^{3a}$, R$^{5a}$ and R$^{7a}$ is other than hydrogen; and when R$^{5a}$ is cyano, then at least one of R$^{2a}$, R$^{3a}$, and R$^{8a}$ is other than hydrogen.

In another embodiment, R$^{7a}$ is alkoxy or alkyl substituted with heterocyclyl and R$^{8a}$ is alkyl.

Another embodiment of Formula (II), wherein R$^{7a}$ is alkoxy or alkyl substituted with heterocyclyl and R$^{8a}$ is alkyl.

Another embodiment of Formula (II), wherein
R$^{2a}$ is hydrogen or halogen;
R$^{3a}$ is hydrogen, or halogen;
R$^{5a}$ is hydrogen or cyano;
R$^{7a}$ is alkyl optionally substituted with heterocyclyl, —NR'—SO$_2$-alkyl, —NR'—SO$_2$-haloalkyl, NR'—C(O)-alkyl, NR'—C(O)-heterocyclyl, —NR'—C(O)—NR'-alkyl, or —NR'—C(O)—O— alkyl;
R' is independently hydrogen, C$_1$-C$_4$-alkyl, or C$_3$-C$_6$-cycloalkyl; and
R$^{8a}$ is hydrogen, or C$_{1-6}$alkyl.

Another embodiment of Formula (II), wherein
R$^{2a}$ is hydrogen or halogen;
R$^{3a}$ is hydrogen, or halogen;
R$^{5a}$ is hydrogen or cyano;
R$^{7a}$ is C$_{1-4}$alkyl optionally substituted with heterocyclyl, —NR'—SO$_2$—C$_{1-4}$alkyl, —NR'—SO$_2$-haloC$_{1-4}$alkyl, NR'—C(O)—C$_{1-4}$alkyl, NR'—C(O)-heterocyclyl, —NR'—C(O)—NR'—C$_{1-4}$alkyl, or —NR'—C(O)—O—C$_{1-4}$alkyl;
R' is independently hydrogen, or C$_1$-C$_4$-alkyl; and
R$^{8a}$ is hydrogen, or C$_{1-6}$alkyl.

Another embodiment of Formula (II), wherein
R$^{7a}$ is C$_{1-4}$alkyl substituted with —NR'—SO$_2$—C$_{1-4}$alkyl, —NR'—SO$_2$-haloC$_{1-4}$alkyl, or NR'—C(O)—C$_{1-4}$alkyl;
R' is independently hydrogen, or C$_1$-C$_4$-alkyl; and
R$^{8a}$ is hydrogen, methyl, or ethyl.

In yet another embodiment, the invention pertains, at least in part, to compounds of Formula III:

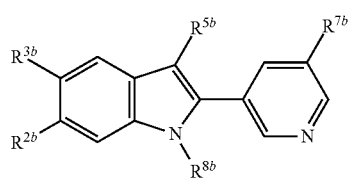

(III)

wherein:
R$^{2b}$ is hydrogen or halogen;
R$^{3b}$ is hydrogen, halogen, or cyano;
R$^{5b}$ is alkyl;
R$^{7b}$ is hydrogen, halogen, alkoxy, —OSO$_2$-heterocyclyl, —O-arylalkyl, —NR'—SO$_2$-alkyl, —NR'—C(O)-alkyl, —NR'—C(O)—NR'-alkyl, —NR'—C(O)—O-alkyl, haloalkyl, or alkyl optionally substituted with heterocyclyl, —NR'—SO$_2$-alkyl, —NR'—SO$_2$-haloalkyl, NR'—C(O)-alkyl, —NR'—C(O)—NR'-alkyl, NR'—C(O)-heterocyclyl, or —NR'—C(O)—O-alkyl;
R$^{8b}$ is hydrogen, alkyl, hydroxyalkyl, -alkyl-OC(O)-alkyl, carboxylate, alkoxycarbonyl, or arylalkyl substituted with alkyl, or aroyl substituted with cyano and/or alkyl, or -alkyl-O-aryl substituted with alkoxycarbonyl;
each R' is independently hydrogen, C$_1$-C$_4$-alkyl, or C$_3$-C$_6$-cycloalkyl; and pharmaceutically acceptable salts, polymorphs, rotamers, prodrugs, enantiomers, hydrates, and solvates thereof.

Another embodiment of Formula (III), wherein
R$^{2b}$ is hydrogen or halogen;
R$^{3b}$ is hydrogen, halogen, or cyano;
R$^{5b}$ is C$_{1-4}$alkyl;
R$^{7b}$ is hydrogen, halogen, C$_{1-4}$alkoxy, —OSO$_2$-heterocyclyl, —O-arylalkyl, —NR'—SO$_2$—C$_{1-4}$alkyl, —NR'—C(O)—C$_{1-4}$alkyl, —NR'—C(O)—NR'—C$_{1-4}$alkyl, —NR'—C(O)—O-alkyl, haloalkyl, or C$_{1-4}$alkyl optionally substituted with heterocyclyl, —NR'—SO$_2$—C$_{1-4}$alkyl, —NR'—SO$_2$-halo C$_{1-4}$alkyl, NR'—C(O)—C$_{1-4}$alkyl, —NR'—C(O)—NR'—C$_{1-4}$alkyl, NR'—C(O)-heterocyclyl, or —NR'—C(O)—O—C$_{1-4}$alkyl;
R$^{8b}$ is hydrogen, C$_{1-4}$alkyl, hydroxyalkyl, —C$_{1-4}$alkyl-OC(O)—C$_{1-4}$alkyl, carboxylate, alkoxycarbonyl, or arylalkyl substituted with C$_{1-4}$alkyl, or aroyl substituted with cyano and/or C$_{1-4}$alkyl, or —C$_{1-4}$alkyl-O-aryl substituted with alkoxycarbonyl;
each R' is independently hydrogen, C$_1$-C$_4$-alkyl, or C$_3$-C$_6$-cycloalkyl; and pharmaceutically acceptable salts, polymorphs, rotamers, prodrugs, enantiomers, hydrates, and solvates thereof.

Another embodiment of Formula (III), wherein
R$^{2b}$ is hydrogen or halogen;
R$^{3b}$ is hydrogen, halogen, or cyano;
R$^{5b}$ is methyl, ethyl or isopropyl;
R$^{7b}$ is C$_{1-4}$alkyl substituted with —NR'—SO$_2$—C$_{1-4}$alkyl, —NR'—SO$_2$-haloC$_{1-4}$alkyl, NR'—C(O)—C$_{1-4}$alkyl, or —NR'—C(O)—NR'—C$_{1-4}$alkyl;
R$^{8b}$ is hydrogen, methyl or ethyl;
each R' is independently hydrogen, or C$_1$-C$_4$-alkyl.

In yet another embodiment, the invention pertains, at least in part, to compounds of Formula IV:

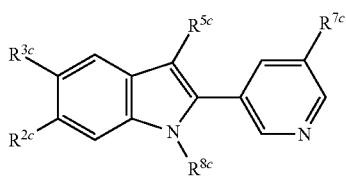

wherein:
$R^{2c}$ is hydrogen or halogen;
$R^{3c}$ is hydrogen, halogen, or cyano;
$R^{5c}$ is cyano; and
$R^{7c}$ is hydrogen, halogen alkoxy, —OSO$_2$-heterocyclyl, —O-arylalkyl, —NR'—SO$_2$-alkyl, —NR'—C(O)-alkyl, —NR'—C(O)—NR'-alkyl, —NR'—C(O)—O-alkyl or alkyl optionally substituted with heterocyclyl, —NR'—SO$_2$-alkyl, —NR'—SO$_2$-haloalkyl, NR'—C(O)-alkyl, NR'—C(O)-heterocyclyl, —NR'—C(O)—NR'-alkyl, or —NR'—C(O)—O-alkyl;
$R^{8c}$ is alkyl;
each R' is independently hydrogen, $C_1$-$C_4$-alkyl, or $C_3$-$C_6$-cycloalkyl; and pharmaceutically acceptable salts, polymorphs, rotamers, prodrugs, enantiomers, hydrates, and solvates thereof.

Another embodiment of Formula (IV), wherein
$R^{2c}$ is hydrogen or halogen;
$R^{3c}$ is hydrogen, halogen, or cyano;
$R^{5c}$ is cyano; and
$R^{7c}$ is hydrogen, halogen, $C_{1-4}$alkoxy, —OSO$_2$-heterocyclyl, —O-arylalkyl, —NR'—SO$_2$—$C_{1-4}$ alkyl, —NR'—C(O)—$C_{1-4}$ alkyl, —NR'—C(O)—NR'—$C_{1-4}$ alkyl, —NR'—C(O)—O—$C_{1-4}$ alkyl or $C_{1-4}$ alkyl optionally substituted with heterocyclyl, —NR'—SO$_2$—$C_{1-4}$ alkyl, —NR'—SO$_2$-halo $C_{1-4}$ alkyl, NR'—C(O)—$C_{1-4}$ alkyl, NR'—C(O)-heterocyclyl, —NR'—C(O)—NR'—$C_{1-4}$ alkyl, or —NR'—C(O)—O—$C_{1-4}$ alkyl;
$R^{8c}$ is $C_{1-4}$ alkyl;
each R' is independently hydrogen, $C_1$-$C_4$-alkyl, or $C_3$-$C_6$-cycloalkyl; and pharmaceutically acceptable salts, polymorphs, rotamers, prodrugs, enantiomers, hydrates, and solvates thereof.

Another embodiment of Formula (IV), wherein
$R^{2c}$ is hydrogen or halogen;
$R^{3c}$ is hydrogen, or halogen;
$R^{5c}$ is cyano; and
$R^{7c}$ is $C_{1-4}$ alkyl optionally substituted with —NR'—SO$_2$—$C_{1-4}$ alkyl, —NR'—SO$_2$-halo $C_{1-4}$ alkyl, NR'—C(O)—$C_{1-4}$ alkyl;
$R^{8c}$ is $C_{1-4}$ alkyl;
each R' is independently hydrogen or $C_1$-$C_4$-alkyl.

Another embodiment of Formula (IV), wherein
$R^{7c}$ is $C_{1-4}$ alkyl substituted with —NR'—SO$_2$—$C_{1-4}$ alkyl, —NR'—SO$_2$-halo $C_{1-4}$ alkyl, NR'—C(O)—$C_{1-4}$ alkyl; and
each R' is independently hydrogen, methyl, ethyl or propyl.

DEFINITIONS

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, and cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls," the latter of which refers to alkyl moieties having substituents replacing a hydrogen on one or more carbons of the hydrocarbon backbone. Such substituents can include, for example, alkenyl, alkynyl, halogen, hydroxy, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, etc. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heterocycles," "heteroaryls" or "heteroaromatics."

Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl. A heteroaryl group may be mono-, bi-, tri-, or polycyclic.

The term "heteroaryl" also refers to a group in which a heteroaromatic ring is fused to one or more aryl, cycloaliphatic, or heterocyclyl rings, where the radical or point of attachment is on the heteroaromatic ring. Non-limiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or I-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

The aromatic ring of an "aryl" or "heteroaryl" group can be substituted at one or more ring positions with such substituents as described above, as for example, halogen, hydroxy, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, and cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ or straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls," the latter of which refers to alkenyl moieties having substituents replacing a hydrogen on one or more carbons of the hydrocarbon backbone. Such substituents can include, for example, alkyl groups, alkynyl groups, halogens, hydroxy, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls," the latter of which refers to alkynyl moieties having substituents replacing a hydrogen on one or more carbons of the hydrocarbon backbone. Such substituents can include, for example, alkyl groups, alkynyl groups, halogens, hydroxy, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, the term "lower alkyl" means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxy, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "acyl" includes compounds and moieties which contain the acyl radical ($CH_3CO$—) or a carbonyl group. It includes substituted acyl moieties. The term "substituted acyl" includes acyl groups where one or more of the hydrogen atoms are replaced by for example, alkyl groups, alkynyl groups, halogens, hydroxy, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc. It includes substituted aroyl moieties. The term "substituted aroyl" includes aroyl groups where one or more of the hydrogen atoms are replaced by for example, alkyl groups, alkynyl groups, halogens, hydroxy, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The terms "alkoxyalkyl," "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "carbamoyl" includes $H_2NC(O)$—, alkyl-NHC(O)—, $(alkyl)_2NC(O)$—, aryl-NHC(O)—, alkyl(aryl)-NC(O)—, heteroaryl-NHC(O)—, alkyl(heteroaryl)-NC(O)—, aryl-alkyl-NHC(O)—, alkyl(aryl-alkyl)-NC(O)—, etc. The term includes substituted carbamoyl moieties.

The term "sulfonyl" includes R—$SO_2$—, wherein R is hydrogen, alkyl, aryl, heteroaryl, aryl-alkyl, heteroaryl-alkyl, alkoxy, aryloxy, cycloalkyl, or heterocyclyl.

The term "sulfonamido" includes alkyl-S(O)$_2$—NH—, aryl-S(O)$_2$—NH—, aryl-alkyl-S(O)$_2$—NH—, heteroaryl-S(O)$_2$—NH—, heteroaryl-alkyl-S(O)$_2$—NH—, alkyl-S(O)$_2$—N(alkyl)-, aryl-S(O)$_2$—N(alkyl)-, aryl-alkyl-S(O)$_2$—N(alkyl)-, heteroaryl-S(O)$_2$—N(alkyl)-, heteroaryl-alkyl-S(O)$_2$—N(alkyl)-, etc. The term includes substituted carbamoyl moieties The term "heterocyclyl" or "heterocyclo" includes an optionally substituted, saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, etc.

The term "heterocyclyl" includes heterocyclic groups as defined herein substituted with 1, 2 or 3 substituents such as alkyl, hydroxy (or protected hydroxy), halo, oxo (e.g., =O), amino, alkylamino or dialkylamino, alkoxy, cycloalkyl, carboxyl, heterocyclooxy, wherein heterocyclooxy denotes a heterocyclic group bonded through an oxygen bridge, alkyl-O—C(O)—, mercapto, nitro, cyano, sulfamoyl or sulfonamide, aryl, alkyl-C(O)—O—, aryl-C(O)—O—, aryl-S—, aryloxy, alkyl-S—, formyl (e.g., HC(O)—), carbamoyl, aryl-alkyl-, and aryl substituted with alkyl, cycloalkyl, alkoxy, hydroxy, amino, alkyl-C(O)—NH—, alkylamino, dialkylamino or halogen.

The term "sulfamoyl" includes $H_2NS(O)_2$—, alkyl-NHS(O)$_2$—, $(alkyl)_2NS(O)_2$—, aryl-NHS(O)$_2$—, alkyl(aryl)-NS(O)$_2$—, $(aryl)_2NS(O)_2$—, heteroaryl-NHS(O)$_2$—, (aryl-alkyl)-NHS(O)$_2$—, (heteroaryl-alkyl)-NHS(O)$_2$—, etc. The term includes substituted sulfamoyl moieties.

The term "aryloxy" includes both an —O-aryl and an —O-heteroaryl group, wherein aryl and heteroaryl are defined herein. The term includes substituted aryloxy moieties.

The term "amine" or "amino" includes compounds where a nitrogen atom is covalently bonded to at least one carbon or heteroatom. The term includes "alkyl amino" which comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group. The term "amine" or "amino" also includes substituted moieties.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino). The term "amide," "amido" or "aminocarbonyl" also includes substituted moieties.

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom. The term also includes substituted moieties.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group. The term also includes substituted moieties.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above. The term also includes substituted moieties.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group. The term also includes substituted moieties.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms are termed "bridged" rings. Each of the rings of the polycycle can be substituted with such substituents as described above, as for example, halogen, hydroxy, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxy, phosphate, phosphonato, phosphinato, cyano, amido, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

The term "isomers" refers to different compounds that have the same molecular formula but differ in arrangement and configuration of the atoms. Moreover, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)-, or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

The recitation of ranges of values in the present application are merely intended to serve as a shorthand method of referring individually to each separate value falling within the range.

Any asymmetric carbon atom on the compounds of the present invention can be present in the (R)-, (S)- or (R,S)-configuration, preferably in the (R)- or (S)-configuration. Substituents at atoms with unsaturated bonds may, if possible, be present in cis-(Z)- or trans-(E)-form. Therefore, the compounds of the present invention can be in the form of one of the possible isomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the imidazolyl moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

The term "pharmaceutically acceptable salts" includes salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, etc. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, etc. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, etc.; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, etc., specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences*, 20th ed., Mack Publishing Company, Easton, Pa., (1985).

When a basic group is present in the compounds of the present invention, the compounds can be converted into acid addition salts thereof, in particular, acid addition salts with the pyridinyl moiety of the structure, preferably pharmaceutically acceptable salts thereof. These are formed, with inorganic acids or organic acids. Suitable inorganic acids include but are not limited to, hydrochloric acid, sulfuric acid, a phosphoric or hydrohalic acid. Suitable organic acids include but are not limited to, carboxylic acids, such as ($C_1$-$C_4$)alkanecarboxylic acids which, for example, are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, organic sulfonic acids, such as ($C_1$-$C_4$)alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

When an acidic group is present in the compounds of the present invention, the compounds can be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine, etc. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

When both a basic group and an acid group are present in the same molecule, the compounds of the present invention can also form internal salts.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

The present invention includes all pharmaceutically acceptable isotopically-labeled compounds of the invention, i.e. Agents of the Invention, wherein (1) one or more atoms are replaced by atoms having the same atomic number, but an atomic mass or mass number different from the atomic mass or mass number usually found in nature, and/or (2) the isotopic ratio of one or more atoms is different from the naturally occurring ratio.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labeled Agents of the Invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled Agents of the Invention can generally be prepared by conventional techniques known to those skilled in the art or by processes analogous to those described in the accompanying Examples and Preparations using an appropriate isotopically-labeled reagents in place of the non-labeled reagent previously employed.

The present invention also provides prodrug moieties of the compounds of the present invention that convert in vivo to the compounds of the present invention. A prodrug moiety is an active or inactive compound that is modified chemically through in vivo physiological action, such as hydrolysis, metabolism, etc., into a compound of this invention following administration of the prodrug to a subject. The term "prodrug moiety" includes moieties which can be metabolized in vivo to a hydroxy group and moieties which may advantageously remain esterified in vivo. Preferably, the prodrugs moieties are metabolized in vivo by esterases or by other mechanisms to hydroxy groups or other advantageous groups. Examples of prodrugs and their uses are well known in the art (See, e.g., Berge et al. (1977) "Pharmaceutical Salts" *J. Pharm. Sci.* 66:1-19). The prodrugs can be prepared in situ during the final isolation and purification of the compounds, or by separately reacting the purified compound in its free acid form or hydroxy with a suitable esterifying agent. Hydroxy groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

The suitability and techniques involved in making and using prodrugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds are inactive or have low activity compared to the corresponding active drug compound that contains one or more protective groups and are converted to an active form by metabolism or solvolysis. Both the active drug form and any released metabolic products should have acceptably low toxicity. Typically, the formation of active drug compound involves a metabolic process or reaction that is one of the follow types:

1. Oxidative reactions, such as oxidation of alcohol, carbonyl, and acid functions, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

2. Reductive reactions, such as reduction of carbonyl groups, reduction of alcoholic groups and carbon-carbon double bonds, reduction of nitrogen-containing functions groups, and other reduction reactions.

3. Reactions without change in the state of oxidation, such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. See, Cheng et al., US20040077595, incorporated herein by reference. Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxy groups with lipophilic carboxylic acids, or of carboxylic acid groups with alcohols, e.g., aliphatic alcohols. Wermuth, *The Practice of Medicinal Chemistry*, Ch. 31-32, Ed. Werriuth, Academic Press, San Diego, Calif., 2001.

Exemplary prodrugs are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester, etc. conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole, etc., have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

In view of the close relationship between the compounds, the compounds in the form of their salts and the prodrugs, any reference to the compounds of the present invention is to be understood as referring also to the corresponding prodrugs of the compounds of the present invention, as appropriate and expedient.

Furthermore, the compounds of the present invention, including their salts, can also be obtained in the form of their hydrates, or include other solvents used for their crystallization.

Compounds of the present invention are prepared from commonly available compounds using procedures known to those skilled in the art, including any one or more of the following conditions without limitation:

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, etc.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Generally, enantiomers of the compounds of the present invention can be prepared by methods known to those skilled in the art to resolve racemic mixtures, such as by formation and recrystallization of diastereomeric salts or by chiral chromotography or HPLC separation utilizing chiral stationery phases.

In starting compounds and intermediates which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxy groups are those that can be converted under mild conditions into free amino thiol, carboxyl and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, NY (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, room temperature or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

ABBREVIATIONS

ATP: adenosine 5'-triphosphate
BINAP: racemic 2,2'-bis(diphenylphosphino)-1,1'-binaphthyl
BOC: tertiary butyl carboxy
br: broad
bs: broad singlet
calcd: calculated
d: doublet
DAST: (diethylamino)sulfur trifluoride
dd: doublet of doublets
DCM: dichloromethane
DIEA: diethylisopropylamine
DME: 1,4-dimethoxyethane
DMF: N,N-dimethylformamide
DMSO: dimethylsulfoxide
DPPA: diphenylphosphorylazide
DTT: dithiothreitol
EDTA: ethylenediamine tetraacetic acid
ESI: electrospray ionization
EtOAc: ethyl acetate
h: hour(s)
HATU: O-(7-azobenzotriazol-1-yl)-1,1,3,3-tetramethyluroniumhexafluorophosphate
HOBt: 1-hydroxy-7-azabenzotriazole
HPLC: high pressure liquid chromatography
LCMS: liquid chromatography and mass spectrometry
MeOD: methanol-d4
MeOH: methanol
MS: mass spectrometry
m: multiplet
min: minutes
m/z: mass to charge ratio
n.d.: not determined
NMR: nuclear magnetic resonance
ppm: parts per million
Pr: propyl
PyBOP: benzotriazol-1-yloxy Tripyrrolidinophosphoniumhexafluorophosphate
rt: room temperature
s: singlet
t: triplet
TFA: trifluoroacetic acid THF: tetrahydrofuran
TLC: thin layer chromatography
Tris•HCl: aminotris(hydroxymethyl) methane hydrochloride Methods for Synthesizing Compounds of the Invention The compounds of the invention can be synthesized using the methods described in the following schemes, examples, and by using art recognized techniques. All compounds described herein are included in the invention as compounds. Compounds of the invention may be synthesized according to at least one of the methods described in schemes 1-7.

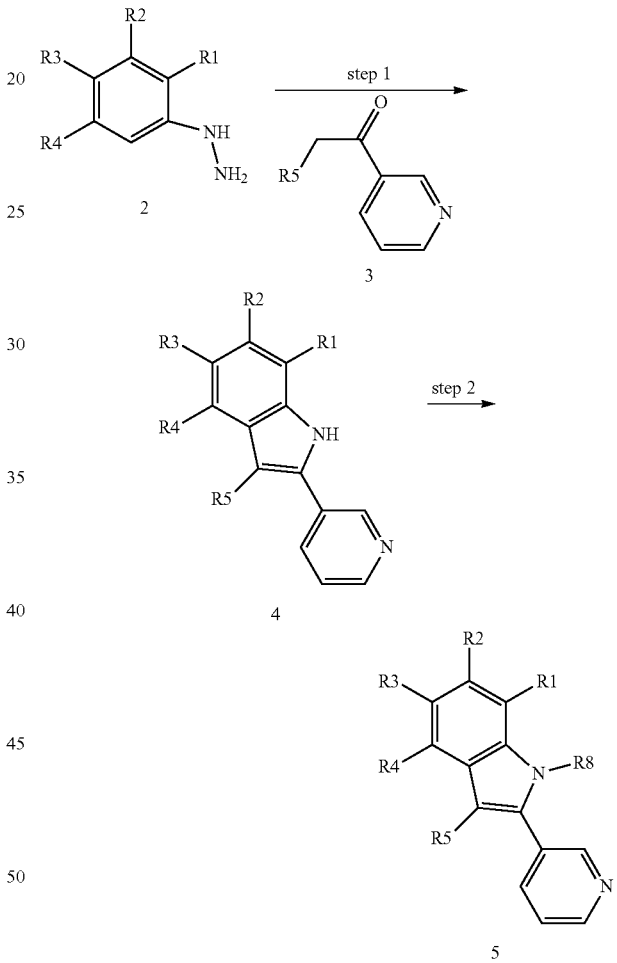

In step 1, the appropriate hydrazine derivative 2 is heated with 3-acetylpyridine derivative 3 in a solvent, e.g. ethanol, resulting in the formation of the corresponding hydrazone, which upon addition of an acid, e.g. hydrogen chloride, undergoes a Fisher reaction to give indole 4. Pyridine 3 can be conveniently prepared from nicotinic acid, via formation of the Weinreb amide and subsequent addition of the appropriate Grignard reagent, e.g. n-propyl magnesium bromide. In step 2, indole 4 is deprotonated with a strong base, such as potassium hexamethyldisilamide, and the resulting anion is trapped with the appropriate electrophilic reagent, e.g. an acid chloride, a chloroformate, an alkyl bromide, an alkyl chloride or an alkyl iodide, to give indole 5. Appropriate transformation of R8 in 5 leads to further analogs. For example, if R8 contains an ester, the ester can be hydrolyzed to the corresponding carboxylic acid. In another example, if R8 contains a nitrile, the nitrile can be reacted with azide to give the corresponding tetrazole.

disilamide, and the resulting anion is trapped with the appropriate electrophilic reagent, e.g. an acid chloride, a chloroformate, an alpha,beta-unsaturated ketone or ester, an alkyl bromide, an alkyl chloride or an alkyl iodide, to give indole 9. Appropriate transformation of R8 in 9 leads to further analogs. For example, if R8 contains an ester, the ester can be hydrolyzed to the corresponding carboxylic acid. In another example, if R8 contains a nitrile, the nitrile can be reacted with azide to give the corresponding tetrazole.

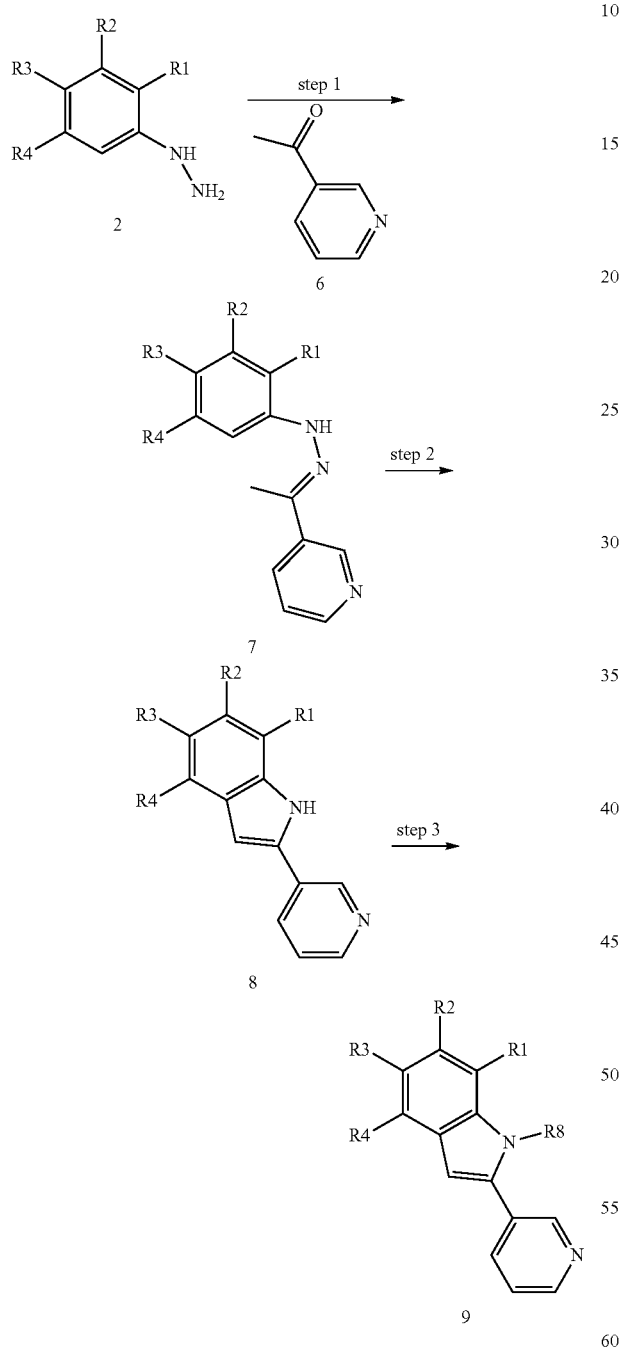

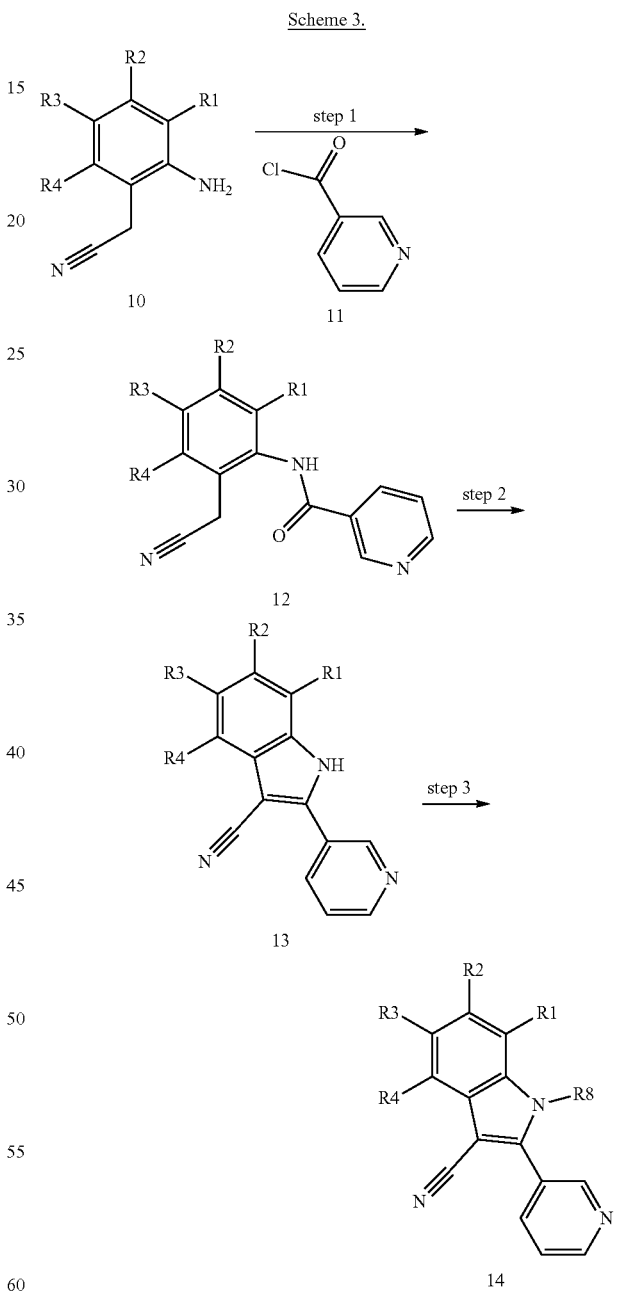

In step 1, the appropriate hydrazine derivative 2 is heated with 3-acetylpyridine 6 in a solvent, e.g. ethanol, resulting in the formation of the corresponding hydrazone 7. In step 2, 7 is heated, neat, with polyphosphoric acid, preferably between 160° C. and 220° C., to give indole 8. In step 3, indole 4 is deprotonated with a strong base, e.g. potassium hexamethyl- In step 1, the appropriate aniline derivative 10 is coupled with nicotinyl chloride in the presence of an amine base, e.g. diisopropylethylamine, to give amide 12. In step 2, heating of 12 in the presence of a strong base, e.g. sodium hydride, gives indole 13. In step 3, indole 13 is deprotonated with a strong base, e.g. sodium hydride, and the resulting anion is trapped with the appropriate electrophilic reagent, e.g. methyl iodide, to give indole 14.

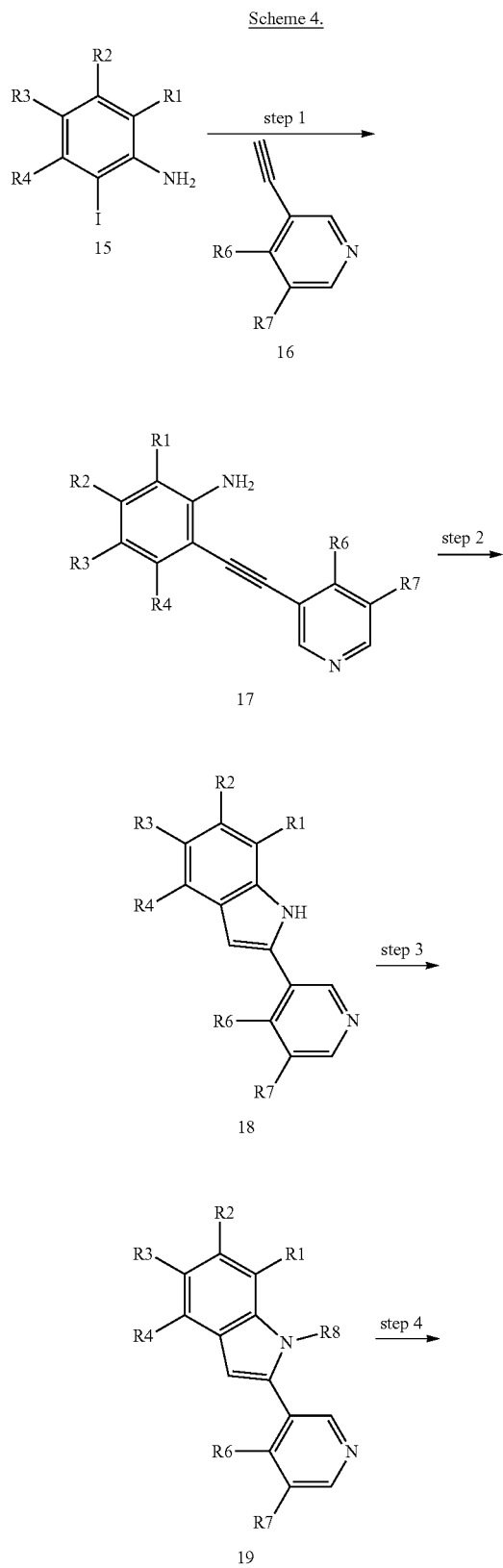

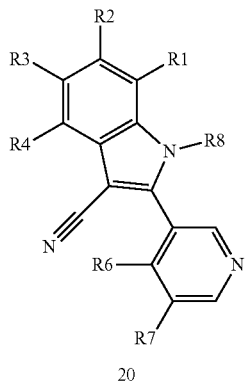

Step 1 involves the reaction of an iodoaniline derivative 15 and acetylene derivative 16 in the presence of palladium salts, e.g. $PdCl_2(PPh_3)_2$, copper salts, preferably copper iodide, in an amine solvent, preferably triethylamine, to give alkyne 17. In step 2, treatment of aniline 17 with a base, e.g. potassium tert-butoxide, in a polar solvent, preferably N-methylpyrolidinone, gives indole 18. In step 3, indole 18 is deprotonated with a strong base, e.g. sodium hydride, and the resulting anion is trapped with the appropriate electrophilic reagent, e.g. an alkyl chloride, or an alpha,beta-unsaturated ketone to give indole 19. Optionally, indole 19 can be reacted with chlorosulfonyl isocyanate, followed with dimethylformamide, as in step 4, to give indole 20. Appropriate transformations of R8 in 19 lead to further analogs. For example, if R8 contains an ester, the ester can be hydrolyzed to the corresponding carboxylic acid.

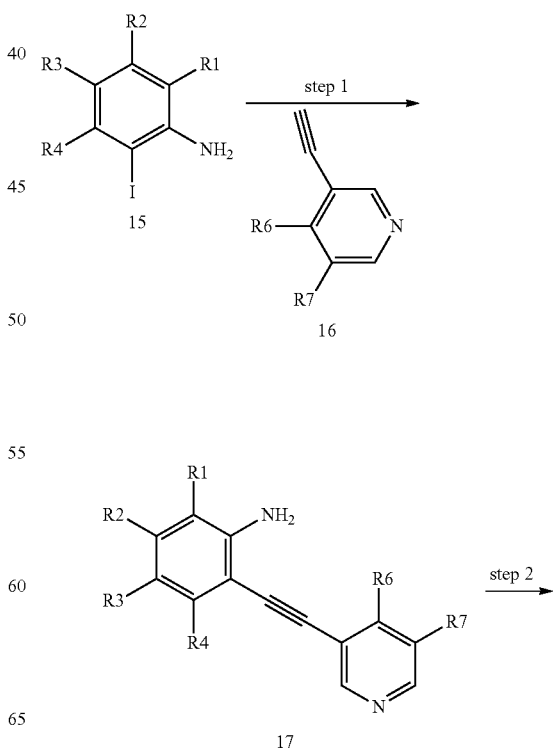

29

-continued

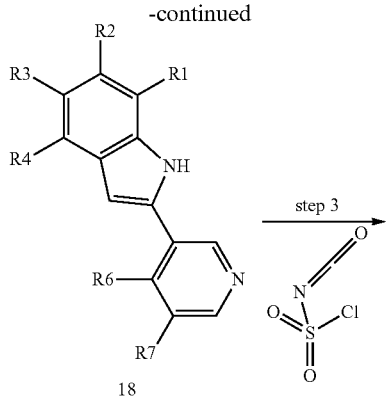

18

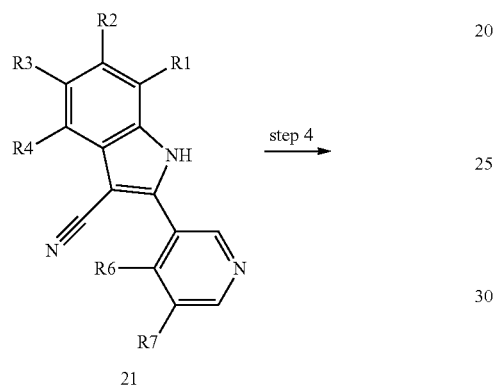

21

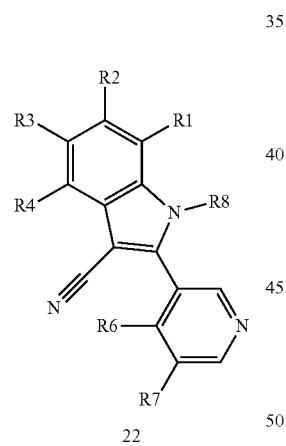

22

30

Scheme 6.

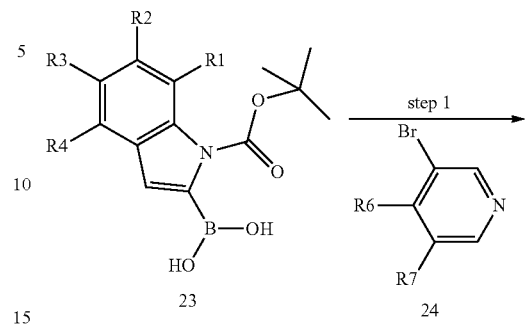

23   24

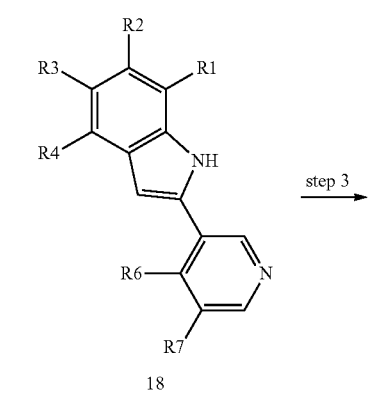

25

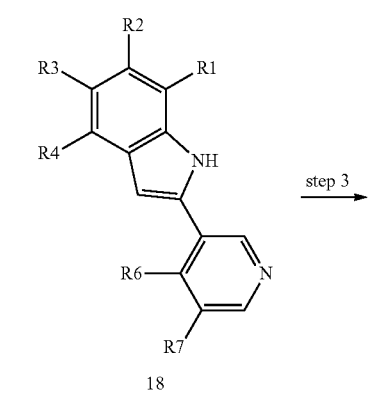

18

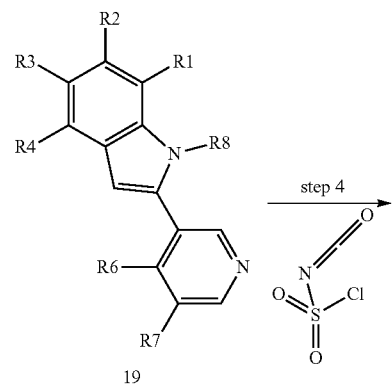

19

Step 1 involves the reaction of an iodoaniline derivative 15 and acetylene derivative 16 in the presence of palladium salts, e.g. PdCl$_2$(PPh$_3$)$_2$, copper salts, e.g. copper iodide, in an amine solvent, e.g. triethylamine, to give alkyne 17. In step 2, treatment of aniline 17 with a base, e.g. potassium tert-butoxide, in a polar solvent, e.g. N-methylpyrolidinone, gives indole 18. In step 3, indole 18 can be reacted with chlorosulfonyl isocyanate, followed with dimethylformamide, to give indole 21. In step 4, indole 21 is deprotonated with a strong base, e.g. sodium hydride, and the resulting anion is trapped with the appropriate electrophilic reagent, e.g. methyl iodide to give indole 22.

31
-continued

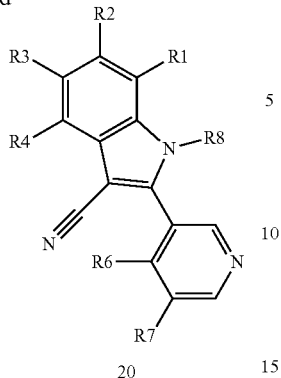

In step 1, the appropriate N-Boc-2-indole boronic acid 23 is reacted with the appropriate 3-bromopyridine 24 in the presence of palladium salts, e.g. $Pd_2dba_3$, ligands, e.g. s-Phos, and a base, e.g. potassium phosphate, in an organic solvent, e.g. toluene, to give indole 25. In step 2, the carbamate is cleaved, e.g. using trifluoroacetic acid or silica gel. In step 3, indole 18 is deprotonated with a strong base, e.g. sodium hydride, and the resulting anion is trapped with the appropriate electrophilic reagent, e.g. methyl iodide to give indole 19. Alternatively, indole 18 can be heated with dimethylcarbonate in the presence of a base, e.g. potassium carbonate, to give indole 19, where R8 is methyl. Optionally, indole 19 can be reacted with chlorosulfonyl isocyanate, followed with dimethylformamide, as in step 4, to give indole 20. Appropriate transformations of R6 and R7 in 19 or 20 lead to further analogs.

Scheme 7.

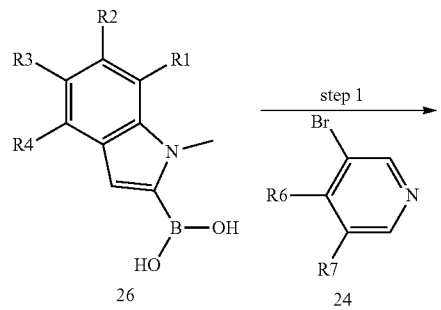

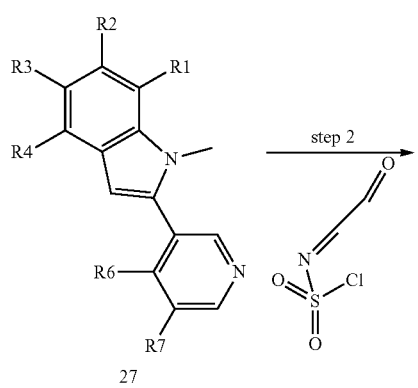

32
-continued

In step 1, the appropriate N-methyl-2-indole boronic acid 26 is reacted with the appropriate heterocycle 24 in the presence of palladium salts, e.g. $Pd_2dba_3$, ligands, e.g. s-Phos, and a base, e.g. potassium phosphate, in an organic solvent, e.g. toluene, to give indole 27. Optionally, indole 27 can be reacted with chlorosulfonyl isocyanate, followed with dimethylformamide, as in step 2, to give indole 28. Appropriate transformations of R6 and R7 in 27 or 28 lead to further analogs.

Methods of the Invention

The invention pertains, at least in part, to methods for treating a subject for a disorder or disease, by administering to a subject a therapeutically effective amount of a compound of Formula I:

(I)

wherein:

$R^{1a}$, $R^{2a}$, $R^{3a}$, and $R^{4a}$ are each independently hydrogen, halogen, cyano, hydroxy, alkoxy, alkyl, alkenyl, or alkoxycarbonyl;

$R^{5a}$ is hydrogen halogen, cyano, alkyl, alkenyl, arylalkyl, heteroarylalkyl, aminocarbonyl, alkylaminocarbonyl, carboxylate, alkoxycarbonyl, heterocyclylcarbonyl, aryl, or heteroaryl;

$R^{6a}$ and $R^{7a}$ are each independently hydrogen, halogen, hydroxy, alkoxy, amino, alkyl, sulfonyl, —O-sulfonyl, alkylamino, heterocyclyl, aminocarbonyl, carboxylate, or alkoxycarbonyl;

$R^{8a}$ is hydrogen, alkyl, arylalkyl, heteroarylalkyl, alkoxycarbonyl, sulfonyl, aroyl, aryl, or heteroaryl; and pharmaceutically acceptable salts, polymorphs, rotamers, prodrugs, enantiomers, hydrates, and solvates thereof, with the proviso that at least one of $R^{1a}$-$R^{8a}$ is other than hydrogen; and when $R^{5a}$ is cyano or lower alkyl optionally substituted with cyano, —C(O)-piperidine, amino, alkylamino, dialkylamino, carboxylate, alkoxycarbonyl, aminocarbonyl, or heterocyclyl, then at least one of $R^{1a}$-$R^{4a}$ and $R^{6a}$-$R^{8a}$ is other than hydrogen; and when $R^{7a}$ is imidazolyl, then at least one of $R^{1a}$-$R^{6a}$ and $R^{8a}$ is other than hydrogen; and when $R^{8a}$ is alkyl, arylalkyl or alkoxycarbonyl, then at least one of $R^{1a}$-$R^{7a}$ is other than hydrogen; and when $R^{5a}$ is lower alkyl and $R^{8a}$ is alkyl substituted with carboxylate or $PO_3R^{21}R^{22}$ wherein $R^{21}$ and $R^{22}$ are each independently hydrogen or lower alkyl, then at least one of $R^{1a}$-$R^{4a}$ and $R^{6a}$ and $R^{7a}$ is other than hydrogen; and when $R^{3a}$ is halogen and $R^{5a}$ and $R^{8a}$ are independently lower alkyl optionally substituted with carboxylate, alkoxycarbonyl, or —C(O)-piperidine, then at least one of $R^{1a}$, $R^{2a}$, $R^{4a}$, $R^{6a}$ and $R^{7a}$ is other than hydrogen; and when $R^{3a}$ is halogen or lower alkyl and $R^{5a}$ is lower alkyl substituted with dialkylamino, dialkylaminocarbonyl, carboxylate, alkoxycarbonyl or aminocarbonyl, then at least one of $R^{1a}$, $R^{2a}$, $R^{4a}$, and $R^{6a}$-$R^{8a}$ is other than hydrogen; and when $R^{2a}$ and $R^{3a}$ are each alkoxy and $R^{5a}$ is cyano, then at least one of $R^{1a}$, $R^{4a}$, and $R^{6a}$-$R^{8a}$ is other than hydrogen; and when $R^{3a}$ is alkyl substituted with aroyl, and $R^5$ and $R^8$ are each independently hydrogen or lower alkyl, then at least one of $R^{1a}$, $R^{2a}$, and $R^{4a}$ is other than hydrogen, such that said disorder or disease in said subject is treated.

In one embodiment, the invention pertains, at least in part, to methods for treating a subject for a disorder or disease, by administering to a subject a therapeutically effective amount of a compound of Formula II:

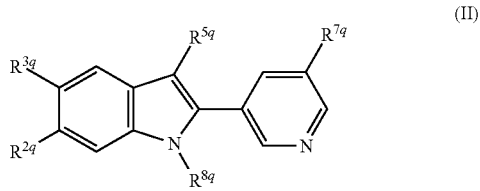

wherein:
$R^{2q}$ is hydrogen or halogen;
$R^{3q}$ is hydrogen, halogen, or cyano;
$R^{5q}$ is hydrogen, alkyl, or cyano;
$R^{7q}$ is hydrogen, halogen, alkoxy, —OSO$_2$-heterocyclyl, —O-arylalkyl, —NR'—SO$_2$-alkyl, —NR'—C(O)-alkyl, —NR'—C(O)—NR'-alkyl, —NR'—C(O)—O-alkyl, haloalkyl, or alkyl optionally substituted with heterocyclyl, —NR'—SO$_2$-alkyl, —NR'—SO$_2$-haloalkyl, NR'—C(O)-alkyl, NR'—C(O)-heterocyclyl, —NR'—C(O)—NR'-alkyl, or —NR'—C(O)—O-alkyl;
$R^{8q}$ is hydrogen, alkyl, hydroxyalkyl, -alkyl-OC(O)-alkyl, carboxylate, alkoxycarbonyl, or arylalkyl substituted with alkyl, or aroyl substituted with cyano and/or alkyl, or -alkyl-O-aryl substituted with alkoxycarbonyl;
each R' is independently hydrogen, $C_1$-$C_4$-alkyl, or $C_3$-$C_6$-cycloalkyl and pharmaceutically acceptable salts, polymorphs, rotamers, prodrugs, enantiomers, hydrates, and solvates thereof, with the proviso that at least one of $R^{2q}$, $R^{3q}$, $R^{5q}$, $R^{7q}$ and $R^{8q}$ is other than hydrogen, such that said disorder or disease in said subject is treated.

In another embodiment, the invention pertains, at least in part, to methods for treating a subject for a disorder or disease, by administering to a subject a therapeutically effective amount of a compound of Formulae III or IV, and pharmaceutically acceptable salts, polymorphs, rotamers, prodrugs, enantiomers, hydrates, and solvates thereof, such that said disorder or disease in said subject is treated.

The term "disorder" or "disease" includes any pathological condition, derangement, or abnormality of function of a part, organ, or system of an organism resulting from various causes, such as infection, genetic defect, or environmental stress, and characterized by an identifiable group of signs or symptoms; and any morbid physical or mental state. See Dorland's Illustrated Medical Dictionary, (W.B. Saunders Co. 27th ed. 1988).

In another embodiment, the disorder or disease is a disease selected from, hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries.

The invention also pertains, at least in part, to methods of inhibiting aldosterone synthase activity in a subject, by administering to a subject a therapeutically effective amount of a compound of Formula I:

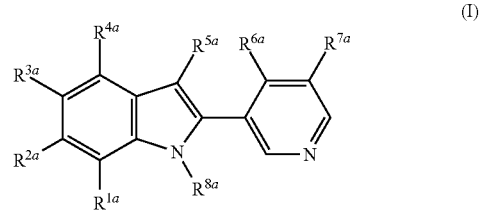

wherein:
$R^{1a}$, $R^{2a}$, $R^{3a}$, and $R^{4a}$ are each independently hydrogen, halogen, cyano, hydroxy, alkoxy, alkyl, alkenyl, or alkoxycarbonyl;
$R^{5a}$ is hydrogen halogen, cyano, alkyl, alkenyl, arylalkyl, heteroarylalkyl, aminocarbonyl, alkylaminocarbonyl, carboxylate, alkoxycarbonyl, heterocyclylcarbonyl, aryl, or heteroaryl;
$R^{6a}$ and $R^{7a}$ are each independently hydrogen, halogen, hydroxy, alkoxy, amino, alkyl, sulfonyl, —O-sulfonyl, alkylamino, heterocyclyl, aminocarbonyl, carboxylate, or alkoxycarbonyl;
$R^{8a}$ is hydrogen, alkyl, arylalkyl, heteroarylalkyl, alkoxycarbonyl, sulfonyl, aroyl, aryl, or heteroaryl; and pharmaceutically acceptable salts, polymorphs, rotamers, prodrugs, enantiomers, hydrates, and solvates thereof, such that aldosterone synthase activity is inhibited.

The invention also pertains, at least in part, to methods of inhibiting aldosterone synthase activity in a subject, by administering to a subject a therapeutically effective amount of a compound of Formula II:

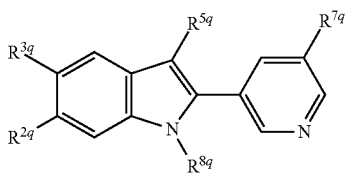

wherein:
R$^{2q}$ is hydrogen or halogen;
R$^{3q}$ is hydrogen, halogen, or cyano;
R$^{5q}$ is hydrogen, alkyl, or cyano;
R$^{7q}$ is hydrogen, halogen, alkoxy, —OSO$_2$-heterocyclyl, —O-arylalkyl, —NR'—SO$_2$-alkyl, —NR'—C(O)-alkyl, —NR'—C(O)—NR'-alkyl, —NR'—C(O)—O-alkyl, haloalkyl, or alkyl optionally substituted with heterocyclyl, —NR'—SO$_2$-alkyl, —NR'—SO$_2$-haloalkyl, NR'—C(O)-alkyl, NR'—C(O)-heterocyclyl, —NR'—C(O)—NR'-alkyl, or —NR'—C(O)—O-alkyl;
R$^{8q}$ is hydrogen, alkyl, hydroxyalkyl, -alkyl-OC(O)-alkyl, carboxylate, alkoxycarbonyl, or arylalkyl substituted with alkyl, or aroyl substituted with cyano and/or alkyl, or -alkyl-O-aryl substituted with alkoxycarbonyl;
each R' is independently hydrogen, C$_1$-C$_4$-alkyl, or C$_3$-C$_6$-cycloalkyl, and pharmaceutically acceptable salts, polymorphs, rotamers, prodrugs, enantiomers, hydrates, and solvates thereof, such that aldosterone synthase activity is inhibited.

In one embodiment, the invention pertains, at least in part, to methods of inhibiting aldosterone synthase activity in a subject, by administering to a subject a therapeutically effective amount of a compound of Formulae III or IV, such that aldosterone synthase activity is inhibited.

Another embodiment of the present invention includes methods for treating an aldosterone synthase associated state, by administering to a subject a therapeutically effective amount of a compound of Formula I:

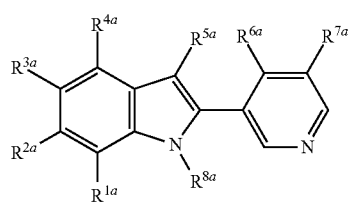

wherein:
R$^{1a}$, R$^{2a}$, R$^{3a}$, and R$^{4a}$ are each independently hydrogen, halogen, cyano, hydroxy, alkoxy, alkyl, alkenyl, or alkoxycarbonyl;
R$^{5a}$ is hydrogen halogen, cyano, alkyl, alkenyl, arylalkyl, heteroarylalkyl, aminocarbonyl, alkylaminocarbonyl, carboxylate, alkoxycarbonyl, heterocyclylcarbonyl, aryl, or heteroaryl;
R$^{6a}$ and R$^{7a}$ are each independently hydrogen, halogen, hydroxy, alkoxy, amino, alkyl, sulfonyl, —O-sulfonyl, alkylamino, heterocyclyl, aminocarbonyl, carboxylate, or alkoxycarbonyl;
R$^{8a}$ is hydrogen, alkyl, arylalkyl, heteroarylalkyl, alkoxycarbonyl, sulfonyl, aroyl, aryl, or heteroaryl; and pharmaceutically acceptable salts, polymorphs, rotamers, prodrugs, enantiomers, hydrates, and solvates thereof, such that said aldosterone synthase associated state in said subject is treated.

Yet another embodiment of the present invention includes methods of treating an aldosterone synthase associated state, by administering to a subject a therapeutically effective amount of a compound of Formula II:

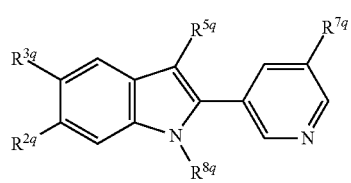

wherein:
R$^{2q}$ is hydrogen or halogen;
R$^{3q}$ is hydrogen, halogen, or cyano;
R$^{5q}$ is hydrogen, alkyl, or cyano;
R$^{7q}$ is hydrogen, halogen, alkoxy, —OSO$_2$-heterocyclyl, —O-arylalkyl, —NR'—SO$_2$-alkyl, —NR'—C(O)-alkyl, —NR'—C(O)—NR'-alkyl, —NR'—C(O)—O-alkyl, haloalkyl, or alkyl optionally substituted with heterocyclyl, —NR'—SO$_2$-alkyl, —NR'—SO$_2$-haloalkyl, NR'—C(O)-alkyl, NR'—C(O)-heterocyclyl, —NR'—C(O)—NR'-alkyl, or —NR'—C(O)—O-alkyl;
R$^{8q}$ is hydrogen, alkyl, hydroxyalkyl, -alkyl-OC(O)-alkyl, carboxylate, alkoxycarbonyl, or arylalkyl substituted with alkyl, or aroyl substituted with cyano and/or alkyl, or -alkyl-O-aryl substituted with alkoxycarbonyl;
each R' is independently hydrogen, C$_1$-C$_4$-alkyl, or C$_3$-C$_6$-cycloalkyl, and pharmaceutically acceptable salts, polymorphs, rotamers, prodrugs, enantiomers, hydrates, and solvates thereof, such that said aldosterone synthase associated state in said subject is treated.

Yet another embodiment of the present invention includes methods of treating an aldosterone synthase associated state, by administering to a subject a therapeutically effective amount of a compound of Formula III or IV, such that said aldosterone synthase associated state in said subject is treated.

The term "aldosterone synthase associated state" refers to a state, disease, or disorder which can be treated by the modulation, (e.g., inhibition) of aldosterone synthase. Aldosterone synthase is a mitcohcondrial cytochrome P450 enzyme catalyzing the last step of aldosterone production in the adrenal cortex, i.e., the conversion of 11-deoxycorticosterone to aldosterone. Aldosterone synthase has been demonstrated to be expressed in all cardiovascular tissues such as heart, umbilical cord, mesenteric and pulmonary arteries, aorta, endothelium and vascular cells. Moreover, the expression of aldosterone synthase is closely correlated with aldosterone production in cells. It has been observed that elevations of aldosterone activity induces different diseases such as congestive heart failure, myocardial fibrosis, ventricular arrhythmia and other adverse effects, etc.

Examples of aldosterone synthase associated states include hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, and fibrinoid necrosis of coronary arteries.

In one embodiment, the aldosterone synthase associated state is characterized by abnormal activity of aldosterone synthase and/or abnormal expression of aldosterone synthase.

The term "abnormal" includes an activity or feature which differs from a normal activity or feature.

The term "abnormal activity" includes an activity which differs from the activity of the wild-type or native gene or protein, or which differs from the activity of the gene or protein in a healthy subject. The abnormal activity can be stronger or weaker than the normal activity.

In one embodiment, the "abnormal activity" includes the abnormal (either over- or under-) production of mRNA transcribed from a gene. In another embodiment, the "abnormal activity" includes the abnormal (either over- or under-) production of polypeptide from a gene. In another embodiment, the abnormal activity refers to a level of a mRNA or polypeptide that is different from a normal level of said mRNA or polypeptide by about 15%, about 25%, about 35%, about 50%, about 65%, about 85%, about 100% or greater. Preferably, the abnormal level of the mRNA or polypeptide can be either higher or lower than the normal level of said mRNA or polypeptide. Yet in another embodiment, the abnormal activity refers to functional activity of a protein that is different from a normal activity of the wild-type protein. Preferably, the abnormal activity can be stronger or weaker than the normal activity. Preferably, the abnormal activity is due to the mutations in the corresponding gene, and the mutations can be in the coding region of the gene or non-coding regions such as transcriptional promoter regions. The mutations can be substitutions, deletions, insertions.

The compounds of the present invention, as aldosterone synthase inhibiting compounds, are useful for treatment of a disorder or disease mediated by aldosterone synthase or responsive to inhibition of aldosterone synthase. In particular, the compounds of the present invention are useful for treatment of a aldosterone synthase associated state including hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, and fibrinoid necrosis of coronary arteries.

The term "aldosterone synthase inhibiting compound" includes compounds which reduce the activity of aldosterone synthase, e.g., the ability of aldosterone synthase to synthesize aldosterone, in vivo or in vitro. In one embodiment, the aldosterone synthase inhibiting compounds are aldosterone synthesis inhibiting compounds.

The term "inhibition" or "inhibiting" includes the reduction or suppression of a given condition, symptom, or disorder, or disease, or a significant decrease in the baseline activity of a biological activity or process. In one embodiment, the condition or symptom or disorder or disease is mediated by aldosterone synthase activity. In another embodiment, the condition or symptom or disorder or disease is associated with the abnormal activity of aldosterone synthase, or the condition or symptom or disorder or disease is associated with the abnormal expression of aldosterone synthase.

The term "subject" includes animals (e.g., mammals). A subject also refers to for example, primates (e.g., humans, including males and females), cows, sheep, goats, horses, dogs, cats, rabbits, rats, mice, fish, birds, etc.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by aldosterone synthase, or (ii) associated with aldosterone synthase activity, or (iii) characterized by abnormal activity of aldosterone synthase; or (2) reduce or inhibit the activity of aldosterone synthase; or (3) reduce or inhibit the expression of aldosterone synthase. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of aldosterone synthase; or at least partially reduce or inhibit the expression of aldosterone synthase.

The effective amount can vary depending on such factors as the size and weight of the subject, the type of illness, or the particular organic compound. For example, the choice of the organic compound can affect what constitutes an "effective amount." One of ordinary skill in the art would be able to study the aforementioned factors and make the determination regarding the effective amount of the organic compound without undue experimentation.

The term "treating" or "treatment" of any disease or disorder includes curing as well as ameliorating at least one symptom of the state, disease, or disorder (e.g., the aldosterone synthase associated state). The term may also include alleviating or ameliorating at least one physical parameter including those which may not be discernible by the patient; or modulating the disease or disorder, either physically, (e.g., stabilization of a discernible symptom), physiologically, (e.g., stabilization of a physical parameter), or both. The terms may also include preventing or delaying the onset or development or progression of the disease or disorder.

A further embodiment includes methods for treating an aldosterone synthase associated disorder or disease in a subject by administering to a subject an effective amount of a compound of the invention (e.g., a compound of Formulae I-IV, or a compound otherwise described herein) in combination with a second agent, such that the subject is treated for said aldosterone synthase associated disorder.

The disorder or disease may be characterized by an abnormal activity of aldosterone synthase or abnormal expression of aldosterone synthase.

In one embodiment the disorder or disease includes but is not limited to hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, and fibrinoid necrosis of coronary arteries.

In one embodiment, the invention pertains, at least in part, to methods for treating a subject for heart failure, congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, fibrinoid necrosis of coronary arteries, renal dysfunction, liver diseases, cerebrovascular diseases, vascular diseases, retinopathy, neuropathy, insulinopathy, edema, endothelial dysfunction, baroreceptor dysfunction, migraine headaches, or hypertension, comprising administering to said subject an effective amount of a compound of Formula I:

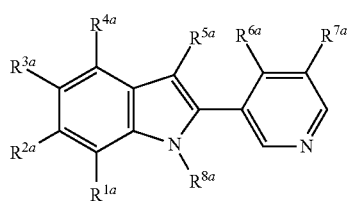

(I)

wherein:
$R^{1a}$, $R^{2a}$, $R^{3a}$, and $R^{4a}$ are each independently hydrogen, halogen, cyano, hydroxy, alkoxy, alkyl, alkenyl, or alkoxycarbonyl;

$R^{5a}$ is hydrogen halogen, cyano, alkyl, alkenyl, arylalkyl, heteroarylalkyl, aminocarbonyl, alkylaminocarbonyl, carboxylate, alkoxycarbonyl, heterocyclylcarbonyl, aryl, or heteroaryl;

$R^{6a}$ and $R^{7a}$ are each independently hydrogen, halogen, hydroxy, alkoxy, amino, alkyl, sulfonyl, —O-sulfonyl, alkylamino, heterocyclyl, aminocarbonyl, carboxylate, or alkoxycarbonyl;

$R^{8a}$ is hydrogen, alkyl, arylalkyl, heteroarylalkyl, alkoxycarbonyl, sulfonyl, aroyl, aryl, or heteroaryl; and pharmaceutically acceptable salts, polymorphs, rotamers, prodrugs, enantiomers, hydrates, and solvates thereof, such that said subject is treated.

In another embodiment, the invention pertains, at least in part, to methods for treating a subject for heart failure, congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, fibrinoid necrosis of coronary arteries, renal dysfunction, liver diseases, cerebrovascular diseases, vascular diseases, retinopathy, neuropathy, insulinopathy, edema, endothelial dysfunction, baroreceptor dysfunction, migraine headaches, or hypertension, comprising administering to said subject an effective amount of a compound of Formula II:

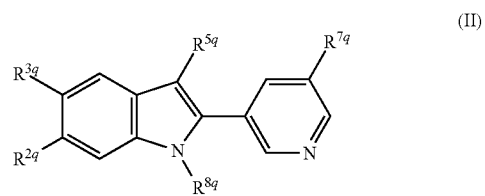

(II)

wherein:
$R^{2q}$ is hydrogen or halogen;
$R^{3q}$ is hydrogen, halogen, or cyano;
$R^{5q}$ is hydrogen, alkyl, or cyano;
$R^{7q}$ is hydrogen, halogen, alkoxy, —OSO₂-heterocyclyl, —O-arylalkyl, —NR'—SO₂-alkyl, —NR'—C(O)-alkyl, —NR'—C(O)—NR'-alkyl, —NR'—C(O)—O-alkyl, haloalkyl, or alkyl optionally substituted with heterocyclyl, —NR'—SO₂-alkyl, —NR'—SO₂-haloalkyl, NR'—C(O)-alkyl, NR'—C(O)-heterocyclyl, —NR'—C(O)—NR'-alkyl, or —NR'—C(O)—O-alkyl;

$R^{8q}$ is hydrogen, alkyl, hydroxyalkyl, -alkyl-OC(O)-alkyl, carboxylate, alkoxycarbonyl, or arylalkyl substituted with alkyl, or aroyl substituted with cyano and/or alkyl, or -alkyl-O-aryl substituted with alkoxycarbonyl;
each R' is independently hydrogen, $C_1$-$C_4$-alkyl, or $C_3$-$C_6$-cycloalkyl, and pharmaceutically acceptable salts, polymorphs, rotamers, prodrugs, enantiomers, hydrates, and solvates thereof, such that said subject is treated.

In yet another embodiment, the invention pertains, at least in part, to methods for treating a subject for heart failure, congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, fibrinoid necrosis of coronary arteries, renal dysfunction, liver diseases, cerebrovascular diseases, vascular diseases, retinopathy, neuropathy, insulinopathy, edema, endothelial dysfunction, baroreceptor dysfunction, migraine headaches, or hypertension, comprising administering to said subject an effective amount of a compound of Formula III or IV, and pharmaceutically acceptable salts, polymorphs, rotamers, prodrugs, enantiomers, hydrates, and solvates thereof, such that said subject is treated.

In still another embodiment, the invention pertains, at least in part, to methods wherein the compound of the invention (e.g., a compound of Formulae I-IV or a compound otherwise described herein) is administered in combination with a second agent.

The term "in combination with" a second agent or treatment includes co-administration of the compound of the invention (e.g., a compound of Formulae I-IV or a compound otherwise described herein) with the second agent or treatment, administration of the compound of the invention first, followed by the second agent or treatment and administration of the second agent or treatment first, followed by the compound of the invention.

The term "second agent" includes any agent which is known in the art to treat, prevent, or reduce the symptoms of a disease or disorder described herein, e.g., an aldosterone synthase associated disorder, such as, for example, hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertropic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, and fibrinoid necrosis of coronary arteries. Furthermore, the second agent may be any agent of benefit to the patient when administered in combination with the administration of a compound of the invention.

Examples of second agents include HMG-Co-A reductase inhibitors, angiotensin II receptor antagonists, angiotensin converting enzyme (ACE) Inhibitors, calcium channel blockers (CCB), dual angiotensin converting enzyme/neutral endopeptidase (ACE/NEP) inhibitors, endothelin antagonists, renin inhibitors, diuretics, ApoA-I mimics, anti-diabetic agents, obesity-reducing agents, aldosterone receptor blockers, endothelin receptor blockers, and CETP inhibitors.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, pharmaceutically acceptables salt thereof.

The term "calcium channel blocker (CCB)" includes dihydropyridines (DHPs) and non-DHPs (e.g., diltiazem-type and verapamil-type CCBs). Examples include amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "dual angiotensin converting enzyme/neutral endopetidase (ACE/NEP) inhibitor" includes omapatrilate (cf. EP 629627), fasidotril or fasidotrilate, or pharmaceutically acceptable salts thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R*,2R*)]]-1-[(1,1-dimethylethoxy)carbonyl]-L-proly l-L-phenylalanyl-N-[2-hydroxy-5-methyl-1-(2-methylpropyl)-4-[[[2-methyl-1-[[(2-pyridinylmethyl)amino]carbonyl]butyl]amino]carbonyl]hexyl]-N-alfa-methyl-L-histidinamide); terlakiren (chemical name: [R—(R*,S*)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); and zankiren (chemical name: [1S-[1R*[R*(R*)],2S*,3R*]]-N-[1-(cyclohexylmethyl)-2,3-dihydroxy-5-methylhexyl]-alfa-[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

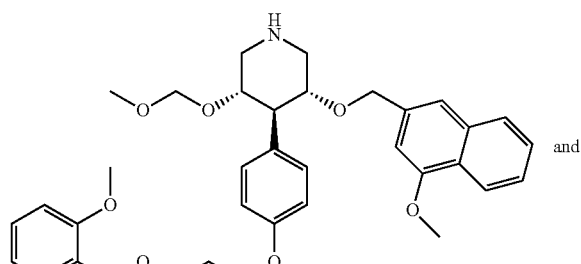

(A)

and

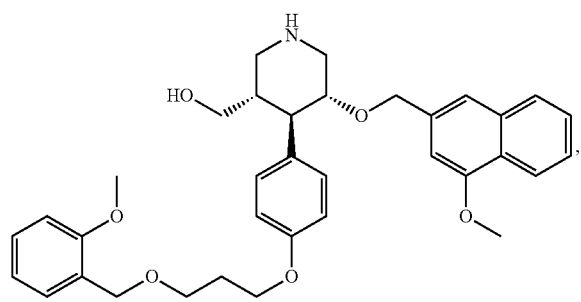

(B)

pharmaceutically acceptable salts thereof.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F)

The term "anti-diabetic agent" includes insulin secretion enhancers that promote the secretion of insulin from pancreatic β-cells. Examples include biguanide derivatives (e.g., metformin), sulfonylureas (SU) (e.g., tolbutamide, chlorpropamide, tolazamide, acetohexamide, 4-chloro-N-[(1-pyrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine](cf. EP 196222 and EP 526171) of the formula

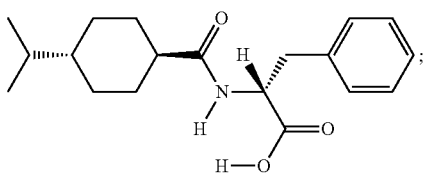 [SMILES: CC(C)[C@H]1CC[C@H](C(=O)N[C@H](Cc2ccccc2)C(=O)O)CC1]

repaglinide [(S)-2-ethoxy-4-{2-[[3-methyl-1-[2-(1-piperidinyl)phenyl]butyl]amino]-2-oxoethyl}benzoic acid](cf. EP 589874, EP 147850 A2, in particular Example 11 on page 61, and EP 207331 A1); calcium (2S)-2-benzyl-3-(cis-hexahydro-2-isoindolinylcarbonyl)-propionate dihydrate (e.g., mitiglinide (cf. EP 507534)); and glimepiride (cf. EP 31058). Further examples include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is an insulinotropic protein which is described, e.g., by W. E. Schmidt et al. in *Diabetologia*, 28, 1985, 704-707 and in U.S. Pat. No. 5,705,483.

The term "GLP-1 agonists" includes variants and analogs of GLP-1(7-36)NH$_2$ which are disclosed in particular in U.S. Pat. No. 5,120,712, U.S. Pat. No. 5,118,666, U.S. Pat. No. 5,512,549, WO 91/11457 and by C. Orskov et al in J. Biol. Chem. 264 (1989) 12826. Further examples include GLP-1 (7-37), in which compound the carboxy-terminal amide functionality of Arg$^{36}$ is displaced with Gly at the 37$^{th}$ position of the GLP-1(7-36)NH$_2$ molecule and variants and analogs thereof including GLN$^9$-GLP-1 (7-37), D-GLN$^9$-GLP-1(7-37), acetyl LYS$^9$-GLP-1(7-37), LYS$^{18}$-GLP-1 (7-37) and, in particular, GLP-1 (7-37)OH, VAL$^8$-GLP-1(7-37), GLY$^8$-GLP-1 (7-37), THR$^8$-GLP-1 (7-37), MET$^8$-GLP-1 (7-37) and 4-imidazopropionyl-GLP-1. Special preference is also given to the GLP agonist analog exendin-4, described by Greig et al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenyl]methyl}-thiazolidine-2,4-dione, 5-[3-(4-chlorophenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluorobenzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPAR agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; α$_2$-adrenergic antagonists; and pharmaceutically acceptable salts thereof.

The term "obesity-reducing agent" includes lipase inhibitors (e.g., orlistat) and appetite suppressants (e.g., sibutramine and phentermine).

The term "aldosterone receptor blocker" includes spironolactone and eplerenone.

The term "endothelin receptor blocker" includes bosentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. No. 6,140,343 and U.S. Pat. No. 6,197,786 (e.g., [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot.*, 49(8): 815-816 (1996), and *Bioorg. Med. Chem. Lett.*; 6:1951-1954 (1996), respectively. Furthermore, the CETP inhibitors also include those disclosed in WO2000/017165, WO2005/095409 and WO2005/097806.

Pharmaceutical Compositions of the Invention

The invention also pertains to pharmaceutical compositions comprising an effective amount of a compound of Formula I:

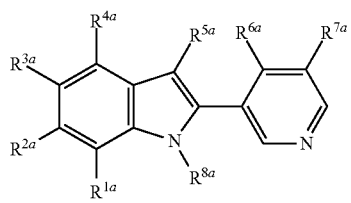

(I)

wherein:

$R^{1a}$, $R^{2a}$, $R^{3a}$, and $R^{4a}$ are each independently hydrogen, halogen, cyano, hydroxy, alkoxy, alkyl, alkenyl, or alkoxycarbonyl;

$R^{5a}$ is hydrogen halogen, cyano, alkyl, alkenyl, arylalkyl, heteroarylalkyl, aminocarbonyl, alkylaminocarbonyl, carboxylate, alkoxycarbonyl, heterocyclylcarbonyl, aryl, or heteroaryl;

$R^{6a}$ and $R^{7a}$ are each independently hydrogen, halogen, hydroxy, alkoxy, amino, alkyl, sulfonyl, —O-sulfonyl, alkylamino, heterocyclyl, aminocarbonyl, carboxylate, or alkoxycarbonyl;

$R^{8a}$ is hydrogen, alkyl, arylalkyl, heteroarylalkyl, alkoxycarbonyl, sulfonyl, aroyl, aryl, or heteroaryl; and pharmaceutically acceptable salts, polymorphs, rotamers, prodrugs, enantiomers, hydrates, and solvates thereof;

with the proviso that at least one of $R^{1a}$-$R^{8a}$ is other than hydrogen; and when $R^{5a}$ is cyano or lower alkyl optionally substituted with cyano, —C(O)-piperidine, amino, alkylamino, dialkylamino, carboxylate, alkoxycarbonyl, aminocarbonyl, or heterocyclyl, then at least one of $R^{1a}$-$R^{4a}$ and $R^{6a}$-$R^{8a}$ is other than hydrogen; and when $R^{7a}$ is imidazolyl, then at least one of $R^{1a}$-$R^{6a}$ and $R^{8a}$ is other than hydrogen; and when $R^{8a}$ is alkyl, arylalkyl or alkoxycarbonyl, then at least one of $R^{1a}$-$R^{7a}$ is other than hydrogen; and when $R^{5a}$ is lower alkyl and $R^{8a}$ is alkyl substituted with carboxylate or $PO_3R^{21}R^{22}$ wherein $R^{21}$ and $R^{22}$ are each independently hydrogen or lower alkyl, then at least one of $R^{1a}$-$R^{4a}$ and $R^{6a}$ and $R^{7a}$ is other than hydrogen; and when $R^{3a}$ is halogen and $R^{5a}$ and $R^{8a}$ are independently lower alkyl optionally substituted with carboxylate, alkoxycarbonyl, or —C(O)-piperidine, then at least one of $R^{1a}$, $R^{2a}$, $R^{4a}$, $R^{6a}$ and $R^{7a}$ is other than hydrogen; and when $R^{3a}$ is halogen or lower alkyl and $R^{5a}$ is lower alkyl substituted with dialkylamino, dialkylaminocarbonyl, carboxylate, alkoxycarbonyl or aminocarbonyl, then at least one of $R^{1a}$, $R^{2a}$, $R^{4a}$, and $R^{6a}$-$R^{8a}$ is other than hydrogen; and when $R^{2a}$ and $R^{3a}$ are each alkoxy and $R^{5a}$ is cyano, then at least one of $R^{1a}$, $R^{4a}$, and $R^{6a}$-$R^{8a}$ is other than hydrogen; and when $R^{3a}$ is alkyl substituted with aroyl, and $R^5$ and $R^8$ are each independently hydrogen or lower alkyl, then at least one of $R^{1a}$, $R^{2a}$, and $R^{4a}$ is other than hydrogen, wherein said effective amount is effective to treat an aldosterone synthase associated state.

In another embodiment, the invention pertains to pharmaceutical compositions comprising an effective amount of a compound of Formula II:

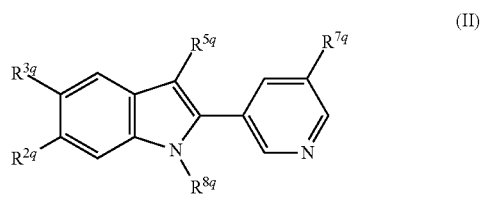

(II)

wherein:

$R^{2q}$ is hydrogen or halogen;

$R^{3q}$ is hydrogen, halogen, or cyano;

$R^{5q}$ is hydrogen, alkyl, or cyano;

$R^{7q}$ is hydrogen, halogen, alkoxy, —OSO$_2$-heterocyclyl, —O-arylalkyl, —NR'—SO$_2$-alkyl, —NR'—C(O)-alkyl, —NR'—C(O)—NR'-alkyl, —NR'—C(O)—O-alkyl, haloalkyl, or alkyl optionally substituted with heterocyclyl, —NR'—SO$_2$-alkyl, —NR'—SO$_2$-haloalkyl, NR'—C(O)-alkyl, NR'—C(O)-heterocyclyl, —NR'—C(O)—NR'-alkyl, or —NR'—C(O)—O-alkyl;

$R^{8q}$ is hydrogen, alkyl, hydroxyalkyl, -alkyl-OC(O)-alkyl, carboxylate, alkoxycarbonyl, or arylalkyl substituted with alkyl, or aroyl substituted with cyano and/or alkyl, or -alkyl-O-aryl substituted with alkoxycarbonyl;

each R' is independently hydrogen, $C_1$-$C_4$-alkyl, or $C_3$-$C_6$-cycloalkyl, with the proviso that at least one of $R^{2q}$, $R^{3q}$, $R^{5q}$, $R^{7q}$ and $R^{8q}$ is other than hydrogen, wherein said effective amount is effective to treat an aldosterone synthase associated state.

In still another embodiment, the invention pertains to pharmaceutical compositions comprising an effective amount of a compound of Formula III or IV, wherein said effective amount is effective to treat an aldosterone synthase associated state.

The pharmaceutical composition or combination of the present invention can be in unit dosage of about 1-1000 mg of active ingredients for a subject of about 50-70 kg, preferably about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and about $10^{-9}$ molar concentrations, or between about $10^{-6}$ molar and about $10^{-9}$ molar concentrations.

The activities of a compound according to the present invention can be assessed by both in vitro and in vivo methods.

The term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, wetting agents, emulsifiers, buffers, disintegration agents, lubricants, coatings, sweetening agents, flavoring agents, dyes, such like materials and combinations thereof, as would be known to one of ordinary skill in the art (see, for example, Remington's Pharmaceutical Sciences, $18^{th}$ Ed. Mack Printing Company, 1990, pp. 1289-1329, incorporated herein by reference). Except insofar as any conventional carrier is incompatible with the active ingredient, its use in the therapeutic or pharmaceutical compositions is contemplated. Suitable pharmaceutically acceptable carriers include but are not limited to water, salt solutions, alcohol, vegetable oils, polyethylene glycols, gelatin, lactose, amylase, magnesium stearate, talc, silicic aid, viscous paraffin, perfume oil, fatty acid monoglycerides and diglycerides, petroethral fatty acid esters, hydroxymethyl-cellulose, polyvinylpyrrolidone, etc.

The pharmaceutical compositions of the invention can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

In certain embodiments, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure, and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable compositions for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays, etc. They are thus particularly suited for use in topical, including cosmetic, formulations well-known in the art. Such may contain solubilizers, stabilizers, tonicity enhancing agents, buffers and preservatives.

The present invention further provides anhydrous pharmaceutical compositions and dosage forms comprising the compounds of the present invention as active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

One embodiment of the invention includes a pharmaceutical composition as described above in combination with a second agent and a pharmaceutical carrier.

In yet another embodiment, the invention pertains, at least in part, to compounds of Formula I:

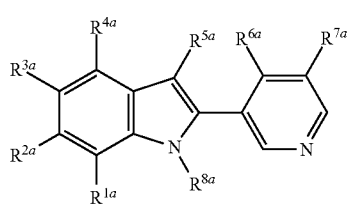

(I)

wherein:

$R^{1a}$, $R^{2a}$, $R^{3a}$, and $R^{4a}$ are each independently hydrogen, halogen, cyano, hydroxy, alkoxy, alkyl, alkenyl, or alkoxycarbonyl;

$R^{5a}$ is hydrogen halogen, cyano, alkyl, alkenyl, arylalkyl, heteroarylalkyl, aminocarbonyl, alkylaminocarbonyl, carboxylate, alkoxycarbonyl, heterocyclylcarbonyl, aryl, or heteroaryl;

$R^{6a}$ and $R^{7a}$ are each independently hydrogen, halogen, hydroxy, alkoxy, amino, alkyl, sulfonyl, —O-sulfonyl, alkylamino, heterocyclyl, aminocarbonyl, carboxylate, or alkoxycarbonyl;

$R^{8a}$ is hydrogen, alkyl, arylalkyl, heteroarylalkyl, alkoxycarbonyl, sulfonyl, aroyl, aryl, or heteroaryl; and pharmaceutically acceptable salts, polymorphs, rotamers, prodrugs, enantiomers, hydrates, and solvates thereof;

with the proviso that at least one of $R^{1a}$-$R^{8a}$ is other than hydrogen; and when $R^{5a}$ is cyano or lower alkyl optionally substituted with cyano, —C(O)-piperidine, amino, alkylamino, dialkylamino, carboxylate, alkoxycarbonyl, aminocarbonyl, or heterocyclyl, then at least one of $R^{1a}$-$R^{4a}$ and $R^{6a}$-$R^{8a}$ is other than hydrogen; and when $R^{7a}$ is imidazolyl, then at least one of $R^{1a}$-$R^{6a}$ and $R^{8a}$ is other than hydrogen; and when $R^{8a}$ is alkyl, arylalkyl or alkoxycarbonyl, then at least one of $R^{1a}$-$R^{7a}$ is other than hydrogen; and when $R^{5a}$ is lower alkyl and $R^{8a}$ is alkyl substituted with carboxylate or $PO_3R^{21}R^{22}$ wherein $R^{21}$ and $R^{22}$ are each independently hydrogen or lower alkyl, then at least one of $R^{1a}$-$R^{4a}$ and $R^{6a}$ and $R^{7a}$ is other than hydrogen; and when $R^{3a}$ is halogen and $R^{5a}$ and $R^{8a}$ are independently lower alkyl optionally substituted with carboxylate, alkoxycarbonyl, or —C(O)-piperidine, then at least one of $R^{1a}$, $R^{2a}$, $R^{4a}$, $R^{6a}$ and $R^{7a}$ is other than hydrogen; and when $R^{3a}$ is halogen or lower alkyl and $R^{5a}$ is lower alkyl substituted with dialkylamino, dialkylaminocarbonyl, carboxylate, alkoxycarbonyl or aminocarbonyl, then at least one of $R^{1a}$, $R^{2a}$, $R^{4a}$, and $R^{6a}$-$R^{8a}$ is other than hydrogen; and when $R^{2a}$ and $R^{3a}$ are each alkoxy and $R^{5a}$ is cyano, then at least one of $R^{1a}$, $R^{4a}$, and $R^{6a}$-$R^{8a}$ is other than hydrogen; and when $R^{3a}$ is alkyl substituted with aroyl, and $R^5$ and $R^8$ are each independently hydrogen or lower alkyl, then at least one of $R^{1a}$, $R^{2a}$, and $R^{4a}$ is other than hydrogen, for use in therapy.

In still another embodiment, the invention pertains, at least in part, to compounds of Formula II:

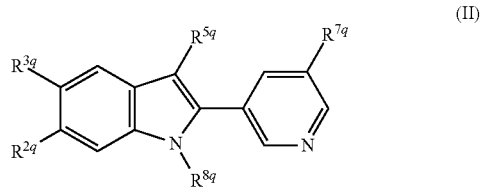

(II)

wherein:

$R^{2q}$ is hydrogen or halogen;

$R^{3q}$ is hydrogen, halogen, or cyano;

$R^{5q}$ is hydrogen, alkyl, or cyano;

$R^{7q}$ is hydrogen, halogen, alkoxy, —OSO$_2$-heterocyclyl, —O-arylalkyl, —NR'—SO$_2$-alkyl, —NR'—C(O)-alkyl, —NR'—C(O)—NR'-alkyl, —NR'—C(O)—O-alkyl, haloalkyl, or alkyl optionally substituted with heterocyclyl, —NR'—SO$_2$-alkyl, —NR'—SO$_2$-haloalkyl, NR'—C(O)-alkyl, NR'—C(O)-heterocyclyl, —NR'—C(O)—NR'-alkyl, or —NR'—C(O)—O-alkyl;

$R^{8q}$ is hydrogen, alkyl, hydroxyalkyl, -alkyl-OC(O)-alkyl, carboxylate, alkoxycarbonyl, or arylalkyl substituted with alkyl, or aroyl substituted with cyano and/or alkyl, or -alkyl-O-aryl substituted with alkoxycarbonyl;

each R' is independently hydrogen, $C_1$-$C_4$-alkyl, or $C_3$-$C_6$-cycloalkyl, with the proviso that at least one of $R^{2q}$, $R^{3q}$, $R^{5q}$, $R^{7q}$ and $R^{8q}$ is other than hydrogen, for use in therapy.

Another embodiment of the invention pertains, at least in part, to compounds of Formula III or IV, for use in therapy.

Still another embodiment of the invention pertains, at least in part, to the use of compounds of Formula (I), (II), (III) or (IV), as described above, and the compounds of the examples, for the preparation of a pharmaceutical composition for the treatment of a disorder or disease in a subject mediated by the inhibition of aldosterone synthase.

In yet another embodiment, the invention pertains, at least in part, to compounds of Formula (I), (II), (III) or (IV), as described above, and the compounds of the examples, for use as a medicament.

Another embodiment of the invention pertains, at least in part, to pharmaceutical compositions, as described above, for use as a medicament.

In another embodiment, the invention pertains, at least in part, to the use of pharmaceutical compositions, as described above, for the preparation of a medicament for the treatment of a disorder or disease in a subject mediated by the inhibition of aldosterone synthase.

Another embodiment of the invention pertains, at least in part, to methods of treating a disorder or disease mediated by aldosterone synthase in a mammal, by administering to the mammal in need thereof a therapeutically effective amount of a compound of Formula (I), (II), (III) or (IV), as described above and in the examples.

Another embodiment of the invention pertains to kits comprising, a pharmaceutical composition as described above, packaged with instructions for use of the pharmaceutical composition in the treatment of an aldosterone synthase associated state in a subject in need thereof.

EXEMPLIFICATION OF THE INVENTION

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

Example 1

3-Methyl-2-pyridin-3-yl-1H-indole hydrochloride

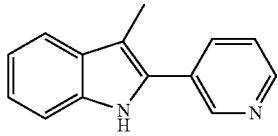 [SMILES: Cc1c(-c2cccnc2)[nH]c2ccccc12]

3-Methyl-2-pyridin-3-yl-1H-indole hydrochloride is synthesized based on the method described in U.S. Pat. No. 3,468,894. A flask is charged with 3-propionylpyridine (1.004 g, 7.279 mmol), phenylhydrazine hydrochloride (1.010 g, 6.915 mmol) and ethanol (15 mL). The mixture is heated to reflux for 1 h and cooled to room temperature. To a portion of the reaction mixture (2.5 mL) is added HCl (4M in dioxane, 1 mL, 4 mmol) and the mixture is heated to reflux. After 3 h, the mixture is concentrated in vacuo. The solid is dissolved in the minimum amount of boiling methanol (17 mL) and allowed to cool slowly to room temperature. A solid precipitates and after cooling to 0° C. for 30 min, the yellow solid is filtered off, washed with portions of cold methanol and dried under high vacuum to give 3-methyl-2-pyridin-3-yl-1H-indole hydrochloride as yellow needles. $^1$H NMR (400 MHz, MeOD) δ ppm (HCl salt) 2.56 (s, 3H), 7.09-7.13 (m, 1H), 7.23-7.26 (m, 1H), 7.43 (d, J=8.1 Hz, 1H), 7.63 (d, J=8.1 Hz, 1H), 8.14-8.18 (m, 1H), 8.74 (d, J=5.8 Hz, 1H), 8.83-8.85 (m, 1H), 9.08 (s, 1H).

Example 2

5-Chloro-3-methyl-2-pyridin-3-yl-1H-indole hydrochloride

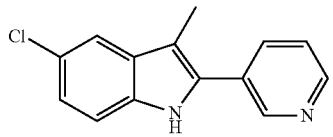 [SMILES: Cc1c(-c2cccnc2)[nH]c2ccc(Cl)cc12]

5-Chloro-3-methyl-2-pyridin-3-yl-1H-indole hydrochloride is synthesized based on the method described in U.S. Pat. No. 3,468,894. (4-Chloro-phenyl)-hydrazine hydrochloride (3.0 g, 16.8 mmol) and 3-propionylpyridine (2.4 g, 17.6 mmol) in ethanol (45 mL) is heated to reflux for 6 h. The mixture is then cooled to room temperature and added to HCl (4M in 1,4-dioxane, 17.6 mL). The resulting mixture is heated to reflux for 24 h. The mixture is then cooled to room temperature and the yellow precipitate is filtered and washed with methanol (10 mL) three times to give 5-chloro-3-methyl-2-pyridin-3-yl-1H-indole hydrochloride as a yellow solid. MS (ESI) m/z 243.0 and 244.9 (M+H)$^+$.

Example 3

5-Fluoro-3-methyl-2-pyridin-3-yl-1H-indole hydrochloride

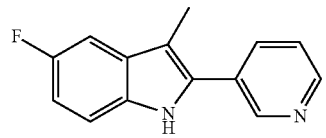 [SMILES: Cc1c(-c2cccnc2)[nH]c2ccc(F)cc12]

(4-Fluoro-phenyl)-hydrazine hydrochloride is processed according to the procedure described in Example 2 to give 5-fluoro-3-methyl-2-pyridin-3-yl-1H-indole hydrochloride. MS (ESI) m/z 227.0 (M+H)$^+$.

Example 4

4- and 6-Fluoro-3-methyl-2-pyridin-3-yl-1H-indole hydrochloride

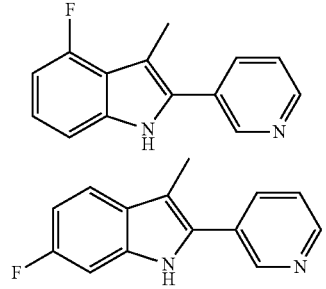

(3-Fluoro-phenyl)-hydrazine hydrochloride is processed according to the procedure described in Example 2 to give a mixture of 4-fluoro-3-methyl-2-pyridin-3-yl-1H-indole hydrochloride and 6-fluoro-3-methyl-2-pyridin-3-yl-1H-indole hydrochloride. MS (ESI) m/z 227.0 (M+H)$^+$.

Example 5

4- and 6-Chloro-3-methyl-2-pyridin-3-yl-1H-indole hydrochloride

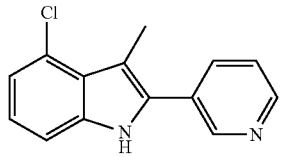

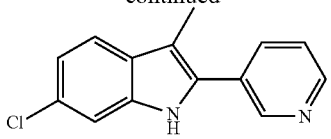

(3-Chloro-phenyl)-hydrazine hydrochloride is processed according to the procedure described in Example 2 to give a mixture of 4-chloro-3-methyl-2-pyridin-3-yl-1H-indole hydrochloride and 6-chloro-3-methyl-2-pyridin-3-yl-1H-indole hydrochloride. MS (ESI) m/z 242.96 and 244.98 (M+H)+.

Example 6

(a) 5-Bromo-3-methyl-2-pyridin-3-yl-1H-indole

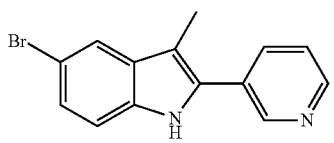 [SMILES: Cc1c(-c2cccnc2)[nH]c2ccc(Br)cc12]

To a suspension of 4-bromophenylhydrazine hydrochloride (10.00 g, 42.95 mmol) in anhydrous ethanol (200 mL) is added 3-propionylpyridine (7.51 g, 42.95 mmol) and the mixture is stirred at reflux for 30 min. 4M HCl in 1,4-dioxane (42.9 mL) is added to the yellow solution and stirring is continued at reflux overnight. The reaction mixture is cooled with an ice-water bath and the yellow precipitate is filtered through a sintered funnel to give 5-bromo-3-methyl-2-pyridin-3-yl-1H-indole hydrochloride as a yellow solid. The product is dissolved in methanol (100 mL) and treated with sodium methoxide to give the free base, which is used in the next step without further purification.

(b) 3-Methyl-2-pyridin-3-yl-1H-indole-5-carbonitrile

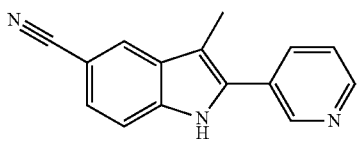 [SMILES: Cc1c(-c2cccnc2)[nH]c2ccc(C#N)cc12]

5-Bromo-3-methyl-2-pyridin-3-yl-1H-indole (5.0 g, 16.7 mmol) and copper (I) cyanide (1.9 g, 20.1 mmol) are placed in a round bottom flask which is flushed with $N_2$. N-Methylpyrrolidinone (40 mL) is added via syringe. The resulting mixture is heated to 200° C. under $N_2$ with vigorous stirring overnight. The mixture is cooled to room temperature and dichloromethane (200 mL) is added. The mixture is filtered through a pad of celite. The filtrate is washed with 10% aqueous ammonia in saturated aqueous ammonium chloride. The aqueous phase is extracted with dichloromethane. The combined organic phase is dried over sodium sulfate and concentrated. The residue is purified by silica gel flash chromatography (ethyl acetate-heptane, 0:1 to 1:0) to give 3-methyl-2-pyridin-3-yl-1H-indole-5-carbonitrile. $^1$H NMR (400 MHz, DMSO-$d_6$) δ ppm 2.45 (s, 3H), 7.45-7.60 (m, 3H), 8.06-8.11 (m, 1H), 8.15 (s, 1H), 8.60 (dd, J=4.8, 1.5 Hz, 1H), 8.91 (d, J=1.5 Hz, 1H), 11.94 (br. s., 1H). HRMS (ESI) m/z 234.1031 [(M+H)+ Calcd for $C_{15}H_{11}N_3$, 234.1031].

Example 7

(a) N-(4-Fluoro-phenyl)-N-[1-pyridin-3-yl-eth-(Z)-ylidene]-hydrazine

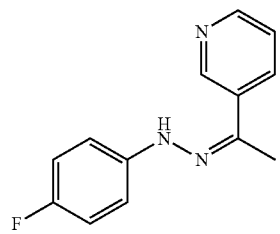 [SMILES: C/C(=N/Nc1ccc(F)cc1)c1cccnc1]

3-Acetylpyridine (5.00 g, 40.45 mmol) and 4-fluorophenylhydrazine hydrochloride (6.44 g, 38.43 mmol) are suspended in ethanol (70 mL) and heated to reflux. After 1 h, HCl (4M in dioxane, 150 mL, 600 mmol) is added and the mixture is heated to reflux for 16 h. The mixture is concentrated in vacuo and taken up in a little ethanol. The solid is filtered off and washed with ethanol to give a yellow solid. The filtrate is concentrated to dryness. The resulting solid is washed with small amounts of ice-cold ethanol and filtered off. The two fractions are combined and used in the next step without further purification.

(b) 5-Fluoro-2-pyridin-3-yl-indole

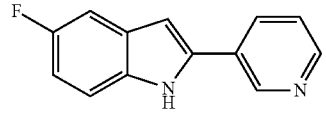

A flask is charged with polyphosphoric acid (1.2 g) and N-(4-fluoro-phenyl)-N'-[1-pyridin-3-yl-eth-(Z)-ylidene]-hydrazine (1.0 g) is added. The mixture is stirred with a thermometer and heated to 160° C. (internal temperature), whereupon the paste is allowed to cool to 100° C. Water (90 mL) and ethyl acetate are added and the mixture is vigorously stirred until a discrete yellow precipitate is obtained. The precipitate is filtered off and the two phases are separated. The ethyl acetate phase is discarded. The solids and aqueous phase are combined and 1M aqueous NaOH is added, followed with chloroform, and the mixture is vigorously stirred until full dissolution. The aqueous phase is extracted with chloroform and the combined organic phase is dried over $MgSO_4$ and concentrated in vacuo. The residue is purified by silica gel flash chromatography (ethyl acetate-heptane, 7:3 to 9:1) to give as a brown solid. MS (ESI) m/z 213 (M+H)+.

Example 8

(a) N-(4-Bromo-phenyl)-N-[1-pyridin-3-yl-eth-(Z)-ylidene]-hydrazine hydrochloride

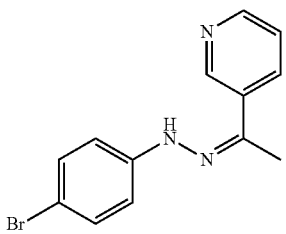 [SMILES: C/C(=N/Nc1ccc(Br)cc1)c1cccnc1]

To a solution of 4-bromophenylhydrazine hydrochloride (11.5 g, 50 mmol) in anhydrous ethanol (200 mL) is added 3-acetylpyridine (6.1 g, 50 mmol). The mixture is heated to 90° C. and stirred for 3 h, cooled to room temperature and filtered through a sintered glass funnel. The solid is washed with ethanol and placed under high vacuum overnight to give N-(4-bromo-phenyl)-N'-[1-pyridin-3-yl-eth-(Z)-ylidene]-hydrazine hydrochloride as a yellow solid.

(b) 2-Pyridin-3-yl-1H-indole-5-carbonitrile

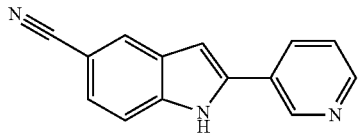 [SMILES: N#Cc1ccc2[nH]c(-c3cccnc3)cc2c1]

A flask fitted with a mechanical stirrer is charged with polyphosphoric acid (15 g) and N-(4-bromo-phenyl)-N'-[1-pyridin-3-yl-eth-(Z)-ylidene]-hydrazine hydrochloride (18 g) is heated to 210° C. (oil bath temperature) for 1 h. The paste is allowed to cool to ambient temperature and 1M aqueous NaOH is added, followed with chloroform, and the mixture is vigorously stirred until full dissolution. The aqueous phase is extracted with chloroform and the combined organic phase is dried over MgSO$_4$ and concentrated in vacuo to give 5-bromo-2-pyridin-3-yl-1H-indole as a brown solid which is used without further purification.

5-Bromo-2-pyridin-3-yl-1H-indole (7.0 g, 21.8 mmol) and copper (I) cyanide (2.3 g, 26.1 mmol) are placed in a round bottom flask which is flushed with N$_2$. N-Methylpyrrolidinone (40 mL) is added via syringe. The resulting mixture is heated to 160° C. under N$_2$ with vigorous stirring overnight. The mixture is cooled to room temperature and poured into 10% aqueous ammonia in saturated aqueous ammonium chloride (300 mL). The aqueous phase is extracted with dichloromethane (100 mL) five times. The combined organic phase is dried over sodium sulfate and concentrated. The residue is purified by silica gel flash chromatography (ethyl acetate-heptane, 0:1 to 1:0) to give 2-pyridin-3-yl-1H-indole-5-carbonitrile. $^1$H NMR (400 MHz, DMSO-d$_6$) δ ppm 7.20 (s, 1H), 7.48 (dd, J=8.3, 1.5 Hz, 1H), 7.51-7.55 (m, 1H), 7.59 (d, J=8.6 Hz, 1H), 8.12 (s, 1H), 8.25-8.29 (m, 1H), 8.56 (dd, J=4.8, 1.5 Hz, 1H), 9.14 (d, J=1.8 Hz, 1H), 12.27 (s, 1H). HRMS (ESI) m/z 220.0869 [(M+H)$^+$ Calcd for C$_{14}$H$_9$N$_3$, 220.0875].

Example 9

1-Benzyl-3-methyl-2-pyridin-3-yl-1H-indole

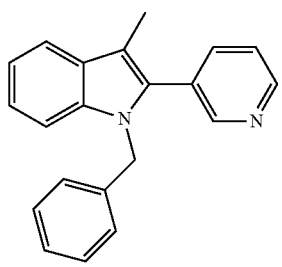 [SMILES: Cc1c(-c2cccnc2)n(Cc2ccccc2)c2ccccc12]

3-Methyl-2-pyridin-3-yl-1H-indole hydrochloride (Example 1, 0.110 g, 0.445 mmol) is suspended in THF (3 mL) and cooled to 0° C. KHMDS (0.5M in toluene, 2 mL, 1 mmol) is added dropwise, the cooling bath is lowered and the mixture is stirred at room temperature for 15 min, whereupon it is lowered in the ice-water bath. Benzyl bromide (0.093 g, 0.534 mmol) is added dropwise. After 3 h, additional benzyl bromide (0.046 g, 0.267 mmol) is added, and upon reaction completion, the mixture is quenched with 1M aqueous HCl and diluted with ethyl acetate. The aqueous phase is extracted and the combined organic phase is dried over MgSO$_4$, filtered and concentrated in vacuo. Purification of the residue by silica gel flash chromatography (dichloromethane-methanol, 99:1) affords 1-benzyl-3-methyl-2-pyridin-3-yl-1H-indole as a pale yellow solid. $^1$H NMR (400 MHz, MeOD) δ ppm 2.18 (s, 3H), 5.19 (s, 2H), 6.69-6.71 (m, 2H), 7.01-7.11 (m, 5H), 7.21 (d, J=8.1 Hz, 1H), 7.37-7.41 (m, 1H), 7.52 (d, J=7.8 Hz, 1H), 7.67-7.70 (m, 1H), 8.36 (s, 1H), 8.43-8.45 (m, 1H). MS (ESI) m/z 299 (M+H)$^+$.

Example 10

3-Methyl-1-(5-methyl-isoxazol-3-ylmethyl)-2-pyridin-3-yl-1H-indole hydrochloride

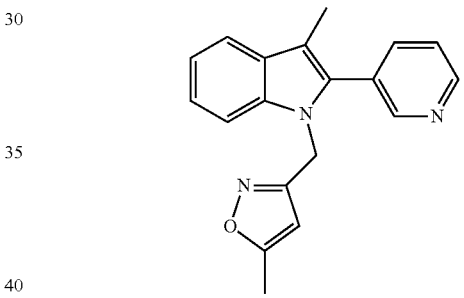

A flask is charged with 3-methyl-2-pyridin-3-yl-1H-indole hydrochloride (Example 1, 0.100 g, 0.408 mmol) in THF (2.5 mL) and cooled to 0° C. KHMDS (0.5 M in toluene, 1.8 mL, 0.898 mmol) is added and the mixture is stirred at room temperature for 30 min, followed by addition of 3-bromomethyl-5-methyl-isoxazole (0.144 g, 0.817 mmol). The reaction mixture is stirred for 0.5 h, then quenched with saturated ammonium chloride solution and extracted with ethyl acetate. The organic layer is dried over sodium sulfate and concentrated in vacuo. The residue is purified by reverse phase HPLC with Xbridge Shield RP18 column and a 0.1% aqueous NH$_4$OH in acetonitrile gradientto afford 3-methyl-1-(5-methyl-isoxazol-3-ylmethyl)-2-pyridin-3-yl-1H-indole product as a colorless oil. The oil is dissolved in diethyl ether and few drops of concentrated HCl are added. The volatiles are removed in vacuo and the reside is lyophilized to afford the product as a yellow solid. $^1$H NMR (400 MHz, MeOD) δ ppm (HCl salt) 2.30 (s, 3H), 2.31 (s, 3H), 5.30 (s, 2H), 5.67 (s, 1H), 7.18 (t, J=8.0 Hz, 1H), 7.27 (ddd, J=7.6, 1.1 Hz, 1H), 7.45 (d, J=8.1 Hz, 1H), 7.56-7.69 (m, 2H), 7.99 (dt, J=8.0, 1.9, 1.8 Hz, 1H), 8.56-8.68 (m, 2H). HRMS (ESI) m/z 304.1440 [(M+H)+ Calcd for $C_{19}H_{18}N_3O$, 304.1450].

Example 11

4-(5-Chloro-3-methyl-2-pyridin-3-yl-1H-indol-1-ylmethyl)-benzoic acid methyl ester

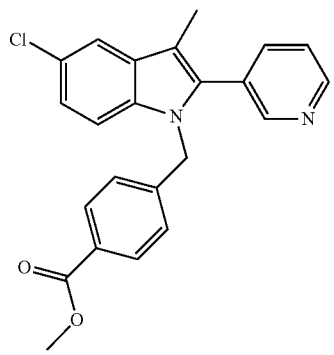 [SMILES: COC(=O)c1ccc(Cn2c(-c3cccnc3)c(C)c3cc(Cl)ccc32)cc1]

To a solution of 5-chloro-3-methyl-2-pyridin-3-yl-1H-indole hydrochloride (Example 2, 558 mg, 2.0 mmol) in THF (20 mL) is added 0.5 M KHMDS in toluene (8.8 mL, 4.4 mmol) and the mixture is stirred at room temperature for 30 min, whereupon 4-bromomethyl-benzoic acid methyl ester (916 mg, 4.0 mmol). The reaction mixture is stirred for 3 h. Methanol is added to quench the reaction and the solvents are removed in vacuo. The residue is purified by flash chromatography with 1-3% methanol in dichloromethane to give 4-(5-chloro-3-methyl-2-pyridin-3-yl-1H-indol-1-ylmethyl)-benzoic acid methyl ester. MS (ESI) m/z 391.3 and 393.3 (M+H)+.

Example 12

4-(6-Fluoro-3-methyl-2-pyridin-3-yl-1H-indol-1-ylmethyl)-benzoic acid methyl ester

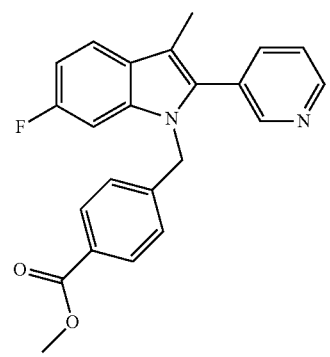 [SMILES: COC(=O)c1ccc(Cn2c(-c3cccnc3)c(C)c3ccc(F)cc32)cc1]

The mixture of 4- and 6-fluoro-3-methyl-2-pyridin-3-yl-1H-indole hydrochloride (Example 4) and 4-bromomethyl-benzoic acid methyl ester are processed according to the method described in Example 11. Separation of the regioisomers is done on an X-Bridge RP18 eluting with a 30-70% gradient of acetonitrile in 0.1% NH4OH to give 4-(6-fluoro-3-methyl-2-pyridin-3-yl-1H-indol-1-ylmethyl)-benzoic acid methyl ester. 1H NMR (400 MHz, CDCl3) δ ppm 2.30 (s, 3H), 3.90 (s, 3H), 5.22 (s, 2H), 6.86 (dd, J=9.8, 2.1 Hz, 1H), 6.93-7.00 (m, 3H), 7.34-7.38 (m, 1H), 7.55-7.61 (m, 2H), 7.90-7.92 (m, 1H), 7.92-7.94 (m, 1H), 8.59 (dd, J=2.3, 0.9 Hz, 1H), 8.63 (dd, J=4.9, 1.6 Hz, 1H). HRMS (ESI) m/z 375.1498 [(M+H)+ Calcd for $C_{23}H_{20}FN_2O_2$, 375.1509].

Example 13

4-(4-Fluoro-3-methyl-2-pyridin-3-yl-1H-indol-1-ylmethyl)-benzoic acid methyl ester

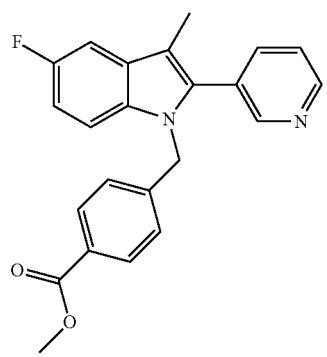 [SMILES: COC(=O)c1ccc(Cn2c(-c3cccnc3)c(C)c3cc(F)ccc32)cc1]

The method described in Example 12 also yields 4-(4-fluoro-3-methyl-2-pyridin-3-yl-1H-indol-1-ylmethyl)-benzoic acid methyl ester. MS (ESI) m/z 375.2 (M+H)+.

Example 14

3-(5-Chloro-3-methyl-2-pyridin-3-yl-1H-indol-1-ylmethyl)-benzonitrile

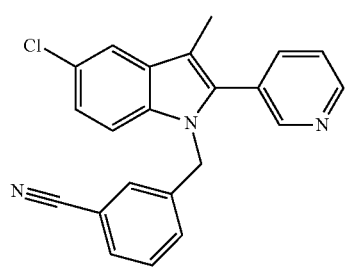 [SMILES: Cc1c(-c2cccnc2)n(Cc2cccc(C#N)c2)c2ccc(Cl)cc12]

5-Chloro-3-methyl-2-pyridin-3-yl-1H-indole hydrochloride (Example 2) and 3-bromomethyl-benzonitrile are processed according to the method described in Example 11 to give 3-(5-chloro-3-methyl-2-pyridin-3-yl-1H-indol-1-ylmethyl)-benzonitrile. 1H NMR (400 MHz, MeOD) δ ppm 2.25 (s, 3H), 5.36 (s, 2H), 7.03 (d, J=7.8 Hz, 1H), 7.14 (s, 1H), 7.18 (dd, J=8.6, 2.0 Hz, 1H), 7.33 (d, J=8.6 Hz, 1H), 7.36 (t, J=7.7 Hz, 1H), 7.49-7.56 (m, 2H), 7.62 (d, J=2.0 Hz, 1H), 7.81 (dt, J=7.8, 1.9 Hz, 1H), 8.47 (d, J=2.3 Hz, 1H), 8.58 (dd, J=5.1, 1.8 Hz, 1H). HRMS (ESI) m/z 358.1102 [(M+H)⁺ Calcd for C$_{22}$H$_{17}$ClN$_3$, 358.1111].

Example 15

3-(6-Fluoro-3-methyl-2-pyridin-3-yl-1H-indol-1-ylmethyl)-benzonitrile hydrochloride

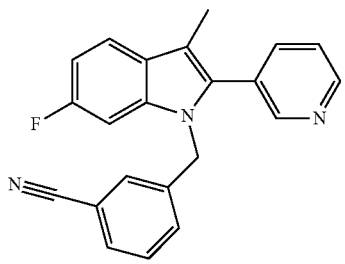 [SMILES: Cc1c(-c2cccnc2)n(Cc2cccc(C#N)c2)c2cc(F)ccc12]

The mixture of 4- and 6-fluoro-3-methyl-2-pyridin-3-yl-1H-indole hydrochloride (Example 4) and 3-bromomethyl-benzonitrile are processed according to the method described in Example 11. Separation of the regioisomers is done on a Chiralcel® OD eluting with heptane-isopropanol 4:1 to give 3-(6-fluoro-3-methyl-2-pyridin-3-yl-1H-indol-1-ylmethyl)-benzonitrile. $^1$H NMR (400 MHz, DMSO-d$_6$) δ ppm (HCl salt) 2.23 (s, 3H), 5.41 (s, 2H), 6.96-7.06 (m, 2H), 7.27 (s, 1H), 7.37-7.43 (m, 2H), 7.62-7.69 (m, 2H), 7.81 (t, J=6.3 Hz, 1H), 8.17 (d, J=7.3 Hz, 1H), 8.75-8.82 (m, 2H). HRMS (ESI) m/z 342.1405 [(M+H)⁺ Calcd for C$_{22}$H$_{17}$FN$_3$: 342.1407]

Example 16

3-(4-Fluoro-3-methyl-2-pyridin-3-yl-1H-indol-1-ylmethyl)-benzonitrile hydrochloride

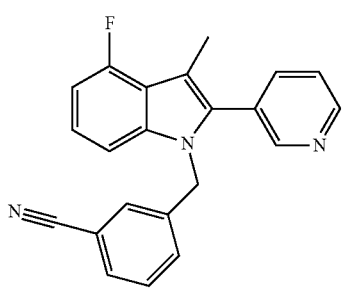 [SMILES: Cc1c(-c2cccnc2)n(Cc2cccc(C#N)c2)c2cccc(F)c12]

The mixture of 4- and 6-fluoro-3-methyl-2-pyridin-3-yl-1H-indole hydrochloride (Example 4) and 3-bromomethyl-benzonitrile are processed according to the method described in Example 11. Separation of the regioisomers is done on a Chiralcel® OD eluting with heptane-isopropanol 4:1 to give 3-(4-fluoro-3-methyl-2-pyridin-3-yl-1H-indol-1-ylmethyl)-benzonitrile. $^1$H NMR (400 MHz, DMSO-d$_6$) δ ppm (HCl salt) 2.33 (s, 3H), 5.41 (s, 2H), 6.87 (dd, J=11.4, 7.8 Hz, 1H), 7.06 (d, J=7.1 Hz, 1H), 7.12-7.21 (m, 1H), 7.26-7.34 (m, 2H), 7.42 (t, J=7.7 Hz, 1H), 7.66 (d, J=7.6 Hz, 1H), 7.81 (dd, J=7.2, 5.2 Hz, 1H), 8.18 (d, J=7.3 Hz, 1H), 8.79 (br. s., 2H). HRMS (ESI) m/z 342.1407 [(M+H)⁺ Calcd for C$_{22}$H$_{17}$FN$_3$: 342.1407].

Example 17

4-(5-Chloro-3-methyl-2-pyridin-3-yl-1H-indol-1-ylmethyl)-benzonitrile

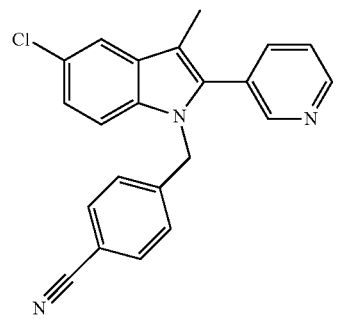 [SMILES: Cc1c(-c2cccnc2)n(Cc2ccc(C#N)cc2)c2ccc(Cl)cc12]

5-Chloro-3-methyl-2-pyridin-3-yl-1H-indole hydrochloride (Example 2) and 4-bromomethyl-benzonitrile are processed according to the method described in Example 11 to give 4-(5-chloro-3-methyl-2-pyridin-3-yl-1H-indol-1-ylmethyl)-benzonitrile. $^1$H NMR (400 MHz, MeOD) δ ppm 2.28 (s, 3H), 5.42 (s, 2H), 6.98 (d, J=8.3 Hz, 1H), 7.20 (dd, J=8.6, 2.0 Hz, 1H), 7.34 (d, J=8.8 Hz, 1H), 7.55 (dd, J=7.8, 5.1 Hz, 1H), 7.57-7.62 (m, 2H), 7.66 (d, J=2.0 Hz, 1H), 7.84 (dt, J=7.8, 1.9 Hz, 1H), 8.50 (d, J=2.0 Hz, 1H), 8.60 (dd, J=4.9, 1.6 Hz, 1H). HRMS (ESI) m/z 358.1120 [(M+H)⁺ Calcd for C$_{22}$H$_{17}$ClN$_3$: 358.1111].

Example 18

4-(4-Fluoro-3-methyl-2-pyridin-3-yl-1H-indol-1-ylmethyl)-benzonitrile hydrochloride

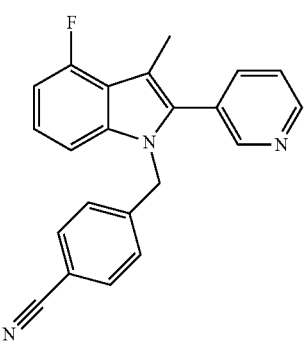 [SMILES: Cc1c(-c2cccnc2)n(Cc2ccc(C#N)cc2)c2cccc(F)c12]

The mixture of 4- and 6-fluoro-3-methyl-2-pyridin-3-yl-1H-indole hydrochloride (Example 4) and 4-bromomethyl-benzonitrile are processed according to the method described in Example 11. Separation of the regioisomers is done on a Chiralcel® OD eluting with heptane-isopropanol 4:1 to give 4-(4-fluoro-3-methyl-2-pyridin-3-yl-1H-indol-1-ylmethyl)-benzonitrile. $^1$H NMR (400 MHz, DMSO-d$_6$) δ ppm (HCl salt) 2.34 (s, 3H), 5.46 (s, 2H), 6.87 (dd, J=11.4, 7.8 Hz, 1H), 6.96 (d, J=8.6 Hz, 2H), 7.11-7.20 (m, 1H), 7.29 (d, J=8.1 Hz, 1H), 7.68 (d, J=8.3 Hz, 2H), 7.72-7.80 (m, 1H), 8.05-8.14 (m, 1H), 8.71-8.79 (m, 2H). HRMS (ESI) m/z 342.1407 [(M+H)+ Calcd for C22H17FN3: 342.1407].

Example 19

4-(6-Fluoro-3-methyl-2-pyridin-3-yl-1H-indol-1-ylmethyl)-benzonitrile

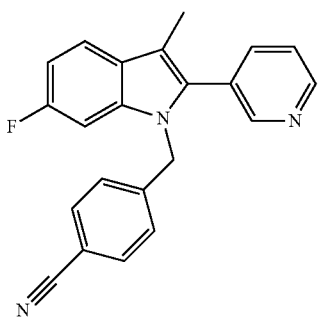 [SMILES: Cc1c(-c2cccnc2)n(Cc2ccc(C#N)cc2)c2cc(F)ccc12]

The mixture of 4- and 6-fluoro-3-methyl-2-pyridin-3-yl-1H-indole hydrochloride (Example 4) and 4-bromomethyl-benzonitrile are processed according to the method described in Example 11. Separation of the regioisomers is done on a Chiralcel® OD eluting with heptane-isopropanol 4:1 to give 4-(6-fluoro-3-methyl-2-pyridin-3-yl-1H-indol-1-ylmethyl)-benzonitrile. $^1$H NMR (400 MHz, CDCl$_3$) δ ppm 2.30 (s, 3H), 5.22 (s, 2H), 6.83 (dd, J=9.7, 2.1 Hz, 1H), 6.93-7.01 (m, 3H), 7.36 (dd, J=7.6, 5.1 Hz, 1H), 7.49-7.63 (m, 4H), 8.56 (d, J=1.3 Hz, 1H), 8.64 (d, J=3.5 Hz, 1H). HRMS (ESI) m/z 342.1390 [(M+H)+ Calcd for C22H17FN3: 342.1407].

Example 20

1-(4-Methanesulfonyl-benzyl)-3-methyl-2-pyridin-3-yl-1H-indole

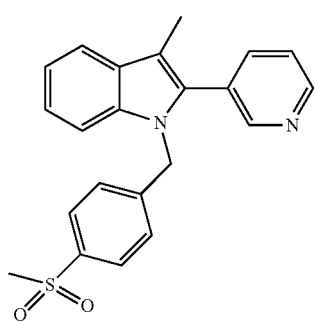 [SMILES: Cc1c(-c2cccnc2)n(Cc2ccc(S(C)(=O)=O)cc2)c2ccccc12]

3-Methyl-2-pyridin-3-yl-1H-indole hydrochloride (Example 1) and 1-bromomethyl-4-methanesulfonyl-benzene are processed according to the method described in Example 11 to give 1-(4-methanesulfonyl-benzyl)-3-methyl-2-pyridin-3-yl-1H-indole. $^1$H NMR (400 MHz, MeOD) δ ppm 2.33 (s, 3H), 3.08 (s, 3H), 5.46 (s, 2H), 7.08 (d, J=8.1 Hz, 2H), 7.18 (t, J=7.3 Hz, 1H), 7.24 (t, J=7.6 Hz, 1H), 7.34 (d, J=8.1 Hz, 1H), 7.55 (dd, J=7.8, 4.8 Hz, 1H), 7.68 (d, J=7.8 Hz, 1H), 7.81 (d, J=8.3 Hz, 2H), 7.85 (dt, J=7.8, 1.9 Hz, 1H), 8.52 (d, J=2.3 Hz, 1H), 8.59 (dd, J=4.9, 1.6 Hz, 1H). HRMS (ESI) m/z 377.1318 [(M+H)+ Calcd for C22H21N2O2S: 377.1324].

Example 21

5-Chloro-1-(4-methanesulfonyl-benzyl)-3-methyl-2-pyridin-3-yl-1H-indole

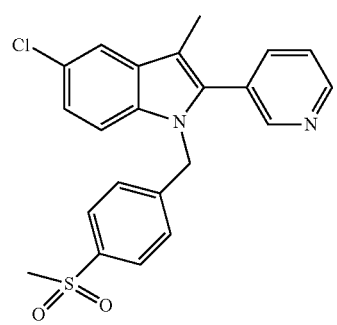 [SMILES: Cc1c(-c2cccnc2)n(Cc2ccc(S(C)(=O)=O)cc2)c2ccc(Cl)cc12]

5-Chloro-3-methyl-2-pyridin-3-yl-1H-indole hydrochloride (Example 2) and 1-bromomethyl-4-methanesulfonyl-benzene are processed according to the method described in Example 11 to give 5-chloro-1-(4-methanesulfonyl-benzyl)-3-methyl-2-pyridin-3-yl-1H-indole. $^1$H NMR (400 MHz, MeOD) δ ppm 2.29 (s, 3H), 3.09 (s, 3H), 5.46 (s, 2H), 7.20 (dd, J=8.6, 2.0 Hz, 1H), 7.34 (d, J=8.8 Hz, 1H), 7.53-7.57 (m, 1H), 7.66 (d, J=1.8 Hz, 1H), 7.79-7.84 (m, 1H), 7.86 (dt, J=7.9, 2.0 Hz, 1H), 8.52 (dd, J=2.3, 1.0 Hz, 1H), 8.61 (dd, J=5.1, 1.8 Hz, 1H). HRMS (ESI) m/z 411.0927 [(M+H)+ Calcd for C22H20N2O2SCl: 411.0934].

Example 22

1-(3-Benzyloxy-benzyl)-3-methyl-2-pyridin-3-yl-1H-indole hydrochloride

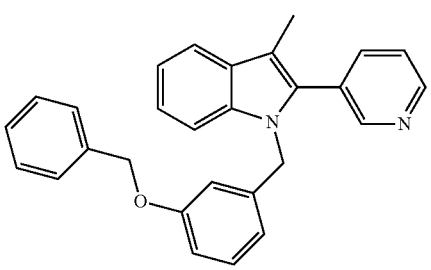 [SMILES: Cc1c(-c2cccnc2)n(Cc2cccc(OCc3ccccc3)c2)c2ccccc12]

3-Methyl-2-pyridin-3-yl-1H-indole hydrochloride (Example 1) and 1-benzyloxy-4-bromomethyl-benzene are processed according to the method described in Example 11 to give 1-(3-benzyloxy-benzyl)-3-methyl-2-pyridin-3-yl-1H-indole. $^1$H NMR (400 MHz, MeOD) δ ppm (HCl salt) 2.31 (s, 3H), 4.91 (s, 2H), 5.28 (s, 2H), 6.37 (s, 1H), 6.45 (d, J=7.6 Hz, 1H), 6.82 (dd, J=8.2, 2.1 Hz, 1H), 7.12 (t, J=7.8 Hz, 1H), 7.16-7.22 (m, 1H), 7.22-7.38 (m, 7H), 7.61 (dd, J=8.0, 5.2 Hz, 1H), 7.68 (d, J=7.8 Hz, 1H), 7.85 (dt, J=8.0, 1.8 Hz, 1H), 8.46

(d, J=1.3 Hz, 1H), 8.60 (dd, J=5.1, 1.5 Hz, 1H). HRMS (ESI) m/z 405.1969 [(M+H)+ Calcd for $C_{28}H_{25}N_2O$: 405.1967].

Example 23

(a) 5-Formyl-2-methylsulfanyl-benzonitrile

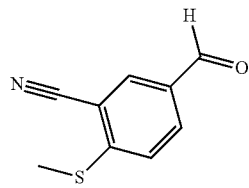

A flask is charged with 5-fluoro-2-formyl-benzonitrile (0.200 g, 1.34 mmol), potassium carbonate (0.371 g, 0.268 mmol), sodium thiomethoxide (0.142 g, 2.01 mmol) and DMF (20 mL). The mixture is stirred at room temperature for 10 min, then diluted with ethyl acetate and washed with water. The organic layer is dried over sodium sulfate and concentrated in vacuo to afford 5-formyl-2-methylsulfanyl-benzonitrile as a yellow color solid. $^1$H NMR (400 MHz, $CDCl_3$) δ ppm 2.64 (s, 3H), 7.41 (d, J=8.3 Hz, 1H), 8.01 (dd, J=8.5, 1.9 Hz, 1H), 8.07 (d, J=1.8 Hz, 1H), 9.95 (s, 1H).

(b) 5-Hydroxymethyl-2-methylsulfanyl-benzonitrile

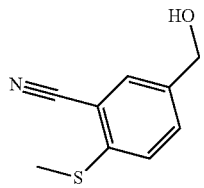

A flask is charged with 5-formyl-2-methylsulfanyl-benzonitrile (1.0 g, 5.68 mmol) in MeOH (20 mL) and cooled to 0° C. Sodium borohydride (1.07 g, 28.40 mmol) is added and the mixture is stirred at room temperature for 2 h, followed by removal of solvent in vacuo. The residue is re-dissolved in dichloromethane and washed with water twice. The organic layer is dried over sodium sulfate and concentrated in vacuo to afford 5-hydroxymethyl-2-methylsulfanyl-benzonitrile as a white solid. $^1$H NMR (400 MHz, $CDCl_3$) δ ppm 2.57 (s, 3H), 4.70 (d, J=5.1 Hz, 2H), 7.33 (d, J=8.3 Hz, 1H), 7.53 (dd, J=8.3, 1.0 Hz, 1H), 7.62 (s, 1H).

(c) 5-Hydroxymethyl-2-methanesulfonyl-benzonitrile

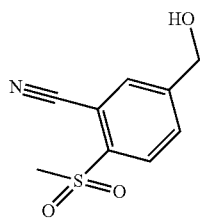

A flask is charged with 5-hydroxymethyl-2-methylsulfanyl-benzonitrile (0.866 g, 4.86 mmol) in a mixture of MeOH (10 mL) and water (10 mL). Oxone (7.47 g, 12.16 mmol) is added and the mixture is stirred at room temperature for 16 h. The residue is acidified to pH 1 using aqueous 1M HCl and then extracted with dichloromethane twice. The organic layer is dried over sodium sulfate and concentrated in vacuo to afford 5-hydroxymethyl-2-methanesulfonyl-benzonitrile as a white solid. $^1$H NMR (400 MHz, $CDCl_3$) δ ppm 3.28 (s, 3H), 4.89 (s, 2H), 7.80 (d, J=8.1 Hz, 1H), 7.95 (s, 1H), 8.18 (d, J=8.1 Hz, 1H).

(d) 5-Bromomethyl-2-methanesulfonyl-benzonitrile

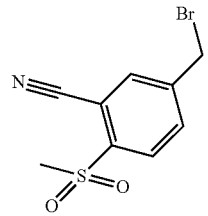

A flask is charged with 5-hydroxymethyl-2-methylsulfonyl-benzonitrile (0.788 g, 3.73 mmol) in toluene (5 mL) and heated at 40° C. $PBr_3$ (0.175 mL, 1.86 mmol) is added and the reaction is refluxed for 0.5 h. It is then cooled to room temperature, diluted with dichloromethane and washed with water. The aqueous layer is extracted with dichloromethane. The combined organic layer is dried over sodium sulfate and concentrated in vacuo to afford 5-bromomethyl-2-methanesulfonyl-benzonitrile as a white solid. $^1$H NMR (400 MHz, $CDCl_3$) δ ppm 3.28 (s, 3H), 4.89 (s, 2H), 7.80 (d, J=8.3 Hz, 1H), 7.94 (s, 1H), 8.18 (d, J=8.1 Hz, 1H).

(e) 2-Methanesulfonyl-5-(3-methyl-2-pyridin-3-yl-indol-1-ylmethyl)-benzonitrile

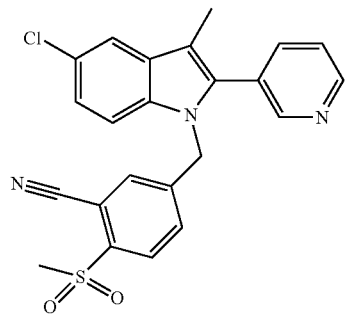 [SMILES: Cc1c(-c2cccnc2)n(Cc2ccc(S(C)(=O)=O)c(C#N)c2)c2ccc(Cl)cc12]

The product in Example 1 is processed according to the method described in Example 11 to give 2-methanesulfonyl-5-(3-methyl-2-pyridin-3-yl-indol-1-ylmethyl)-benzonitrile. $^1$H NMR (400 MHz, MeOD) δ ppm 2.35 (s, 3H), 3.27 (s, 3H), 5.53 (s, 2H), 7.19-7.31 (m, 3H), 7.37 (d, J=8.1 Hz, 1H), 7.51 (d, J=1.3 Hz, 1H), 7.65 (dd, J=7.8, 5.1 Hz, 1H), 7.71 (d, J=7.6 Hz, 1H), 7.98 (d, J=7.6 Hz, 1H), 8.02 (d, J=8.1 Hz, 1H), 8.60 (d, J=1.8 Hz, 1H), 8.65 (dd, J=5.1, 1.5 Hz, 1H). HRMS (ESI) m/z 402.1269 [(M+H)+ Calcd for $C_{23}H_{20}N_3O_2S$: 402.1276].

Example 24

(a) N-methyl-N-methoxy-nicotinamide

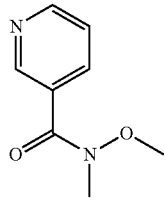

A flask is charged with nicotinic acid (5.0 g, 40.6 mmol). Thionyl chloride (30.0 mL) is added and the reaction is refluxed for 1 h. It is then cooled to room temperature and concentrated in vacuo. The residue is dissolved in anhydrous dichloromethane (30 mL) and O,N-dimethyl-hydroxylamine (4.35 g, 44.0 mmol) is added, followed by addition of triethylamine (14.15 g, 100.0 mmol). The reaction mixture is stirred at room temperature for 1.5 h. It is then washed with water and the aqueous phase is extracted with dichloromethane. The combined organic layer is dried over sodium sulfate and concentrated in vacuo to afford N-methyl-N-methoxy-nicotinamide as a brown oil. MS (ESI) m/z 167.0 (M+H)$^+$.

(b) 1-Pyridin-3-yl-butan-1-one

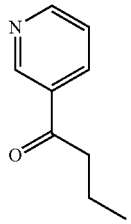

A flask is charged with N-methyl-N-methoxy-nicotinamide (1.0 g, 6.02 mmol) and THF (10 mL). Propyl magnesium chloride (2M in THF, 3.31 mL, 6.62 mmol) is added and the mixture is stirred at room temperature overnight. It is quenched with saturated sodium bicarbonate solution and extracted with dichloromethane. The combined organic layer is dried over sodium sulfate and concentrated in vacuo to afford 1-pyridin-3-yl-butan-1-one as a yellow oil. $^1$H NMR (400 MHz, CDCl$_3$) δ ppm 1.03 (t, J=7.5 Hz, 3H), 1.74-1.87 (m, 2H), 2.97 (t, J=7.3 Hz, 2H), 7.42 (dd, J=8.0, 4.9 Hz, 1H), 8.24 (dt, J=8.0, 2.0, 1.9 Hz, 1H), 8.78 (dd, J=4.9, 2.0 Hz, 1H), 9.18 (d, J=2.0 Hz, 1H).

(c) 3-Ethyl-2-pyridin-3-yl-1H-indole

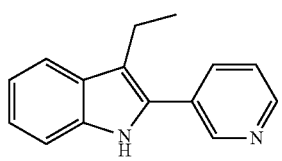 [SMILES: CCc1c(-c2cccnc2)[nH]c2ccccc12]

A flask is charged with phenylhydrazine (0.873 g, 6.46 mmol) and EtOH (14 mL). 1-Pyridin-3-yl-butan-1-one (0.914 g, 6.13 mmol) is added and the reaction is refluxed for 1 h. After cooling to room temperature, HCl (4M in 1,4-dioxane, 6.45 mL, 25.83 mmol) is added. The reaction mixture is refluxed for 4 h. After cooling to room temperature, the precipitate formed is filtered to afford 3-ethyl-2-pyridin-3-yl-1H-indole as a yellow solid. MS (ESI) m/z 223.0 (M+H)$^+$.

(d) 2-Methanesulfonyl-5-(3-ethyl-2-pyridin-3-yl-indol-1-ylmethyl)-benzonitrile

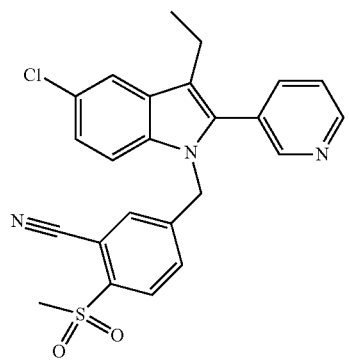 [SMILES: CCc1c(-c2cccnc2)n(Cc2ccc(S(C)(=O)=O)c(C#N)c2)c2ccc(Cl)cc12]

3-Ethyl-2-pyridin-3-yl-1H-indole and 2-methanesulfonyl-5-(3-ethyl-2-pyridin-3-yl-indol-1-ylmethyl)-benzonitrile (Example 23d) are processed according to the method described in Example 11 to give 2-methanesulfonyl-5-(3-ethyl-2-pyridin-3-yl-indol-1-ylmethyl)-benzonitrile. $^1$H NMR (400 MHz, MeOD) δ ppm 1.27 (t, J=7.6 Hz, 3H), 2.77 (q, J=7.6 Hz, 2H), 3.27 (s, 3H), 5.49 (s, 2H), 7.14-7.31 (m, 3H), 7.37 (d, J=8.1 Hz, 1H), 7.49 (s, 1H), 7.57 (dd, J=7.8, 5.1 Hz, 1H), 7.74 (d, J=7.8 Hz, 1H), 7.86 (dt, J=7.8, 1.8 Hz, 1H), 8.03 (d, J=8.3 Hz, 1H), 8.51 (d, J=2.0 Hz, 1H), 8.62 (dd, J=4.9, 1.4 Hz, 1H). HRMS (ESI) m/z 416.1424 [(M+H)$^+$ Calcd for C$_{24}$H$_{22}$N$_3$O$_2$S: 416.1433].

Example 25

3-Fluoro-4-(3-methyl-2-pyridin-3-yl-1H-indol-1-ylmethyl)-benzonitrile

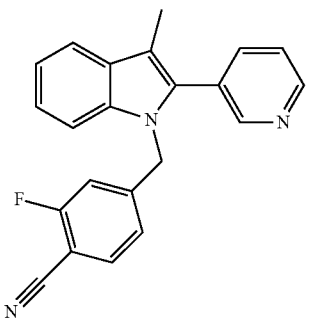 [SMILES: Cc1c(-c2cccnc2)n(Cc2ccc(C#N)c(F)c2)c2ccccc12]

A flask is charged with 3-methyl-2-pyridin-3-yl-1H-indole hydrochloride (Example 1, 0.080 g, 0.326 mmol) and DMF (1.5 mL), and 60% NaH in mineral oil (0.028 g, 0.719 mmol) is added. The mixture is stirred at room temperature for 20 min, followed by addition of 4-bromomethyl-3-fluoro-benzonitrile (0.175 g, 0.817 mmol). The reaction mixture stirred at room temperature for 30 min. The residue is diluted with DMF (1.5 mL), filtered and purified by reverse phase HPLC with Xbridge Shield RP18 column and a 0.1% aqueous NH$_4$OH in acetonitrile gradient to afford 3-fluoro-4-(3-methyl-2-pyridin-3-yl-indol-1-ylmethyl)-benzonitrile as a yellow solid. $^1$H NMR (400 MHz, MeOD) δ ppm 2.32 (s, 3H), 5.47 (s, 2H), 6.62 (t, J=7.6 Hz, 1H), 7.20 (t, J=7.5 Hz, 1H), 7.27 (t, J=7.6 Hz, 1H), 7.38 (d, J=8.1 Hz, 2H), 7.50 (d, J=9.9 Hz, 1H), 7.56 (dd, J=7.8, 4.8 Hz, 1H), 7.68 (d, J=7.8 Hz, 1H), 7.86 (dd, J=7.8, 1.8 Hz, 1H), 8.52 (s, 1H), 8.60 (dd, J=4.9, 1.6 Hz, 1H). HRMS (ESI) m/z 342.1394 [(M+H)$^+$ Calcd for C$_{22}$H$_{17}$FN$_3$: 342.1407].

Example 26

3-(3-methyl-2-pyridin-3-yl-1H-indol-1-ylmethyl)-benzonitrile

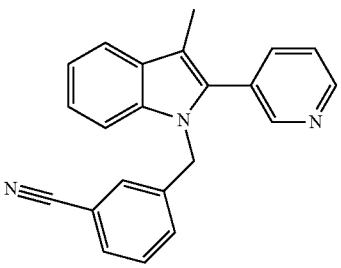 [SMILES: Cc1c(-c2cccnc2)n(Cc2cccc(C#N)c2)c2ccccc12]

3-Methyl-2-pyridin-3-yl-1H-indole hydrochloride (Example 1) and 3-bromomethyl-benzonitrile are processed according to the method described in Example 25 to give 3-(3-methyl-2-pyridin-3-yl-1H-indol-1-ylmethyl)-benzonitrile. $^1$H NMR (400 MHz, MeOD) δ ppm 2.33 (s, 3H), 5.41 (s, 2H), 7.08 (d, J=8.1 Hz, 1H), 7.16 (s, 1H), 7.20 (t, J=7.2 Hz, 1H), 7.27 (ddd, J=7.6, 1.0 Hz, 1H), 7.37 (d, J=5.8 Hz, 1H), 7.38-7.42 (m, 1H), 7.54-7.57 (m, 1H), 7.57 (s, 1H), 7.68 (d, J=7.8 Hz, 1H), 7.85 (dt, J=7.8, 1.9 Hz, 1H), 8.50 (d, J=2.0 Hz, 1H), 8.60 (dd, J=4.8, 1.5 Hz, 1H). HRMS (ESI) m/z 324.1491 [(M+H)$^+$ Calcd for C$_{22}$H$_{18}$N$_3$: 324.1501].

Example 27

4-(3-Methyl-2-pyridin-3-yl-1H-indol-1-ylmethyl)-benzonitrile

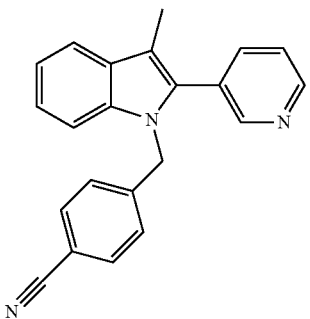 [SMILES: Cc1c(-c2cccnc2)n(Cc2ccc(C#N)cc2)c2ccccc12]

3-Methyl-2-pyridin-3-yl-1H-indole hydrochloride (Example 1) and 4-bromomethyl-benzonitrile are processed according to the method described in Example 25 to give 4-(3-methyl-2-pyridin-3-yl-1H-indol-1-ylmethyl)-benzonitrile. $^1$H NMR (400 MHz, MeOD) δ ppm 2.32 (s, 3H), 5.43 (s, 2H), 6.99 (d, J=8.6 Hz, 2H), 7.13-7.21 (m, 1H), 7.25 (ddd, J=7.6, 1.3 Hz, 1H), 7.34 (d, J=8.1 Hz, 1H), 7.54 (dd, J=8.0, 4.9 Hz, 2H), 7.58 (d, J=8.3 Hz, 1H), 7.67 (d, J=7.6 Hz, 1H), 7.84 (dt, J=7.9, 2.0 Hz, 1H), 8.50 (d, J=1.5 Hz, 1H), 8.59 (dd, J=4.9, 1.6 Hz, 1H). HRMS (ESI) m/z 324.1501 [(M+H)$^+$ Calcd for C$_{22}$H$_{18}$N$_3$: 324.1501].

Example 28

1-(2-Fluoro-4-methoxy-benzyl)-3-methyl-2-pyridin-3-yl-1H-indole hydrochloride

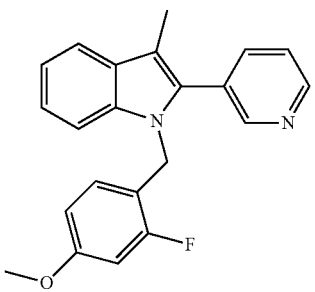 [SMILES: COc1ccc(Cn2c(-c3cccnc3)c(C)c3ccccc32)c(F)c1]

3-Methyl-2-pyridin-3-yl-1H-indole hydrochloride (Example 1) and 4-bromomethyl-2-fluoro-1-methoxy-benzene are processed according to the method described in Example 25 to give 1-(2-fluoro-4-methoxy-benzyl)-3-methyl-2-pyridin-3-yl-1H-indole hydrochloride. $^1$H NMR (400 MHz, MeOD) δ ppm (HCl salt) 2.38 (s, 3H), 3.82 (s, 3H), 5.35 (s, 2H), 6.54-6.62 (m, 2H), 6.94 (t, J=8.6 Hz, 1H), 7.22 (ddd, J=7.5, 0.9 Hz, 1H), 7.33 (ddd, J=7.6, 1.1 Hz, 1H), 7.45 (d, J=8.3 Hz, 1H), 7.72 (d, J=7.8 Hz, 1H), 8.12 (dd, J=8.2, 5.7 Hz, 1H), 8.54 (dt, J=8.1, 1.6 Hz, 1H), 8.80-8.89 (m, 2H). HRMS (ESI) m/z 347.1568 [(M+H)$^+$ Calcd for C$_{22}$H$_{20}$FN$_2$O: 347.1560].

Example 29

4-(5-chloro-3-methyl-2-pyridin-3-yl-1H-indol-1-ylmethyl)-benzoic acid

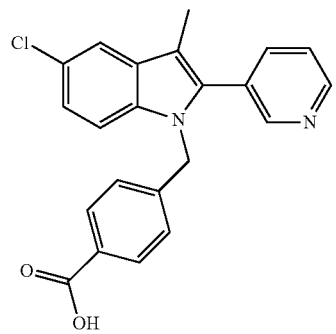 [SMILES: Cc1c(-c2cccnc2)n(Cc2ccc(C(=O)O)cc2)c2ccc(Cl)cc12]

4-(5-Chloro-3-methyl-2-pyridin-3-yl-1H-indol-1-ylmethyl)-benzoic acid methyl ester (Example 11, 200 mg, 0.51 mmol) in methanol (5 mL) is added to 5M aqueous NaOH (1 mL, 5 mmol) and the mixture is stirred at room temperature for 5 h. Concentrated HCl (4.4 mL) is added to neutralize the reaction mixture and the solvents are removed in vacuo. The residue is redissolved in methanol and purified by reverse phase HPLC with Xbridge Shield RP18 column and a 0.1% NH$_4$OH in acetonitrile gradient to afford 4-(5-chloro-3-methyl-2-pyridin-3-yl-1H-indol-1-ylmethyl)-benzoic acid. $^1$H NMR (400 MHz, MeOD) δ ppm 2.25 (s, 3H), 5.34 (s, 2H), 6.82 (d, J=8.1 Hz, 2H), 7.15 (dd, J=8.6, 2.0 Hz, 1H), 7.31 (d, J=8.6 Hz, 1H), 7.50 (dd, J=7.7, 4.9 Hz, 1H), 7.61 (d, J=2.0 Hz, 1H), 7.78-7.80 (m, 1H), 7.81 (d, J=8.1 Hz, 2H), 8.50 (s, 1H), 8.56 (br. s, 1H). HRMS (ESI) m/z 377.1072 [(M+H)$^+$ Calcd for C$_{22}$H$_{18}$ClN$_2$O$_2$: 377.1057].

Example 30

4-(5-Fluoro-3-methyl-2-pyridin-3-yl-1H-indol-1-ylmethyl)-benzoic acid

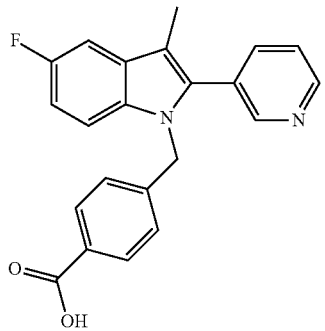 [SMILES: Cc1c(-c2cccnc2)n(Cc2ccc(C(=O)O)cc2)c2ccc(F)cc12]

5-Fluoro-3-methyl-2-pyridin-3-yl-1H-indole (Example 3) is processed according to the method in Example 11 to give 4-(5-fluoro-3-methyl-2-pyridin-3-yl-1H-indol-1-ylmethyl)-benzoic acid methyl ester. 4-(5-Fluoro-3-methyl-2-pyridin-3-yl-1H-indol-1-ylmethyl)-benzoic acid methyl ester is processed according to the method described in Example 29 to give 4-(5-fluoro-3-methyl-2-pyridin-3-yl-1H-indol-1-ylmethyl)-benzoic acid. $^1$H NMR (400 MHz, MeOD) δ ppm 2.25 (s, 3H), 5.36 (s, 2H), 6.88 (d, J=8.6 Hz, 2H), 6.94-7.00 (m, 1H), 7.28-7.29 (m, 1H), 7.30-7.32 (m, 1H), 7.49-7.53 (m, 1H), 7.78-7.82 (m, 1H), 7.82-7.86 (m, 2H), 8.47-8.49 (m, 1H), 8.56 (dd, J=4.9, 1.6 Hz, 1H). HRMS (ESI) m/z 361.1360 [(M+H)$^+$ Calcd for C$_{22}$H$_{18}$FN$_2$O$_2$: 361.1352].

Example 31

4-(6-Chloro-3-methyl-2-pyridin-3-yl-1H-indol-1-ylmethyl)-benzoic acid

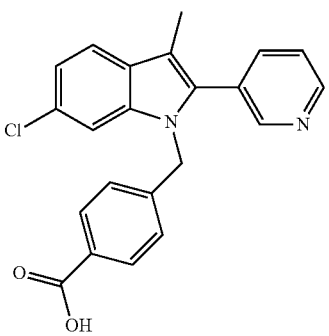 [SMILES: Cc1c(-c2cccnc2)n(Cc2ccc(C(=O)O)cc2)c2cc(Cl)ccc12]

A mixture of 4- and 6-chloro-3-methyl-2-pyridin-3-yl-1H-indole (Example 5) is processed according to the method in Example 11 to give 4-(6-chloro-3-methyl-2-pyridin-3-yl-1H-indol-1-ylmethyl)-benzoic acid methyl ester and 4-(4-chloro-3-methyl-2-pyridin-3-yl-1H-indol-1-ylmethyl)-benzoic acid methyl ester. This mixture is processed according to the method described in Example 29 to give 4-(6-chloro-3-methyl-2-pyridin-3-yl-1H-indol-1-ylmethyl)-benzoic acid after reverse-phase HPLC purification. $^1$H NMR (400 MHz, MeOD) δ ppm (TFA salt) 2.30 (s, 3H), 5.41 (s, 2H), 6.89 (d, J=8.6 Hz, 2H), 7.15 (dd, J=8.3, 1.8 Hz, 1H), 7.44 (d, J=1.8 Hz, 1H), 7.64 (d, J=8.6 Hz, 1H), 7.81-7.88 (m, 3H), 8.20-8.27 (m, 1H), 8.68 (br. s., 1H), 8.70-8.73 (m, 1H). HRMS (ESI) m/z 377.1050 [(M+H)$^+$ Calcd for C$_{22}$H$_{18}$ClN$_2$O$_2$: 377.1057].

Example 32

4-(6-Fluoro-3-methyl-2-pyridin-3-yl-1H-indol-1-ylmethyl)-benzoic acid

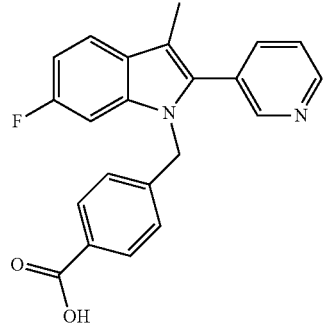 [SMILES: Cc1c(-c2cccnc2)n(Cc2ccc(C(=O)O)cc2)c2cc(F)ccc12]

4-(6-Fluoro-3-methyl-2-pyridin-3-yl-1H-indol-1-ylmethyl)-benzoic acid methyl ester (Example 12) is processed according to the method described in Example 29 to give 4-(6-fluoro-3-methyl-2-pyridin-3-yl-1H-indol-1-ylmethyl)-benzoic acid. $^1$H NMR (400 MHz, MeOD) δ ppm (TFA salt) 2.31 (s, 3H), 5.40 (s, 2H), 6.90 (d, J=8.6 Hz, 2H), 6.93-7.00 (m, 1H), 7.15 (dd, J=10.0, 2.1 Hz, 1H), 7.65 (dd, J=8.8, 5.3 Hz, 1H), 7.86 (d, J=8.6 Hz, 2H), 7.88-7.92 (m, 1H), 8.27-8.31 (m, 1H), 8.70 (d, J=1.8 Hz, 1H), 8.72 (dd, J=5.6, 1.5 Hz, 1H). HRMS (ESI) m/z 361.1360 [(M+H)$^+$ Calcd for C$_{22}$H$_{18}$FN$_2$O$_2$: 361.1352].

Example 33

4-(4-Fluoro-3-methyl-2-pyridin-3-yl-1H-indol-1-ylmethyl)-benzoic acid

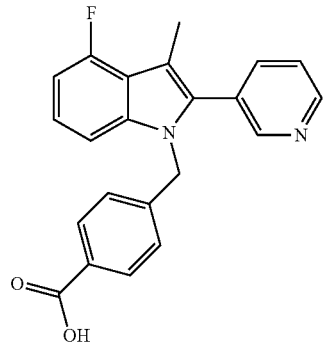 [SMILES: Cc1c(-c2cccnc2)n(Cc2ccc(C(=O)O)cc2)c2cccc(F)c12]

4-(4-Fluoro-3-methyl-2-pyridin-3-yl-1H-indol-1-ylmethyl)-benzoic acid methyl ester (Example 13) is processed according to the method described in Example 29 to give 4-(4-fluoro-3-methyl-2-pyridin-3-yl-1H-indol-1-ylmethyl)-benzoic acid. $^1$H NMR (400 MHz, DMSO-$d_6$) δ ppm 2.32 (s, 3H), 5.37 (s, 2H), 6.81-6.88 (m, 3H), 7.08-7.15 (m, 1H), 7.26 (d, J=8.1 Hz, 1H), 7.50 (dd, J=7.8, 4.8 Hz, 1H), 7.74 (d, J=8.3 Hz, 2H), 7.77-7.81 (m, 1H), 8.55 (d, J=1.5 Hz, 1H), 8.62 (dd, J=4.9, 1.6 Hz, 1H). MS (ESI) m/z 361.09 (M+H)$^+$.

Example 34

4-(5-Cyano-3-methyl-2-pyridin-3-yl-1H-indol-1-ylmethyl)-benzoic acid

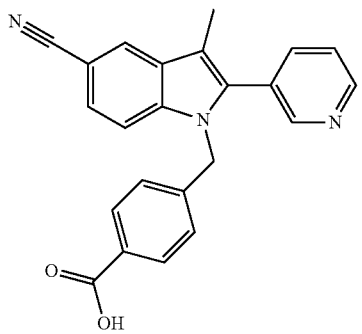 [SMILES: Cc1c(-c2cccnc2)n(Cc2ccc(C(=O)O)cc2)c2ccc(C#N)cc12]

5-Cyano-3-methyl-2-pyridin-3-yl-indole (Example 6) is processed according to the method described in Example 11 to give 4-(5-cyano-3-methyl-2-pyridin-3-yl-indol-1-ylmethyl)-benzoic acid methyl ester. To a solution of 4-(5-cyano-3-methyl-2-pyridin-3-yl-indol-1-ylmethyl)-benzoic acid methyl ester (80 mg, 0.21 mmol) in methanol (5 mL) and THF (5 mL) is added 1M aqueous lithium hydroxide (2.5 mL, 2.5 mmol) and the mixture is stirred overnight at ambient temperature. The volatiles are removed in vacuo and the residue is redissolved in DMF and purified by Xbridge RP18 with a gradient of 0.1% aqueous ammonium hydroxide in acetonitrile to give 4-(5-cyano-3-methyl-2-pyridin-3-yl-indol-1-yl-methyl)-benzoic acid. $^1$H NMR (400 MHz, DMSO-$d_6$) δ ppm 2.25 (s, 3H), 5.40 (s, 2H), 6.71 (d, J=8.1 Hz, 2H), 7.47-7.55 (m, 2H), 7.66 (t, J=8.6 Hz, 3H), 7.79-7.83 (m, 1H), 8.20 (d, J=1.3 Hz, 1H), 8.58 (d, J=1.5 Hz, 1H), 8.64 (dd, J=4.8, 1.5 Hz, 1H). HRMS (ESI) m/z 368.1396 [(M+H)$^+$ Calcd for $C_{23}H_{18}N_3O_2$: 368.1399].

Example 35

3-(5-Chloro-3-methyl-2-pyridin-3-yl-indol-1-ylmethyl)-benzoic acid

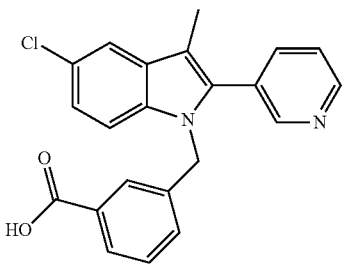 [SMILES: Cc1c(-c2cccnc2)n(Cc2cccc(C(=O)O)c2)c2ccc(Cl)cc12]

3-(5-Chloro-3-methyl-2-pyridin-3-yl-indol-1-ylmethyl)-benzonitrile (Example 14, 200 mg, 0.56 mmol) in acetic acid (3 mL) is added to a 20% HCl aqueous solution (3 mL). The reaction mixture is refluxed for 3 days. The volatiles are removed in vacuo and the residue is redissolved in methanol and purified by reverse phase HPLC with Xbridge Shield RP18 and a gradient of 0.1% NH$_4$OH in acetonitrile to give 3-(5-chloro-3-methyl-2-pyridin-3-yl-indol-1-ylmethyl)-benzoic acid. $^1$H NMR (400 MHz, DMSO-$d_6$) δ ppm 2.21 (s, 3H), 5.36 (s, 2H), 6.83 (d, J=7.1 Hz, 1H), 7.13-7.23 (m, 2H), 7.43-7.52 (m, 3H), 7.64-7.70 (m, 2H), 7.74-7.81 (m, 1H), 8.55 (s, 1H), 8.61-8.62 (m, 1H). HRMS (ESI) m/z 377.1058 [(M+H)$^+$ Calcd for $C_{22}H_{18}ClN_2O_2$: 377.1057].

Example 36

(a) 4-Bromomethyl-2,6-dimethyl-benzoic acid ethyl ester

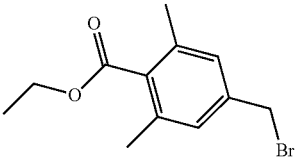

Ethyl 2,4,6-trimethylbenzene (4.20 g, 21.41 mmol) and N-bromosuccinimide (4.23 g, 23.55 mmol) are taken up in carbon tetrachloride (200 mL), and benzoyl peroxide (0.53 g, 2.14 mmol) is added. The suspension is heated to reflux. After 4 h, the mixture is diluted with dichloromethane, washed with saturated aqueous sodium bicarbonate, water and brine, dried and concentrated in vacuo. The residue is purified by silica gel flash chromatography (heptane-ethyl acetate, 1 to 5%) to give partially purified 4-bromomethyl-2,6-dimethyl-benzoic acid ethyl ester, which is taken in the next step without further purification.

(b) 2,6-Dimethyl-4-(5-chloro-3-methyl-2-pyridin-3-yl-indol-1-ylmethyl)-benzoic acid ethyl ester

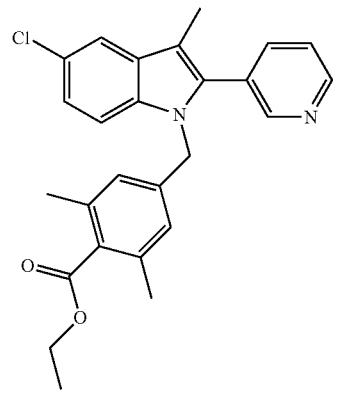 [SMILES: CCOC(=O)c1c(C)cc(Cn2c(-c3cccnc3)c(C)c3cc(Cl)ccc32)cc1C]

5-Chloro-3-methyl-2-pyridin-3-yl-1H-indole (Example 2, 1.350 g, 4.659 mmol) is suspended in THF (40 mL) and cooled to 0° C. KHMDS (0.5M in toluene, 32.6 mL, 16.3 mmol) is added dropwise. After 1 h, 4-bromomethyl-2,6-dimethyl-benzoic acid ethyl ester (4.95 g, 18.2 mmol) in THF (10 mL) is added dropwise. The mixture is allowed to warm to room temperature overnight. The mixture is then quenched with saturated aqueous ammonium chloride and diluted with dichloromethane. The aqueous phase is extracted with ethyl acetate, dried over MgSO$_4$, filtered and concentrated in vacuo. Purification of the residue by silica gel chromatography (dichloromethane-methanol, 1:0 to 99:1 to 49:1 to 97:3) affords 2,6-dimethyl-4-(5-chloro-3-methyl-2-pyridin-3-yl-indol-1-ylmethyl)-benzoic acid ethyl ester as an orange solid. MS (ESI) m/z 399 (M+H)$^+$.

(c) 2,6-Dimethyl-4-(5-chloro-3-methyl-2-pyridin-3-yl-indol-1-ylmethyl)-benzoic acid

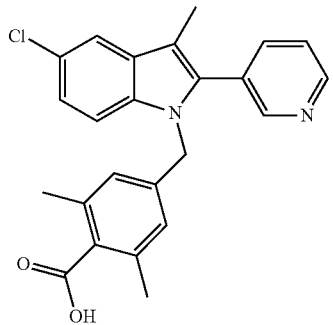 [SMILES: Cc1cc(Cn2c(-c3cccnc3)c(C)c3cc(Cl)ccc32)cc(C)c1C(=O)O]

To a refluxing solution of lithium iodide (0.218 g, 1.626 mmol) in 2,6-lutidine (5 mL) is added 2,6-dimethyl-4-(5-chloro-3-methyl-2-pyridin-3-yl-indol-1-ylmethyl)-benzoic acid ethyl ester (0.176 g, 0.407 mmol). The reaction is refluxed overnight. It is cooled to room temperature, acidified to pH 1 using 1M aqueous HCl solution and extracted with dichloromethane. The organic layer is dried over sodium sulfate and concentrated in vacuo. The residue is purified by reverse phase HPLC with Xbridge Shield RP18 column and a 0.1% aqueous NH$_4$OH in acetonitrile gradient to afford 2,6-dimethyl-4-(5-chloro-3-methyl-2-pyridin-3-yl-indol-1-ylmethyl)-benzoic acid as a solid. $^1$H NMR (400 MHz, MeOD) δ ppm 2.22 (s, 6H), 2.28 (s, 3H), 5.22 (s, 2H), 6.49 (s, 2H), 7.15 (dd, J=8.6, 2.0 Hz, 1H), 7.30 (d, J=8.8 Hz, 1H), 7.51-7.57 (m, 1H), 7.61 (d, J=1.8 Hz, 1H), 7.81 (dt, J=8.1, 2.0, 1.8 Hz, 1H), 8.58 (d, J=1.3 Hz, 1H), 8.61 (dd, J=4.9, 1.6 Hz, 1H). HRMS (ESI) m/z 405.1379 [(M+H)$^+$ Calcd for C$_{24}$H$_{21}$ClN$_2$O$_2$: 405.1370].

Example 37

5-Chloro-3-methyl-2-pyridin-3-yl-1-[4-(2H-tetrazol-5-yl)-benzyl]-1H-indole

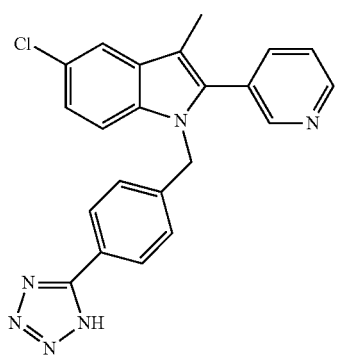 [SMILES: Cc1c(-c2cccnc2)n(Cc2ccc(-c3nnn[nH]3)cc2)c2ccc(Cl)cc12]

To a solution of 4-(5-chloro-3-methyl-2-pyridin-3-yl-indol-1-ylmethyl)-benzonitrile (Example 17, 179 mg, 0.5 mmol) in DMF (5 mL) is added sodium azide (97 mg, 1.5 mmol) and ammonium chloride (80 mg, 1.5 mmol) and the mixture is heated to 120° C. The reaction mixture is cooled to room temperature and filtered. The filtrate is purified by reverse phase HPLC with Xbridge C18 and a gradient of 0.1% NH$_4$OH in acetonitrile to give 5-chloro-3-methyl-2-pyridin-3-yl-1-[4-(2H-tetrazol-5-yl)-benzyl]-1H-indole. $^1$H NMR (400 MHz, DMSO-d$_6$) δ ppm 2.21 (s, 3H), 5.34 (s, 2H), 6.81 (d, J=8.1 Hz, 2H), 7.11 (br. s., 1H), 7.17 (dd, J=8.7, 2.1 Hz, 1H), 7.48-7.53 (m, 2H), 7.67 (d, J=2.0 Hz, 1H), 7.77 (d, J=8.3 Hz, 2H), 7.80-7.84 (m, 1H), 8.60 (d, J=1.5 Hz, 1H), 8.62 (dd, J=4.8, 1.5 Hz, 1H). HRMS (ESI) m/z 401.1276 [(M+H)$^+$ Calcd for C$_{22}$H$_{18}$N$_6$Cl: 401.1281].

Example 38

3-(3-Methyl-2-pyridin-3-yl-indole-1-carbonyl)-benzonitrile

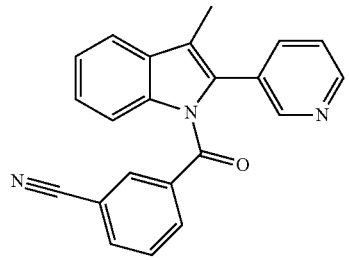 [SMILES: Cc1c(-c2cccnc2)n(C(=O)c2cccc(C#N)c2)c2ccccc12]

A flask is charged with 3-methyl-2-pyridin-3-yl-1H-indole hydrochloride (Example 1, 0.100 g, 0.408 mmol) in THF (2.5 mL) and cooled to 0° C. KHMDS (0.5 M in toluene, 1.8 mL, 0.898 mmol) is added and the mixture is stirred at room temperature for 30 min, followed by addition of 3-cyano-benzoyl chloride (0.135 g, 0.817 mmol). The reaction mixture is stirred for 0.5 h, then quenched with saturated ammonium chloride and extracted with ethyl acetate. The organic layer is dried over sodium sulfate and concentrated in vacuo. The residue is purified by reverse phase HPLC with Xbridge Shield RP18 column and a 0.1% aqueous NH$_4$OH in acetonitrile gradient to afford 3-(3-methyl-2-pyridin-3-yl-indole-1-carbonyl)-benzonitrile product as a yellow solid. $^1$H NMR (400 MHz, MeOD) δ ppm 2.31 (s, 3H), 7.32 (ddd, J=7.9, 4.9, 0.9 Hz, 1H), 7.37-7.44 (m, 2H), 7.66-7.70 (m, 4H), 7.71-7.76 (m, 2H), 7.85-7.91 (m, 1H), 8.37 (dd, J=5.1, 1.5 Hz, 1H), 8.46 (dd, J=2.3, 0.8 Hz, 1H). HRMS (ESI) m/z 338.1293 [(M+H)$^+$ Calcd for C$_{22}$H$_{16}$N$_3$O: 338.1293].

Example 39

4-(3-Methyl-2-pyridin-3-yl-indole-1-carbonyl)-benzonitrile

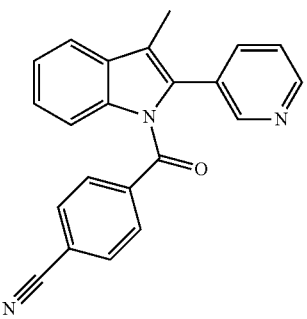 [SMILES: Cc1c(-c2cccnc2)n(C(=O)c2ccc(C#N)cc2)c2ccccc12]

4-Cyano-benzoyl chloride is processed according to the method described in Example 38 to give 4-(3-methyl-2-pyridin-3-yl-indol-1-carbonyl)-benzonitrile. $^1$H NMR (400 MHz, MeOD) δ ppm 2.32 (s, 3H), 7.32 (dd, J=7.8, 5.1 Hz, 1H), 7.37-7.45 (m, 2H), 7.49 (t, J=7.8 Hz, 1H), 7.66-7.79 (m, 3H), 7.79-7.83 (m, 1H), 7.86-7.93 (m, 2H), 8.34 (dd, J=4.8, 1.5 Hz, 1H), 8.47 (d, J=1.5 Hz, 1H). HRMS (ESI) m/z 338.1292 [(M+H)$^+$ Calcd for C$_{22}$H$_{16}$N$_3$O: 338.1293].

Example 40

(3-Methyl-2-pyridin-3-yl-indol-1-yl)-phenyl-methanone

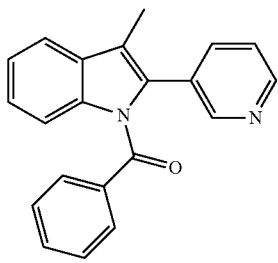 [SMILES: Cc1c(-c2cccnc2)n(C(=O)c2ccccc2)c2ccccc12]

3-Methyl-2-pyridin-3-yl-1H-indole hydrochloride and benzoyl chloride are processed according to the method described in Example 38 to give (3-methyl-2-pyridin-3-yl-indol-1-yl)-phenyl-methanone. $^1$H NMR (400 MHz, MeOD) δ ppm 2.33 (s, 3H), 7.26-7.40 (m, 5H), 7.45-7.52 (m, 1H), 7.57 (d, J=1.3 Hz, 1H), 7.59 (s, 1H), 7.63 (dd, J=7.1, 1.3 Hz, 1H), 7.68-7.73 (m, 1H), 7.75 (dt, J=7.8, 1.9 Hz, 1H), 8.33 (dd, J=5.1, 1.5 Hz, 1H), 8.47 (d, J=1.3 Hz, 2H). HRMS (ESI) m/z 313.1337 [(M+H)$^+$ Calcd for C$_{21}$H$_{17}$N$_2$O: 313.1341].

Example 41

3-(5-Cyano-3-methyl-2-pyridin-3-yl-indole-1-carbonyl)-benzonitrile

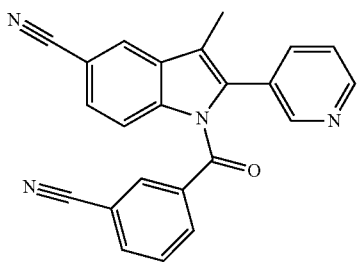 [SMILES: Cc1c(-c2cccnc2)n(C(=O)c2cccc(C#N)c2)c2ccc(C#N)cc12]

KHMDS (0.5 M in toluene, 1.46 mL, 0.73 mmol) is added to a solution of 3-methyl-2-pyridin-3-yl-1H-indole-5-carbonitrile (Example 6, 122 mg, 0.480 mmol) in THF (10 mL) at room temperature. After 5 min, 3-cyanobenzoyl chloride (178 mg, 1.08 mmol) is added. The mixture is stirred under N$_2$ for 1 h, whereupon aqueous ammonium chloride (0.5 mL) is added. The solvents are removed in vacuo and the residue is purified by Xbridge RP18 with a 0.1% aqueous ammonium hydroxide in acetonitrile gradient to give 1-(3-cyano-benzoyl)-3-methyl-2-pyridin-3-yl-1H-indole-5-carbonitrile. $^1$H NMR (400 MHz, CDCl$_3$) δ ppm 2.35 (s, 3H), 7.37-7.44 (m, 1H), 7.47-7.52 (m, 1H), 7.60-7.64 (m, 1H), 7.68-7.83 (m, 5H), 8.01 (d, J=1.5 Hz, 1H), 8.51 (d, J=4.5 Hz, 1H), 8.53 (s, 1H). HRMS (ESI) m/z 363.1247 [(M+H)$^+$ Calcd for C$_{23}$H$_{15}$N$_4$O: 363.1246].

Example 42

1-(3-Cyano-benzoyl)-2-pyridin-3-yl-1H-indole-5-carbonitrile

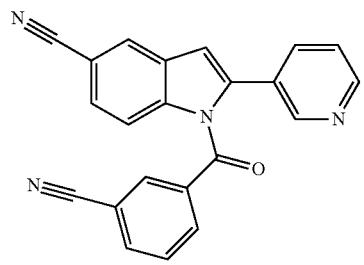 [SMILES: N#Cc1cccc(C(=O)n2c(-c3cccnc3)cc3cc(C#N)ccc32)c1]

To a solution of 2-pyridin-3-yl-1H-indole-5-carbonitrile (Example 8, 210 mg, 0.96 mmol) in THF (20 mL) at room temperature is added 0.5 M KHMDS in toluene (4.10 mL, 2.05 mmol). After 30 min, 3-cyanobenzoyl chloride (510 mg, 3.08 mmol) is added. The mixture is stirred under N$_2$ overnight. The reaction is quenched with aqueous ammonium chloride and the volatiles are removed in vacuo. The residue is redissolved in dichloromethane and poured into saturated aqueous sodium bicarbonate (100 mL). Extraction with dichloromethane, drying over sodium sulfate followed by concentration affords a residue which is purified on an XBridge RP18 using a 0.1% ammonium hydroxide in acetonitrile gradient. Further purification by silica gel flash chromatography (heptane-ethyl acetate, 3:2 to 2:3) affords 1-(3-cyano-benzoyl)-2-pyridin-3-yl-1H-indole-5-carbonitrile. $^1$H NMR (400 MHz, DMSO-d$_6$) δ ppm 7.20 (d, J=0.5 Hz, 1H), 7.22-7.26 (m, 1H), 7.55 (t, J=7.8 Hz, 1H), 7.73-7.79 (m, 2H), 7.84 (d, 1H), 7.92-7.98 (m, 2H), 8.11 (t, J=1.5 Hz, 1H), 8.29-8.33 (m, 1H), 8.39 (dd, J=4.8, 1.5 Hz, 1H), 8.60 (dd, J=2.3, 0.8 Hz, 1H). HRMS (ESI) m/z 349.1106 [(M+H)$^+$ Calcd for C$_{22}$H$_{13}$N$_4$O: 349.1089].

Example 43

4-(5-Cyano-2-pyridin-3-yl-indole-1-carbonyl)-benzoic acid methyl ester

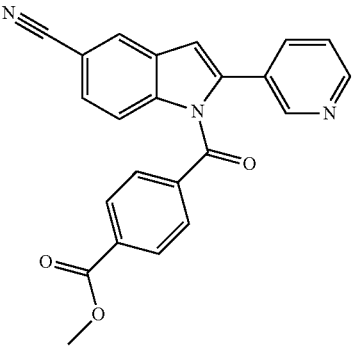 [SMILES: COC(=O)c1ccc(C(=O)n2c(-c3cccnc3)cc3cc(C#N)ccc32)cc1]

To a solution of 2-pyridin-3-yl-1H-indole-5-carbonitrile (Example 8, 240 mg, 1.09 mmol) in THF (10 mL) at room temperature is added 0.5 M KHMDS in toluene (4.0 mL, 2.0 mmol). After 30 min, 4-chlorocarbonyl-benzoic acid methyl ester (400 mg, 2.0 mmol) is added. The mixture is stirred under N₂ for 1 h. The reaction is quenched with aqueous sodium bicarbonate and the volatiles are removed in vacuo. Purification by silica gel flash chromatography using a heptane-ethyl acetate gradient affords 4-(5-cyano-2-pyridin-3-yl-indole-1-carbonyl)-benzoic acid methyl ester. $^1$H NMR (400 MHz, MeOD) δ ppm 3.90 (s, 3H), 7.12 (s, 1H), 7.26 (dd, J=8.0, 4.9 Hz, 1H), 7.63-7.72 (m, 3H), 7.77-7.81 (m, 1H), 7.91-7.96 (m, 3H), 8.17 (d, J=1.5 Hz, 1H), 8.32 (dd, J=4.8, 1.5 Hz, 1H), 8.56 (d, J=2.3 Hz, 1H). HRMS (ESI) m/z 382.1186 [(M+H)⁺ Calcd for $C_{23}H_{16}N_3O_3$: 382.1192].

Example 44

(a) 4-(5-Cyano-2-pyridin-3-yl-indole-1-carbonyl)-benzoic acid tert-butyl ester

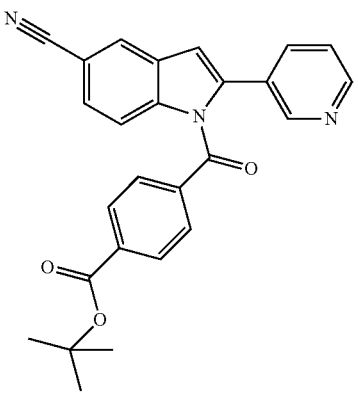 [SMILES: CC(C)(C)OC(=O)c1ccc(C(=O)n2c(-c3cccnc3)cc3cc(C#N)ccc32)cc1]

To 2-pyridin-3-yl-1H-indole-5-carbonitrile (575 mg, 2.62 mmol), 4-(butoxycarbonyl)benzoic acid (700 mg, 3.15 mmol) and DMAP (780 mg, 3.93 mmol) in DMF (30 mL) is added DCC (811 mg, 3.93 mmol). The reaction is stirred for 3 days and the mixture is poured into water (50 mL) and extracted with ethyl acetate, dried over Na₂SO₄ and concentrated. The residue is purified by silica gel flash chromatography (ethyl acetate-heptane gradient) to give 4-(5-cyano-2-pyridin-3-yl-indole-1-carbonyl)-benzoic acid tert-butyl ester as a white solid. MS (ESI) m/z 424 (M+H)⁺.

(b) 4-(5-cyano-2-pyridin-3-yl-indole-1-carbonyl)-benzoic acid

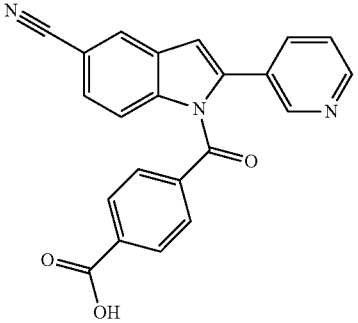 [SMILES: N#Cc1ccc2c(c1)cc(-c1cccnc1)n2C(=O)c1ccc(C(=O)O)cc1]

4-(5-Cyano-2-pyridin-3-yl-indole-1-carbonyl)-benzoic acid tert-butyl ester (100 mg) is dissolved in TFA (3 mL) and stirred at ambient temperature for 1 h. The solvent is removed in vacuo and the residue is triturated with diethyl ether twice. The residue is purified by reverse phase HPLC with Sunfire C18 and a gradient of acetonitrile in 0.1% aqueous TFA to afford 4-(5-cyano-2-pyridin-3-yl-indole-1-carbonyl)-benzoic acid as a white solid. $^1$H NMR (400 MHz, DMSO-d₆) δ ppm (TFA salt) 7.24 (s, 1H), 7.28 (dd, J=7.9, 4.9 Hz, 1H), 7.73-7.77 (m, 4H), 7.81 (dt, J=8.1, 1.9, 1.8 Hz, 1H), 7.87-7.91 (m, 2H), 8.32 (t, J=1.1 Hz, 1H), 8.41 (dd, J=4.9, 1.6 Hz, 1H), 8.63-8.65 (m, 1H), 13.40 (br. s., 1H). HRMS (ESI) m/z 366.0868 [(M+H)⁺ Calcd for $C_{22}H_{14}N_3O_3$: 366.0879].

Example 45

1-(4-cyano-3-methyl-benzoyl)-2-pyridin-3-yl-1H-indole-5-carbonitrile

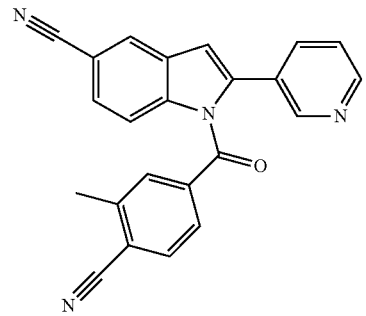 [SMILES: Cc1cc(C(=O)n2c(-c3cccnc3)cc3cc(C#N)ccc32)ccc1C#N]

4-Cyano-3-methyl-benzoic acid is synthesized based on the method described in patent EP1512687A1. To a solution of 2-pyridin-3-yl-1H-indole-5-carbonitrile (20 mg, 0.09 mmol), 4-dimethylaminopyridine (22 mg, 0.01 mmol) and 4-cyano-3-methyl-benzoic acid (29 mg, 0.18 mmol) at 0° C. in dichloromethane (2 mL) is added DCC (38 mg, 0.18 mmol). After stirring for 10 min the reaction is warmed to room temperature. A precipitate forms and stirring is continued for 16 h. The mixture is filtered and the filtrate is diluted with dichloromethane (10 mL), washed with water and a saturated sodium chloride solution. The combined organic extracts are dried over sodium sulfate, filtered, and concentrated. The resulting residue is purified by silica gel flash chromatography (ethyl acetate-heptane, 0:1 to 1:1) to furnish 1-(4-cyano-3-methyl-benzoyl)-2-pyridin-3-yl-1H-indole-5-carbonitrile. $^1$H NMR (400 MHz, CDCl₃) δ ppm 2.47 (s, 3H), 6.91 (s, 1H), 7.14 (dd, J=8.0, 4.9 Hz, 1H), 7.43-7.48 (m, 2H), 7.49-7.54 (m, 2H), 7.61 (dd, J=8.7, 1.6 Hz, 1H), 7.93 (d, J=8.6 Hz, 1H), 8.03 (d, J=1.0 Hz, 1H), 8.44 (dd, J=4.8, 1.5 Hz, 1H), 8.55 (d, J=1.8 Hz, 1H). HRMS (ESI) m/z 363.1245 [(M+H)⁺: Calcd for $C_{23}H_{15}N_4O$: 363.1246].

Example 46

3-(5-Cyano-2-pyridin-3-yl-indole-1-carbonyl)-benzoic acid tert-butyl ester

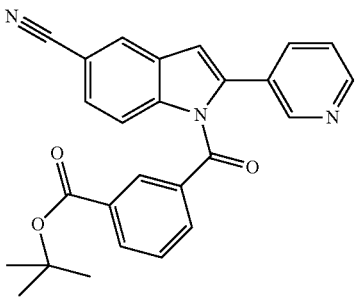 [SMILES: CC(C)(C)OC(=O)c1cccc(C(=O)n2c(-c3cccnc3)cc3cc(C#N)ccc32)c1]

Isophthalic acid mono-tert-butyl ester is processed according to the method described in Example 45 to give 3-(5-cyano-2-pyridin-3-yl-indole-1-carbonyl)-benzoic acid tert-butyl ester. ¹H NMR (400 MHz, CDCl₃) δ ppm 1.58 (s, 9H), 6.91 (s, 1H), 7.10 (dd, J=7.6, 5.1 Hz, 1H), 7.40 (t, J=7.8 Hz, 1H), 7.52-7.59 (m, 2H), 7.81 (dt, J=7.9, 1.5, 1.3 Hz, 1H), 7.85 (d, J=8.7 Hz, 1H), 8.02-8.06 (m, 2H), 8.09 (t, J=1.6 Hz, 1H), 8.40 (d, J=3.4 Hz, 1H), 8.58 (d, J=1.8 Hz, 1H). HRMS (ESI) m/z 424.1662 [(M+H)⁺: Calcd for C₂₆H₂₂N₃O₃: 424.1661].

Example 47

1-(3-Methyl-benzoyl)-2-pyridin-3-yl-1H-indole-5-carbonitrile

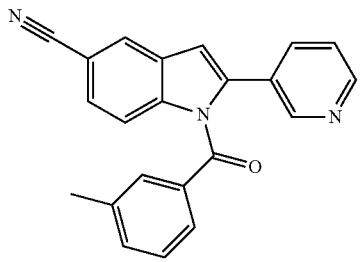 [SMILES: Cc1cccc(C(=O)n2c(-c3cccnc3)cc3cc(C#N)ccc32)c1]

3-Methylbenzoic acid is processed according to the method described in Example 45 to give 1-(3-methyl-benzoyl)-2-pyridin-3-yl-1H-indole-5-carbonitrile. ¹H NMR (400 MHz, CDCl₃) δ ppm 2.29 (s, 3H), 6.89 (s, 1H), 7.14 (dd, J=8.0, 4.9 Hz, 1H), 7.19-7.24 (m, 1H), 7.27-7.31 (m, 1H), 7.39-7.44 (m, 2H), 7.50-7.57 (m, 2H), 7.71 (d, J=8.6 Hz, 1 H), 8.01 (d, J=1.0 Hz, 1H), 8.42 (dd, J=4.8, 1.5 Hz, 1H), 8.62 (d, J=1.8 Hz, 1H). HRMS (ESI) m/z 338.1289 [(M+H)⁺: Calcd for C₂₂H₁₆N₃O: 338.1293]

Example 48

1-(3,4-Dimethyl-benzoyl)-2-pyridin-3-yl-1H-indole-5-carbonitrile

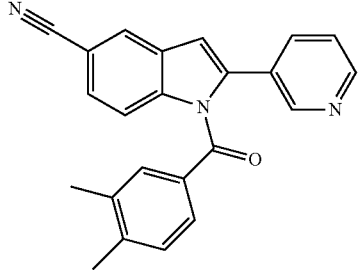 [SMILES: Cc1ccc(C(=O)n2c(-c3cccnc3)cc3cc(C#N)ccc32)cc1C]

3,4-Dimethylbenzoic acid is processed according to the method described in Example 45 to give 1-(3,4-dimethyl-benzoyl)-2-pyridin-3-yl-1H-indole-5-carbonitrile. ¹H NMR (400 MHz, CDCl₃) δ ppm 2.21 (s, 3H), 2.26 (s, 3H), 6.89 (s, 1H), 7.10 (d, J=7.8 Hz, 1H), 7.15 (dd, J=7.5, 5.2 Hz, 1H), 7.37-7.43 (m, 2H), 7.49 (dd, J=8.6, 1.5 Hz, 1H), 7.57 (dt, J=8.3, 2.0, 1.6 Hz, 1H), 7.61 (d, J=8.8 Hz, 1H), 8.01 (d, J=2.0 Hz, 1H), 8.44 (dd, J=4.8, 1.5 Hz, 1H), 8.64 (d, J=2.3 Hz, 1H). HRMS (ESI) m/z 352.1458 [(M+H)⁺: Calcd for C₂₃H₁₈N₃O: 352.1450].

Example 49

1-(4-Methoxy-benzoyl)-2-pyridin-3-yl-1H-indole-5-carbonitrile

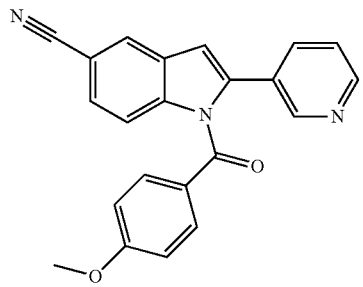 [SMILES: COc1ccc(C(=O)n2c(-c3cccnc3)cc3cc(C#N)ccc32)cc1]

4-Methoxybenzoic acid is processed according to the method described in Example 45 to give 1-(4-methoxy-benzoyl)-2-pyridin-3-yl-1H-indole-5-carbonitrile. ¹H NMR (400 MHz, CDCl₃) δ ppm 3.83 (s, 3H), 6.81-6.85 (m, 2H), 6.90 (s, 1H), 7.18 (dd, J=7.8, 3.0 Hz, 1H), 7.49 (dd, J=8.6, 1.5 Hz, 1H), 7.58-7.62 (m, 2H), 7.62-7.66 (m, 2H), 8.01 (d, J=1.5 Hz, 1H), 8.46 (dd, J=4.8, 1.5 Hz, 1H), 8.66 (d, J=3.0 Hz, 1H). HRMS (ESI) m/z 354.1225 [(M+H)⁺: Calcd for C₂₂H₁₆N₃O₂: 354.1243].

Example 50

1-(3-Methoxy-benzoyl)-2-pyridin-3-yl-1H-indole-5-carbonitrile

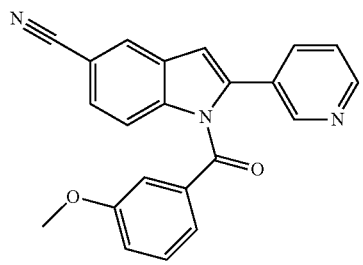 [SMILES: COc1cccc(C(=O)n2c(-c3cccnc3)cc3cc(C#N)ccc32)c1]

3-Methoxybenzoic acid is processed according to the method described in Example 45 to give 1-(3-methoxy-benzoyl)-2-pyridin-3-yl-1H-indole-5-carbonitrile. ¹H NMR (400 MHz, CDCl₃) δ ppm 3.78 (s, 3H), 6.89 (s, 1H), 7.02 (ddd, J=8.2, 2.6, 1.1 Hz, 1H), 7.13-7.18 (m, 3H), 7.23 (d, J=8.1 Hz, 1H), 7.52 (dd, J=8.6, 1.5 Hz, 1H), 7.57 (dt, J=8.0, 1.9 Hz, 1H), 7.69 (d, J=8.8 Hz, 1H), 8.01 (d, J=1.0 Hz, 1H), 8.45 (dd, J=4.8, 1.5 Hz, 1H), 8.64 (d, J=2.3 Hz, 1H). HRMS (ESI) m/z 354.1231 [(M+H)⁺: Calcd for C₂₂H₁₆N₃O₂: 354.1243].

Example 51

1-(3,4-Dimethoxy-benzoyl)-2-pyridin-3-yl-1H-indole-5-carbonitrile

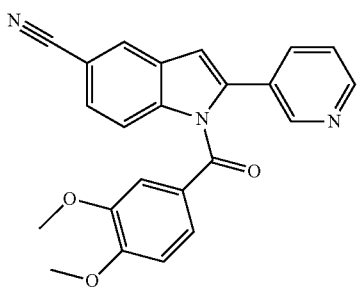 [SMILES: COc1ccc(C(=O)n2c(-c3cccnc3)cc3cc(C#N)ccc32)cc1OC]

3,4-Dimethoxybenzoic acid is processed according to the method described in Example 45 to give 1-(3,4-dimethoxybenzoyl)-2-pyridin-3-yl-1H-indole-5-carbonitrile. $^1$H NMR (400 MHz, CDCl$_3$) δ ppm 3.87 (s, 3H), 3.90 (s, 3H), 6.75 (d, J=8.6 Hz, 1H), 6.92 (s, 1H), 7.19 (dd, J=7.8, 4.3 Hz, 1H), 7.22 (dd, J=8.5, 2.2 Hz, 1H), 7.29 (d, J=2.0 Hz, 1H), 7.50 (dd, J=8.7, 1.6 Hz, 1H), 7.58-7.63 (m, 2H), 8.02 (d, J=1.0 Hz, 1H), 8.47 (dd, J=4.8, 1.5 Hz, 1H), 8.68 (dd, J=2.3, 0.8 Hz, 1H). HRMS (ESI) m/z 384.1349 [(M+H)$^+$: Calcd for C$_{23}$H$_{18}$N$_3$O$_3$: 384.1348].

Example 52

1-(3-Ethyl-benzoyl)-2-pyridin-3-yl-1H-indole-5-carbonitrile

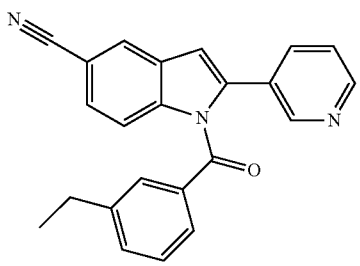 [SMILES: CCc1cccc(C(=O)n2c(-c3cccnc3)cc3cc(C#N)ccc32)c1]

3-Ethylbenzoic acid is processed according to the method described in Example 45 to give 1-(3-ethyl-benzoyl)-2-pyridin-3-yl-1H-indole-5-carbonitrile. $^1$H NMR (400 MHz, CDCl$_3$) δ ppm 1.16 (t, J=7.6 Hz, 3H), 2.58 (q, J=7.6 Hz, 2H), 6.89 (s, 1H), 7.12 (dd, J=8.0, 4.9 Hz, 1H), 7.22-7.25 (m, 1H), 7.29-7.33 (m, 1H), 7.40 (s, 1H), 7.43-7.47 (m, 1H), 7.51-7.57 (m, 2H), 7.73 (d, J=8.8 Hz, 1H), 8.02 (d, J=1.0 Hz, 1H), 8.42 (dd, J=4.8, 1.5 Hz, 1H), 8.63 (d, J=1.8 Hz, 1H). HRMS (ESI) m/z 352.1443 [(M+H)$^+$: Calcd for C$_{23}$H$_{18}$N$_3$O: 352.1450].

Example 53

1-(3,5-Dimethyl-benzoyl)-2-pyridin-3-yl-1H-indole-5-carbonitrile

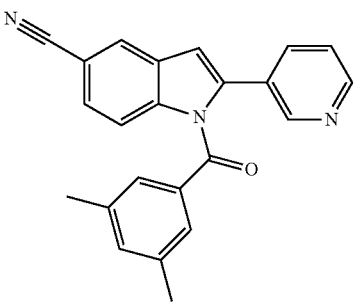 [SMILES: Cc1cc(C)cc(C(=O)n2c(-c3cccnc3)cc3cc(C#N)ccc32)c1]

To a solution of 2-pyridin-3-yl-1H-indole-5-carbonitrile (Example 8, 200 mg, 0.913 mmol) at 0° C. in THF (6 mL) is added 60% sodium hydride (72 mg, 1.826 mmol) and the mixture is stirred for 10 min at 0° C. The reaction mixture is then warmed to room temperature and stirred for 30 min. 3,5-Dimethyl-benzoyl chloride (460 mg, 2.740 mmol) in THF (2 mL) is added dropwise at 0° C. and the reaction is stirred at room temperature for 1 h. The reaction is quenched by adding saturated sodium bicarbonate. The THF is removed under vacuum, and the resulting residue is purified by silica gel flash chromatography (ethyl acetate-heptane, 0:1 to 1:1). The resulting product is further purified by HPLC using an X-bridge RP18 and an acetonitrile-0.1% ammonia hydroxide gradient to yield 1-(3,5-dimethyl-benzoyl)-2-pyridine-3-yl-1H-indole-5-carbonitrile. $^1$H NMR (400 MHz, CDCl$_3$) δ ppm 2.25 (s, 6H), 6.88 (s, 1H), 7.10 (s, 1H), 7.14 (dd, J=7.6, 5.3 Hz, 1H), 7.22 (s, 2H), 7.50-7.56 (m, 2H), 7.70 (d, J=8.8 Hz, 1H), 8.01 (s, 1H), 8.43 (dd, J=4.8, 1.5 Hz, 1H), 8.62 (s, 1H). HRMS (ESI) m/z 352.1452 [(M+H)$^+$: Calcd for C$_{23}$H$_{18}$N$_3$O: 352.1450].

Example 54

(a) 5-Bromo-2-methyl-benzoic acid tert-butyl ester

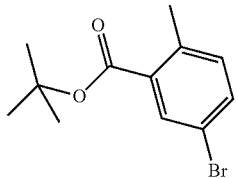

To a suspension of anhydrous magnesium sulfate (4.5 g, 37.28 mmol) in dichloromethane (37 mL) is added concentrated H$_2$SO$_4$ (516 μl, 9.302 mmol) and the mixture is stirred vigorously for 15 min. 5-Bromo-2-methyl-benzoic acid (2 g, 9.302 mmol) is added, followed by t-butanol (4.39 mL, 46.51 mmol). The flask is capped tightly and stirred at room temperature for 24 h. After adding saturated sodium bicarbonate, the resulting solution is extracted with ethyl acetate. The organic layer is washed with a saturated sodium chloride solution, dried over sodium sulfate, filtered and concentrated. The resulting residue is purified by silica gel flash chromatography (ethyl acetate-heptane, 0:1 to 3:7) to furnish 5-bromo-2-methyl-benzoic acid tert-butyl ester. $^1$H NMR (400 MHz, DMSO-d$_6$) δ ppm 1.59 (s, 9H), 2.51 (s, 3H), 7.08 (d, J=8.1 Hz, 1H), 7.46 (dd, J=8.3, 2.3 Hz, 1H), 7.92 (d, J=2.3 Hz, 1H)

(b) 4-Methyl-isophthalic acid 3-tert-butyl ester

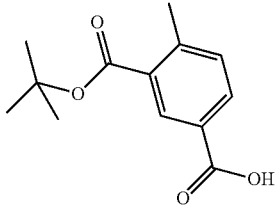 [SMILES: Cc1ccc(C(=O)O)cc1C(=O)OC(C)(C)C]

n-Butyllithium (1.6M in hexane, 1.29 mL, 1.975 mmol) is slowly added to 5-bromo-2-methyl-benzoic acid tert-butyl ester (511 mg, 1.884 mmol) in THF (18 mL) at −78° C. under N$_2$. The reaction mixture is stirred at −78° C. for 30 min. Carbon dioxide gas is bubbled through the solution until the solution color changes to orange. After stirring at −78° C. for 10 min, the reaction mixture is warmed to room temperature. The reaction is quenched with saturated ammonium chloride, extracted with ethyl acetate, dried over sodium sulfate, filtered and concentrated. The resulting residue is purified by silica gel flash chromatography (ethyl acetate-heptane, 0:1 to 1:1) to furnish 4-methyl-isophthalic acid 3-tert-butyl ester. $^1$H NMR (400 MHz, CDCl$_3$) δ ppm 1.62 (s, 9H), 2.65 (s, 3H), 7.33 (d, J=7.83 Hz, 1H), 8.07 (dd, J=7.96, 1.89 Hz, 1H), 8.52 (d, J=2.02 Hz, 1H).

(c) 5-(5-Cyano-2-pyridin-3-yl-indole-1-carbonyl)-2-methyl-benzoic acid tert-butyl ester

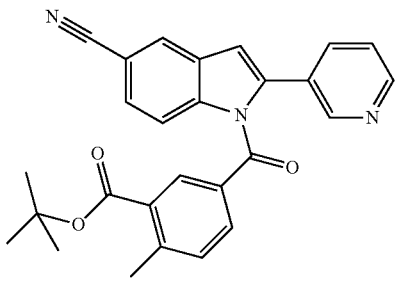 [SMILES: Cc1ccc(C(=O)n2c(-c3cccnc3)cc3cc(C#N)ccc32)cc1C(=O)OC(C)(C)C]

4-methyl-isophthalic acid 3-tert-butyl ester is processed according to the method described in Example 45 to give 5-(5-cyano-2-pyridin-3-yl-indole-1-carbonyl)-2-methyl-benzoic acid tert-butyl ester. $^1$H NMR (400 MHz, CDCl$_3$) δ ppm 1.57 (s, 9H), 2.55 (s, 3H), 6.91 (s, 1H), 7.13 (dd, J=7.83, 4.29 Hz, 1H), 7.20 (d, J=8.08 Hz, 1H), 7.53-7.58 (m, 2H), 7.66 (dd, J=7.96, 2.15 Hz, 1H), 7.76 (d, J=8.59 Hz, 1H), 7.98 (d, J=2.02 Hz, 1H), 8.02 (d, J=1.01 Hz, 1H), 8.43 (dd, J=4.80, 1.52 Hz, 1H), 8.61 (d, J=2.27 Hz, 1H).

(d) 5-(5-Cyano-2-pyridin-3-yl-indole-1-carbonyl)-2-methyl-benzoic acid

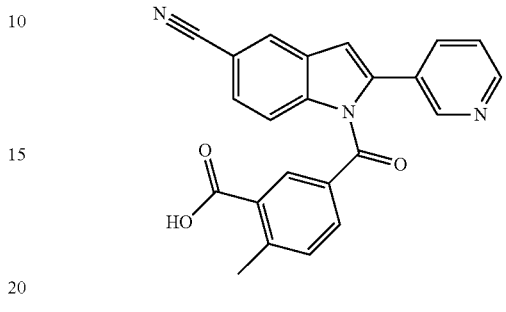

5-(5-Cyano-2-pyridin-3-yl-indole-1-carbonyl)-2-methyl-benzoic acid tert-butyl ester is dissolved in trifluoroacetic acid (3 mL), and stirred at room temperature for 1 h. After removing the solvent, the residue is purified by HPLC with an X-bridge Phenyl using acetonitrile-0.1% trifluoroacetic acid as an eluent to yield 5-(5-cyano-2-pyridin-3-yl-indole-1-carbonyl)-2-methyl-benzoic acid. $^1$H NMR (400 MHz, DMSO-d$_6$) δ ppm (TFA salt) 2.59 (s, 3H), 7.32 (s, 1H), 7.39-7.44 (m, 2H), 7.71-7.75 (m, 1H), 7.76-7.79 (m, 1H), 7.81 (dd, J=7.8, 2.0 Hz, 1H), 7.92 (dt, J=8.0, 1.8 Hz, 1H), 8.11 (d, J=2.0 Hz, 1H), 8.38 (d, J=1.5 Hz, 1H), 8.52 (dd, J=5.0, 1.5 Hz, 1H), 8.74 (d, J=2.0 Hz, 1H). HRMS (ESI) m/z 382.1202 [(M+H)$^+$ Calcd for C$_{23}$H$_{16}$N$_3$O$_3$: 382.1192].

Example 55

3-(5-Cyano-2-pyridin-3-yl-indole-1-carbonyl)-benzoic acid

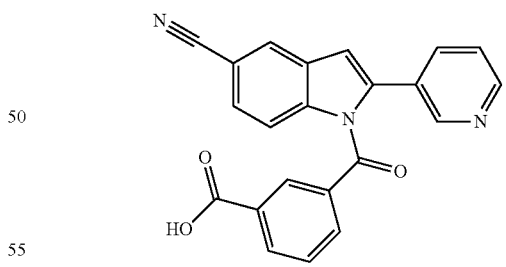

3-(5-cyano-2-pyridin-3-yl-indole-1-carbonyl)-benzoic acid tert-butyl ester (Example 46) is processed according to the method described in Example 54d to give 5-(5-cyano-2-pyridin-3-yl-indole-1-carbonyl)-2-methyl-benzoic acid. $^1$H NMR (400 MHz, DMSO-d$_6$) δ ppm (TFA salt) 7.16-7.21 (m, 2H), 7.43 (t, J=7.8 Hz, 1H), 7.67 (dd, J=8.7, 1.64 Hz, 1H), 7.71-7.75 (m, 2H), 7.82 (dt, J=8.0, 1.5, 1.3 Hz, 1H), 7.97 (dt, J=7.8, 1.4 Hz, 1H), 8.00 (t, J=1.5 Hz, 1H), 8.25 (d, J=1.0 Hz, 1H), 8.32 (dd, J=4.8, 1.5 Hz, 1H), 8.55 (d, J=1.6 Hz, 1H). HRMS (ESI) m/z 368.1040 [(M+H)+ Calcd for $C_{22}H_{14}N_3O_3$: 368.1035]

Example 56

1-(3-Cyano-benzenesulfonyl)-2-pyridin-3-yl-1H-indole-5-carbonitrile

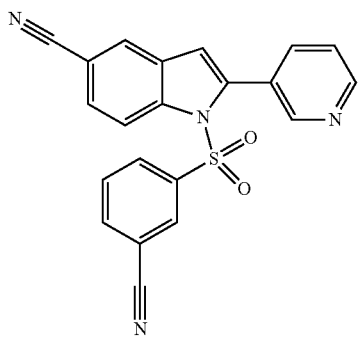 [SMILES: N#Cc1cccc(S(=O)(=O)n2c(-c3cccnc3)cc3cc(C#N)ccc32)c1]

To a solution of 2-pyridin-3-yl-1H-indole-5-carbonitrile (Example 8, 300 mg, 1.37 mmol) at 0° C. in DMF (12 mL) is added 60% sodium hydride (82 mg, 2.06 mmol) and the mixture stirred for 10 min at 0° C. The reaction mixture is then warmed to room temperature and stirred for 30 min. 3-Cyanobenzenesulfonyl chloride (552 mg, 2.74 mmol) in DMF (2 mL) is added dropwise at 0° C. and the reaction is stirred at room temperature for 1 h. The reaction is quenched by adding water (1 mL). The resulting mixture is purified by HPLC X-bridge RP18 using acetonitrile-0.1% ammonia hydroxide as an eluent to yield 1-(3-cyano-benzenesulfonyl)2-pyridin-3-yl-1H-indole-5-carbonitrile. $^1$H NMR (400 MHz, CDCl$_3$) δ ppm 7.11 (s, 1H), 7.54 (dd, J=7.8, 4.8 Hz, 1H), 7.66 (dd, J=8.1, 2.0 Hz, 1H), 7.72 (t, J=7.7 Hz, 1H), 7.86 (dd, J=8.7, 1.6 Hz, 1H), 7.94 (t, J=1.5 Hz, 1H), 7.98 (dt, J=8.2, 2.0, 1.8 Hz, 1H), 8.16 (dd, J=7.6, 1.3 Hz, 1H), 8.19 (d, J=1.0 Hz, 1H), 8.34 (d, J=8.6 Hz, 1H), 8.67 (d, J=2.8 Hz, 1H), 8.71 (dd, J=4.9, 1.6 Hz, 1H). HRMS (ESI) m/z 385.0763 [(M+H)+ Calcd for $C_{21}H_{13}N_4O_2S$: 385.0759].

Example 57

3-Methyl-1-(2-phenoxy-ethyl)-2-pyridin-3-yl-1H-indole-5-carbonitrile

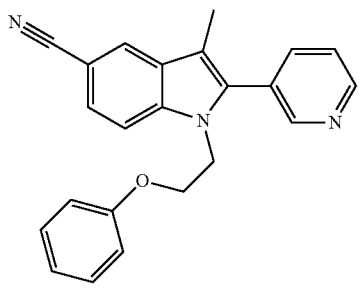 [SMILES: Cc1c(-c2cccnc2)n(CCOc2ccccc2)c2ccc(C#N)cc12]

To a solution of 3-methyl-2-pyridin-3-yl-1H-indole-5-carbonitrile (Example 6, 47 mg, 0.20 mmol) in THF (5 mL) at room temperature is added KHMDS (0.5 M in toluene, 0.60 mL, 0.30 mmol) followed with (2-bromo-ethoxy)-benzene (90 mg, 0.45 mmol). The mixture is stirred under N$_2$ for 2 days and aqueous ammonium chloride (1 mL) is added to quench the reaction. The volatiles are removed in vacuo and the residue is purified by silica gel flash chromatography (ethyl acetate-heptane, 1:4 to 1:0) to give 3-methyl-1-(2-phenoxy-ethyl)-2-pyridin-3-yl-1H-indole-5-carbonitrile. $^1$H NMR (400 MHz, CDCl$_3$) δ ppm 2.25 (s, 3H), 4.10 (t, J=5.2 Hz, 2H), 4.46 (t, J=5.3 Hz, 2H), 6.66 (d, J=7.8 Hz, 2H), 6.93 (t, J=7.3 Hz, 1H), 7.17-7.25 (m, 2H), 7.51-7.57 (m, 2H), 7.59-7.65 (m, 1H), 7.95 (d, J=8.6 Hz, 1H), 7.98 (s, 1H), 8.74-8.79 (m, 2H). HRMS (ESI) m/z 354.1618 [(M+H)+ Calcd for $C_{23}H_{20}N_3O$: 354.1606].

Example 58

1-(2-Phenoxy-ethyl)-2-pyridin-3-yl-1H-indole-5-carbonitrile

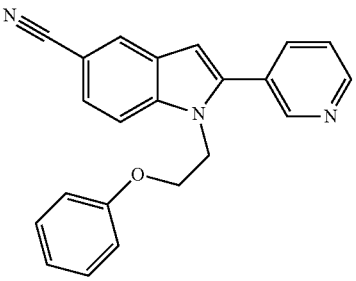 [SMILES: N#Cc1ccc2c(c1)cc(-c1cccnc1)n2CCOc1ccccc1]

(2-Bromo-ethoxy)-benzene and 2-pyridin-3-yl-1H-indole-5-carbonitrile (Example 8) are processed according to the method described in Example 57 to give 1-(2-phenoxy-ethyl)-2-pyridin-3-yl-1H-indole-5-carbonitrile. $^1$H NMR (400 MHz, MeOD) δ ppm 4.19 (t, J=5.2 Hz, 2H), 4.67 (t, J=5.1 Hz, 2H), 6.63 (d, J=7.8 Hz, 2H), 6.77 (s, 1H), 6.84 (t, J=7.5 Hz, 1H), 7.10-7.17 (m, 2H), 7.53 (dd, J=8.6, 1.8 Hz, 1H), 7.55-7.60 (m, 1H), 7.77 (d, J=8.6 Hz, 1H), 8.05 (s, 1H), 8.08-8.13 (m, 1H), 8.63 (dd, J=4.9, 1.6 Hz, 1H), 8.79 (d, J=1.5 Hz, 1H). HRMS (ESI) m/z 340.1453 [(M+H)+ Calcd for $C_{22}H_{18}N_3O$: 340.1450].

Example 59

3-Methyl-1-(2-phenoxy-ethyl)-2-pyridin-3-yl-1H-indole

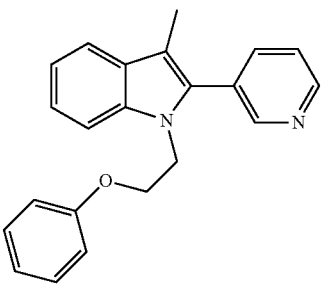 [SMILES: Cc1c(-c2cccnc2)n(CCOc2ccccc2)c2ccccc12]

A flask is charged with 3-methyl-2-pyridin-3-yl-1H-indole hydrochloride (Example 1, 0.100 g, 0.408 mmol) and DMF (2 mL). The solution is cooled to 0° C. and 60% NaH in mineral oil (0.036 g, 0.898 mmol) is added. The mixture is stirred at room temperature for 20 min followed by addition of (2-bromo-ethoxy)-benzene (0.205 mL, 1.021 mmol). The mixture is stirred at room temperature for 5 h, whereupon it is concentrated in vacuo. The residue is purified by reverse phase HPLC with Xbridge Shield RP18 column and a gradient of 0.1% aqueous TFA in acetonitrile to afford 3-methyl-1-(2-phenoxy-ethyl)-2-pyridin-3-yl-1H-indole as a yellow trifluoro acetate salt. $^1$H NMR (400 MHz, MeOD) δ ppm (TFA salt) 2.29 (s, 3H), 4.18 (t, J=5.2 Hz, 2H), 4.55 (t, J=5.1 Hz, 2H), 6.64 (d, J=7.8 Hz, 2H), 6.87 (t, J=7.5 Hz, 1H), 7.11-7.22 (m, 3H), 7.33 (ddd, J=7.6, 1.1 Hz, 1H), 7.58 (d, J=8.3 Hz, 1H), 7.64 (d, J=7.8 Hz, 1H), 7.96 (dd, J=8.0, 5.4 Hz, 1H), 8.44 (dt, J=8.0, 1.9, 1.8 Hz, 1H), 8.77 (dd, J=5.6, 1.3 Hz, 1H), 8.89 (d, J=1.8 Hz, 1H). HRMS (ESI) m/z 329.1646 [(M+H)$^+$ Calcd for $C_{22}H_{21}N_2O$: 329.1654].

Example 60

(a) 3-(2-Bromo-ethoxy)-benzoic acid methyl ester

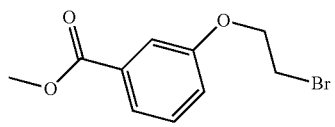

A flask is charged with 3-hydroxybenzoic acid methyl ester (2.54 g, 16.0 mmol) and acetone (50 mL). 1,2-Dibromo-ethane (5.69 mL, 66.0 mmol) and potassium carbonate (2.76 g, 19.0 mmol) are added and the mixture is refluxed for 24 h. The reaction mixture is then cooled to room temperature. The solids are filtered off and the filtrate concentrated in vacuo. The residue is purified by silica gel flash chromatography (heptane-ethyl acetate, 3:1) to afford 3-(2-bromo-ethoxy)-benzoic acid methyl ester as a colorless oil. $^1$H NMR (400 MHz, CDCl$_3$) δ ppm 3.66 (t, J=6.2 Hz, 2H), 3.93 (s, 3H), 4.35 (t, J=6.2 Hz, 2H), 7.14 (m, 1H) 7.37 (m, 1H) 7.57 (m, 1H) 7.68 (m, 1H).

(b) 3-[2-(5-Cyano-3-methyl-2-pyridin-3-yl-indol-1-yl)-ethoxy]-benzoic acid methyl ester

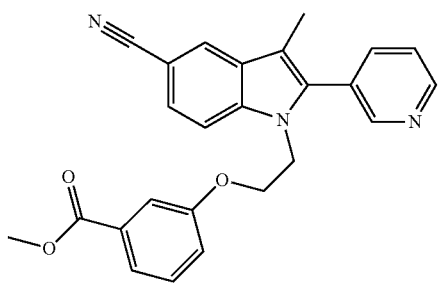 [SMILES: COC(=O)c1cccc(OCCn2c(-c3cccnc3)c(C)c3cc(C#N)ccc32)c1]

3-(2-Bromo-ethoxy)-benzoic acid methyl ester and 5-cyano-3-methyl-2-pyridin-3-yl-indol-1-yl (Example 6) are processed according to the method described in Example 59 to give 3-[2-(5-cyano-3-methyl-2-pyridin-3-yl-indol-1-yl)-ethoxy]-benzoic acid methyl ester. $^1$H NMR (400 MHz, MeOD) δ ppm 2.26 (s, 3H), 3.90 (s, 3H), 4.22 (t, J=4.9 Hz, 2H), 4.60 (t, J=5.1 Hz, 2H), 6.91 (dd, J=7.8, 2.3 Hz, 1H), 7.21-7.24 (m, 1H), 7.28 (t, J=8.0 Hz, 1H), 7.52-7.59 (m, 2H), 7.65 (dd, J=7.8, 5.1 Hz, 1H), 7.76 (d, J=8.6 Hz, 1H), 7.98-8.09 (m, 2H), 8.56-8.77 (m, 2H). HRMS (ESI) m/z 412.1664 [(M+H)$^+$ Calcd for $C_{25}H_{22}N_3O_3$: 412.1661].

Example 61

(a) 4-(2-Bromo-ethoxy)-benzoic acid methyl ester

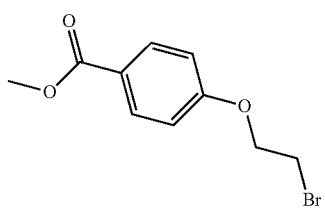

4-Hydroxybenzoic acid methyl ester is processed according to the method described in Example 60a to give 4-(2-Bromo-ethoxy)-benzoic acid methyl ester.

(b) 4-[2-(5-Cyano-3-methyl-2-pyridin-3-yl-indol-1-yl)-ethoxy]-benzoic acid methyl ester

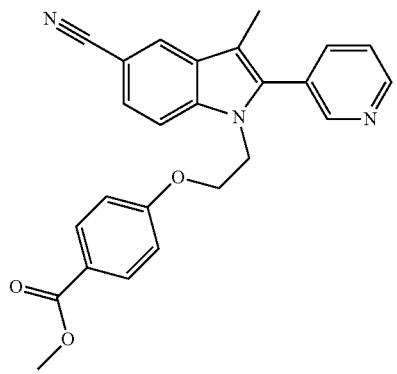 [SMILES: COC(=O)c1ccc(OCCn2c(-c3cccnc3)c(C)c3cc(C#N)ccc32)cc1]

4-(2-Bromo-ethoxy)-benzoic acid methyl ester and 5-cyano-3-methyl-2-pyridin-3-yl-indol-1-yl (Example 6) are processed according to the method described in Example 59 to give 4-[2-(5-cyano-3-methyl-2-pyridin-3-yl-indol-1-yl)-ethoxy]-benzoic acid methyl ester. $^1$H NMR (400 MHz, MeOD) δ ppm 2.28 (s, 3H), 3.87 (s, 3H), 4.24 (t, J=5.1 Hz, 2H), 4.61 (t, J=5.1 Hz, 2H), 6.73-6.79 (m, 2H), 7.58 (dd, J=8.5, 1.6 Hz, 1H), 7.66 (ddd, J=7.9, 5.0, 0.8 Hz, 1H), 7.77 (dd, J=8.6, 0.5 Hz, 1H), 7.85-7.88 (m, 1H), 7.88-7.90 (m, 1H), 8.03 (dt, J=8.1, 1.9, 1.8 Hz, 1H), 8.07 (dd, J=1.5, 0.6 Hz, 1H), 8.52-8.84 (m, 2H). HRMS (ESI) m/z 412.1660 [(M+H)+ Calcd for $C_{25}H_{22}N_3O_3$: 412.1661].

Example 62

4-[2-(5-Cyano-3-methyl-2-pyridin-3-yl-indol-1-yl)-ethoxy]-benzoic acid

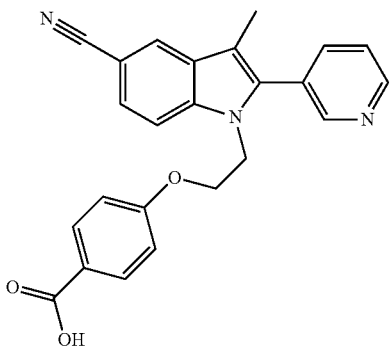 [SMILES: Cc1c(-c2cccnc2)n(CCOc2ccc(C(=O)O)cc2)c2ccc(C#N)cc12]

A flask is charged with 4-[2-(5-cyano-3-methyl-2-pyridin-3-yl-indol-1-yl)-ethoxy]-benzoic acid methyl ester (Example 61, 0.150 g, 0.36 mmol) in MeOH (5 mL). Aqueous lithium hydroxide (1 M, 0.912 mL, 0.912 mmol) is added and the mixture is refluxed overnight. The reaction mixture is then acidified to pH 1 using 1 M aqueous HCl solution and the methanol is removed in vacuo. The resulting solution is extracted with ethyl acetate. The organic layer is dried over sodium sulfate, filtered and concentrated. The resulting residue is purified by silica gel flash chromatography (dichloromethane-methanol, 9:1) to afford 4-[2-(5-cyano-3-methyl-2-pyridin-3-yl-indol-1-yl)-ethoxy]-benzoic acid as a white solid. $^1$H NMR (400 MHz, MeOD) δ ppm 2.27 (s, 3H), 4.22 (t, J=5.1 Hz, 2H), 4.60 (t, J=5.2 Hz, 2H), 6.72 (d, J=8.8 Hz, 2H), 7.57 (dd, J=8.6, 1.5 Hz, 1H), 7.62-7.72 (m, 1H), 7.76 (d, J=8.6 Hz, 1H), 7.86 (d, J=8.6 Hz, 2H), 8.02 (d, J=7.8 Hz, 1H), 8.07 (s, 1H), 8.72 (br. s., 2H). HRMS (ESI) m/z 398.1487 [(M+H)+ Calcd for $C_{24}H_{20}N_3O_3$: 398.1505].

Example 63

(a) 4-[2-(5-Chloro-3-methyl-2-pyridin-3-yl-indol-1-yl)-ethoxy]-benzoic acid methyl ester

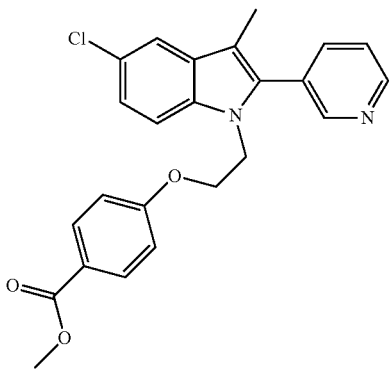 [SMILES: COC(=O)c1ccc(OCCn2c(-c3cccnc3)c(C)c3cc(Cl)ccc32)cc1]

4-(2-Bromo-ethoxy)-benzoic acid methyl ester (Example 61a) and 5-chloro-3-methyl-2-pyridin-3-yl-indol-1-yl (Example 2) are processed according to the method described in Example 59 to give 4-[2-(5-chloro-3-methyl-2-pyridin-3-yl-indol-1-yl)-ethoxy]-benzoic acid methyl ester. MS (ESI) m/z 421.01.

(b) 4-[2-(5-Chloro-3-methyl-2-pyridin-3-yl-indol-1-yl)-ethoxy]-benzoic acid

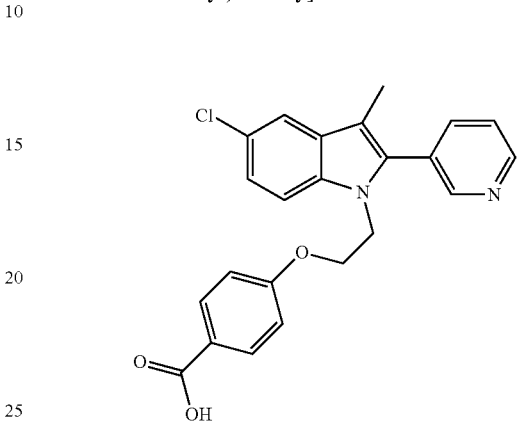

4-[2-(5-Chloro-3-methyl-2-pyridin-3-yl-indol-1-yl)-ethoxy]-benzoic acid methyl ester is processed according to the method described in Example 62 to give 4-[2-(5-chloro-3-methyl-2-pyridin-3-yl-indol-1-yl)-ethoxy]-benzoic acid. $^1$H NMR (400 MHz, MeOD) δ ppm 2.22 (s, 3H), 4.21 (t, J=5.1 Hz, 2H), 4.54 (t, J=5.1 Hz, 2H), 6.73 (d, J=8.8 Hz, 2H), 7.25 (dd, J=8.7, 2.1 Hz, 1H), 7.56 (d, J=8.6 Hz, 1H), 7.59 (d, J=2.0 Hz, 1H), 7.61-7.67 (m, 1H), 7.87 (d, J=8.8 Hz, 2H), 7.99 (d, J=7.8 Hz, 1H), 8.68 (br. s., 2H); HRMS (ESI) m/z 407.1157 [(M+H)+ Calcd for $C_{23}H_{20}ClN_2O_3$: 407.1162].

Example 64

2-(5-Chloro-3-methyl-2-pyridin-3-yl-indol-1-yl)-ethanol

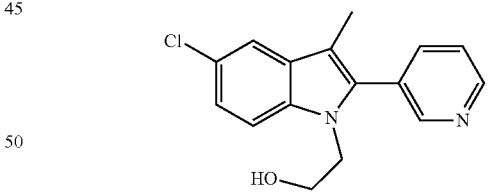

A flask is charged with 5-chloro-3-methyl-2-pyridin-3-yl-1H-indole hydrochloride (Example 2, 1.0 g, 3.58 mmol) and THF (20 mL) and cooled to 0° C. KHMDS (0.5 M in toluene, 17.9 mL, 8.95 mmol) is added and the mixture is stirred at room temperature for 30 min, followed by addition of (2-chloro-ethoxy)-trimethylsilane (1.06 mL, 8.95 mmol). The reaction mixture is stirred for 48 h at 60° C. After cooling to room temperature, aqueous 1M HCl (30 mL) is added and the mixture is stirred at room temperature for 30 min, then washed with water and extracted with ethyl acetate twice. The organic layer is dried over sodium sulfate and concentrated in vacuo. The residue is purified by silica gel flash chromatography (heptane-ethyl acetate, 1:4) to afford 2-(5-chloro-3-methyl-2-pyridin-3-yl-indol-1-yl)-ethanol as a solid. $^1$H NMR (400 MHz, MeOD) δ ppm 2.22 (s, 3H), 3.69 (t, J=5.9 Hz, 2H), 4.18 (t, J=5.8 Hz, 2H), 7.21 (dd, J=8.6, 2.0 Hz, 1H), 7.47 (d, J=8.6 Hz, 1H), 7.57 (d, J=1.8 Hz, 1H), 7.61-7.67 (m, 1H), 8.01 (dt, J=7.9, 2.0 Hz, 1H), 8.61-8.71 (m, 2H). HRMS (ESI) m/z 287.0953 [(M+H)$^+$ Calcd for $C_{16}H_{16}ClN_2O$: 287.0951].

Example 65

2,2-Dimethyl-propionic acid 5-chloro-3-methyl-2-pyridin-3-yl-indol-1-ylmethyl ester

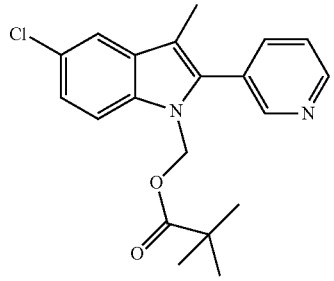 [SMILES: Cc1c(-c2cccnc2)n(COC(=O)C(C)(C)C)c2ccc(Cl)cc12]

A flask is charged with 5-chloro-3-methyl-2-pyridin-3-yl-1H-indole hydrochloride (Example 2, 1.0 g, 3.58 mmol) and THF (20 mL) and cooled to 0° C. KHMDS (0.5 M in toluene, 17.9 mL, 8.95 mmol) is added and the mixture is stirred at room temperature for 30 min, followed by addition of 2,2-dimethyl-propionic acid chloromethyl ester (2.58 mL, 8.95 mmol). The reaction mixture is stirred at room temperature for 3.5 h, then washed with water and extracted with ethyl acetate twice. The organic layer is dried over sodium sulfate and concentrated in vacuo. The residue is purified by silica gel flash chromatography (heptane-ethyl acetate, 1:1) to afford an oil, which is taken up in diethyl ether. A few drops of concentrated HCl are added. Evaporation of the solvent and lyophilization give 2,2-dimethyl-propionic acid 5-chloro-3-methyl-2-pyridin-3-yl-indol-1-ylmethyl ester as a solid. $^1$H NMR (400 MHz, MeOD) δ ppm (HCl salt) 1.12 (s, 9H), 2.27 (s, 3H), 6.06 (s, 2H), 7.30 (dd, J=8.6, 2.0 Hz, 1H), 7.60 (s, 1H), 7.63 (d, J=2.3 Hz, 1H), 7.74 (dd, J=7.8, 5.1 Hz, 1H), 8.01-8.16 (m, 1H), 8.64-8.79 (m, 2H). HRMS (ESI) m/z 357.1121 [(M+H)$^+$ Calcd for $C_{20}H_{22}ClN_2O_2$: 357.1127].

Example 66

2-(5-Chloro-3-methyl-2-pyridin-3-yl-indol-1-yl)-methanol

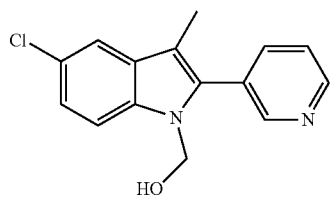 [SMILES: Cc1c(-c2cccnc2)n(CO)c2ccc(Cl)cc12]

A flask is charged with 2,2-dimethyl-propionic acid 5-chloro-3-methyl-2-pyridin-3-yl-indol-1-ylmethyl ester (Example 65, 0.607 g, 1.684 mmol) and dichloromethane (10 mL) and cooled to −78° C. DIBAL-H (1M in hexane, 4.21 mL, 4.21 mmol) is added and the mixture is stirred at −78° C. for 1 h. The reaction is quenched with MeOH (1 mL) and then washed with saturated aqueous sodium potassium tartrate and extracted with ethyl acetate. The organic layer is dried over sodium sulfate and concentrated in vacuo, to give a residue which is purified by silica gel flash chromatography (heptane-ethyl acetate, 3:7) to afford (5-chloro-3-methyl-2-pyridin-3-yl-indol-1-yl)-methanol as a white color solid. $^1$H NMR (400 MHz, MeOD) δ ppm 2.27 (s, 3H), 5.46 (s, 2H), 7.25 (dd, J=8.6, 2.0 Hz, 1H), 7.55 (s, 1H), 7.58 (s, 1H), 7.59 (d, J=2.0 Hz, 1H), 7.62-7.67 (m, 1H), 8.08 (dt, J=8.1, 2.0, 1.8 Hz, 1H), 8.66 (dd, J=4.9, 1.6 Hz, 1H), 8.75 (d, J=1.3 Hz, 1H). HRMS (ESI) m/z 273.0807 [(M+H)$^+$ Calcd for $C_{15}H_{14}ClN_2O$: 273.0795].

Example 67

2-(5-Cyano-3-methyl-2-pyridin-3-yl-indol-1-yl)-methanol

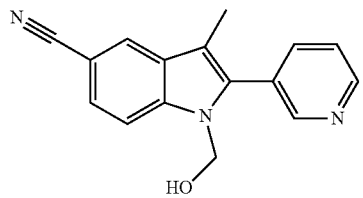 [SMILES: Cc1c(-c2cccnc2)n(CO)c2ccc(C#N)cc12]

A mixture of 5-cyano-3-methyl-2-pyridin-3-yl-indole (Example 6, 0.200 g, 0.587 mmol) in formaldehyde (4.0 mL) is refluxed for 5 h. The reaction is cooled to room temperature, diluted with ethyl acetate and washed with water. The organic layer is dried over sodium sulfate and concentrated in vacuo, to give a residue which is purified by silica gel flash chromatography (dichloromethane-acetonitrile, 7:3) and further purified by reverse phase HPLC with an Xbridge Shield RP18 column and a gradient of 0.1% aqueous TFA in acetonitrile to afford 2-(5-cyano-3-methyl-2-pyridin-3-yl-indol-1-yl)-methanol as the trifluoroacetate salt. $^1$H NMR (400 MHz, MeOD) δ ppm (TFA salt) 2.37 (s, 3H), 5.54 (s, 2H), 7.61 (dd, J=8.6, 1.5 Hz, 1H), 7.78 (d, J=8.6 Hz, 1H), 8.01 (dd, J=7.3, 5.3 Hz, 1H), 8.12 (d, J=1.0 Hz, 1H), 8.54 (dt, J=7.9, 1.9 Hz, 1H), 8.85 (dd, J=5.4, 1.4 Hz, 1H), 9.01 (d, J=1.5 Hz, 1H). HRMS (ESI) m/z 264.1134 [(M+H)$^+$ Calcd for $C_{16}H_{14}N_3O$: 264.1137].

Example 68

2,2-Dimethyl-propionic acid 5-cyano-3-methyl-2-pyridin-3-yl-indol-1-ylmethyl ester

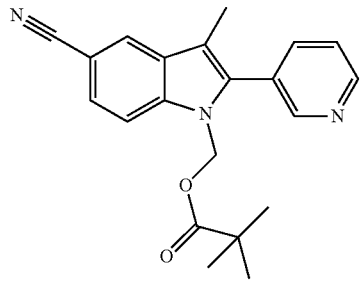 [SMILES: Cc1c(-c2cccnc2)n(COC(=O)C(C)(C)C)c2ccc(C#N)cc12]

A flask is charged with 3-methyl-2-pyridin-3-yl-1H-indole-5-carbonitrile (Example 6, 0.200 g, 0.856 mmol) and DMF (10 mL). The mixture is cooled to 0° C. and 60% NaH in mineral oil (0.086 g, 2.14 mmol) is added. The mixture is stirred at room temperature for 20 min followed by addition of 2,2-dimethyl-propionic acid chloromethyl ester (0.310 mL, 2.14 mmol). After stirring at room temperature for 1.5 h, the mixture is diluted with ethyl acetate and washed with water. The organic layer is dried over sodium sulfate and concentrated in vacuo. The residue is purified by reverse phase HPLC with Xbridge Shield RP18 column and a 0.1% aqueous NH$_4$OH in acetonitrile gradient to afford 2,2-dimethyl-propionic acid 5-cyano-3-methyl-2-pyridin-3-yl-indol-1-ylmethyl ester product as a white solid. $^1$H NMR (400 MHz, MeOD) δ ppm 1.12 (s, 9H), 2.31 (s, 3H), 6.10 (s, 2H), 7.62 (dd, J=8.5, 1.6 Hz, 1H), 7.68 (ddd, J=7.9, 5.0, 0.8 Hz, 1H), 7.81 (d, J=8.6 Hz, 1H), 8.04 (dt, J=8.1, 2.0, 1.8 Hz, 1H), 8.09 (d, J=1.0 Hz, 1H), 8.66-8.76 (m, 2H). HRMS (ESI) m/z 348.1700 [(M+H)$^+$ Calcd for C$_{21}$H$_{22}$N$_3$O$_2$: 348.1712].

Example 69

(a) N-Hydroxymethyl-2,2-dimethyl-propionamide

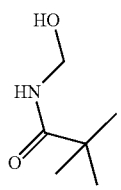

A flask is charged with 2,2-dimethyl-propionamide (1.00 g, 9.98 mmol), p-formaldehyde (0.736 g, 9.98 mmol), and potassium carbonate (0.054 g, 3.95 mmol). The reaction mixture is stirred at 75° C. for 16 h, whereupon it is cooled to room temperature and diluted with acetone. Filtration and concentration of the filtrate give a residue which is purified by silica gel flash chromatography (heptane-ethyl acetate, 4:1) to afford N-hydroxymethyl-2,2-dimethyl-propionamide as a white solid. $^1$H NMR (400 MHz, CDCl$_3$) δ ppm 1.25 (s, 9H), 4.73 (d, J=7.1 Hz, 2H).

(b) N-Chloromethyl-2,2-dimethyl-propionamide

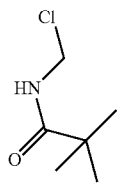

A flask is charged with N-hydroxymethyl-2,2-dimethyl-propionamide (0.500 g, 3.81 mmol) and dichloromethane (4 mL). Oxalyl chloride (0.8 mL, 9.52 mmol) is added and the reaction mixture is stirred at room temperature for 2 h. Concentration in vacuo gives N-chloromethyl-2,2-dimethyl-propionamide as a white solid. $^1$H NMR (400 MHz, CDCl$_3$) δ ppm 1.23 (s, 9H), 5.31 (s, 2H).

(c) N-(5-Cyano-3-methyl-2-pyridin-3-yl-indol-1-ylmethyl)-2,2-dimethyl-propionamide

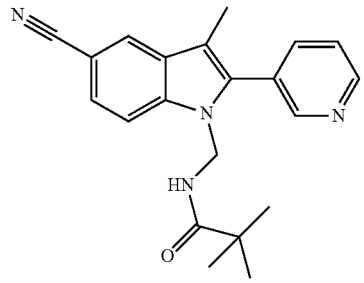 [SMILES: Cc1c(-c2cccnc2)n(CNC(=O)C(C)(C)C)c2ccc(C#N)cc12]

N-Chloromethyl-2,2-dimethyl-propionamide and 3-methyl-2-pyridin-3-yl-1H-indole-5-carbonitrile (Example 6) are processed according to the method described in Example 68 to give N-(5-cyano-3-methyl-2-pyridin-3-yl-indol-1-ylmethyl)-2,2-dimethyl-propionamide. $^1$H NMR (400 MHz, MeOD) δ ppm 1.06 (s, 9H), 2.27 (s, 3H), 5.54 (s, 2H), 7.55 (dd, J=8.6, 1.8 Hz, 1H), 7.66 (ddd, J=7.9, 5.0, 1.0 Hz, 1H), 7.81 (d, J=8.6 Hz, 1H), 8.01-8.09 (m, 2H), 8.65-8.73 (m, 2H). HRMS (ESI) m/z 347.1863 [(M+H)$^+$ Calcd for C$_{21}$H$_{23}$N$_4$O: 347.1872].

Example 70

(a) 1-Chloromethoxy-2,2-dimethyl-propane

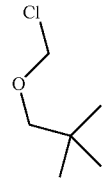

A 2-neck flask is charged with formaldehyde (1.1 g, 36.8 mmol), 2,2-dimethyl-propan-1-ol (2.5 g, 28.3 mmol) and toluene (50 mL). The reaction mixture is cooled to −20° C. and HCl gas is bubbled through for 30 min. Sodium sulfate (5.9 g) is added to the reaction mixture, which is then stirred at −10° C. overnight, warmed to 0° C. and stirred for another 5 h. The solids are filtered off and the filtrate is concentrated in vacuo to afford 1-chloromethoxy-2,2-dimethyl-propane as a colorless oil. $^1$H NMR (400 MHz, CDCl$_3$) δ ppm 0.95 (s, 9H), 3.36 (s, 2H), 5.54 (s, 2H).

(b) 1-(2,2-Dimethyl-propoxymethyl)-3-methyl-2-pyridin-3-yl-1H-indole-5-carbonitrile

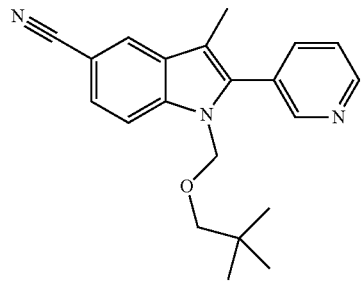 [SMILES: Cc1c(-c2cccnc2)n(COCC(C)(C)C)c2ccc(C#N)cc12]

3-Methyl-2-pyridin-3-yl-1H-indole-5-carbonitrile (Example 6) and 1-chloromethoxy-2,2-dimethyl-propane are processed according to the method described in Example 68 to give 1-(2,2-dimethyl-propoxymethyl)-3-methyl-2-pyridin-3-yl-1H-indole-5-carbonitrile. $^1$H NMR (400 MHz, MeOD) δ ppm 0.84 (s, 9H), 2.33 (s, 3H), 3.04 (s, 2H), 5.48 (s, 2H), 7.59 (dd, J=8.6, 1.5 Hz, 1H), 7.66 (ddd, J=8.0, 4.9, 1.0 Hz, 1H), 7.77 (dd, J=8.6, 0.5 Hz, 1H), 8.07 (dt, J=7.8, 1.9 Hz, 1H), 8.09 (dd, J=1.5, 0.8 Hz, 1H), 8.70 (dd, J=4.9, 1.6 Hz, 1H), 8.75 (dd, J=2.3, 0.8 Hz, 1H). HRMS (ESI) m/z 334.1914 [(M+H)$^+$ Calcd for $C_{21}H_{24}N_3O$: 334.1919].

Example 71

(5-Cyano-3-methyl-2-pyridin-3-yl-indol-1-yl)-acetic acid tert-butyl ester

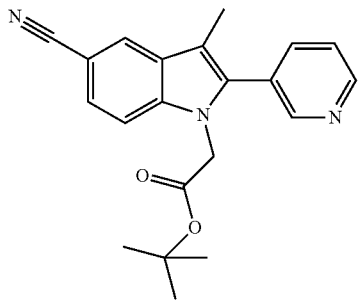 [SMILES: Cc1c(-c2cccnc2)n(CC(=O)OC(C)(C)C)c2ccc(C#N)cc12]

3-Methyl-2-pyridin-3-yl-1H-indole-5-carbonitrile (Example 6) and tert-butyl bromoacetate are processed according to the method described in Example 68 to give (5-cyano-3-methyl-2-pyridin-3-yl-indol-1-yl)-acetic acid tert-butyl ester. $^1$H NMR (400 MHz, MeOD) δ ppm 1.38 (s, 9H), 2.31 (s, 3H), 4.83 (s, 2H), 7.56 (d, J=1.3 Hz, 2H), 7.66 (ddd, J=7.8, 4.9, 0.9 Hz, 1H), 7.95 (dt, J=7.8, 1.9 Hz, 1H), 8.09 (s, 1H), 8.63 (d, J=1.3 Hz, 1H), 8.71 (dd, J=4.9, 1.6 Hz, 1H). HRMS (ESI) m/z 348.1719 [(M+H)$^+$ Calcd for $C_{21}H_{22}N_3O_2$: 348.1712].

Example 72

(a) Chloromethoxy-acetic acid ethyl ester

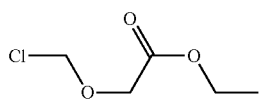

Chloromethoxy-acetic acid ethyl ester is prepared according to the method described in *Heterocycles* 2005, 65, 1967. A 2-neck flask is charged with formaldehyde (0.747 g, 24.9 mol), hydroxy-acetic acid ethyl ester (2.0 g, 19.2 mmol) and toluene (50 mL). The reaction mixture is cooled to −20° C., and HCl gas is bubbled through it for 30 min. Sodium sulfate (4 g) is added to the reaction mixture, which is then stirred at −10° C. overnight, warmed to 0° C. and stirred for another 5 h. The solids are filtered off and the filtrate is concentrated in vacuo to afford chloromethoxy-acetic acid ethyl ester as a colorless oil.

(b) (5-Chloro-3-methyl-2-pyridin-3-yl-indol-1-ylmethoxy)-acetic acid ethyl ester

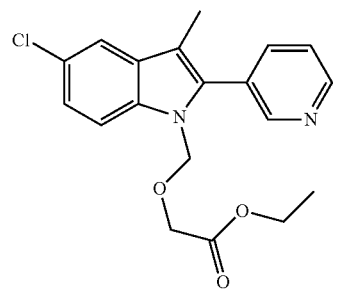 [SMILES: CCOC(=O)COCn1c(-c2cccnc2)c(C)c2cc(Cl)ccc21]

A flask is charged with 5-chloro-3-methyl-2-pyridin-3-yl-1H-indole hydrochloride (Example 2) (0.930 g, 3.33 mmol) in THF (20 mL) and cooled to 0° C. KHMDS (0.5 M in toluene, 16.65 mL, 8.32 mmol) is added and the mixture is stirred at room temperature for 30 min, followed by addition of chloromethoxy-acetic acid ethyl ester (1.27 g, 8.32 mmol). The reaction mixture is stirred for 3 h, then washed with water and extracted with ethyl acetate. The organic layer is dried over sodium sulfate and concentrated in vacuo to give a residue which is purified by silica gel flash chromatography (dichloromethane-methanol, 19:1) to afford (5-chloro-3-methyl-2-pyridinyl-indol-1-ylmethoxy)-acetic acid ethyl ester as a solid. MS (ESI) m/z 359.2 (M+H)$^+$.

(c) (5-Chloro-3-methyl-2-pyridin-3-yl-indol-1-ylmethoxy)-acetic acid

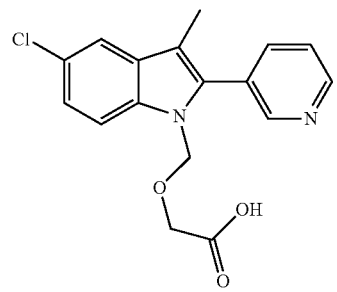 [SMILES: Cc1c(-c2cccnc2)n(COCC(=O)O)c2ccc(Cl)cc12]

A flask is charged with (5-chloro-3-methyl-2-pyridinyl-indol-1-ylmethoxy)-acetic acid ethyl ester (0.622 g, 1.737 mmol) in MeOH (10 mL). Aqueous lithium hydroxide (1M, 4.34 mL, 4.34 mmol) is added and the mixture is stirred at room temperature for 1.5 h. The reaction mixture is acidified to pH 1 using 1M aqueous HCl. The precipitate is filtered and re-crystallized in MeOH to afford (5-chloro-3-methyl-2-phenyl-indol-1-ylmethoxy)-acetic acid as a white solid. $^1$H NMR (400 MHz, MeOD) δ ppm 2.27 (s, 3H), 4.02 (s, 2H), 5.54 (s, 2H), 7.27 (dd, J=8.8, 2.0 Hz, 1H), 7.59-7.68 (m, 3H), 8.10 (ddd, J=8.0, 1.9, 1.8 Hz, 1H), 8.67 (dd, J=4.9, 1.6 Hz, 1H), 8.74 (d, J=1.5 Hz, 1H). HRMS (ESI) m/z 331.0849 [(M+H)+ Calcd for $C_{17}H_{16}ClN_2O_3$: 331.0849].

Example 73

2-(5-Chloro-3-methyl-2-pyridin-3-yl-indol-1-yl-methoxy)-ethanol

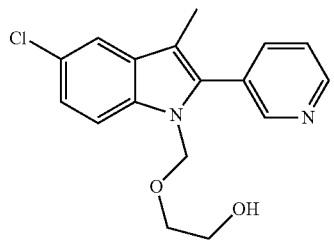 [SMILES: Cc1c(-c2cccnc2)n(COCCO)c2ccc(Cl)cc12]

A flask is charged with (5-chloro-3-methyl-2-pyridin-3-yl-indol-1-ylmethoxy)-acetic acid ethyl ester (Example 72b, 1.00 g, 2.79 mmol) and THF (10 mL). The reaction mixture is cooled to 0° C. and lithium aluminum hydride (1M in THF, 6.98 mL, 6.98 mmol) is added. After stirring for 1 h at room temperature, the mixture is quenched with water (0.3 mL), followed with 16% aqueous NaOH (0.3 mL). Water (1 mL) is added and stirring is continued for 10 min. The solids are filtered off and the filtrate is concentrated in vacuo. The residue is purified by silica gel flash chromatography (dichloromethane-acetonitrile, 3:1), followed by a purification on Chiralcel® IA column (heptane-EtOH, 9:1) to afford 2-(5-chloro-3-methyl-2-pyridin-3-yl-indol-1-ylmethoxy)-ethanol as a white solid. $^1$H NMR (400 MHz, MeOD) δ ppm 2.27 (s, 3H), 3.42-3.49 (m, 2H), 3.60 (t, J=4.8 Hz, 2H), 5.47 (s, 2H), 7.27 (dd, J=8.7, 1.9 Hz, 1H), 7.57-7.62 (m, 2H), 7.64 (dd, J=8.0, 4.9 Hz, 1H), 8.10 (dt, J=7.8, 1.9 Hz, 1H), 8.66 (dd, J=4.9, 1.6 Hz, 1H), 8.74 (d, J=1.3 Hz, 1H). HRMS (ESI) m/z 317.1056 [(M+H)+ Calcd for $C_{17}H_{17}ClN_2O_2$: 317.1507].

Example 74

(a) 3-(5-Chloro-3-methyl-2-pyridin-3-yl-indol-1-yl)-propionic acid

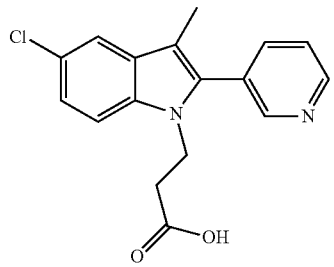 [SMILES: Cc1c(-c2cccnc2)n(CCC(=O)O)c2ccc(Cl)cc12]

A flask is charged with 5-chloro-3-methyl-2-pyridin-3-yl-1H-indole hydrochloride (Example 2, 0.700 g, 2.50 mmol) in DMF (7 mL) and cooled to 0° C. Potassium tert-butoxide (0.740 mg, 6.26 mmol) is added and the mixture is stirred at room temperature for 30 min, then lowered back into the ice bath. Acrylic acid methyl ester (0.680 mL, 7.52 mmol) is added, and the reaction mixture is stirred for 1.5 h. The reaction mixture is acidified to pH 1 using 1M aqueous HCl and extracted with ethyl acetate. The organic layer is dried over sodium sulfate and concentrated in vacuo to give a residue which is purified by silica gel flash chromatography (dichloromethane-methanol, 9:1) to afford 3-(5-chloro-3-methyl-2-pyridinyl-indol-1-yl)-propionic acid as a white solid. MS (ESI) m/z 315.18 (M+H)+

(b) 3-(5-Chloro-3-methyl-2-pyridin-3-yl-indol-1-yl)-propan-1-ol

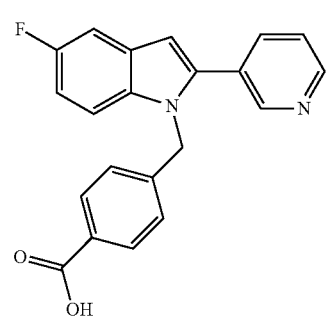 [SMILES: O=C(O)c1ccc(Cn2c(-c3cccnc3)cc3cc(F)ccc32)cc1]

A flask is charged with 3-(5-chloro-3-methyl-2-pyridinyl-indol-1-yl)-propionic acid (0.344 g, 1.09 mmol) and THF (10 mL). The reaction mixture is cooled to 0° C. and LAH (1M in THF, 2.73 mL, 2.73 mmol) is added. After stirring at room temperature for 30 min, the mixture is cooled to 0° C., quenched with aqueous $NaHCO_3$ and extracted with ethyl acetate. The organic layer is dried over sodium sulfate and concentrated in vacuo to give a residue which is purified by silica gel flash chromatography (dichloromethane-methanol, 19:1) to afford 3-(5-chloro-3-methyl-2-pyridinyl-indol-1-yl)-propan-1-ol as a white solid. $^1$H NMR (400 MHz, MeOD) δ ppm 1.71-1.82 (m, 2H), 2.23 (s, 3H), 3.38 (t, J=6.1 Hz, 2H), 4.18-4.24 (m, 2H), 7.21 (dd, J=8.8, 2.0 Hz, 1H), 7.49 (d, J=8.6 Hz, 1H), 7.57 (d, J=1.8 Hz, 1H), 7.65 (ddd, J=7.9, 5.0, 1.0 Hz, 1H), 7.98 (ddd, J=8.1, 2.0, 1.8 Hz, 1H), 8.65 (dd, J=2.3, 0.8 Hz, 1H), 8.67 (dd, J=5.1, 1.8 Hz, 1H). HRMS (ESI) m/z 301.1108 [(M+H)+ Calcd for $C_{17}H_{18}ClN_2O$: 301.1108].

Example 75

4-(5-Fluoro-2-pyridin-3-yl-indol-1-ylmethyl)-benzoic acid

A flask is charged with NaH (0.284 g, 7.093 mmol) and DMSO (1.5 mL). 5-Fluoro-2-pyridin-3-yl-indole (Example 7, 0.112 g, 0.507 mmol) in DMSO (0.5 mL) is added. The flask and syringes are rinsed with DMSO (2 times 0.5 mL). After 10 min, ethyl 4-(bromomethyl)benzoate (0.192 g, 0.760 mmol) is added neat. After 10 min, water is added. The resulting precipitate is filtered through a sintered funnel and washed with water and dichloromethane to give 4-(5-fluoro-2-pyridin-3-yl-indol-1-ylmethyl)-benzoic acid as an off-white solid. $^1$H NMR (400 MHz, MeOD) δ ppm (sodium salt) 5.49 (s, 2H), 6.77 (s, 1H), 6.92 (d, J=8.1 Hz, 2H), 6.95-7.00 (m, 1H), 7.31-7.37 (m, 2H), 7.49 (dd, J=7.7, 5.2 Hz, 1H), 7.85 (d, J=8.1 Hz, 2H), 7.87-7.92 (m, 1H), 8.56 (dd, J=4.9, 1.5 Hz, 1H), 8.68 (d, J=1.5 Hz, 1H). HRMS (ESI) m/z 347.1212 [(M+H)$^+$ Calcd for C$_{21}$H$_{16}$FN$_2$O$_2$: 347.1196].

Example 76

2,2-Dimethyl-propionic acid 5-cyano-2-pyridin-3-yl-indol-1-ylmethyl ester

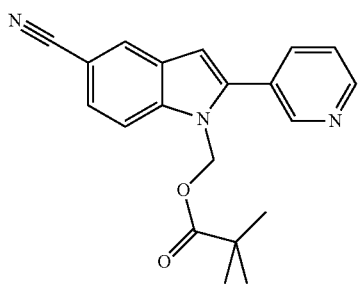 [SMILES: CC(C)(C)C(=O)OCn1c(-c2cccnc2)cc2cc(C#N)ccc21]

To a solution of 2-pyridin-3-yl-1H-indole-5-carbonitrile (Example 8, 210 mg, 1.37 mmol) in THF (20 mL) at room temperature is added 0.5 M KHMDS in toluene (4.1 mL, 2.05 mmol). After 30 min, chloromethyl pivalate (510 mg, 3.08 mmol) is added. The mixture is stirred under N$_2$ for 1 h. Saturated aqueous sodium bicarbonate (0.5 mL) is added to quench the reaction. Silica gel is added to the mixture and the solvents are removed in vacuo. The residue is purified by silica gel flash chromatography (ethyl acetate-heptane, 0:1 to 1:0). Further purification by HPLC using an Xbridge RP18 with a gradient of 0.1% aqueous ammonium hydroxide in acetonitrile gives 2,2-dimethyl-propionic acid 5-cyano-2-pyridin-3-yl-indol-1-ylmethyl ester as a white solid. $^1$H NMR (400 MHz, CDCl$_3$) δ ppm 1.20 (s, 9H), 6.08 (s, 2H), 6.77 (s, 1H), 7.49 (ddd, J=7.8, 4.8, 0.8 Hz, 1H), 7.56 (dd, J=8.6, 1.8 Hz, 1H), 7.68 (d, J=8.6 Hz, 1H), 7.94 (ddd, J=7.9, 2.0 Hz, 1H), 8.01 (dd, J=1.5, 0.5 Hz, 1H), 8.75 (dd, J=4.8, 1.8 Hz, 1H), 8.87 (d, J=1.5 Hz, 1H). HRMS (ESI) m/z 334.1566 [(M+H)$^+$ Calcd for C$_{20}$H$_{20}$N$_3$O$_2$: 334.1556].

Example 77

(a) 4,4-Dimethyl-pent-1-en-3-one

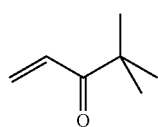

This procedure is adapted from *Tetrahedron Lett.* 1978, 32, 2955. A flask is charged with 3,3-dimethyl-butan-2-one (1.00 g, 9.98 mmol), p-formaldehyde (1.34 g, 44.9 mmol), N-methylanilinium trifluoroacetate (3.31 g, 14.9 mmol) and THF (10 mL). The reaction mixture is refluxed for 16 h, followed by addition of additional quantities of p-formaldehyde (0.674 g, 22.45 mmol), and N-methylanilinium trifluoroacetate (1.64 g, 7.48 mmol). After another 5.5 h at reflux, the mixture is cooled to room temperature and pentane (20 mL) is added. A brown oil collects at the bottom of the flask. The supernatant is removed and pentane (25 mL) is added. After decantation, the supernatant is removed. The supernatants are combined and concentrated in vacuo to afford 4,4-dimethyl-pent-1-en-3-one as a colorless oil. $^1$H NMR (400 MHz, CDCl$_3$) δ ppm 1.18 (s, 9H), 5.68 (dd, J=10.4, 2.0 Hz, 1H), 6.36 (dd, J=16.9, 2.0 Hz, 1H), 6.83 (dd, J=16.9, 10.4 Hz, 1H).

(b) 1-(4,4-Dimethyl-3-oxo-pentyl)-2-pyridin-3-yl-1H-indole-5-carbonitrile

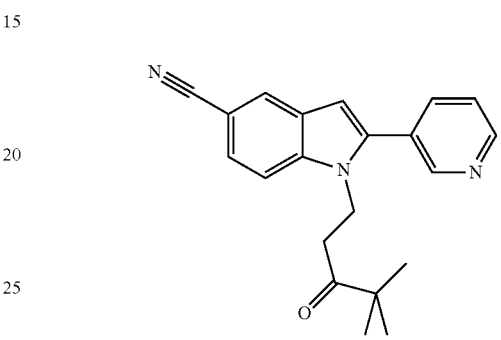

To a solution of 2-pyridin-3-yl-1H-indole-5-carbonitrile (Example 8, 0.225 g, 1.026 mmol) in DMSO (5 mL) is added potassium tert-butoxide (0.182 g, 1.53 mmol) and the mixture is stirred at room temperature for 0.5 h. 4,4-Dimethyl-pent-1-en-3-one (0.345 g, 3.078 mmol) is added and the mixture is stirred at 50° C. overnight. Dilution with ethyl acetate gives a solution which is washed with water twice, dried over sodium sulfate and concentrated in vacuo. The residue is purified by Xbridge Shield RP18 with a gradient of acetonitrile in 0.1% NH$_4$OH to give an oil. Addition of diethyl ether and a few drops of concentrated HCl, followed by lyophilization affords 1-(4,4-dimethyl-3-oxo-pentyl)-2-pyridin-3-yl-1H-indole-5-carbonitrile as a light yellow color solid. $^1$H NMR (400 MHz, MeOD) δ ppm (HCl salt) 0.90 (s, 9H), 2.94 (t, J=6.4 Hz, 2H), 4.61 (t, J=6.6 Hz, 2H), 6.88 (s, 1H), 7.59 (dd, J=8.7, 1.6 Hz, 1H), 7.77 (d, J=8.6 Hz, 1H), 7.93 (dd, J=8.0, 5.4 Hz, 1H), 8.10 (d, J=1.0 Hz, 1H), 8.44 (dt, J=7.9, 1.7 Hz, 1H), 8.82 (dd, J=5.3, 1.3 Hz, 1H), 8.96 (d, J=1.8 Hz, 1H). HRMS (ESI) m/z 332.1762 [(M+H)$^+$ Calcd for C$_{21}$H$_{22}$N$_3$O: 332.1763].

Example 78

(a) 3,3-dimethyl-azetidin-2-one

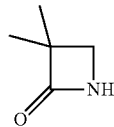

A 250 mL Parr glass vessel is charged with Rh/Al$_2$O$_3$ (2.33 g, 1.13 mmol) and ethyl 2,2-dimethylcyanoacetate (2.0 g) dissolved in ethanol (90 mL). The flask is evacuated and filled with hydrogen (50 psi) and the mixture is shaken under 50 psi of hydrogen. After 48 h, the mixture is filtered and concentrated in vacuo (50 Torr, 35° C., 30 min) to give a crude mixture which is dissolved in anhydrous ether (60 mL) under nitrogen and cooled to 0° C. LHMDS (1.0M in THF, 10 mL, 10 mmol) is added dropwise and the cooling bath is removed. After 2 h, the mixture is cooled to 0° C. and quenched with 1M aqueous sodium bisulfate and diluted with ether. The organic phase is washed with 1M aqueous sodium bisulfate and brine. The pH of the combined aqueous phase is adjusted to 14 with 4M aqueous sodium hydroxide and the aqueous phase is repeatedly extracted with dichloromethane. The dichloromethane phase is dried over magnesium sulfate, filtered and concentrated in vacuo to give a residue which is purified by silica gel flash chromatography (ethyl acetate) to give 3,3-dimethyl-azetidin-2-one as a colorless oil. $^1$H NMR (400 MHz, CDCl$_3$) δ ppm 1.34 (s, 6H), 3.13 (s, 2H).

(b) 1-hydroxymethyl-3,3-dimethyl-azetidin-2-one

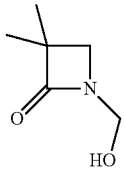

A flask is charged with 3,3-dimethyl-azetidin-2-one (0.159 g, 1.524 mmol), aqueous formaldehyde (37% wt., 0.124 g, 1.524 mmol) and crushed potassium carbonate (0.009 g, 0.061 mmol). The flask is lowered in a pre-heated oil bath (75° C.). After 15 min, the flask is removed from the oil bath and allowed to stand at room temperature. After 2 h, the mixture is taken up in acetone, dried over magnesium sulfate and filtered through a plug of silica gel. Concentration in vacuo (30° C., 40 Torr) gives 1-hydroxymethyl-3,3-dimethyl-azetidin-2-one, which is used in the next step without further purification. $^1$H NMR (400 MHz, CDCl$_3$) δ ppm 1.32 (s, 6H), 3.23 (s, 2H), 4.69 (d, J=7.5 Hz, 2H).

(c) 1-(3,3-dimethyl-2-oxo-azetidin-1-ylmethyl)-2-pyridin-3-yl-1H-indole-5-carbonitrile

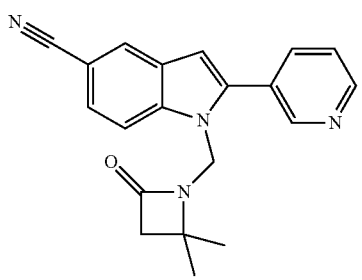 [SMILES: CC1(C)CC(=O)N1Cn1c(-c2cccnc2)cc2cc(C#N)ccc21]

A flask is charged with 1-hydroxymethyl-3,3-dimethyl-azetidin-2-one (0.179 g, 1.317 mmol) and dichloromethane (5 mL), and thionyl chloride (0.63 g, 5.27 mmol) is added. The mixture is stirred at room temperature overnight and concentrated in vacuo to yield an oil, which is redissolved in DMF (0.8 mL). 2-Pyridin-3-yl-1H-indole-5-carbonitrile (Example 8, 0.213 g, 0.922 mmol) is dissolved in DMF (5 mL), cooled to 0° C., and NaH (0.053 g, 1.317 mmol) is added portionwise. After 30 min, the chloride solution is added. After 1 h, NaH (0.027 g, 0.67 mmol) is added and the mixture is stirred overnight. The mixture is quenched with a few drops of water and diluted with methanol and DMSO. The mixture is purified on Xbridge C18 eluting with a 9:1 to 1:9 water-acetonitrile gradient to give 1-(3,3-dimethyl-2-oxo-azetidin-1-ylmethyl)-2-pyridin-3-yl-1H-indole-5-carbonitrile. $^1$H NMR (400 MHz, CDCl$_3$) δ ppm 1.18 (s, 6H), 2.82 (s, 2H), 5.47 (s, 2H), 6.71 (s, 1H), 7.47-7.51 (m, 1H), 7.56 (dd, J=8.6, 1.5 Hz, 1H), 7.73 (d, J=8.6 Hz, 1H), 7.80-7.83 (m, 1H), 8.01 (d, J=1.5 Hz, 1H), 8.75-8.76 (m, 2H). HRMS (ESI) m/z 331.1558 [(M+H)$^+$ Calcd for C$_{20}$H$_{19}$N$_4$O: 331.1559].

Example 79

5-Fluoro-3-methyl-2-pyridin-3-yl-indole-1-carboxylic acid isopropyl ester

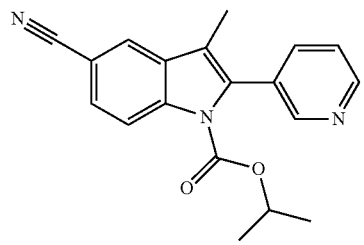 [SMILES: Cc1c(-c2cccnc2)n(C(=O)OC(C)C)c2ccc(C#N)cc12]

5-Fluoro-3-methyl-2-pyridin-3-yl-indole (Example 3, 0.246 g, 1.044 mmol) is dissolved in DMF (9 mL). NaH (60%, 0.054 g, 1.357 mmol) is added and the mixture is stirred for 1 h, whereupon isopropylchloroformate (1.0M in toluene 2.1 mL, 2.1 mmol) is added. The mixture is stirred overnight, quenched with saturated aqueous sodium bicarbonate and extracted with ethyl acetate. The organic phase is dried over MgSO$_4$ and concentrated in vacuo to give a residue, which is purified by silica gel flash chromatography (ethyl acetate-heptane, 1:4 to 2:3) to give 5-fluoro-3-methyl-2-pyridin-3-yl-indole-1-carboxylic acid isopropyl ester as a pale yellow solid. $^1$H NMR (400 MHz, MeOD) δ ppm 1.07 (d, J=6.3 Hz, 6H), 2.12 (s, 3H), 4.93-5.04 (m, 1H), 7.09-7.17 (m, 1H), 7.30 (dd, J=8.8, 2.3 Hz, 1H), 7.54-7.59 (m, 1H), 7.84-7.89 (m, 1H), 8.23 (dd, J=9.1, 4.5 Hz, 1H), 8.53-8.56 (m, 1H), 8.61 (dd, J=4.5, 1.6 Hz, 1H). HRMS (ESI) m/z 313.1353 [(M+H)$^+$ Calcd for C$_{18}$H$_{18}$FN$_2$O$_2$: 313.1352].

Example 80

5-Cyano-3-methyl-2-pyridin-3-yl-indole-1-carboxylic acid tert-butyl ester

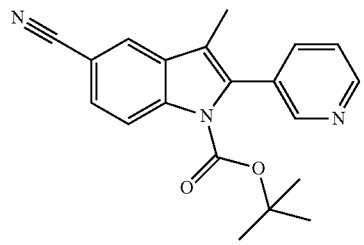 [SMILES: Cc1c(-c2cccnc2)n(C(=O)OC(C)(C)C)c2ccc(C#N)cc12]

To a solution of 3-methyl-2-pyridin-3-yl-1H-indole-5-carbonitrile (Example 6, 96 mg, 0.40 mmol) in DMF (2 mL) at room temperature is added triethylamine (30 mg, 0.30 mmol), di-tert-butyl carbonate (65 mg, 0.30 mmol) and 4-(N,N-dimethylamino)pyridine (2 mg, 0.020 mmol). The mixture is stirred under $N_2$. The mixture is purified by Xbridge RP18 with a gradient of acetonitrile in 0.1% aqueous ammonium hydroxide to give 5-cyano-3-methyl-2-pyridin-3-yl-indole-1-carboxylic acid tert-butyl ester as a white solid. $^1$H NMR (400 MHz, CDCl$_3$) δ ppm 1.30 (s, 9H), 2.16 (s, 3H), 7.47-7.55 (m, 1H), 7.65 (dd, J=8.7, 1.6 Hz, 1H), 7.76 (d, J=7.3 Hz, 1H), 7.90 (d, J=1.0 Hz, 1H), 8.35 (d, J=8.6 Hz, 1H), 8.63 (d, J=1.8 Hz, 1H), 8.69 (dd, J=5.1, 1.5 Hz, 1H). HRMS (ESI) m/z 334.1566 [(M+H)$^+$ Calcd for $C_{20}H_{20}N_3O_2$: 334.1556].

Example 81

5-Cyano-2-pyridin-3-yl-indole-1-carboxylic acid tert-butyl ester

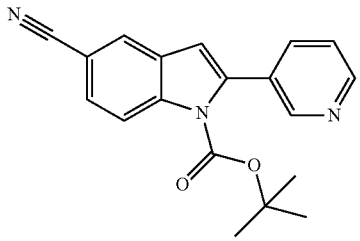 [SMILES: CC(C)(C)OC(=O)n1c(-c2cccnc2)cc2cc(C#N)ccc21]

A mixture of 1-Boc-5-cyanoindole-2-boronic acid (339 mg, 1.19 mmol), 3-bromo-pyridine (150 mg, 93 uL, 0.95 mmol), aqueous sodium carbonate (2M, 0.95 mL, 1.9 mmol) and DME (4 mL) is degassed with nitrogen and PS—Pd (PPh$_3$) (285 mg, 0.11 mmol/g, 0.028 mmol) is added. The resulting mixture is then heated in the microwave at 120° C. for 20 min and at 130° C. for 25 min (three times). The reaction mixture is filtered through a sintered funnel and washed with dichloromethane (50 mL). The filtrate is dried over Na$_2$SO$_4$, filtered, and concentrated. The residue is purified by reverse phase HPLC (5 to 80% acetonitrile-0.1% aqueous ammonia) to give 5-cyano-2-pyridin-3-yl-indole-1-carboxylic acid tert-butyl ester as a solid. $^1$H NMR (400.3 MHz, CDCl$_3$) δ ppm 1.34 (s, 9H), 6.67 (s, 1H), 7.39 (dd, J=4.9, 7.8 Hz, 1H), 7.61 (dd, J=1.6, 8.7 Hz, 1H), 7.74 (m, 1H), 7.92 (s, 1H), 8.35 (d, J=8.7 Hz, 1H), 8.65 (dd, J=1.6 Hz, 4.9 Hz, 1H), 8.69 (d, J=2.2 Hz, 1H). MS (ESI) m/z 320 (M+H)$^+$.

Example 82

5-Fluoro-2-pyridin-3-yl-indole-1-carboxylic acid tert-butyl ester

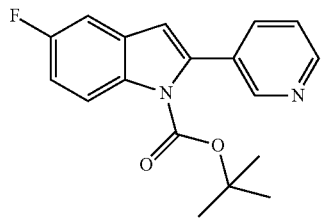 [SMILES: CC(C)(C)OC(=O)n1c(-c2cccnc2)cc2cc(F)ccc21]

To a solution of 5-fluoro-2-pyridin-3-yl-indole (Example 3, 0.100 g, 0.452 mmol) in DMF (1 mL) is added triethylamine (0.083 g, 0.814 mmol), DMAP (0.006 g, 0.045 mmol) and di-tert-butyl carbonate (0.120 g, 0.543 mmol). After 15 h, the mixture is diluted with ethyl acetate and washed with water. The organic phase is dried over MgSO$_4$, filtered and the filtrate is concentrated in vacuo to give a residue which is purified by silica gel chromatography (heptane-ethyl acetate, 9:1 to 4:1) to give 5-fluoro-2-pyridin-3-yl-indole-1-carboxylic acid tert-butyl ester as a yellow oil. Trituration with ether and heptane, followed by standing for several days affords a solid. $^1$H NMR (400 MHz, CDCl$_3$) δ ppm 1.35 (s, 9H), 6.58 (s, 1H), 7.07-7.12 (m, 1H), 7.23 (dd, J=8.6, 2.5 Hz, 1H), 7.36 (dd, J=7.8, 5.1 Hz, 1H), 7.72-7.75 (m, 1H), 8.21 (dd, J=9.1, 4.9 Hz, 1H), 8.62 (dd, J=4.9, 1.5 Hz, 1H), 8.69 (d, J=1.5 Hz, 1H). MS (ESI) m/z 313 (M+H)$^+$.

Example 83

(a) N-(2-Cyanomethyl-phenyl)-nicotinamide

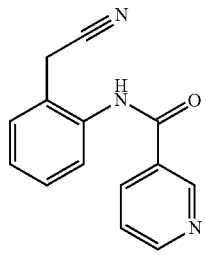 [SMILES: N#CCc1ccccc1NC(=O)c1cccnc1]

2-aminophenylacetonitrile (5.0 g, 37.1 mmol) and nicotinoyl chloride (7.5 g, 40.8 mmol) are taken up in dry dichloromethane (200 mL) and diisopropylethylamine (12.1 g, 92.7 mmol) is added while cooling the mixture with a cold water bath. The mixture is stirred overnight, whereupon it is washed twice with saturated aqueous sodium bicarbonate. The combined aqueous layer is back-extracted with ethyl acetate. The combined organic phase is dried over MgSO$_4$ and concentrated in vacuo to give a residue, which is purified by silica gel flash chromatography (dichloromethane-methanol, 1:0 to 19:1) to give N-(2-cyanomethyl-phenyl)-nicotinamide as an off-white solid. $^1$H NMR (400 MHz, DMSO-d$_6$) δ ppm 4.02 (s, 2H), 7.32-7.37 (m, 1H), 7.39-7.44 (m, 2H), 7.50 (d, J=7.1 Hz, 1H), 7.59 (dd, J=8.1, 4.8 Hz, 1H), 8.30-8.33 (m, 1H), 8.78 (dd, J=4.8, 1.5 Hz, 1H), 9.14 (d, J=1.8 Hz, 1H), 10.36 (s, 1H).

(b) 2-Pyridin-3-yl-1H-indole-3-carbonitrile

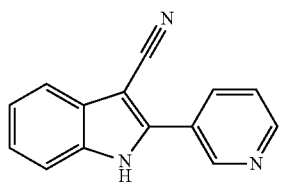 [SMILES: N#Cc1c(-c2cccnc2)[nH]c2ccccc12]

N-(2-cyanomethyl-phenyl)-nicotinamide (0.095 g, 0.384 mmol) is dissolved in DMF (3 mL). NaH (60%, 0.015 g, 0.384 mmol) is added and the mixture is heated to 130° C. After 18 h, the mixture is cooled down, diluted with ethyl acetate, and washed with 1M aqueous sodium hydroxide. The combined washings are back-extracted with ethyl acetate. The combined organic phase is dried over magnesium sulfate, filtered and concentrated in vacuo. The residue is purified by silica gel flash chromatography (dichloromethane-methanol, 99:1 to 19:1) to give 2-pyridin-3-yl-1H-indole-3-carbonitrile as a brown solid. $^1$H NMR (400 MHz, MeOD) δ ppm 7.29-7.32 (m, 1H), 7.34-7.39 (m, 1H), 7.57 (d, J=8.0 Hz, 1H), 7.66 (dd, J=8.0, 4.9 Hz, 1H), 7.70 (d, J=7.8 Hz, 1H), 8.39-8.44 (m, 1H), 8.68 (dd, J=4.8, 1.5 Hz, 1H), 9.15 (d, J=1.5 Hz, 1H).

(c) 1-Methyl-2-pyridin-3-yl-1H-indole-3-carbonitrile

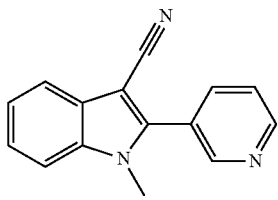 [SMILES: Cn1c(-c2cccnc2)c(C#N)c2ccccc21]

To 2-pyridin-3-yl-1H-indole-3-carbonitrile (1.0 g, 4.56 mmol) in DMF (17 mL) is added 60% sodium hydride in mineral oil (547 mg, 13.68 mmol) and the suspension is stirred for 30 min. Iodomethane (971 mg, 6.84 mmol) is then added to the reaction mixture and stirred at ambient temperature for 1 h. Aqueous NaHCO$_3$ (3 mL) is added and the mixture is concentrated in vacuo. The residue is purified by purified by silica gel flash chromatography (dichloromethane-methanol gradient) to give 1-methyl-2-pyridin-3-yl-1H-indole-3-carbonitrile as a white solid. $^1$H NMR (400 MHz, MeOD) δ ppm 3.83 (s, 3H), 7.35 (t, J=7.5 Hz, 1H), 7.40-7.46 (m, 1H), 7.64 (d, J=8.3 Hz, 1H), 7.67-7.74 (m, 2H), 8.16 (dt, J=8.0, 2.0, 1.9 Hz, 1H), 8.76 (dd, J=5.1, 1.5 Hz, 1H), 8.86 (d, J=1.5 Hz, 1H). HRMS (ESI) m/z 234.1029 [(M+H)$^+$ Calcd for C$_{15}$H$_{12}$N$_3$: 234.1031].

Example 84

1-Ethyl-2-pyridin-3-yl-1H-indole-3-carbonitrile

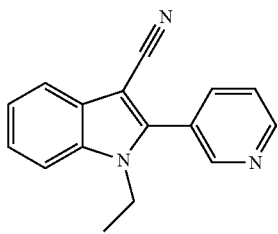 [SMILES: CCn1c(-c2cccnc2)c(C#N)c2ccccc21]

To a solution of N-(2-cyanomethyl-phenyl)-nicotinamide (Example 83a, 400 mg, 1.69 mmol) in DMF (17 mL) is added Cs$_2$CO$_3$ (1.1 g, 3.37 mmol). The reaction is heated to 80° C., at which time a solution of iodoethane (0.14 mL, 1.75 mmol) in DMF (5 mL) is added over 75 min. The temperature is then increased to 100° C. After stirring for an additional 2 h, the reaction is cooled to room temperature and quenched with saturated aqueous NH$_4$Cl, and diluted with ethyl acetate and water. The layers are separated and the aqueous layer is extracted with ethyl acetate. The combined organic extracts are dried over sodium sulfate, filtered, and concentrated. The resulting residue is purified by silica gel flash chromatography (ethyl acetate-heptane, 3:10 to 1:0) to furnish 1-ethyl-2-pyridin-3-yl-1H-indole-3-carbonitrile. $^1$H NMR (400 MHz, CDCl$_3$) δ ppm 1.40 (t, J=7.2 Hz, 3H), 4.22 (q, J=7.2 Hz, 2H), 7.32-7.45 (m, 2H), 7.47-7.51 (m, 1H), 7.54 (dd, J=7.8, 5.6 Hz, 1H), 7.82 (d, J=7.8 Hz, 1H), 7.91-7.98 (m, 1H), 8.78-8.85 (m, 2H). HRMS (ESI) m/z 248.1190 [(M+H)$^+$ Calcd for C$_{16}$H$_{14}$N$_3$: 248.1188].

Example 85

3-(2-Ethoxy-ethyl)-1-ethyl-2-pyridin-3-yl-1H-indole

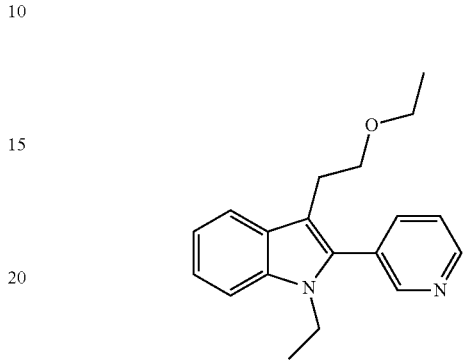

To a solution of 1-ethyl-2-pyridin-3-yl-1H-indole-3-carbonitrile (Example 84, 590 mg, 2.4 mmol) in toluene (20 mL) at −60° C. is added a 1 M solution of DIBAL-H (3.6 mL, 3.6 mmol). The reaction is stirred for 1 h and kept below −40° C. The reaction is then quenched with water (1 mL) and brought to room temperature. Anhydrous sodium sulfate (ca. 2 g) is then added to the reaction mixture. The reaction mixture is filtered through a plug of celite. Sulfuric acid (2M, ca. 5 mL) is added and upon complete conversion to the desired aldehyde, the reaction mixture is brought to pH 8 with the addition of Na$_2$CO$_3$, and extracted with ethyl acetate. The organic extract is washed with brine, dried over Na$_2$SO$_4$, filtered, and concentrated. The resulting 1-ethyl-2-pyridin-3-yl-1H-indole-3-carbaldehyde is used without further purification. To a solution of ethoxymethyltriphenylphosphonium chloride (0.32 g, 0.9 mmol) in THF (3 mL) is added potassium tert-butoxide (1 M in THF, 0.93 mL, 0.93 mmol). The resulting red solution is permitted to stir for 15 min, at which time a solution of 1-ethyl-2-pyridin-3-yl-1H-indole-3-carbaldehyde (75 mg, 0.3 mmol) in THF (3 mL) is added. The reaction is stirred for 1 h, quenched with saturated aqueous NH$_4$Cl, diluted with water and extracted with ethyl acetate. The organic extract is dried over Na$_2$SO$_4$, filtered, and concentrated. The resulting E/Z mixture of 3-(2-ethoxy-vinyl)-1-ethyl-2-pyridin-3-yl-1H-indole is then dissolved in methanol (5 mL) and 10% Pd/C (32 mg, 0.03 mmol) is added. The reaction mixture is stirred under an atmosphere of H$_2$ gas (balloon) for 2 h. The reaction is then filtered through a plug of celite and concentrated to dryness. The resulting residue is purified by silica gel flash chromatography (ethyl acetate-heptane, 0:1 to 2:5) to afford 3-(2-ethoxy-ethyl)-1-ethyl-2-pyridin-3-yl-1H-indole. $^1$H NMR (400 MHz, CDCl$_3$) δ ppm 1.17 (t, J=7.0 Hz, 3H), 1.23 (t, J=7.2 Hz, 3H), 2.94 (t, J=7.3 Hz, 2H), 3.43 (q, J=7.1 Hz, 2H), 3.61 (t, J=7.3 Hz, 2H), 4.05 (q, J=7.3 Hz, 2H), 7.19 (t, J=7.4 Hz, 1H), 7.30 (t, J=7.1 Hz, 1H), 7.40 (d, J=8.3 Hz, 1H), 7.53 (dd, J=7.6, 5.1 Hz, 1H), 7.69 (d, J=7.8 Hz, 1H), 7.92 (d, J=7.8 Hz, 1H), 8.72 (dd, J=4.9, 1.6

Hz, 1H), 8.77 (d, J=1.5 Hz, 1H). HRMS (ESI) m/z 295.1805 [(M+H)+ Calcd for $C_{19}H_{23}N_2O$: 295.1810].

Example 86

(a) 4-Chloro-2-fluoro-6-pyridin-3-ylethynyl-phenylamine

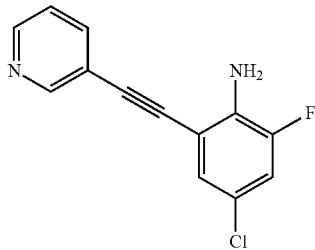 [SMILES: Nc1c(F)cc(Cl)cc1C#Cc1cccnc1]

To a mixture of 3-ethynylpyridine (1.13 g, 11 mmol) and 2-fluoro-4-chloro-6-iodoaniline (2.71 g, 10 mmol) in triethylamine (100 mL) is added $PdCl_2(PPh_3)_2$ (175 mg, 0.25 mmol) and CuI (95 mg, 0.50 mmol) and the mixture is refluxed for 1 h. The solvent is removed in vacuo and the residue is purified by silica gel flash chromatography (dichloromethane-methanol, 1:0 to 24:1) to give 4-chloro-2-fluoro-6-pyridin-3-ylethynyl-phenylamine. MS (ESI) m/z 247 (M+H)+.

(b) 5-Chloro-7-fluoro-2-pyridin-3-yl-1H-indole

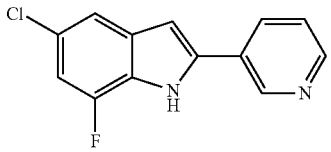 [SMILES: Fc1cc(Cl)cc2cc(-c3cccnc3)[nH]c12]

To a solution of 4-chloro-2-fluoro-6-pyridin-3-ylethynyl-phenylamine (3.1 g, 12.57 mmol) in NMP (40 mL) is added potassium tert-butoxide (2.1 g, 18.85 mmol) and the mixture is stirred overnight. Water (1 mL) is added to quench the reaction and the mixture is poured into water (100 mL). The mixture is extracted with diethyl ether five times. The combined organic phase is partially concentrated, resulting in precipitation of the product, which is filtered through a glass sintered funnel and washed with dichloromethane to afford 5-chloro-7-fluoro-2-pyridin-3-yl-1H-indole as a white solid. $^1$H NMR (400 MHz, DMSO-$d_6$) δ ppm 7.10-7.15 (m, 2H), 7.47-7.53 (m, 2H), 8.31 (dt, J=8.2, 1.9, 1.8 Hz, 1H), 8.55 (d, J=4.3 Hz, 1H), 9.16 (s, 1H), 12.23 (s, 1H).

Example 87

5-Chloro-2-pyridin-3-yl-1H-indole

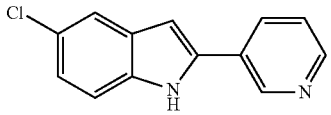 [SMILES: Clc1ccc2[nH]c(-c3cccnc3)cc2c1]

3-Ethynylpyridine and 4-chloro-6-iodoaniline are processed according to the method described in Example 86 to give 5-chloro-2-pyridin-3-yl-1H-indole. $^1$H NMR (400 MHz, MeOD) δ ppm 6.96 (s, 1H), 7.14 (dd, J=8.6, 2.0 Hz, 1H), 7.41 (d, J=8.8 Hz, 1H), 7.54 (dd, J=8.0, 4.9 Hz, 1H), 7.59 (d, J=2.0 Hz, 1H), 8.25 (dt, J=8.0, 1.9 Hz, 1H), 8.50 (d, J=4.5 Hz, 1H), 9.02 (s, 1H). HRMS (ESI) m/z 229.0522 [(M+H)+ Calcd for $C_{13}H_{10}ClN_2$: 229.0533].

Example 88

5,6-Dimethyl-2-pyridin-3-yl-1H-indole

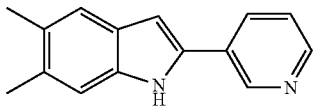 [SMILES: Cc1cc2cc(-c3cccnc3)[nH]c2cc1C]

3-Ethynylpyridine and 3,4-dimethyl-6-iodoaniline are processed according to the method described in Example 86 to give 5,6-dimethyl-2-pyridin-3-yl-1H-indole. MS (ESI) m/z 223.13 (M+H)+.

Example 89

6-Fluoro-2-pyridin-3-yl-1H-indole

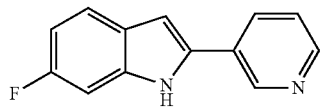 [SMILES: Fc1ccc2cc(-c3cccnc3)[nH]c2c1]

3-Ethynylpyridine and 3-fluoro-6-iodoaniline are processed according to the method described in Example 86 to give 6-fluoro-2-pyridin-3-yl-1H-indole. MS (ESI) m/z 213.0 (M+H)+.

Example 90

(a) 4-Methoxy-pyridine-3-carbaldehyde

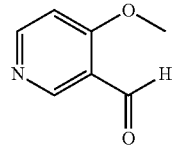

A flask is charged with 1.7M tert-butyllithium in pentane (47.1 mL, 80.1 mmol) and THF (20 mL), and cooled to −78° C. 2-Bromomesitylene (6.0 mL, 39 mmol) is added dropwise. The mixture is stirred for 1 h, and 4-methoxypyridine (3.0 mL, 30 mmol) is added dropwise. The mixture is warmed to −23° C. and stirred for 3 h. The mixture is cooled again to −78° C. and dimethylformamide (3.5 mL, 45 mmol) is added. After 1 h, brine (50 mL) is added to the mixture at −78° C. and warmed to room temperature. The mixture is extracted with ether and the combined organic layer is dried over $Na_2SO_4$. Concentration followed by silica gel chromatography eluting with a 0 to 6% methanol-dichloromethane gradient gives 4-methoxy-pyridine-3-carbaldehyde. $^1$H NMR (400 MHz, CDCl$_3$) δ ppm 4.01 (s, 3H), 6.94 (d, J=5.8 Hz, 1H), 8.65 (d, J=5.8 Hz, 1H), 8.90 (s, 1H), 10.46 (s, 1H).

(b) 3-(2,2-dibromo-vinyl)-4-methoxy-pyridine

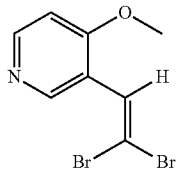

A flask is charged with triphenylphosphine (21.4 g, 81.6 mmol), carbon tetrabromide (13.5 g, 40.8 mmol) and dichloromethane (300 mL). 4-Methoxy-pyridine-3-carbaldehyde (2.8 g, 20.4 mmol) in dichloromethane (300 mL) is added at 0° C. The mixture is stirred at 0° C. for 1 h. The mixture is extracted with saturated aqueous ammonium chloride and the aqueous phase is neutralized with NaHCO$_3$ and extracted with dichloromethane. The organic phase is dried over Na$_2$SO$_4$, concentrated and purified by silica gel chromatography eluting with a 0 to 10% methanol-dichloromethane gradient to give 3-(2,2-dibromo-vinyl)-4-methoxy-pyridine. $^1$H NMR (400 MHz, CDCl$_3$) δ ppm 3.90 (s, 3H), 6.81 (d, J=5.8 Hz, 1H), 7.48 (s, 1H), 8.48 (d, J=5.8 Hz, 1H), 8.76 (s, 1H).

(c) 4-methoxy-3-ethynyl-pyridine

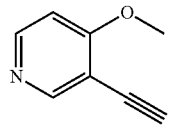

A flask is charged with 3-(2,2-dibromo-vinyl)-4-methoxy-pyridine (3.7 g, 12.63 mmol) and THF (100 mL), and 1.6 M nBuLi in pentane (17.4 mL, 27.79 mmol) is added dropwise at −78° C. The mixture is stirred at −78° C. for 1 h before addition of saturated aqueous NH$_4$Cl (0.5 mL). The mixture is warmed to room temperature and poured into water (100 mL). The mixture is extracted with ethyl acetate and the combined organic phase is dried over Na$_2$SO$_4$. Concentration followed by silica gel flash chromatography eluting with a 0 to 5% methanol-dichloromethane gradient gives 4-methoxy-3-ethynyl-pyridine. $^1$H NMR (400 MHz, CDCl$_3$) δ ppm 3.39 (s, 1H), 3.96 (s, 3H), 6.82 (d, J=5.8 Hz, 1H), 8.46 (d, J=5.8 Hz, 1H), 8.58 (s, 1H).

(d) 2-(4-Methoxy-pyridin-3-yl)-1H-indole-5-carbonitrile

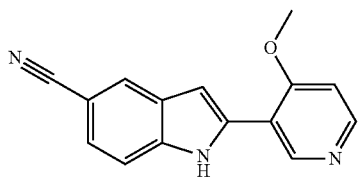 [SMILES: COc1ccncc1-c1cc2cc(C#N)ccc2[nH]1]

4-Methoxy-3-ethynyl-pyridine and 4-cyano-6-iodoaniline are processed according to the method described in Example 86 to give 2-(4-methoxy-pyridin-3-yl)-1H-indole-5-carbonitrile. 2-(4-Methoxy-pyridin-3-yl)-1H-indole-5-carbonitrile is purified by HPLC using an Xbridge Shield RP18 with a gradient of acetonitrile in 0.1% NH$_4$OH. $^1$H NMR (400 MHz, DMSO-d$_6$) δ ppm 4.04 (s, 3H), 7.14 (d, J=1.3 Hz, 1H), 7.25 (d, J=5.8 Hz, 1H), 7.47 (dd, J=8.5, 1.6 Hz, 1H), 7.61 (d, J=8.3 Hz, 1H), 8.11 (s, 1H), 8.47 (d, J=5.8 Hz, 1H), 8.91 (s, 1H), 11.91 (br. s., 1H). HRMS (ESI) m/z 250.0968 [(M+H)$^+$ calcd for C$_{15}$H$_{12}$N$_3$O: 250.0980].

Example 91

2-(5-Chloro-pyridin-3-yl)-1H-indole

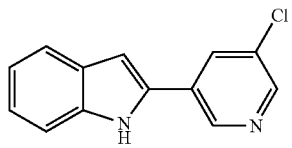 [SMILES: Clc1cncc(-c2cc3ccccc3[nH]2)c1]

A flask is charged with N-Boc-indole-2-boronic acid (0.407 g, 1.55 mmol), 3-chloro-5-bromopyridine (0.200 g, 1.03 mmol), s-phos (0.021 g, 0.05 mmol), potassium phosphate (0.441 g, 2.07 mmol) and toluene (5 mL). The flask is evacuated and filled with N$_2$ thrice and Pd$_2$(dba)$_3$ (0.019 g, 0.02 mmol) is added. The flask is evacuated and filled with N$_2$ thrice. The mixture is refluxed for 1 h, then cooled to room temperature and filtered through celite. The filtrate is concentrated in vacuo to afford 2-(5-chloro-pyridin-3-yl)-indole-1-carboxylic acid tert-butyl ester as an oil. The residue is dissolved in DCM (5 mL) and trifluoroacetic acid (2 mL) is added. The reaction mixture is stirred at room temperature for 4 h, followed with quenching with a saturated sodium bicarbonate solution. Extraction with dichloromethane, drying of the organic layer over sodium sulfate and concentration in vacuo gives a residue which is purified by silica gel flash chromatography (heptane-ethyl acetate, 3:2) to afford 2-(5-chloro-pyridin-3-yl)-1H-indole. $^1$H NMR (400 MHz, MeOD) δ ppm 7.06 (s, 1H), 7.08 (d, J=7.8 Hz, 1H), 7.20 (t, J=7.7 Hz, 1H), 7.45 (d, J=8.3 Hz, 1H), 7.61 (d, J=7.8 Hz, 1H), 8.30 (t, J=2.1 Hz, 1H), 8.47 (d, J=2.3 Hz, 1H), 8.96 (d, J=1.8 Hz, 2H). HRMS (ESI) m/z 229.0542 [(M+H)$^+$ calcd for C$_{13}$H$_{10}$ClN$_2$: 229.0533].

Example 92

2-(5-Fluoro-pyridin-3-yl)-1H-indole

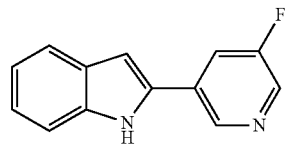 [SMILES: Fc1cncc(-c2cc3ccccc3[nH]2)c1]

3-Fluoro-5-bromopyridine is processed according to the procedure described in Example 91 to give 2-(5-fluoro-pyridin-3-yl)-1H-indole. HRMS (ESI) m/z 213.0834 [(M+H)$^+$ Calcd for C$_{13}$H$_{10}$N$_2$F: 213.0828].

Example 93

5-Methoxy-2-pyridin-3-yl-1H-indole

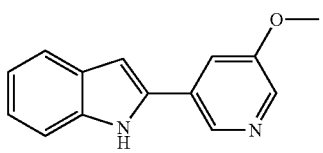 [SMILES: COc1cncc(-c2cc3ccccc3[nH]2)c1]

3-Bromopyridine and N-Boc-5-methoxy-indole-2-boronic acid are processed according to the procedure described in Example 91 to give 5-methoxy-2-pyridin-3-yl-1H-indole. HRMS (ESI) m/z 225.1026 [(M+H)$^+$ Calcd for $C_{14}H_{13}N_2O$: 225.1028]

Example 94

6-Chloro-2-(5-methyl-pyridin-3-yl)-1H-indole

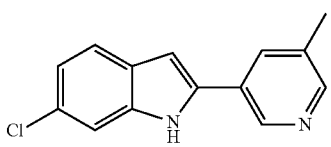 [SMILES: Cc1cncc(-c2cc3ccc(Cl)cc3[nH]2)c1]

3-Methyl-5-bromopyridine and N-Boc-6-chloro-indole-2-boronic acid are processed according to the procedure described in Example 91 to give 6-chloro-2-(5-methyl-pyridin-3-yl)-1H-indole. (ESI) m/z 243.0 (M+H)$^+$.

Example 95

6-Chloro-2-(5-trifluoromethyl-pyridin-3-yl)-1H-indole

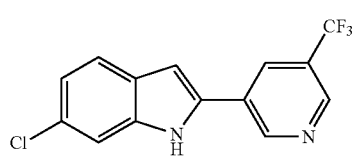 [SMILES: FC(F)(F)c1cncc(-c2cc3ccc(Cl)cc3[nH]2)c1]

3-Trifluoromethyl-5-bromopyridine and N-Boc-6-chloro-indole-2-boronic acid are processed according to the procedure described in Example 91 to give 6-chloro-2-(5-trifluoromethyl-pyridin-3-yl)-1H-indole. (ESI) m/z 297.0 (M+H)$^+$.

Example 96

5-Fluoro-2-(5-fluoro-pyridin-3-yl)-1H-indole

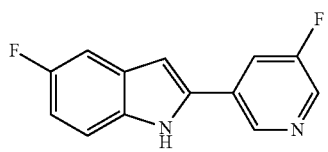 [SMILES: Fc1cncc(-c2cc3cc(F)ccc3[nH]2)c1]

3-Fluoro-5-bromopyridine and N-Boc-5-fluoro-indole-2-boronic acid are processed according to the procedure described in Example 91 to give 5-fluoro-2-(5-fluoro-pyridin-3-yl)-1H-indole. (ESI) m/z 231.04 (M+H)$^+$.

Example 97

6-Chloro-2-pyridin-3-yl-1H-indole

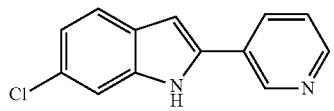 [SMILES: Clc1ccc2cc(-c3cccnc3)[nH]c2c1]

3-Bromopyridine and N-Boc-6-chloro-indole-2-boronic acid are processed according to the procedure described in Example 91 to give 6-chloro-2-pyridin-3-yl-1H-indole. (ESI) m/z 229.0 (M+H)$^+$.

Example 98

2-(5-Benzyloxy-pyridin-3-yl)-6-chloro-1H-indole

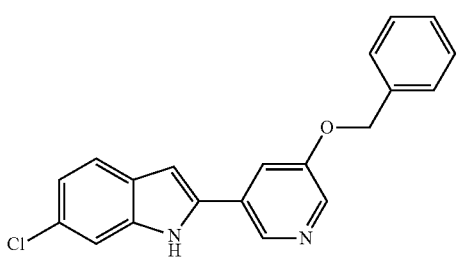 [SMILES: Clc1ccc2cc(-c3cncc(OCc4ccccc4)c3)[nH]c2c1]

A flask is charged with 6-chloro-1-Boc-indole-2-boronic acid (0.839 g, 2.83 mmol), 1-benzyloxy-3-bromo-pyridine (0.500 g, 1.89 mmol), potassium phosphate (1.2 g, 5.67 mmol) and DMF (5 mL). The flask is evacuated and filled with nitrogen thrice and Pd(PPh$_3$)$_4$ (0.164 g, 0.141 mmol) is added. The flask is evacuated and filled with nitrogen thrice again, and heated to 80° C. for 3.5 h. The mixture is then diluted with ethyl acetate and washed with water thrice. The organic layer is dried over sodium sulfate and concentrated in vacuo. The residue is redissolved in DCM (1 mL) and trifluoroacetic acid (2 mL) is added. After 1 h, 4M aqueous NaOH is added and following extraction with DCM, the organic layer is dried over sodium sulfate and concentrated in vacuo. The residue is purified by silica gel flash chromatography (heptane-ethyl acetate, 1:1) to afford 2-(3-benzyloxy-phenyl)-6-chloro-1H-indole as a yellow solid. MS (ESI) m/z 335.07 (M+H)$^+$.

Example 99

2-(5-Ethoxy-pyridin-3-yl)-6-chloro-1H-indole

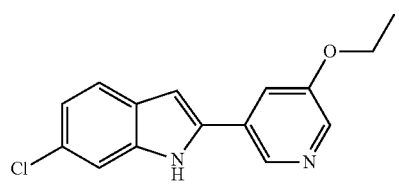 [SMILES: CCOc1cncc(-c2cc3ccc(Cl)cc3[nH]2)c1]

1-Ethoxy-3-bromo-pyridine is processed according to the method described in Example 98 to give 2-(5-ethoxy-pyridin-3-yl)-6-chloro-1H-indole. MS (ESI) m/z 273.27 (M+H)+

Example 100

2-(5-Amino-pyridin-3-yl)-1-methyl-1H-indole

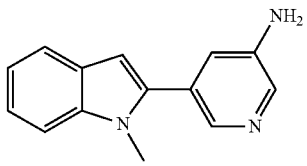 [SMILES: Cn1c(-c2cncc(N)c2)cc2ccccc21]

A flask is charged with 3-amino-5-bromopyridine (0.173 g, 0.950 mmol), N-methyl-indole boronic acid (0.262 g, 1.425 mmol), s-Phos (0.030 g, 0.071 mmol), finely crushed potassium phosphate (0.407 g, 1.900 mmol) and toluene (4 mL). After degassing for 30 min, Pd$_2$dba$_3$ (0.018 g, 0.019 mmol) is added, the flask is flushed with nitrogen and the mixture is heated to 85° C. After 3 h, the mixture is allowed to cool to r.t., diluted with ethyl acetate and filtered through a plug of silica gel (elution with ethyl acetate). The residue is purified by silica gel flash chromatography (heptane-ethyl acetate, 3:7 to 0:1) to give 2-(5-amino-pyridin-3-yl)-1-methyl-1H-indole as an off-white powder. $^1$H NMR (400 MHz, DMSO-d$_6$) δ ppm 3.74 (s, 3H), 5.49 (s, 2H), 6.56 (s, 1H), 7.05-7.09 (m, 1H), 7.09-7.10 (m, 1H), 7.17-7.21 (m, 1H), 7.49 (d, J=7.6 Hz, 1H), 7.57 (d, J=7.6 Hz, 1H), 7.94 (d, J=2.0 Hz, 1H), 7.99 (d, J=2.5 Hz, 1H). MS (ESI) m/z 224 (M+H)+.

Example 101

2-(5-Methoxy-pyridin-3-yl)-1-methyl-1H-indole

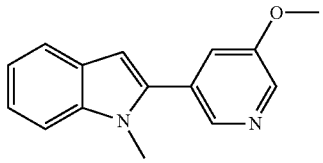 [SMILES: COc1cncc(-c2cc3ccccc3n2C)c1]

5-Methoxy-3-bromo-pyridine is processed according to the method described in Example 100 to give 2-(5-methoxy-pyridin-3-yl)-1-methyl-1H-indole. $^1$H NMR (400 MHz, MeOD) δ ppm 3.82 (s, 3H), 4.00 (s, 3H), 6.69 (d, J=0.8 Hz, 1H), 7.08-7.16 (m, 1H), 7.23-7.30 (m, 1H), 7.47 (dd, J=8.3, 0.8 Hz, 1H), 7.58-7.66 (m, 2H), 8.32 (d, J=2.8 Hz, 1H), 8.37 (d, J=1.6 Hz, 1H). HRMS (ESI) m/z 239.1175 [(M+H)+ Calcd for C$_{15}$H$_{15}$N$_2$O: 239.1184].

Example 102

5-(1-Methyl-1H-indol-2-yl)-nicotinic acid ethyl ester

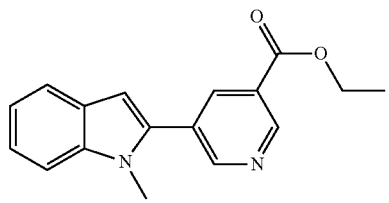 [SMILES: CCOC(=O)c1cncc(-c2cc3ccccc3n2C)c1]

5-Bromo-nicotinic acid ethyl ester is processed according to the method described in Example 100 to give 5-(1-methyl-1H-indol-2-yl)-nicotinic acid ethyl ester. $^1$H NMR (400 MHz, MeOD) δ ppm 1.47 (t, J=7.1 Hz, 3H), 3.83 (s, 3H), 4.50 (q, J=7.1 Hz, 2H), 6.76 (s, 1H), 7.14 (t, J=7.5 Hz, 1H), 7.29 (t, J=7.6 Hz, 1H), 7.50 (d, J=8.3 Hz, 1H), 7.64 (d, J=8.1 Hz, 1H), 8.56 (t, J=2.0 Hz, 1H), 9.00 (d, J=2.0 Hz, 1H), 9.17 (d, J=2.0 Hz, 1H). HRMS (ESI) m/z 281.1297 [(M+H)+ Calcd for C$_{17}$H$_{17}$N$_2$O$_2$: 281.1290].

Example 103

5-(1H-Indol-2-yl)-pyridine-3-carbaldehyde

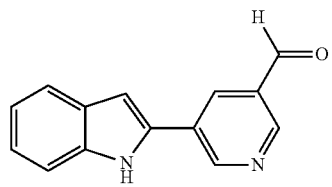 [SMILES: O=Cc1cncc(-c2cc3ccccc3[nH]2)c1]

A flask is charged with 3-bromopyridine-5-carboxaldehyde (4.12 g, 21.48 mmol), N-Boc-indoleboronic acid (8.59 g, 32.23 mmol), s-Phos (0.68 g, 1.61 mmol), finely crushed potassium phosphate (9.21 g, 42.97 mmol) and toluene (70 mL). After degassing for 1 h, Pd$_2$dba$_3$ (0.40 g, 0.43 mmol) is added, the flask is flushed with nitrogen and the mixture is heated to 85° C. After 30 min, the mixture is allowed to cool to r.t., diluted with ethyl acetate and filtered through a plug of silica gel. Silica gel (50 g) is added to the filtrate and the mixture is concentrated in vacuo. The residue is heated to 60° C. with gentle stirring under oil pump vacuum overnight. The mixture is then loaded on a silica gel flash chromatography column and eluted (heptane-ethyl acetate, 4:1 to 2:3) to give 5-(1H-indol-2-yl)-pyridine-3-carbaldehyde. $^1$H NMR (400 MHz, DMSO-d$_6$) δ ppm 7.02-7.08 (m, 1H), 7.14-7.19 (m, 1H), 7.20 (d, J=1.5 Hz, 1H), 7.45 (d, J=8.1 Hz, 1H), 7.59 (d, J=8.1 Hz, 1H), 8.66 (t, J=2.1 Hz, 1H), 9.00 (d, J=1.8 Hz, 1H), 9.39 (d, J=2.3 Hz, 1H), 10.18 (s, 1H), 11.86 (br. s, 1H). MS (ESI) m/z 223.02 (M+H)+.

Example 104

5-(6-Chloro-1H-indol-2-yl)-pyridine-3-carbaldehyde

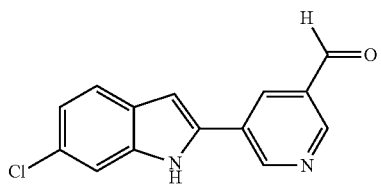 [SMILES: O=Cc1cncc(-c2cc3ccc(Cl)cc3[nH]2)c1]

A flask is charged with N-(tert-butoxycarbonyl)-6-chloro-1H-indol-2-ylboronic acid (8.3 g, 28.1 mmol), 5-bromonicotinaldehyde (4.35 g, 23.4 mmol), K$_3$PO$_4$ (9.94 g, 46.8 mmol), s-Phos (0.480 g, 1.170 mmol) and Pd$_2$(dba)$_3$ (0.429 g, 0.468 mmol), and the flask is flushed with N$_2$. Toluene (250 mL) is added, and the mixture is heated to 85° C. for 1.5 h. The mixture is cooled to room temperature. Ethyl acetate (250 mL) is added and the mixture is filtered through a pad of silica gel, which is washed with EtOAc. Silica gel is added to the combined filtrate, which is concentrated in vacuo. The residue is placed under high vacuum at 63° C. overnight, and after elution with ethyl acetate, 5-(6-chloro-1H-indol-2-yl)-pyridine-3-carbaldehyde is obtained. MS (ESI) m/z 257.0 and 258.9 (M+H)+.

Example 105

(a) 3-Bromo-5-vinyl-pyridine

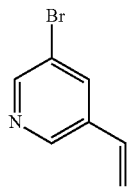

To a solution of methyltriphenylphosphine bromide (3.16 g, 8.87 mmol) in tetrahydrofuran (20 mL) is added sodium hexamethyldisilazane (1M solution in THF, 9.67 mL, 9.67 mmol) dropwise. The reaction mixture is stirred at room temperature for 30 min, whereupon 5-bromo-pyridine-3-carbaldehyde (1.5 g, 8.06 mmol) is added. The reaction mixture is allowed to stir at room temperature for 1 h. The mixture is concentrated and the residue is purified by silica gel flash chromatography (heptane-ethyl acetate, 7:3) to afford 3-bromo-5-vinyl-pyridine as a colorless oil. MS (ESI) m/z 185.91 (M+H)+.

(b) 1-Methyl-2-(5-vinyl-pyridin-3-yl)-1H-indole

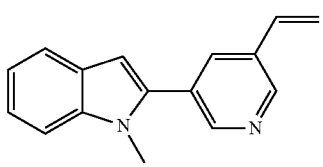 [SMILES: C=Cc1cncc(-c2cc3ccccc3n2C)c1]

3-Bromo-5-vinyl-pyridine is processed according to the method described in Example 100 to give 1-methyl-2-(5-vinyl-pyridin-3-yl)-1H-indole. MS (ESI) m/z 235.40 (M+H)+.

Example 106

(a) (3-Bromo-pyridin-4-yl)-methanol

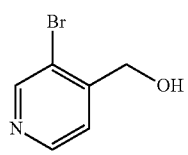

To a solution of 3-bromo-pyridine-4-carbaldehyde (0.500 g, 2.68 mmol) in MeOH (5 mL) at 0° C. is added sodium borohydride (0.122 g, 3.22 mmol). The mixture is stirred at room temperature for 1 h followed by removal of the solvent in vacuo. The residue is redissolved in DCM and washed with water twice. The organic layer is dried over sodium sulfate and concentrated in vacuo to afford (3-bromo-pyridin-4-yl)-methanol as a yellow oil. MS (ESI) m/z 189.9 (M+H)+

(b) [3-(1-Methyl-1H-indol-2-yl)-pyridin-4-yl]-methanol

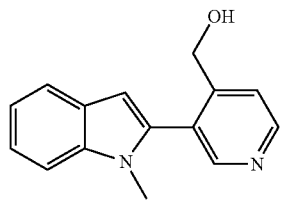 [SMILES: Cn1c(-c2cnccc2CO)cc2ccccc21]

A microwave reactor is charged with 1-methyl-indole-2-boronic acid (1.18 g, 6.78 mmol), (3-bromo-pyridin-4-yl)-methanol (0.850 g, 4.52 mmol), potassium phosphate (1.91 g, 9.04 mmol) and DMF (10 mL). The reactor is evacuated and filled with nitrogen thrice and Pd(PPh$_3$)$_4$ (0.261 g, 0.226 mmol) is added. The reactor is evacuated and filled with nitrogen thrice again. The mixture is heated to 120° C. for 1 h under microwave irradiation, then diluted with ethyl acetate and washed with water thrice. The organic layer is dried over sodium sulfate and concentrated in vacuo to give a residue which is purified by silica gel flash chromatography (dichloromethane-methanol, 19:1) to afford [3-(1-methyl-1H-indol-2-yl)-pyridin-4-yl]-methanol as a white solid. $^1$H NMR (400 MHz, MeOD) δ ppm 3.58 (s, 3H), 4.57 (s, 2H), 6.54 (s, 1H), 7.14 (t, J=7.5 Hz, 1H), 7.27 (ddd, J=7.6, 1.1 Hz, 1H), 7.46 (d, J=8.3 Hz, 1H), 7.62 (d, J=7.8 Hz, 1H), 7.81 (d, J=5.1 Hz, 1H), 8.49 (s, 1H), 8.67 (d, J=5.1 Hz, 1H). HRMS (ESI) m/z 239.1177 [(M+H)+ Calcd for C$_{15}$H$_{15}$N$_2$O: 239.1184].

Example 107

2-(4-Chloro-pyridin-3-yl)-1-methyl-1H-indole

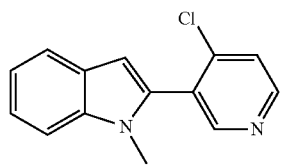 [SMILES: Cn1c(-c2cnccc2Cl)cc2ccccc21]

3-Bromo-4-chloropyridine is processed according to the method described in Example 106b to give 2-(4-chloro-pyridin-3-yl)-1-methyl-1H-indole. $^1$H NMR (400 MHz, MeOD) δ ppm 3.64 (s, 3H), 6.61 (s, 1H), 7.14 (t, J=7.5 Hz, 1H), 7.28 (t, J=7.6 Hz, 1H), 7.47 (d, J=8.3 Hz, 1H), 7.64 (d, J=7.8 Hz, 1H), 7.73 (d, J=5.3 Hz, 1H), 8.62 (d, J=5.6 Hz, 1H), 8.66 (s, 1H). HRMS (ESI) m/z 243.0686 [(M+H)+ Calcd for C$_{14}$H$_{12}$ClN$_2$: 243.0689].

Example 108

2-(5-Hydroxy-pyridin-3-yl)-1-methyl-1H-indole

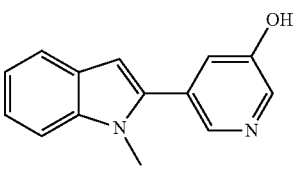 [SMILES: Cn1c(-c2cncc(O)c2)cc2ccccc21]

3-Bromo-5-hydroxypyridine is processed according to the method described in Example 106b to give 2-(5-hydroxy-pyridin-3-yl)-1-methyl-1H-indole. HRMS (ESI) m/z 225.1028 [(M+H)$^+$ Calcd for $C_{14}H_{13}N_2O$: 225.1028].

Example 109

2-(5-Benzyloxy-pyridin-3-yl)-6-chloro-1-methyl-1H-indole

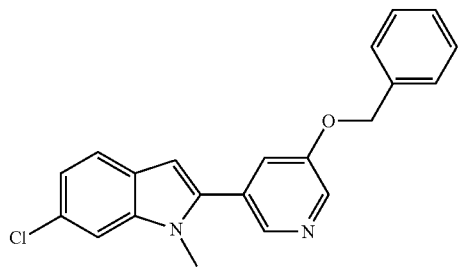 [SMILES: Cn1c(-c2cncc(OCc3ccccc3)c2)cc2ccc(Cl)cc21]

A flask is charged with 2-(5-benzyloxy-pyridin-3-yl)-6-chloro-1H-indole (Example 98, 0.435 g, 1.29 mmol), dimethyl carbonate (0.328 mL, 3.89 mmol), potassium carbonate (0.098 g, 0.714 mmol) and DMF (3 mL). The reaction mixture is stirred at 150° C. overnight. It is then cooled to room temperature, diluted with ethyl acetate and washed with water. The organic layer is dried over sodium sulfate and concentrated in vacuo, to give a residue which is purified by flash chromatography (heptane-ethyl acetate, 1:1) to afford 2-(5-benzyloxy-pyridin-3-yl)-6-chloro-1-methyl-1H-indole as a solid. $^1$H NMR (400 MHz, MeOD) δ ppm 3.70 (s, 3H), 5.31 (s, 2H), 6.67 (d, J=0.8 Hz, 1H), 7.10 (dd, J=8.3, 1.8 Hz, 1H), 7.35-7.40 (m, 1H), 7.41-7.47 (m, 2H), 7.49-7.55 (m, 3H), 7.57 (d, J=8.3 Hz, 1H), 7.64 (dd, J=2.5, 1.8 Hz, 1H), 8.35 (d, J=1.8 Hz, 1H), 8.39 (d, J=2.8 Hz, 1H); HRMS (ESI) m/z 349.1108 [(M+H)$^+$ Calcd for $C_{21}H_{18}ClN_2O$: 349.1108].

Example 110

2-(5-Ethoxy-pyridin-3-yl)-6-chloro-1-methyl-1H-indole

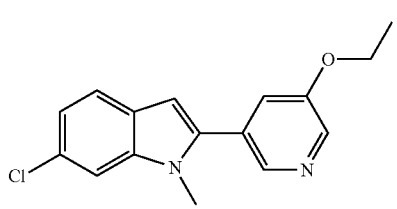 [SMILES: CCOc1cncc(-c2cc3ccc(Cl)cc3n2C)c1]

2-(5-Ethoxy-pyridin-3-yl)-6-chloro-1H-indole (Example 99) is processed according to the method described in Example 109 to give 2-(5-ethoxy-pyridin-3-yl)-6-chloro-1-methyl-1H-indole. MS (ESI) m/z 287.07 (M+H)$^+$.

Example 111

6-Chloro-2-(5-methyl-pyridin-3-yl)-1-methyl-1H-indole

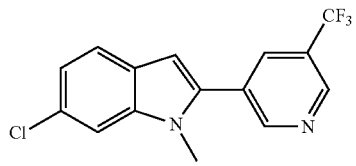 [SMILES: Cn1c(-c2cncc(C(F)(F)F)c2)cc2ccc(Cl)cc21]

6-Chloro-2-(5-methyl-pyridin-3-yl)-1H-indole (Example 94) is processed according to the method described in Example 109 to give 6-chloro-2-(5-methyl-pyridin-3-yl)-1-methyl-1H-indole. MS (ESI) m/z 257.1 (M+H)$^+$.

Example 112

6-Chloro-2-(5-trifluoromethyl-pyridin-3-yl)-1-methyl-1H-indole

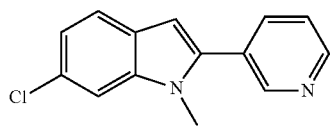 [SMILES: Cn1c(-c2cccnc2)cc2ccc(Cl)cc21]

6-Chloro-2-(5-trifluoromethyl-pyridin-3-yl)-1H-indole (Example 95) is processed according to the method described in Example 109 to give 6-chloro-2-(5-trifluoromethyl-pyridin-3-yl)-1-methyl-1H-indole. MS (ESI) m/z 311.0 (M+H)$^+$.

Example 113

6-Chloro-2-pyridin-3-yl-1-methyl-1H-indole

6-Chloro-2-pyridin-3-yl-1H-indole (Example 97) is processed according to the method described in Example 109 to give 6-chloro-2-pyridin-3-yl-1-methyl-1H-indole. MS (ESI) m/z 243.02 (M+H)$^+$.

Example 114

2-(4-Methoxy-pyridin-3-yl)-1-methyl-1H-indole-5-carbonitrile

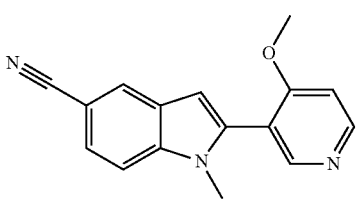 [SMILES: COc1ccncc1-c1cc2cc(C#N)ccc2n1C]

To a solution of 2-(4-methoxy-pyridin-3-yl)-1H-indole-5-carbonitrile (Example 90, 178 mg, 0.649 mmol) in DMF (4 mL) is added 60% sodium hydride in mineral oil (78 mg, 1.95 mmol) and the suspension is stirred for 30 min. Iodomethane (138 mg, 0.97 mmol) is then added to the reaction mixture which is stirred at ambient temperature for 1 h. Aqueous $NaHCO_3$ (3 mL) is added to quench the reaction and the mixture is filtered and purified by HPLC using an Xbridge C18 with a gradient of acetonitrile in 0.1% $NH_4OH$ to afford 2-(4-methoxy-pyridin-3-yl)-1-methyl-1H-indole-5-carbonitrile as a white solid. $^1$H NMR (400 MHz, DMSO-$d_6$) δ ppm 3.59 (s, 3H), 3.89 (s, 3H), 6.67 (s, 1H), 7.27 (d, J=5.8 Hz, 1H), 7.54 (dd, J=8.6, 1.5 Hz, 1H), 7.70 (d, J=8.6 Hz, 1H), 8.11 (d, J=1.1 Hz, 1H), 8.42 (s, 1H), 8.60 (d, J=5.8 Hz, 1H). HRMS (ESI) m/z 264.1138 [(M+H) calcd for $C_{16}H_{14}N_3O$: 264.1137].

Example 115

2-(5-Chloro-pyridin-3-yl)-1-methyl-1H-indole

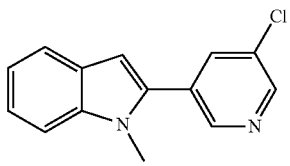 [SMILES: Cn1c(-c2cncc(Cl)c2)cc2ccccc21]

2-(5-Chloro-pyridin-3-yl)-1H-indole (Example 91) is processed according to the method described in Example 114 to give 2-(5-chloro-pyridin-3-yl)-1-methyl-1H-indole. $^1$H NMR (400 MHz, MeOD) δ ppm 3.83 (s, 3H), 6.74 (s, 1H), 7.14 (t, J=7.5 Hz, 1H), 7.25-7.33 (m, 1H), 7.49 (d, J=8.3 Hz, 1H), 7.64 (dd, J=7.8, 0.6 Hz, 1H), 8.14 (t, J=2.7 Hz, 1H), 8.63 (dd, J=2.2, 0.9 Hz, 1H), 8.74 (d, J=1.3 Hz, 1H). HRMS (ESI) m/z 243.0686 [(M+H)$^+$ Calcd for $C_{14}H_{12}ClN_2$: 243.0689].

Example 116

5-Methoxy-1-methyl-2-pyridin-3-yl-1H-indole

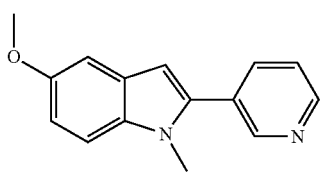 [SMILES: COc1ccc2c(c1)cc(-c1cccnc1)n2C]

5-Methoxy-2-pyridin-3-yl-1H-indole (Example 93) is processed according to the procedure described in Example 114 to give 5-methoxy-1-methyl-2-pyridin-3-yl-1H-indole. $^1$H NMR (400 MHz, MeOD) δ ppm 3.78 (s, 3H), 3.87 (s, 3H), 6.61 (d, J=0.8 Hz, 1H), 6.93 (dd, J=8.9, 2.5 Hz, 1H), 7.14 (d, J=2.4 Hz, 1H), 7.37 (d, J=9.0 Hz, 1H), 7.60 (ddd, J=8.0, 4.9, 0.9 Hz, 1H), 8.06 (dt, J=7.9, 2.2, 1.6 Hz, 1H). HRMS (ESI) m/z 239.1181 [(M+H)$^+$ Calcd for $C_{15}H_{15}N_2O$: 239.1184].

Example 117

2-(5-Fluoro-pyridin-3-yl)-1-methyl-1H-indole

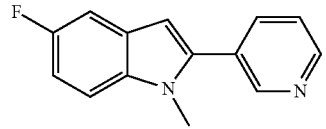 [SMILES: Cn1c(-c2cccnc2)cc2cc(F)ccc21]

2-(5-Fluoro-pyridin-3-yl)-1H-indole (Example 92) is processed according to the procedure described in Example 114 to give 2-(5-fluoro-pyridin-3-yl)-1-methyl-1H-indole. $^1$H NMR (400 MHz, MeOD) δ ppm 3.83 (s, 3H), 6.74 (s, 1H), 7.10-7.17 (m, 1H), 7.26-7.32 (m, 1H), 7.48 (d, J=8.3 Hz, 1H), 7.63 (d, J=7.8 Hz, 1H), 7.91 (ddd, J=9.6, 2.8, 1.8 Hz, 1H), 8.54 (d, J=2.5 Hz, 1H), 8.67 (t, J=1.5 Hz, 1H). HRMS (ESI) m/z 227.0989 [(M+H)$^+$ Calcd for $C_{14}H_{12}FN_2$: 227.0985].

Example 118

5-Fluoro-2-(5-fluoro-pyridin-3-yl)-1-methyl-1H-indole

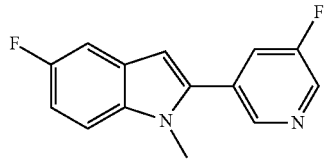 [SMILES: Cn1c(-c2cncc(F)c2)cc2cc(F)ccc21]

5-Fluoro-2-(5-fluoro-pyridin-3-yl)-1H-indole (Example 96) is processed according to the procedure described in Example 114 to give 5-fluoro-2-(5-fluoro-pyridin-3-yl)-1-methyl-1H-indole. (ESI) m/z 245.34 (M+H)$^+$.

Example 119

1,3-Dimethyl-2-(pyridin-3-yl)-1H-indole

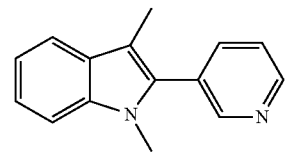 [SMILES: Cc1c(-c2cccnc2)n(C)c2ccccc12]

3-Methyl-2-(pyridin-3-yl)-1H-indole hydrochloride (Example 1) is processed according to the procedure described in Example 114 to give 1,3-dimethyl-2-(pyridin-3-yl)-1H-indole. $^1$H NMR (400 MHz, DMSO-$d_6$) δ ppm 2.23 (s, 3H), 3.62 (s, 3H), 7.06-7.12 (m, 1H), 7.22 (td, J=7.6, 1.1 Hz, 1H), 7.48 (d, J=8.3 Hz, 1H), 7.55-7.61 (m, 2H), 7.93 (dt, J=7.9, 2.0 Hz, 1H), 8.66 (dd, J=4.8, 1.5 Hz, 1H), 8.69 (dd, J=2.3, 0.8 Hz, 1H). HRMS: (ESI) m/z 223.1236 [(M+H)$^+$ Calcd for $C_{15}H_{15}N_2$: 223.1230].

Example 120

5-(6-Chloro-1-methyl-1H-indol-2-yl)-nicotinonitrile

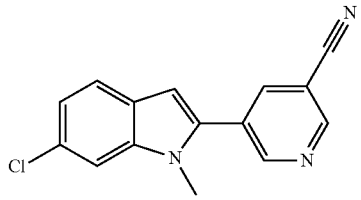 [SMILES: Cn1c(-c2cncc(C#N)c2)cc2ccc(Cl)cc21]

3-Bromo-5-cyano-pyridine and N-Boc-6-chloro-indole-boronic acid are processed according to the procedure described in Example 103 to give 5-(6-chloro-1H-indol-2-yl)-nicotinonitrile, which is processed according to the procedure described in Example 114 to give 5-(6-Chloro-1-methyl-1H-indol-2-yl)-nicotinonitrile. $^1$H NMR (400 MHz, MeOD) δ ppm 3.81 (s, 3H), 6.81 (s, 1H), 7.14 (dd, J=8.6, 1.8 Hz, 1H), 7.56 (s, 1H), 7.61 (d, J=8.3 Hz, 1H), 8.46 (t, J=2.1 Hz, 1H), 8.98 (d, J=2.0 Hz, 1H), 9.06 (d, J=2.0 Hz, 1H). HRMS (ESI) m/z 268.0636 [(M+H)$^+$ Calcd for C$_{15}$H$_{10}$ClN$_3$ 268.0636].

Example 121

(a) 2-(5-bromopyridin-3-yl)-1H-indole

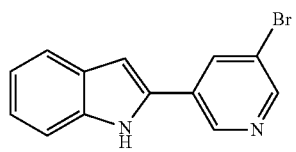 [SMILES: Brc1cncc(-c2cc3ccccc3[nH]2)c1]

A flask containing 1-(tert-butoxycarbonyl)-1H-indol-2-yl-boronic acid (2 g, 7.66 mmol), 3-bromo-5-iodopyridine (1.45 g, 5.11 mmol), 2M K$_2$CO$_3$ in water (5.11 mL, 10.21 mmol), PS—Pd(PPh$_3$)$_4$ (2.84 g, 0.255 mmol) is flushed with N$_2$ and dioxane (50 mL) is added. The mixture is stirred at 60° C. for 3 h, whereupon another portion of 3-bromo-5-iodopyridine (300 mg, 1.06 mmol) is added. The mixture is stirred at 60° C. overnight. The mixture is cooled to room temperature and silica gel (20 g) is added. The suspension is concentrated in vacuo and the residue is placed under high vacuum at 60° C. over the weekend. The mixture is purified by silica chromatography eluting with a 1:9 to 7:3 EtOAc-heptane gradient to give 2-(5-bromopyridin-3-yl)-1H-indole. MS (ESI) m/z 273.0, 275.1 (M+H)$^+$.

(b) 2-(5-Bromopyridin-3-yl)-3-(trifluoromethyl)-1H-indole

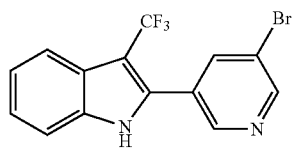 [SMILES: FC(F)(F)c1c(-c2cncc(Br)c2)[nH]c2ccccc12]

A flask is charged with 2-(5-bromopyridin-3-yl)-1H-indole (1.2 g, 4.39 mmol), acetonitrile (100 mL), potassium carbonate (1.2 g, 8.79 mmol) and 5-(trifluoromethyl)-5H-dibenzo[b,d]thiophenium trifluoromethanesulfonate (2.65 g, 6.59 mmol). The flask is lowered into an oil bath preheated to 70° C., and the mixture is stirred under N$_2$ overnight. The mixture is cooled to room temperature and silica gel (10 g) is added. The suspension is concentrated in vacuo and the residue is purified by silica chromatography eluting with a 0 to 30% EtOAc-heptane gradient to give 2-(5-bromopyridin-3-yl)-3-(trifluoromethyl)-1H-indole; $^1$H NMR (400 MHz, DMSO-d$_6$) δ ppm 7.25 (t, J=7.6 Hz, 1H), 7.33 (t, J=7.1 Hz, 1H), 7.55 (d, J=8.1 Hz, 1H), 7.69 (d, J=7.8 Hz, 1H), 8.33 (t, J=2.0 Hz, 1H), 8.79 (d, J=1.8 Hz, 1H), 8.86 (d, J=2.0 Hz, 1H).

(c) 2-(5-Bromopyridin-3-yl)-1-methyl-3-(trifluoromethyl)-1H-indole

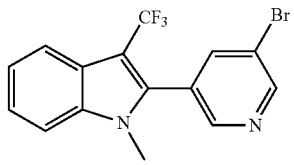 [SMILES: Cn1c(-c2cncc(Br)c2)c(C(F)(F)F)c2ccccc21]

2-(5-Bromopyridin-3-yl)-3-(trifluoromethyl)-1H-indole is processed according to the method described in Example 114 to give 2-(5-bromopyridin-3-yl)-1-methyl-3-(trifluoromethyl)-1H-indole. $^1$H NMR (400 MHz, DMSO-d$_6$) δ ppm 3.62 (s, 3H), 7.30 (t, J=8.0 Hz, 1H), 7.37-7.44 (m, 1H), 7.71 (d, J=8.8 Hz, 2H), 8.36 (t, J=2.0 Hz, 1H), 8.72 (d, J=1.8 Hz, 1H), 8.92 (d, J=2.3 Hz, 1H). HRMS: (ESI) m/z 355.0052 [(M+H)$^+$ Calcd for C$_{15}$H$_{11}$BrF$_3$N$_2$: 355.0052].

Example 122

(a) 5-Chloro-7-fluoro-1-methyl-2-pyridin-3-yl-1H-indole

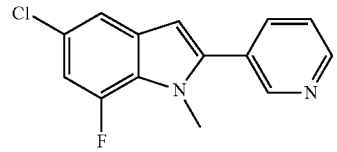 [SMILES: Cn1c(-c2cccnc2)cc2cc(Cl)cc(F)c21]

To a solution of 5-chloro-7-fluoro-2-pyridin-3-yl-1H-indole (Example 86, 276 mg, 1.12 mmol) in DMF (4 mL) is added 60% sodium hydride in mineral oil (120 mg, 3.0 mmol) and the suspension is stirred for 30 min. Iodomethane (213 mg, 1.5 mmol) is then added to the reaction mixture and stirred at ambient temperature for 1 h. Water (2 mL) is added to quench the reaction. The mixture is filtered and purified by HPLC using Xbridge C18 with a gradient of acetonitrile in 0.1% NH$_4$OH to afford 5-chloro-7-fluoro-1-methyl-2-pyridin-3-yl-1H-indole. MS (ESI) m/z 261 (M+H)$^+$.

(b) 5-Chloro-7-fluoro-1-methyl-2-pyridin-3-yl-1H-indole-3-carbonitrile

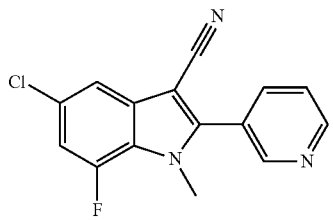 [SMILES: Cn1c(-c2cccnc2)c(C#N)c2cc(Cl)cc(F)c21]

To a solution of 5-chloro-7-fluoro-1-methyl-2-pyridin-3-yl-1H-indole (130 mg, 0.50 mmol) in dichloromethane (10 mL) at ambient temperature is added chlorosulfonyl isocyanate (282 mg, 2.0 mmol) and the mixture is stirred for 11 h, whereupon anhydrous DMF (1 mL) is added. After 1 h, the mixture is concentrated and the residue is purified by HPLC using an Xbridge C18 with a gradient of acetonitrile in 0.1% NH$_4$OH to afford 5-chloro-7-fluoro-1-methyl-2-pyridin-3-yl-1H-indole-3-carbonitrile as a white solid. $^1$H NMR (400 MHz, DMSO-d$_6$) δ ppm 3.89 (d, J=1.8 Hz, 3H), 7.46 (dd, J=12.4, 1.8 Hz, 1H), 7.62 (d, J=1.8 Hz, 1H), 7.71 (dd, J=7.5, 4.4 Hz, 1H), 8.16 (dt, J=8.1, 2.0, 1.8 Hz, 1H), 8.83 (dd, J=4.9, 1.6 Hz, 1H), 8.89 (d, J=1.5 Hz, 1H). HRMS (ESI) m/z 286.0558 [(M+H)$^+$ Calcd for C$_{15}$H$_{10}$ClFN$_3$: 286.0547].

Example 123

2-(5-Chloro-pyridin-3-yl)-1-methyl-1H-indole-3-carbonitrile

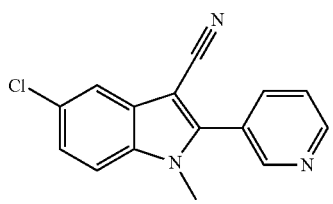 [SMILES: Cn1c(-c2cccnc2)c(C#N)c2cc(Cl)ccc21]

2-(5-Chloro-pyridin-3-yl)-1H-indole (Example 91) is processed according to the method described in Example 122 to give 2-(5-chloro-pyridin-3-yl)-1-methyl-1H-indole-3-carbonitrile. $^1$H NMR (400 MHz, MeOD) δ ppm 3.87 (s, 3H), 7.40 (t, J=7.6 Hz, 1H), 7.48 (ddd, J=7.7, 1.3 Hz, 1H), 7.68 (d, J=8.3 Hz, 1H), 7.75 (d, J=8.1 Hz, 1H), 8.28 (t, J=2.1 Hz, 1H), 8.70-8.90 (m, 2H). HRMS (ESI) m/z 268.0650 [(M+H)$^+$ Calcd for C$_{15}$H$_{11}$ClN$_3$: 268.0641].

Example 124

2-(5-Fluoro-pyridin-3-yl)-1-methyl-1H-indole-3-carbonitrile

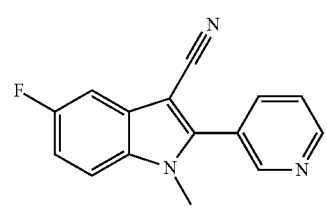 [SMILES: Cn1c(-c2cccnc2)c(C#N)c2cc(F)ccc21]

2-(5-Fluoro-pyridin-3-yl)-1H-indole (Example 92) is processed according to the method described in Example 122 to give 2-(5-fluoro-pyridin-3-yl)-1-methyl-1H-indole-3-carbonitrile. $^1$H NMR (400 MHz, MeOD) δ ppm 3.88 (s, 3H), 7.40 (t, J=7.6 Hz, 1H), 7.48 (ddd, J=7.8, 1.1 Hz, 1H), 7.69 (d, J=8.3 Hz, 1H), 7.76 (d, J=8.1 Hz, 1H), 8.06 (dt, J=9.0, 2.2 Hz, 1H), 8.74 (d, J=2.5 Hz, 1H), 8.77 (s, 1H). HRMS (ESI) m/z 252.0939 [(M+H)$^+$ Calcd for C$_{15}$H$_{11}$FN$_3$: 252.0937].

Example 125

1,5,6-Tri-methyl-2-pyridin-3-yl-1H-indole-3-carbonitrile

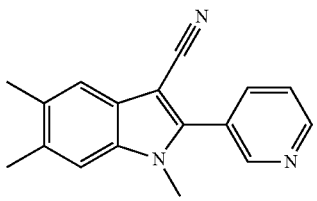 [SMILES: Cc1cc2c(C#N)c(-c3cccnc3)n(C)c2cc1C]

5,6-dimethyl-2-pyridin-3-yl-1H-indole (Example 88) is processed according to the method described in Example 122 to give 1,5,6-tri-methyl-2-pyridin-3-yl-1H-indole-3-carbonitrile. $^1$H NMR (400 MHz, DMSO-d$_6$) δ ppm 2.38 (s, 3H), 2.40 (s, 3H), 3.75 (s, 3H), 7.47 (s, 1H), 7.54 (s, 1H), 7.67 (dd, J=7.8, 4.8 Hz, 1H), 8.14 (dt, J=8.1, 2.0, 1.8 Hz, 1H), 8.78 (dd, J=4.8, 1.8 Hz, 1H), 8.88 (d, J=1.5 Hz, 1H). HRMS (ESI) m/z 262.1352 [(M+H)$^+$ Calcd for C$_{17}$H$_{16}$N$_3$: 262.1344].

Example 126 a) 6-Chloro-2-(5-formyl-pyridin-3-yl)-1-methyl-1H-indole

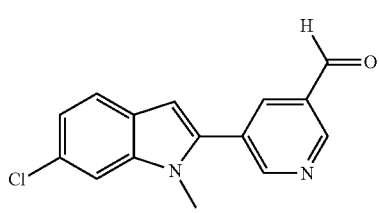 [SMILES: Cn1c(-c2cncc(C=O)c2)cc2ccc(Cl)cc21]

A flask is charged with 5-(6-chloro-1H-indol-2-yl)-pyridine-3-carbaldehyde (Example 104, 7.8 g, 28.9 mmol), MeI (5.33 g, 37.5 mmol) and DMF (300 mL), and 60% NaH in mineral oil (1.386 g, 34.6 mmol) is added at 0° C. The mixture is stirred for 2 h. Water (100 mL) is added. The mixture is extracted with EtOAc twice and the combined organic phase is washed with water (2×200 mL) and brine (200 mL), dried over Na$_2$SO$_4$, filtered and concentrated in vacuo. The residue is purified by silica gel chromatography with a 0 to 2% methanol-DCM gradient to give 6-chloro-2-(5-formyl-pyridin-3-yl)-1-methyl-1H-indole. MS (ESI) m/z 271.0, 272.9 (M+H)$^+$.

b) 6-Chloro-2-(5-formyl-pyridin-3-yl)-1-methyl-1H-indole-3-carbonitrile

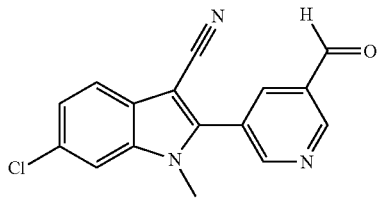 [SMILES: Cn1c(-c2cncc(C=O)c2)c(C#N)c2ccc(Cl)cc21]

A flask is charged with 6-chloro-2-(5-formyl-pyridin-3-yl)-1-methyl-1H-indole (10 g, 36.9 mmol) and acetonitrile (1 L), and chlorosulfonyl isocyanate (15.68 g, 111 mmol) is added at 0° C. The mixture is stirred for 10 min. DMF (18.9 g, 259 mmol) is added at 0° C. The mixture is stirred for 1.5 h. Saturated NaHCO$_3$ (20 mL) and triethylamine (51.5 mL, 369 mmol) are added to the reaction mixture, which is stirred for 10 min. The mixture is concentrated in vacuo to give a residue which is purified by silica gel flash chromatography eluting with a 0 to 5% methanol-DCM gradient to give 6-chloro-2-(5-formyl-pyridin-3-yl)-1-methyl-1H-indole-3-carbonitrile. MS (ESI) m/z 296.0, 297.8 (M+H)$^+$.

Example 127

2-(5-formyl-pyridin-3-yl)-1-methyl-1H-indole-3-carbonitrile

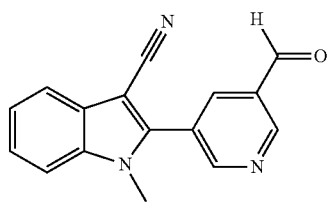 [SMILES: Cn1c(-c2cncc(C=O)c2)c(C#N)c2ccccc21]

5-(1H-indol-2-yl)-pyridine-3-carbaldehyde (Example 103) is processed according to the method described in Example 122 using acetonitrile instead of dichloromethane, to give 2-(5-formyl-pyridin-3-yl)-1-methyl-1H-indole-3-carbonitrile. MS (ESI) m/z 262.02 (M+H)$^+$.

Example 128

2-(4-Chloro-pyridin-3-yl)-1-methyl-1H-indole-3-carbonitrile

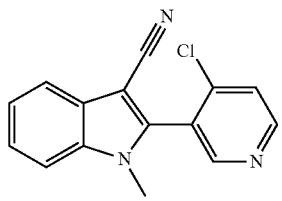

A flask is charged with 2-(4-chloro-pyridin-3-yl)-1-methyl-1H-indole (Example 107, 0.110 g, 0.418 mmol) and dichloromethane (5 mL). Chlorosulfonyl isocyanate (0.091 mL, 1.04 mmol) is added and the reaction is stirred for 2 min, whereupon DMF (1 mL) is added. After another 20 min, the reaction is concentrated in vacuo and the residue is purified by reverse phase HPLC with Xbridge Shield RP18 column and a 0.1% aqueous NH$_4$OH in acetonitrile gradient to afford 2-(4-chloro-pyridin-3-yl)-1H-indole-3-carbonitrile as a solid. $^1$H NMR (400 MHz, MeOD) δ ppm 3.74 (s, 3H), 7.41 (t, J=7.6 Hz, 1H), 7.49 (t, J=7.7 Hz, 1H), 7.69 (d, J=8.3 Hz, 1H), 7.77 (d, J=8.1 Hz, 1H), 7.84 (d, J=5.3 Hz, 1H), 8.61-8.86 (m, 2H). HRMS (ESI) m/z 268.0635 [(M+H)$^+$ Calcd for C$_{15}$H$_{11}$ClN$_3$: 268.0641].

Example 129

2-(5-Methoxy-pyridin-3-yl)-1-methyl-1H-indole-3-carbonitrile

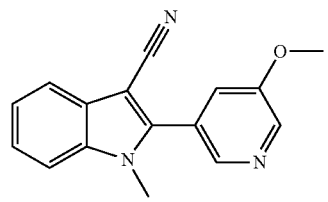 [SMILES: COc1cncc(-c2c(C#N)c3ccccc3n2C)c1]

2-(5-Methoxy-pyridin-3-yl)-1-methyl-1H-indole (Example 101) is processed according to the method described in Example 128 to give 2-(5-methoxy-pyridin-3-yl)-1-methyl-1H-indole-3-carbonitrile. $^1$H NMR (400 MHz, MeOD) δ ppm 3.87 (s, 3H), 4.02 (s, 3H), 7.36-7.42 (m, 1H), 7.47 (td, J=7.8, 1.1 Hz, 1H), 7.67 (d, J=8.3 Hz, 1H), 7.72-7.77 (m, 2H), 8.45 (d, J=1.8 Hz, 1H), 8.49 (d, J=2.8 Hz, 1H). HRMS (ESI) m/z 264.1130 [(M+H)$^+$ Calcd for C$_{16}$H$_{14}$N$_3$O: 264.1137].

Example 130

2-(5-Benzyloxy-pyridin-3-yl)-6-chloro-1-methyl-1H-indole-3-carbonitrile

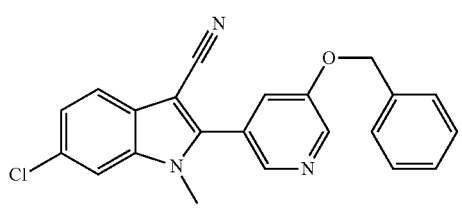 [SMILES: Cn1c(-c2cncc(OCc3ccccc3)c2)c(C#N)c2ccc(Cl)cc21]

2-(5-Benzyloxy-pyridin-3-yl)-6-chloro-1-methyl-1H-indole (Example 109) is processed according to the method described in Example 128 to give 2-(5-benzyloxy-pyridin-3-yl)-6-chloro-1-methyl-1H-indole-3-carbonitrile. $^1$H NMR (400 MHz, MeOD) δ ppm 3.75 (s, 3H), 5.33 (s, 2H), 7.37 (dd, J=8.3, 1.8 Hz, 2H), 7.44 (t, J=7.3 Hz, 2H), 7.54 (d, J=7.1 Hz, 2H), 7.71 (d, J=8.3 Hz, 1H), 7.75 (d, J=1.5 Hz, 1H), 7.78 (dd, J=2.8, 1.8 Hz, 1H), 8.45 (d, J=1.8 Hz, 1H), 8.56 (d, J=2.8 Hz, 1H). HRMS (ESI) m/z 374.1070 [(M+H)$^+$ Calcd for C$_{22}$H$_{17}$ClN$_3$O: 374.1060].

Example 131

2-(5-Ethoxy-pyridin-3-yl)-6-chloro-1-methyl-1H-indole-3-carbonitrile

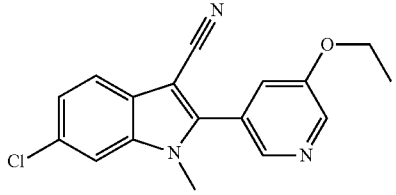 [SMILES: CCOc1cncc(-c2c(C#N)c3ccc(Cl)cc3n2C)c1]

2-(5-Ethoxy-pyridin-3-yl)-6-chloro-1-methyl-1H-indole (Example 110) is processed according to the method described in Example 128 to give 2-(5-ethoxy-pyridin-3-yl)-6-chloro-1-methyl-1H-indole-3-carbonitrile. $^1$H NMR (400 MHz, MeOD) δ ppm 1.51 (t, J=7.1 Hz, 3H), 3.84 (s, 3H), 4.27 (q, J=6.9 Hz, 2H), 7.37 (dd, J=8.6, 1.8 Hz, 1H), 7.66-7.74 (m, 2H), 7.76 (d, J=1.5 Hz, 1H), 8.43 (d, J=1.5 Hz, 1H), 8.47 (d, J=2.8 Hz, 1H). HRMS (ESI) m/z 312.0893 [(M+H)$^+$ Calcd for $C_{17}H_{15}ClN_3O$: 312.0904].

Example 132

6-Chloro-2-(5-methyl-pyridin-3-yl)-1-methyl-1H-indole-3-carbonitrile

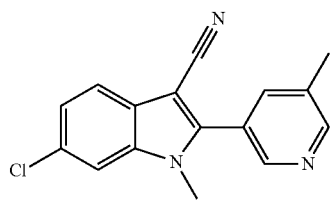 [SMILES: Cc1cncc(-c2c(C#N)c3ccc(Cl)cc3n2C)c1]

6-Chloro-2-(5-methyl-pyridin-3-yl)-1-methyl-1H-indole (Example 111) is processed according to the method described in Example 128 to give 6-chloro-2-(5-methyl-pyridin-3-yl)-1-methyl-1H-indole-3-carbonitrile. $^1$H NMR (400 MHz, DMSO-d$_6$) δ ppm 2.44 (s, 3H), 3.78 (s, 3H), 7.36 (dd, J=8.3, 1.8 Hz, 1H), 7.71 (d, J=8.3 Hz, 1H), 7.95 (d, J=1.5 Hz, 1H), 7.97 (s, 1H), 8.65 (d, J=1.5 Hz, 1H), 8.68 (d, J=2.0 Hz, 1H). HRMS (ESI) m/z 282.0803 [(M+H)$^+$ Calcd for $C_{16}H_{13}ClN_3$: 282.0798].

Example 133

6-Chloro-2-(5-trifluoromethyl-pyridin-3-yl)-1-methyl-1H-indole-3-carbonitrile

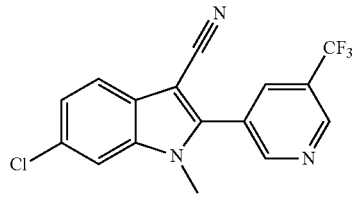 [SMILES: Cn1c(-c2cncc(C(F)(F)F)c2)c(C#N)c2ccc(Cl)cc21]

6-Chloro-2-(5-trifluoromethyl-pyridin-3-yl)-1-methyl-1H-indole (Example 112) is processed according to the method described in Example 128 to give 6-chloro-2-(5-trifluoromethyl-pyridin-3-yl)-1-methyl-1H-indole-3-carbonitrile. $^1$H NMR (400 MHz, DMSO-d$_6$) δ ppm 3.82 (s, 3H), 7.39 (dd, J=8.5, 1.9 Hz, 1H), 7.76 (d, J=8.3 Hz, 1H), 8.00 (d, J=1.8 Hz, 1H), 8.65 (s, 1H), 9.22 (d, J=2.0 Hz, 1H), 9.23 (d, J=1.3 Hz, 1H). HRMS (ESI) m/z 377.0790 [(M+H+CH$_3$CN)$^+$ Calcd for $C_{18}H_{13}ClF_3N_4$: 377.0781].

Example 134

5-Fluoro-2-(5-fluoro-pyridin-3-yl)-1-methyl-1H-indole-3-carbonitrile

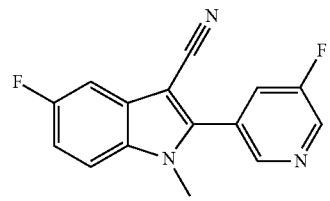 [SMILES: Cn1c(-c2cncc(F)c2)c(C#N)c2cc(F)ccc21]

5-Fluoro-2-(5-fluoro-pyridin-3-yl)-1-methyl-1H-indole (Example 118) is processed according to the method described in Example 128 to give 5-fluoro-2-(5-fluoro-pyridin-3-yl)-1-methyl-1H-indole-3-carbonitrile. $^1$H NMR (400 MHz, MeOD) δ ppm 3.87 (s, 3H), 7.26 (td, J=9.2, 2.4 Hz, 1H), 7.44 (dd, J=8.7, 2.4 Hz, 1H), 7.70 (dd, J=9.1, 4.3 Hz, 1H), 8.06 (dt, J=9.0, 2.4, 2.3 Hz, 1H), 8.72-8.79 (m, 2H). HRMS (ESI) m/z 270.0831 [(M+H)$^+$ Calcd for $C_{15}H_{10}F_2N_3$: 270.0843].

Example 135

5-(3-Cyano-1-methyl-1H-indol-2-yl)-nicotinic acid ethyl ester

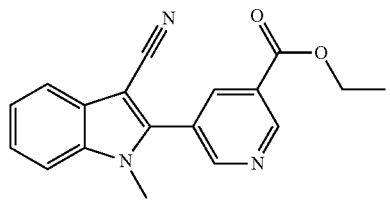 [SMILES: CCOC(=O)c1cncc(-c2c(C#N)c3ccccc3n2C)c1]

The product in Example 102 is processed according to the method described in Example 128 to give 5-(3-cyano-1-methyl-1H-indol-2-yl)-nicotinic acid ethyl ester. $^1$H NMR (400 MHz, MeOD) δ ppm 1.47 (t, J=7.1 Hz, 3H), 3.88 (s, 3H), 4.51 (q, J=7.2 Hz, 2H), 7.40 (t, J=7.6 Hz, 1H), 7.49 (td, J=7.7, 1.3 Hz, 1H), 7.69 (d, J=8.3 Hz, 1H), 7.76 (d, J=7.8 Hz, 1H), 8.69 (t, J=2.0 Hz, 1H), 9.09 (d, J=2.0 Hz, 1H), 9.34 (d, J=2.0 Hz, 1H). HRMS (ESI) m/z 306.1246 [(M+H)$^+$ Calcd for $C_{18}H_{16}N_3O_2$: 306.1243].

Example 136

6-Chloro-2-pyridin-3-yl-1-methyl-1H-indole-3-carbonitrile

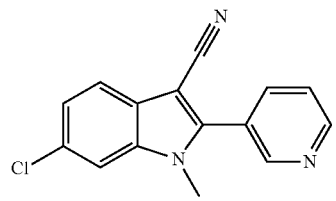 [SMILES: Cn1c(-c2cccnc2)c(C#N)c2ccc(Cl)cc21]

The product in Example 113 is processed according to the method described in Example 128 to give 6-chloro-2-pyridin-3-yl-1-methyl-1H-indole-3-carbonitrile. $^1$H NMR (400 MHz, DMSO-$d_6$) δ ppm 3.79 (s, 3H), 7.37 (dd, J=8.5, 1.9 Hz, 1H), 7.69 (dd, J=7.5, 4.4 Hz, 1H), 7.73 (d, J=8.6 Hz, 1H), 7.98 (d, J=1.5 Hz, 1H), 8.17 (dt, J=8.1, 2.0, 1.8 Hz, 1H), 8.82 (dd, J=4.9, 1.6 Hz, 1H), 8.90 (d, J=1.5 Hz, 1H). HRMS (ESI) m/z 268.0653 [(M+H)$^+$ Calcd for $C_{15}H_{11}ClN_3$: 268.0642].

Example 137

(a) 1-Methyl-2-(5-ethyl-pyridin-3-yl)-1H-indole

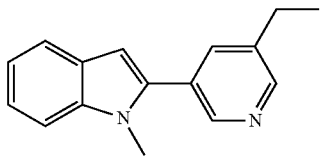 [SMILES: CCc1cncc(-c2cc3ccccc3n2C)c1]

To a solution of 1-methyl-2-(5-vinyl-pyridin-3-yl)-1H-indole (Example 105, 0.473 g, 2.02 mmol) in methanol (10 mL) is added palladium on carbon (0.215 g, 0.202 mmol). The reaction mixture is stirred at 55° C. under $H_2$ for 16 h. It is then cooled to room temperature and filtered through celite. The celite layer is washed with methanol thoroughly and the combined filtrate is concentrated in vacuo. The residue is purified by silica gel flash chromatography (heptane-ethyl acetate, 3:1) to afford 1-methyl-2-(5-ethyl-pyridin-3-yl)-1H-indole as a yellow oil. MS (ESI) m/z 237.24 (M+H)$^+$.

(b) 2-(5-Ethyl-pyridin-3-yl)-1-methyl-1H-indole-3-carbonitrile

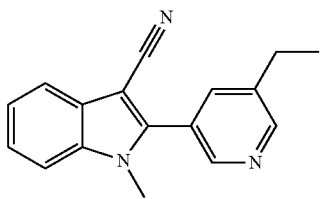 [SMILES: CCc1cncc(-c2c(C#N)c3ccccc3n2C)c1]

1-Methyl-2-(5-ethyl-pyridin-3-yl)-1H-indole is processed according to the method described in Example 128 to give 2-(5-ethyl-pyridin-3-yl)-1-methyl-1H-indole-3-carbonitrile. $^1$H NMR (400 MHz, MeOD) δ ppm 1.40 (t, J=7.6 Hz, 3H), 2.89 (q, J=7.7 Hz, 2H), 3.87 (s, 3H), 7.35-7.43 (m, 1H), 7.43-7.50 (m, 1H), 7.67 (d, J=8.3 Hz, 1H), 7.75 (dd, J=7.9, 0.8 Hz, 1H), 8.06 (t, J=2.1 Hz, 1H), 8.66 (d, J=1.9 Hz, 1H), 8.70 (d, J=2.0 Hz, 1H). HRMS (ESI) m/z 262.1351 [(M+H)$^+$ Calcd for $C_{17}H_{16}N_3$: 262.1344].

Example 138

(a) Methanesulfonic acid 5-bromo-pyridin-3-yl ester

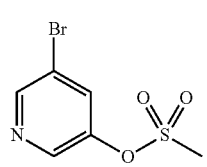

A flask is charged with 5-bromo-pyridin-3-ol (0.200 g, 1.126 mmol), potassium carbonate (0.212 g, 1.487 mmol) and acetone (3 mL). Methanesulfonyl chloride (0.143 g, 1.239 mmol) is then added dropwise. After 2 h, an other portion of methanesulfonyl chloride (0.071 g, 0.61 mmol) is added. After overnight stirring, the suspension is concentrated, diluted with ethyl acetate and filtered through a pad of silica gel. The filtrate is concentrated in vacuo to give a residue, which is purified by silica gel flash chromatography (heptane-ethyl acetate, 4:1 to 7:3) to give a mixture of product and starting material. The fractions are combined, washed three times with saturated aqueous sodium bicarbonate and dried over $MgSO_4$. Concentration in vacuo gives methanesulfonic acid 5-bromo-pyridin-3-yl ester as an oil. $^1$H NMR (400 MHz, CDCl$_3$) δ ppm 3.25 (s, 3H), 7.86 (m, 1H), 8.52 (d, J=2.3 Hz, 1H), 8.67 (d, J=1.8 Hz, 1H).

(b) Methanesulfonic acid 5-(1-methyl-1H-indol-2-yl)-pyridin-3-yl ester

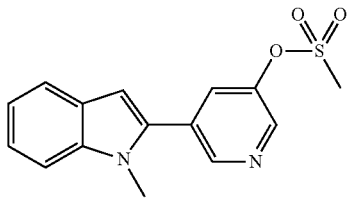 [SMILES: Cn1c(-c2cncc(OS(C)(=O)=O)c2)cc2ccccc21]

Methanesulfonic acid 5-bromo-pyridin-3-yl ester is processed according to the method described in Example 100 to give methanesulfonic acid 5-(1-methyl-1H-indol-2-yl)-pyridin-3-yl ester. (ESI) m/z 303.1 (M+H)$^+$.

(c) Methanesulfonic acid 5-(3-cyano-1-methyl-1H-indol-2-yl)-pyridin-3-yl ester

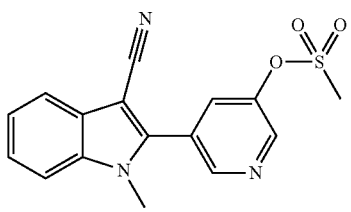 [SMILES: Cn1c(-c2cncc(OS(C)(=O)=O)c2)c(C#N)c2ccccc21]

Methanesulfonic acid 5-(1-methyl-1H-indol-2-yl)-pyridin-3-yl ester is processed according to the method described in Example 128 to give methanesulfonic acid 5-(3-cyano-1-methyl-1H-indol-2-yl)-pyridin-3-yl ester. $^1$H NMR (400 MHz, DMSO-$d_6$) δ ppm 3.57 (s, 3H), 3.84 (s, 3H), 7.35-7.40 (m, 1H), 7.43-7.48 (m, 1H), 7.74 (d, J=7.8 Hz, 1H), 7.79 (d, J=8.3 Hz, 1H), 8.30 (t, J=2.5 Hz, 1H), 8.85 (d, J=2.5 Hz, 1H), 8.94 (d, J=1.8 Hz, 1H). HRMS (ESI) m/z 328.0771 [(M+H)$^+$ Calcd for $C_{16}H_{14}N_3O_3S$: 328.0756].

Example 139

(a) Dimethyl-sulfamic acid 5-bromo-pyridin-3-yl ester

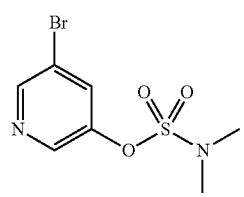

A flask is charged with 5-bromo-pyridin-3-ol (0.200 g, 1.126 mmol), potassium phosphate (0.631 g, 2.884 mmol) and acetone (5 mL) and cooled to 0° C. Dimethylsulfamoyl chloride (0.261 g, 1.802 mmol) is then added dropwise and the cooling bath is removed. After 2 h, the mixture is diluted with acetone, filtered and the filtrate is concentrated in vacuo. The residue is dissolved in THF (30 mL) and polymer-supported trisamine (3.85 mmol/g, 0.7 g, 2.7 mmol) is added. After 1 h, the mixture is filtered. Concentration in vacuo gives a residue which is purified by silica gel flash chromatography (heptane-ethyl acetate, 9:1 to 4:1) to give dimethyl-sulfamic acid 5-bromo-pyridin-3-yl ester as a solid. $^1$H NMR (400 MHz, CDCl$_3$) δ ppm 3.05 (s, 3H), 7.86 (m, 1H), 8.50 (d, J=2.3 Hz, 1H), 8.62 (d, J=1.9 Hz, 1H).

(b) Dimethyl-sulfamic acid 5-(1-methyl-1H-indol-2-yl)-pyridin-3-yl ester

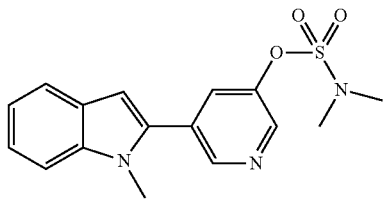 [SMILES: CN(C)S(=O)(=O)Oc1cncc(-c2cc3ccccc3n2C)c1]

Dimethyl-sulfamic acid 5-bromo-pyridin-3-yl ester is processed according to the method described in Example 100 to give dimethyl-sulfamic acid 5-(1-methyl-1H-indol-2-yl)-pyridin-3-yl ester. MS (ESI) m/z 332.1 (M+H)$^+$.

(c) Dimethyl-sulfamic acid 5-(3-cyano-1-methyl-1H-indol-2-yl)-pyridin-3-yl ester

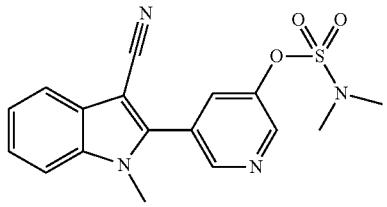 [SMILES: CN(C)S(=O)(=O)Oc1cncc(-c2c(C#N)c3ccccc3n2C)c1]

Dimethyl-sulfamic acid 5-(1-methyl-1H-indol-2-yl)-pyridin-3-yl ester is processed according to the method described in Example 128 to give dimethyl-sulfamic acid 5-(3-cyano-1-methyl-1H-indol-2-yl)-pyridin-3-yl ester. $^1$H NMR (400 MHz, DMSO-d$_6$) δ ppm 2.99 (s, 6H), 3.82 (s, 3H), 7.35-7.40 (m, 1H), 7.43-7.48 (m, 1H), 7.74 (d, J=7.8 Hz, 1H), 7.79 (d, J=8.3 Hz, 1H), 8.24 (dd, J=2.5, 1.8 Hz, 1H), 8.85 (d, J=2.5 Hz, 1H), 8.91 (d, J=1.8 Hz, 1H). HRMS (ESI) m/z 357.1018 [(M+H)$^+$ Calcd for C$_{17}$H$_{17}$N$_4$O$_3$S: 357.1021].

Example 140

6-Fluoro-2-pyridin-3-yl-1H-indole-3-carbonitrile

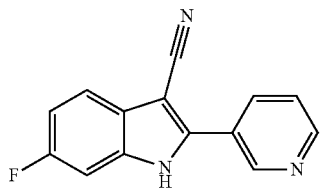 [SMILES: N#Cc1c(-c2cccnc2)[nH]c2cc(F)ccc12]

To a solution of 6-fluoro-2-pyridin-3-yl-1H-indole (Example 89, 212 mg, 1.0 mmol) in dichloromethane (90 mL) at ambient temperature is added chlorosulfonyl isocyanate (0.71 g, 5 mmol) and the mixture is stirred overnight. Anhydrous DMF (1 mL) is added. After 1 h, the solvent is removed in vacuo and the residue purified by HPLC using an Xbridge C18 with a gradient of acetonitrile in 0.1% NH$_4$OH to give 6-fluoro-2-pyridin-3-yl-1H-indole-3-carbonitrile as a white solid. $^1$H NMR (400 MHz, DMSO-d$_6$) δ ppm 7.12-7.21 (m, 1H), 7.39 (dd, J=9.5, 2.4 Hz, 1H), 7.64-7.74 (m, 2H), 8.27-8.35 (m, 1H), 8.73 (dd, J=4.9, 1.6 Hz, 1H), 9.14 (d, J=1.8 Hz, 1H), 12.89 (s, 1H). MS (ESI) m/z 238.0 (M+H)$^+$.

Example 141

2-Pyridin-3-yl-1H-indole-3,5-dicarbonitrile

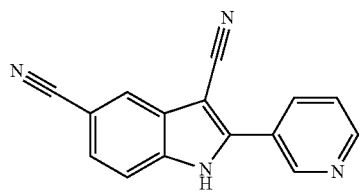 [SMILES: N#Cc1ccc2[nH]c(-c3cccnc3)c(C#N)c2c1]

2-Pyridin-3-yl-1H-indole-5-carbonitrile (Example 8) is processed according to the method described in Example 140, using acetonitrile instead of dichloromethane, to give 2-pyridin-3-yl-1H-indole-3,5-dicarbonitrile. $^1$H NMR (400 MHz, MeOD) δ ppm 7.68 (dd, J=8.6 Hz, 1H), 7.72 (dd, J=8.1, 4.8 Hz, 1H), 7.75 (d, J=8.3 Hz, 1H), 8.17 (s, 1H), 8.47 (dt, J=8.1, 1.9 Hz, 1H), 8.76 (dd, J=4.8, 1.5 Hz, 1H), 9.19 (d, J=1.5 Hz, 1H). HRMS (ESI) m/z 245.0823 [(M+H) calcd for C$_{15}$H$_9$N$_4$: 245.0827].

Example 142

5-Chloro-2-pyridin-3-yl-1H-indole-3-carbonitrile

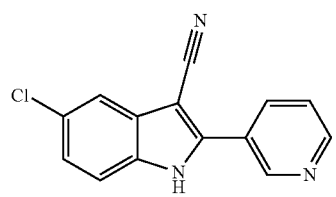 [SMILES: N#Cc1c(-c2cccnc2)[nH]c2ccc(Cl)cc12]

5-Chloro-2-pyridin-3-yl-1H-indole (Example 87) is processed according to the method described in Example 140, using acetonitrile instead of dichloromethane, to give 5-chloro-2-pyridin-3-yl-1H-indole-3-carbonitrile. $^1$H NMR (400 MHz, MeOD) δ ppm 7.36 (dd, J=8.6, 2.0 Hz, 1H), 7.57 (d, J=8.6 Hz, 1H), 7.65-7.77 (m, 2H), 8.43 (dt, J=8.1, 2.0 Hz, 1H), 8.72 (d, J=4.8 Hz, 1H), 9.16 (s, 1H). HRMS (ESI) m/z 254.0495 [(M+H)⁺ calcd for $C_{14}H_9ClN_3$: 254.0485].

Example 143

2-(4-Methoxy-pyridin-3-yl)-1H-indole-3,5-dicarbonitrile

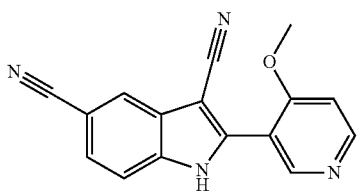 [SMILES: COc1ccncc1-c1[nH]c2ccc(C#N)cc2c1C#N]

2-(4-Methoxy-pyridin-3-yl)-1H-indole-5-carbonitrile (Example 128) is processed according to the method described in Example 140, using acetonitrile instead of dichloromethane, to give 2-(4-methoxy-pyridin-3-yl)-1H-indole-3,5-dicarbonitrile. MS (ESI) m/z 275.08 (M+H)⁺.

Example 144

2-(5-Fluoro-pyridin-3-yl)-1H-indole-3-carbonitrile

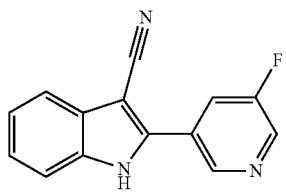 [SMILES: N#Cc1c(-c2cncc(F)c2)[nH]c2ccccc12]

2-(5-Fluoro-pyridin-3-yl)-1H-indole (Example 92) is processed according to the method described in Example 140, using a mixture of dichloromethane and acetonitrile instead of dichloromethane, to give 2-(5-fluoro-pyridin-3-yl)-1H-indole-3-carbonitrile. MS (ESI) m/z 238.0 (M+H)⁺.

Example 145

6-Fluoro-1-methyl-2-pyridin-3-yl-1H-indole-3-carbonitrile

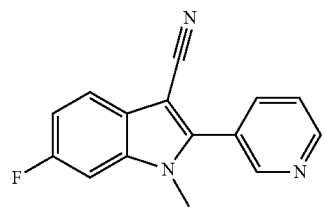 [SMILES: Cn1c(-c2cccnc2)c(C#N)c2ccc(F)cc21]

A flask is charged with 6-fluoro-2-pyridin-3-yl-1H-indole-3-carbonitrile (Example 140, 50 mg, 0.21 mmol) and DMF (2 mL), and 60% sodium hydride (25 mg, 0.63 mmol) is added. The mixture is stirred at room temperature for 30 min before addition of iodomethane (45 mg, 0.315 mmol). After 1 h, saturated NaHCO₃ aqueous solution (3 mL) is added to quench the reaction and the mixture is filtered and purified on Xbridge C18 eluting with a 9:1 to 1:9 water-acetonitrile gradient to give 6-fluoro-1-methyl-2-pyridin-3-yl-1H-indole-3-carbonitrile. ¹H NMR (400 MHz, DMSO-d₆) δ ppm 3.77 (s, 3H), 7.19-7.26 (m, 1H), 7.66-7.76 (m, 3H), 8.14-8.19 (m, 1H), 8.80 (dd, J=4.9, 1.6 Hz, 1H), 8.89 (dd, J=2.3, 0.8 Hz, 1H). HRMS (ESI) m/z 293.1210 [(M+H+CH₃CN)⁺ calcd for $C_{17}H_{14}FN_4$: 293.1203].

Example 146

1-Methyl-2-pyridin-3-yl-1H-indole-3,5-dicarbonitrile

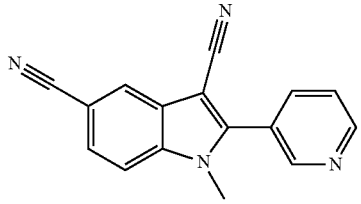 [SMILES: Cn1c(-c2cccnc2)c(C#N)c2cc(C#N)ccc21]

2-Pyridin-3-yl-1H-indole-3,5-dicarbonitrile (Example 141) is processed according to the method described in Example 145 to give 1-methyl-2-pyridin-3-yl-1H-indole-3,5-dicarbonitrile. ¹H NMR (400 MHz, MeOD) δ ppm 3.90 (s, 3H), 7.65-7.79 (m, 2H), 7.87 (d, J=8.6 Hz, 1H), 8.20 (s, 1H), 8.22 (dt, J=8.0, 1.9, 1.8 Hz, 1H), 8.83 (dd, J=4.9, 1.6 Hz, 1H), 8.92 (d, J=2.0 Hz, 1H). HRMS (ESI) m/z 259.0979 [(M+H)⁺ calcd for $C_{16}H_{11}N_4$: 259.0984].

Example 147

5-Chloro-1-methyl-2-pyridin-3-yl-1H-indole-3-carbonitrile

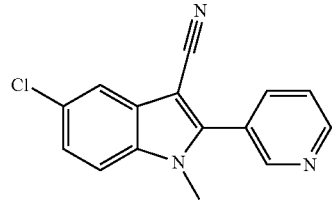 [SMILES: Cn1c(-c2cccnc2)c(C#N)c2cc(Cl)ccc21]

5-Chloro-2-pyridin-3-yl-1H-indole-3-carbonitrile (Example 142) is processed according to the method described in Example 145 to give 5-chloro-1-methyl-2-pyridin-3-yl-1H-indole-3-carbonitrile. ¹H NMR (400 MHz, MeOD) δ ppm 3.86 (s, 3H), 7.44 (dd, J=8.8, 2.0 Hz, 1H), 7.68 (d, J=8.8 Hz, 1H), 7.71-7.81 (m, 2H), 8.20 (dt, J=8.0, 1.9 Hz, 1H), 8.81 (dd, J=4.9, 1.6 Hz, 1H), 8.89 (d, J=1.5 Hz, 1H). HRMS (ESI) m/z 268.0646 [(M+H)⁺ calcd for $C_{15}H_{11}ClN_3$: 268.0641].

Example 148

1-Methyl-2-(4-methoxy-pyridin-3-yl)-1H-indole-3,5-dicarbonitrile

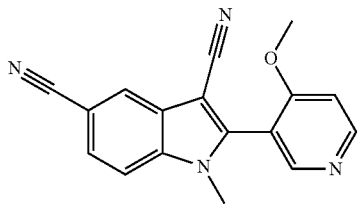 [SMILES: COc1ccncc1-c1c(C#N)c2cc(C#N)ccc2n1C]

2-(4-methoxy-pyridin-3-yl)-1H-indole-3,5-dicarbonitrile (Example 143) is processed according to the method described in Example 145 to give 1-methyl-2-(4-methoxy-pyridin-3-yl)-1H-indole-3,5-dicarbonitrile. $^1$H NMR (400 MHz, DMSO-d$_6$) δ ppm 3.69 (s, 3H), 3.94 (s, 3H), 7.38 (d, J=5.8 Hz, 1H), 7.79 (dd, J=8.6, 1.5 Hz, 1H), 7.95 (dd, J=8.7, 0.6 Hz, 1H), 8.27 (dd, J=1.5, 0.6 Hz, 1H), 8.57 (s, 1H), 8.72 (d, J=5.8 Hz, 1H). HRMS (ESI) m/z 289.1096 [(M+H) calcd for C$_{17}$H$_{13}$N$_4$O: 289.1089].

Example 149

1-Methyl-2-(5-fluoro-pyridin-3-yl)-1H-indole-3-carbonitrile

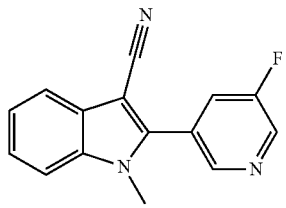 [SMILES: Cn1c(-c2cncc(F)c2)c(C#N)c2ccccc21]

2-(5-Fluoro-pyridin-3-yl)-1H-indole-3-carbonitrile (Example 144) is processed according to the method described in Example 145 to give 1-methyl-2-(5-fluoro-pyridin-3-yl)-1H-indole-3-carbonitrile. $^1$H NMR (400 MHz, DMSO-d$_6$) δ ppm 3.80 (s, 3H), 7.30 (td, J=9.3, 2.5 Hz, 1H), 7.52 (dd, J=9.0, 2.4 Hz, 1H), 7.69 (dd, J=8.0, 4.9 Hz, 1H), 7.82 (dd, J=9.1, 4.3 Hz, 1H), 8.17 (dt, J=8.1, 2.0, 1.8 Hz, 1H), 8.81 (dd, J=4.8, 1.5 Hz, 1H), 8.90 (d, J=1.5 Hz, 1H). HRMS (ESI) m/z 252.0948 [(M+H) calcd for C$_{15}$H$_{11}$FN$_3$: 252.0937].

Example 150

(a) 1-(5-Bromo-pyridin-3-ylmethyl)-morpholine

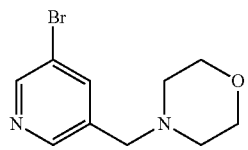 [SMILES: Brc1cncc(CN2CCOCC2)c1]

To a solution of 3-bromo-5-carboxaldehyde pyridine (0.400 g, 2.086 mmol) in dichloroethane (10 mL) at 0° C. is added morpholine (0.275 g, 3.129 mmol), followed with Na(OAc)$_3$BH (0.931 g, 4.172 mmol). After 2 h, the cooling bath is removed. After stirring overnight, the mixture is diluted with dichloromethane (0.2 L) and washed twice with water and brine. The combined aqueous phase is extracted (twice) with dichloromethane. The combined organic phase is dried over MgSO$_4$, filtered and concentrated to give a residue which is purified by silica gel flash chromatography (dichloromethane-methanol, 99:1 to 49:1) gives 1-(5-bromo-pyridin-3-ylmethyl)-morpholine as a colorless oil. MS (ESI) m/z 257 and 259 (M+H)$^+$.

(b) 6-Chloro-2-(5-morpholin-4-ylmethyl-pyridin-3-yl)-1H-indole

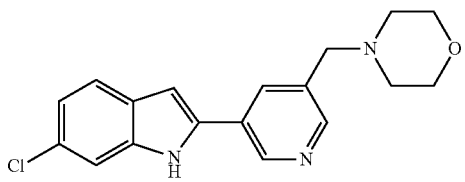 [SMILES: Clc1ccc2cc(-c3cncc(CN4CCOCC4)c3)[nH]c2c1]

1-(5-Bromo-pyridin-3-ylmethyl)-morpholine and 6-chloro-1-Boc-indole-2-boronic acid are processed according to the method described in Example 91 to give 6-chloro-2-(5-morpholin-4-ylmethyl-pyridin-3-yl)-1H-indole. MS (ESI) m/z 328.2 (M+H)$^+$.

(c) 6-Chloro-1-methyl-2-(5-morpholin-4-ylmethyl-pyridin-3-yl)-1H-indole

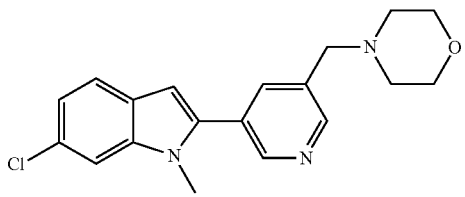 [SMILES: Cn1c(-c2cncc(CN3CCOCC3)c2)cc2ccc(Cl)cc21]

6-chloro-2-(5-morpholin-4-ylmethyl-pyridin-3-yl)-1H-indole is processed according to the method described in Example 109 to afford 6-chloro-1-methyl-2-(5-morpholin-4-ylmethyl-pyridin-3-yl)-1H-indole. $^1$H NMR (400 MHz, MeOD) δ ppm 2.52-2.60 (m, 4H), 3.70 (s, 2H), 3.72-3.77 (m, 4H), 3.79 (s, 3H), 6.70 (s, 1H), 7.11 (dd, J=8.3, 1.8 Hz, 1H), 7.53 (s, 1H), 7.59 (d, J=8.6 Hz, 1H), 8.06 (t, J=2.0 Hz, 1H), 8.60 (d, J=1.8 Hz, 1H), 8.69 (d, J=2.0 Hz, 1H). HRMS (ESI) m/z 342.1369 [(M+H)$^+$ Calcd for C$_{19}$H$_{21}$ClN$_3$O: 342.1373].

Example 151

(a) 1-(5-Bromo-pyridin-3-ylmethyl)-4-methyl-piperazine

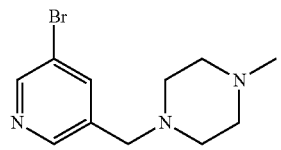

To a solution of 3-bromo-5-carboxaldehyde pyridine (0.400 g, 2.086 mmol) in dichloroethane (10 mL) at 0° C. is added 1-methylpiperazine (0.317 g, 3.129 mmol), followed with Na(OAc)$_3$BH (0.931 g, 4.172 mmol). After 2 h, the cooling bath is removed. After stirring overnight, the mixture is diluted with dichloromethane (0.2 L) and washed with saturated aqueous sodium bicarbonate. The organic phase is dried over MgSO$_4$, filtered and concentrated to give 1-(5-bromo-pyridin-3-ylmethyl)-4-methyl-piperazine as a yellow solid. (ESI) m/z 270 and 272 (M+H)$^+$.

(b) 6-Chloro-2-[5-(4-methyl-piperazin-1-ylmethyl)-pyridin-3-yl]-1H-indole

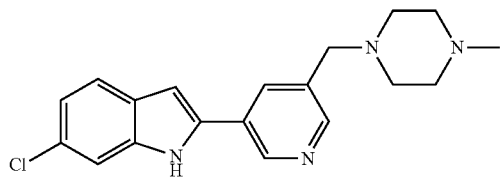 [SMILES: CN1CCN(Cc2cncc(-c3cc4ccc(Cl)cc4[nH]3)c2)CC1]

1-(5-Bromo-pyridin-3-ylmethyl)-4-methyl-piperazine and 6-chloro-1-Boc-indole-2-boronic acid are processed according to the method described in Example 91 to give 6-chloro-2-[5-(4-methyl-piperazin-1-ylmethyl)-pyridin-3-yl]-1H-indole. (ESI) m/z 341.1 (M+H)$^+$.

(c) 6-Chloro-1-methyl-2-[5-(4-methyl-piperazin-1-ylmethyl)-pyridin-3-yl]-1H-indole

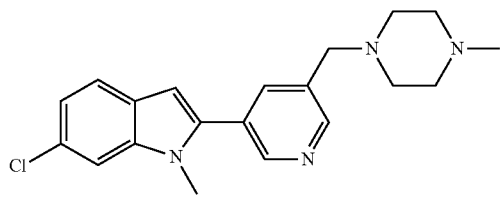 [SMILES: CN1CCN(Cc2cncc(-c3cc4ccc(Cl)cc4n3C)c2)CC1]

6-Chloro-1-methyl-2-[5-(4-methyl-piperazin-1-ylmethyl)-pyridin-3-yl]-1H-indole is processed according to the method described in Example 109 to afford 6-chloro-1-methyl-2-[5-(4-methyl-piperazin-1-ylmethyl)-pyridin-3-yl]-1H-indole. $^1$H NMR (400 MHz, MeOD) δ ppm 2.33 (s, 3H), 2.60 (br. s., 8H), 3.73 (s, 2H), 3.79 (s, 3H), 6.70 (s, 1H), 7.11 (dd, J=8.5, 1.9 Hz, 1H), 7.53 (d, J=1.8 Hz, 1H), 7.59 (d, J=8.3 Hz, 1H), 8.05 (t, J=2.0 Hz, 1H), 8.59 (d, J=2.0 Hz, 1H), 8.69 (d, J=2.0 Hz, 1H). HRMS (ESI) m/z 355.1688 [(M+H)$^+$ Calcd for C$_{20}$H$_{24}$ClN$_4$: 355.1689].

Example 152

6-Chloro-1-methyl-2-(5-morpholin-4-ylmethyl-pyridin-3-yl)-1H-indole-3-carbonitrile

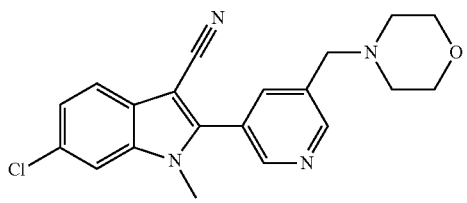 [SMILES: Cn1c(-c2cncc(CN3CCOCC3)c2)c(C#N)c2ccc(Cl)cc21]

6-Chloro-1-methyl-2-(5-morpholin-4-ylmethyl-pyridin-3-yl)-1H-indole (Example 150) is processed according to the method described in Example 128 to give 6-chloro-1-methyl-2-(5-morpholin-4-ylmethyl-pyridin-3-yl)-1H-indole-3-carbonitrile. $^1$H NMR (400 MHz, MeOD) δ ppm 2.51-2.66 (m, 4H), 3.69-3.79 (m, 6H), 3.85 (s, 3H), 7.38 (dd, J=8.3, 1.8 Hz, 1H), 7.72 (d, J=8.3 Hz, 1H), 7.77 (d, J=1.5 Hz, 1H), 8.20 (t, J=2.0 Hz, 1H), 8.77 (dd, J=13.3, 2.1 Hz, 2H). HRMS (ESI) m/z 367.1321 [(M+H)$^+$ Calcd for C$_{20}$H$_{20}$ClN$_4$O: 367.1326].

Example 153

6-Chloro-1-methyl-2-[5-(4-methyl-piperazin-1-ylmethyl)-pyridin-3-yl]-1H-indole-3-carbonitrile

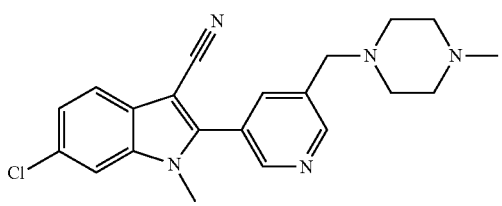 [SMILES: CN1CCN(Cc2cncc(-c3c(C#N)c4ccc(Cl)cc4n3C)c2)CC1]

6-Chloro-1-methyl-2-[5-(4-methyl-piperazin-1-ylmethyl)-pyridin-3-yl]-1H-indole (Example 151) is processed according to the method described in Example 128 to give 6-chloro-1-methyl-2-[5-(4-methyl-piperazin-1-ylmethyl)-pyridin-3-yl]-1H-indole-3-carbonitrile. $^1$H NMR (400 MHz, MeOD) δ ppm 2.34 (s, 3H), 2.61 (br. s., 8H), 3.77 (s, 2H), 3.85 (s, 3H), 7.38 (dd, J=8.6, 1.8 Hz, 1H), 7.72 (d, J=8.6 Hz, 1H), 7.77 (d, J=1.5 Hz, 1H), 8.18 (t, J=2.0 Hz, 1H), 8.75 (d, J=2.0 Hz, 1H), 8.79 (d, J=2.3 Hz, 1H). HRMS (ESI) m/z 380.1624 [(M+H)$^+$ Calcd for C$_{21}$H$_{23}$ClN$_5$: 380.1642].

Example 154

(a) 2-[4-(tert-Butyl-dimethyl-silanyloxymethyl)-pyridin-3-yl]-1-methyl-1H-indole

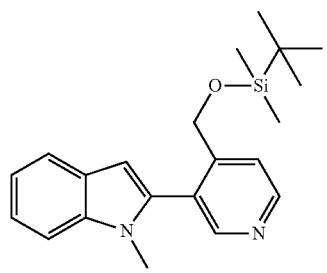 [SMILES: Cn1c(-c2cnccc2CO[Si](C)(C)C(C)(C)C)cc2ccccc21]

A flask is charged with [3-(1-methyl-1H-indol-2-yl)-pyridin-4-yl]-methanol (Example 106, 0.270 g, 1.13 mmol), tert-butyl di-methylsilyl chloride (0.187 g, 1.24 mmol), imidazole (0.231 g, 3.39 mmol), DMAP (0.025 g, 0.193 mmol) and DMF (3 mL). The reaction is stirred at room temperature for 3 h. Water is added and the mixture is extracted with ethyl acetate. The combined organic layer is dried over sodium sulfate and concentrated in vacuo to afford 2-[4-(tert-butyl-dimethyl-silanyloxymethyl)-pyridin-3-yl]-1-methyl-1H-indole as an oil, which is used in the next step with no further purification. MS (ESI) m/z 353.31 (M+H)$^+$ (b) 2-(4-Hydroxymethyl-pyridin-3-yl)-1-methyl-1H-indole-3-carbonitrile

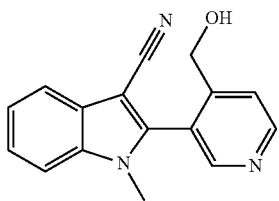 [SMILES: Cn1c(-c2cnccc2CO)c(C#N)c2ccccc21]

To a solution of 2-[4-(tert-butyl-dimethyl-silanyloxymethyl)-pyridin-3-yl]-1-methyl-1H-indole (0.263 g, 0.747 mmol) in DCM (5 mL) is added chlorosulfonyl isocyanate (0.162 mL, 1.867 mmol). After 5 min, DMF (1 mL) is added. After another 30 min, the reaction is concentrated under vacuo to afford 2-[4-(tert-butyl-dimethyl-silanyloxymethyl)-pyridin-3-yl]-1-methyl-1H-indole-3-carbonitrile as a light yellow solid, which is redissolved in DCM (3 mL). 4 M HCl in 1,4-dioxane (1 mL) is added, and the mixture is stirred at room temperature for 30 min. Purification by reverse phase HPLC with Xbridge Shield RP18 column and a 0.1% aqueous NH$_4$OH in acetonitrile gradient affords 2-(4-hydroxymethyl-pyridin-3-yl)-1-methyl-1H-indole-3-carbonitrile as a solid. $^1$H NMR (400 MHz, MeOD) δ ppm 3.67 (s, 3H), 4.44-4.67 (m, 2H), 7.39 (t, J=7.6 Hz, 1H), 7.47 (t, J=8.3 Hz, 1H), 7.66 (d, J=8.3 Hz, 1H), 7.74 (d, J=7.8 Hz, 1H), 7.87 (d, J=5.3 Hz, 1H), 8.60 (s, 1H), 8.80 (d, J=5.3 Hz, 1H). HRMS (ESI) m/z 264.1142 [(M+H)$^+$ Calcd for C$_{16}$H$_{14}$N$_3$O: 264.11379].

Example 155

3-Bromo-2-(4-hydroxy-pyridin-3-yl)-1H-indole-5-carbonitrile

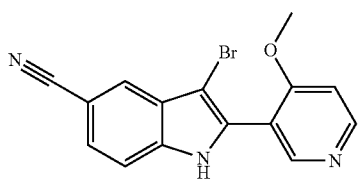 [SMILES: COc1ccncc1-c1[nH]c2ccc(C#N)cc2c1Br]

A flask is charged with 2-(4-methoxy-pyridin-3-yl)-1H-indole-5-carbonitrile (Example 90, 190 mg, 0.80 mmol) and DCE (8 mL), and 1.0 M BBr$_3$ in DCM (4.8 mL, 4.8 mmol) is added. The mixture is stirred at room temperature overnight. The reaction mixture is poured into saturated aqueous NaHCO$_3$ and extracted with DCM. The aqueous phase is concentrated, acidified with 1M HCl in water and concentrated in vacuo. The residue is purified with an Xbridge C18 eluting with a 1:9 to 9:1 acetonitrile-water gradient to give 3-bromo-2-(4-hydroxy-pyridin-3-yl)-1H-indole-5-carbonitrile. $^1$H NMR (400 MHz, DMSO-d$_6$) δ ppm 6.40 (d, J=7.1 Hz, 1H), 7.48 (dd, J=8.5, 1.6 Hz, 1H), 7.71 (d, J=8.6 Hz, 1H), 7.81 (dd, J=7.1, 1.3 Hz, 1H), 7.86 (d, J=1.0 Hz, 1H), 8.67 (d, J=1.3 Hz, 1H). HRMS (ESI) m/z 313.9932 [(M+H) calcd for C$_{14}$H$_9$BrN$_3$O: 313.9929].

Example 156

(a) 5-(1-Methyl-1H-indol-2-yl)-nicotinic acid

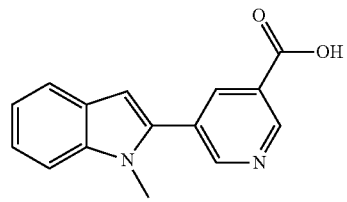 [SMILES: Cn1c(-c2cncc(C(=O)O)c2)cc2ccccc21]

To a solution of 5-(1-methyl-1H-indol-2-yl)-nicotinic acid ethyl ester (Example 102, 0.156 g, 0.55 mmol) and MeOH (5 mL) is added aqueous 1M LiOH (1.4 mL, 1.39 mmol). The reaction is stirred at room temperature for 2.5 h. Purification by reverse phase HPLC with Xbridge Shield RP18 column and a 0.1% aqueous NH$_4$OH in acetonitrile gradient gives 5-(1-methyl-1H-indol-2-yl)-nicotinic acid. MS (ESI) m/z 253.34 (M+H)$^+$.

(b) 5-(1-Methyl-1H-indol-2-yl)-nicotinamide

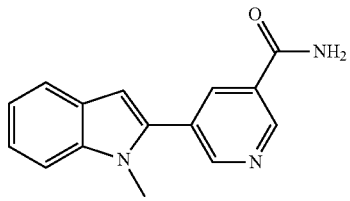 [SMILES: Cn1c(-c2cncc(C(N)=O)c2)cc2ccccc21]

A flask is charged with 5-(1-methyl-1H-indol-2-yl)-nicotinic acid (0.037 g, 0.146 mmol), HOBT (0.024 g, 0.175 mmol), EDCl (0.034 g, 0.175 mmol), DIPEA (0.076 mL, 0.439 mmol) and DMF (3 mL). Ammonium chloride (0.012 g, 0.219 mmol) is added and the reaction is stirred at room temperature overnight. Purification by reverse phase HPLC with Xbridge Shield RP18 column and a 0.1% aqueous NH$_4$OH in acetonitrile gradient gives 5-(1-methyl-1H-indol-2-yl)-nicotinamide. $^1$H NMR (400 MHz, MeOD) δ ppm 3.85 (s, 3H), 6.77 (d, J=0.6 Hz, 1H), 7.08-7.19 (m, 1H), 7.29 (ddd, J=8.2, 7.1, 1.1 Hz, 1H), 7.50 (dd, J=8.3, 0.7 Hz, 1H), 7.65 (d, J=8.0 Hz, 1H), 8.49 (t, J=2.1 Hz, 1H), 8.95 (d, J=2.1 Hz, 1H), 9.09 (d, J=2.1 Hz, 1H). HRMS (ESI) m/z 252.1145 [(M+H)$^+$ Calcd for C$_{15}$H$_{14}$N$_3$O: 252.1137].

Example 157

2-[5-(1-Methyl-1H-indol-2-yl)-pyridin-3-yloxy]-ethanol

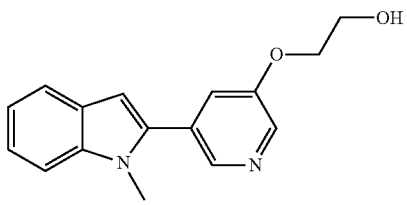 [SMILES: Cn1c(-c2cncc(OCCO)c2)cc2ccccc21]

To a solution of 5-(1-methyl-1H-indol-2-yl)-pyridin-3-ol (Example 108, 0.300 g, 1.33 mmol), potassium carbonate (0.462 g, 3.34 mmol) and DMF (3 mL) is added (2-chloroethoxy)-trimethylsilane (0.324 mL, 2.00 mmol) and the reaction is stirred at 70° C. overnight and at 100° C. for another 24 h. It is then cooled to room temperature, diluted with ethyl acetate and washed with water. The organic layer is dried over sodium sulfate and concentrated in vacuo to afford a residue which is purified by reverse phase HPLC with Xbridge Shield RP18 column and a gradient of 0.1% aqueous $NH_4OH$ in acetonitrile. The resulting oil is dissolved in diethyl ether and a few drops of concentrated HCl are added. Lyophilization gives 2-[5-(1-methyl-1H-indol-2-yl)-pyridin-3-yloxy]-ethanol as the HCl salt. $^1$H NMR (400 MHz, MeOD) δ ppm (HCl salt) 3.78 (s, 3H), 3.93 (t, J=4.8 Hz, 2H), 4.22 (t, J=4.5 Hz, 2H), 6.65 (s, 1H), 7.09 (t, J=7.5 Hz, 1H), 7.23 (ddd, J=7.6, 1.1 Hz, 1H), 7.44 (d, J=8.1 Hz, 1H), 7.58 (d, J=7.8 Hz, 1H), 7.62 (dd, J=2.8, 1.8 Hz, 1H), 8.31 (d, J=2.8 Hz, 1H), 8.34 (d, J=1.5 Hz, 1H). HRMS (ESI) m/z 269.1302 [(M+H)$^+$ Calcd for $C_{16}H_{17}N_2O_2$: 269.1290].

Example 158

(a) 6-Chloro-2-(5-hydroxy-pyridin-3-yl)-indole-1-carboxylic acid tert-butyl ester

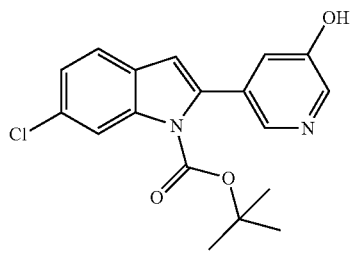 [SMILES: CC(C)(C)OC(=O)n1c(-c2cncc(O)c2)cc2ccc(Cl)cc21]

A microwave flask is charged with 6-chloro-1-Boc-indole-2-boronic acid (1.91 g, 6.46 mmol), 3-hydroxy-5-bromopyridine (0.750 g, 4.31 mmol), potassium phosphate (1.83 g, 8.62 mmol) and DMF (15 mL). The flask is evacuated and filled with nitrogen thrice and Pd(PPh$_3$)$_4$ (0.250 g, 0.215 mmol) is added. The flask is evacuated and filled with nitrogen thrice again, and heated to 110° C. under microwave irradiation for 45 min. Pd(PPh$_3$)$_4$ (0.100 g, 0.086 mmol) is added and the vial is heated again to 110° C. under microwave irradiation for 45 min. The mixture is then diluted with ethyl acetate and washed with water thrice. The organic layer is dried over sodium sulfate and concentrated in vacuo. The residue is purified by silica gel flash chromatography (dichloromethane-methanol, 19:1) to afford 6-chloro-2-(5-hydroxy-pyridin-3-yl)-indole-1-carboxylic acid tert-butyl ester as a solid. MS (ESI) m/z 345.06 (M+H)$^+$ (b) 6-Chloro-2-(5-diethylsulfamoyloxy-pyridin-3-yl)-indole-1-carboxylic acid tert-butyl ester

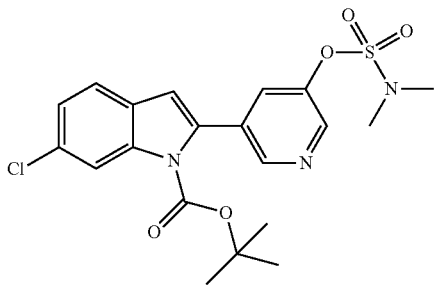 [SMILES: CN(C)S(=O)(=O)Oc1cncc(-c2cc3ccc(Cl)cc3n2C(=O)OC(C)(C)C)c1]

A flask is charged with 6-chloro-2-(5-hydroxy-pyridin-3-yl)-indole-1-carboxylic acid tert-butyl ester (0.200 g, 0.581 mmol) and acetone (5 mL). Diethylaminosulfamoyl chloride (0.150 g, 0.872 mmol) and potassium phosphate (0.308 g, 1.45 mmol) are added and the reaction is stirred at room temperature overnight. The mixture is then concentrated in vacuo. The residue is dissolved in DCM and washed with water. The organic layer is dried over sodium sulfate and concentrated to afford 6-chloro-2-(5-diethylsulfamoyloxy-pyridin-3-yl)-indole-1-carboxylic acid tert-butyl ester as an oil, which is used without further purification. MS (ESI) m/z 480.1 (M+H)$^+$.

(c) Diethyl-sulfamic acid 5-(6-chloro-1H-indol-2-yl)-pyridin-3-yl ester

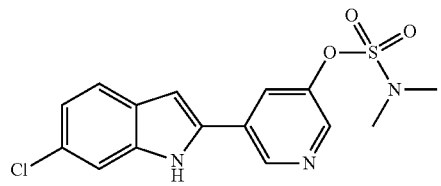 [SMILES: CN(C)S(=O)(=O)Oc1cncc(-c2cc3ccc(Cl)cc3[nH]2)c1]

6-Chloro-2-(5-diethylsulfamoyloxy-pyridin-3-yl)-indole-1-carboxylic acid tert-butyl ester is redissolved in DCM (2 mL) and trifluoroacetic acid (2 mL) is added. After 1 h, saturated aqueous sodium bicarbonate is added and following extraction with dichloromethane, the organic layer is dried over sodium sulfate and concentrated to give diethyl-sulfamic acid 5-(6-chloro-1H-indol-2-yl)-pyridin-3-yl ester, which is used in the next step without further purification. MS (ESI) m/z 378.1 (M+H)$^+$ (d) Diethyl-sulfamic acid 5-(6-chloro-1-methyl-1H-indol-2-yl)-pyridin-3-yl ester

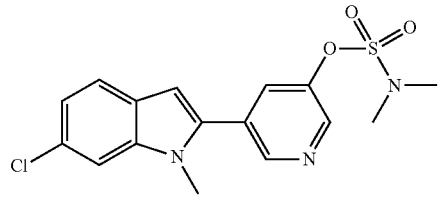 [SMILES: CN(C)S(=O)(=O)Oc1cncc(-c2cc3ccc(Cl)cc3n2C)c1]

A flask is charged with diethyl-sulfamic acid 5-(6-chloro-1H-indol-2-yl)-pyridin-3-yl ester (0.175 g, 0.560 mmol) and DMF (5 mL). Dimethyl carbonate (0.116 mL, 1.38 mmol) and potassium carbonate (0.035 g, 0.253 mmol) are added and the reaction is stirred at 150° C. overnight. The reaction mixture is cooled to room temperature, diluted with ethyl acetate and washed with water. The organic layer is dried over sodium sulfate and concentrated in vacuo. The residue is purified by flash chromatography (heptane-ethyl acetate, 3:1)

to afford diethyl-sulfamic acid 5-(6-chloro-1-methyl-1H-indol-2-yl)-pyridin-3-yl ester as a yellow solid. MS (ESI) m/z 394.04 (M+H)+

(e) Diethyl-sulfamic acid 5-(6-chloro-3-cyano-1-methyl-1H-indol-2-yl)-pyridin-3-yl ester

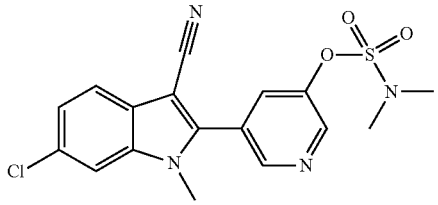 [SMILES: CN(C)S(=O)(=O)Oc1cncc(-c2c(C#N)c3ccc(Cl)cc3n2C)c1]

Diethyl-sulfamic acid 5-(6-chloro-1-methyl-1H-indol-2-yl)-pyridin-3-yl ester is processed according to the method described in Example 128 to give diethyl-sulfamic acid 5-(6-chloro-3-cyano-1-methyl-1H-indol-2-yl)-pyridin-3-yl ester. $^1$H NMR (400 MHz, MeOD) δ ppm 1.28 (t, J=7.2 Hz, 6H), 3.51 (q, J=7.1 Hz, 4H), 3.85 (s, 3H), 7.39 (dd, J=8.5, 1.9 Hz, 1H), 7.74 (d, J=8.6 Hz, 1H), 7.78 (d, J=1.8 Hz, 1H), 8.15 (t, J=2.0 Hz, 1H), 8.77 (d, J=2.5 Hz, 1H), 8.84 (d, J=1.8 Hz, 1H). HRMS (ESI) m/z 419.0966 [(M+H)+ Calcd for $C_{19}H_{20}ClN_4O_3S$: 419.0945].

Example 159

(a) N-Ethyl-N-benzylaminosulfamoyl chloride

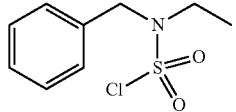

To a solution of sulfuryl chloride (1.19 mL, 14.8 mmol) in dichloromethane (10 mL) is added N-ethyl-N-benzylamine (2.0 g, 14.7 mmol) at −10° C. The cooling bath is removed after 30 min and the mixture is stirred overnight. The mixture is washed with water and following back-extraction with DCM, the combined organic layer is dried over sodium sulfate and concentrated in vacuo to give N-ethyl-N-benzylaminosulfamoyl chloride. $^1$H NMR (400 MHz, CDCl$_3$) δ ppm 1.19 (t, J=7.2 Hz, 3H), 3.40 (q, J=7.3 Hz, 2H), 4.50 (br. s., 2H), 7.32-7.48 (m, 5H).

(b) Benzyl-ethyl-sulfamic acid 5-(6-chloro-1H-indol-2-yl)-pyridin-3-yl ester

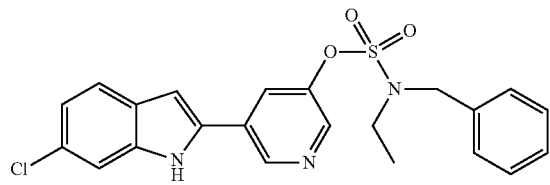 [SMILES: CCN(Cc1ccccc1)S(=O)(=O)Oc1cncc(-c2cc3ccc(Cl)cc3[nH]2)c1]

N-Ethyl-N-benzylaminosulfamoyl chloride and 6-chloro-2-(5-hydroxy-pyridin-3-yl)-indole-1-carboxylic acid tert-butyl ester (Example 158a) are processed according to the method described in Example 158b to give 2-[5-(benzyl-ethyl-sulfamoyloxy)-pyridin-3-yl]-6-chloro-indole-1-carboxylic acid tert-butyl ester. The crude product is loaded onto silica gel and heated to 50° C. overnight under vacuum. Elution with heptane-ethanol, 1:1 affords benzyl-ethyl-sulfamic acid 5-(6-chloro-1H-indol-2-yl)-pyridin-3-yl ester. MS (ESI) m/z 442.1 (M+H)+.

(c) Benzyl-ethyl-sulfamic acid 5-(6-chloro-1-methyl-1H-indol-2-yl)-pyridin-3-yl ester

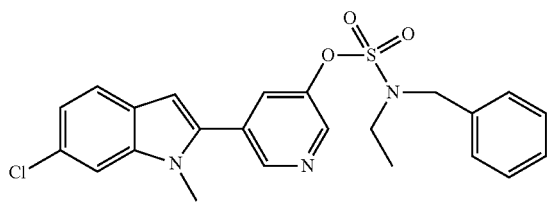 [SMILES: CCN(Cc1ccccc1)S(=O)(=O)Oc1cncc(-c2cc3ccc(Cl)cc3n2C)c1]

Benzyl-ethyl-sulfamic acid 5-(6-chloro-1H-indol-2-yl)-pyridin-3-yl ester is processed according to the method described in Example 114 to give benzyl-ethyl-sulfamic acid 5-(6-chloro-1-methyl-1H-indol-2-yl)-pyridin-3-yl ester. MS (ESI) m/z 456.0 (M+H)+

(d) Benzyl-ethyl-sulfamic acid 5-(6-chloro-3-cyano-1-methyl-1H-indol-2-yl)-pyridin-3-yl ester

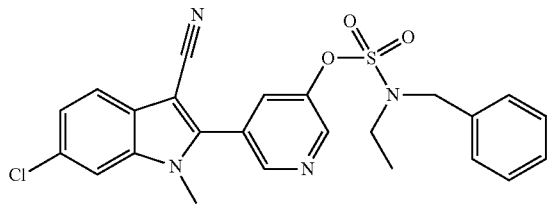 [SMILES: CCN(Cc1ccccc1)S(=O)(=O)Oc1cncc(-c2c(C#N)c3ccc(Cl)cc3n2C)c1]

Benzyl-ethyl-sulfamic acid 5-(6-chloro-1-methyl-1H-indol-2-yl)-pyridin-3-yl ester is processed according to the method described in Example 128 to give benzyl-ethyl-sulfamic acid 5-(6-chloro-3-cyano-1-methyl-1H-indol-2-yl)-pyridin-3-yl ester. $^1$H NMR (400 MHz, MeOD) δ ppm 1.15 (t, J=7.2 Hz, 3H), 3.43 (q, J=7.1 Hz, 2H), 3.82 (s, 3H), 4.61 (s, 2H), 7.27-7.47 (m, 6H), 7.73 (d, J=8.6 Hz, 1H), 7.77 (d, J=1.5 Hz, 1H), 8.06 (t, J=2.5 Hz, 1H), 8.72 (d, J=2.5 Hz, 1H), 8.83 (d, J=1.8 Hz, 1H). HRMS (ESI) m/z 481.1085 [(M+H)+ Calcd for $C_{24}H_{22}ClN_4O_3S$: 481.1101].

Example 160

(a) Morpholine-4-sulfonic acid 5-bromo-pyridin-3-yl ester

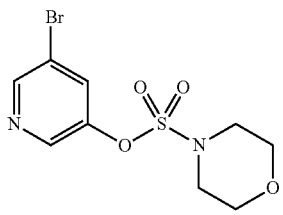 [SMILES: O=S(=O)(Oc1cncc(Br)c1)N1CCOCC1]

A flask is charged with 5-bromo-pyridin-3-ol (0.310 g, 1.78 mmol), potassium phosphate (0.982 g, 4.63 mmol) and acetone (10 mL), and morpholine-4-sulfonyl chloride (0.529 g, 2.85 mmol) is added dropwise at 0° C. The mixture is stirred at room temperature overnight. Saturated NaHCO$_3$ in water (1 mL) is added and the mixture is concentrated in vacuo. The residue is purified on silica gel chromatography eluting with a 9:1 to 4:1 heptane-ethyl acetate gradient to give morpholine-4-sulfonic acid 5-bromo-pyridin-3-yl ester. MS (ESI) m/z 322.9 and 324.9 (M+H)$^+$.

(b) Morpholine-4-sulfonic acid 5-(1-methyl-1H-indol-2-yl)-pyridin-3-yl ester

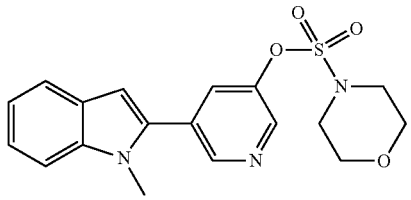 [SMILES: Cn1c(-c2cncc(OS(=O)(=O)N3CCOCC3)c2)cc2ccccc21]

Morpholine-4-sulfonic acid 5-bromo-pyridin-3-yl ester and N-methyl-indoleboronic acid are processed according to the method described in Example 100 to give morpholine-4-sulfonic acid 5-(1-methyl-1H-indol-2-yl)-pyridin-3-yl ester. MS (ESI) m/z 374.1 (M+H)$^+$ (c) Morpholine-4-sulfonic acid 5-(3-cyano-1-methyl-1H-indol-2-yl)-pyridin-3-yl ester

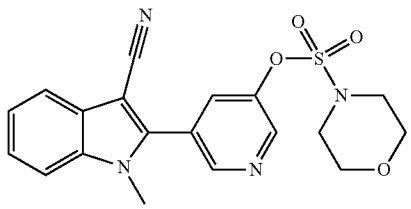 [SMILES: Cn1c(-c2cncc(OS(=O)(=O)N3CCOCC3)c2)c(C#N)c2ccccc21]

Morpholine-4-sulfonic acid 5-(1-methyl-1H-indol-2-yl)-pyridin-3-yl ester is processed according to the method described in Example 128 to give morpholine-4-sulfonic acid 5-(3-cyano-1-methyl-1H-indol-2-yl)-pyridin-3-yl ester. $^1$H NMR (400 MHz, DMSO-d$_6$) δ ppm 3.38-3.43 (m, 4H), 3.66-3.70 (m, 4H), 3.81 (s, 3H), 7.34-7.39 (m, 1H), 7.42-7.48 (m, 1H), 7.73 (d, J=7.8 Hz, 1H), 7.78 (d, J=8.3 Hz, 1H), 8.26 (dd, J=2.5, 2.0 Hz, 1H), 8.86 (d, J=2.5 Hz, 1H), 8.90 (d, J=1.8 Hz, 1H). HRMS (ESI) m/z 399.1124 [(M+H)$^+$ Calcd for C$_{19}$H$_{19}$N$_4$O$_4$S: 399.1127].

Example 161

(a) 4-Methyl-piperazine-1-sulfonic acid 5-bromo-pyridin-3-yl ester

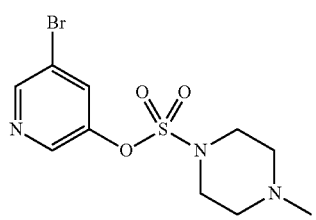 [SMILES: CN1CCN(S(=O)(=O)Oc2cncc(Br)c2)CC1]

4-Methyl-piperazine-1-sulfonyl chloride is processed according to the method described in Example 160a to give 4-methyl-piperazine-1-sulfonic acid 5-bromo-pyridin-3-yl ester. MS (ESI) m/z 335.9 and 337.9 (M+H)$^+$.

(b) 4-Methyl-piperazine-1-sulfonic acid 5-(1-methyl-1H-indol-2-yl)-pyridin-3-yl ester

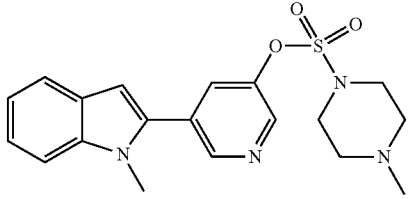 [SMILES: CN1CCN(S(=O)(=O)Oc2cncc(-c3cc4ccccc4n3C)c2)CC1]

4-Methyl-piperazine-1-sulfonic acid 5-bromo-pyridin-3-yl ester and N-methyl-indoleboronic acid are processed according to the method described in Example 100 to give 4-Methyl-piperazine-1-sulfonic acid 5-(1-methyl-1H-indol-2-yl)-pyridin-3-yl ester. MS (ESI) m/z 387.1 (M+H)$^+$.

(c) 4-Methyl-piperazine-1-sulfonic acid 5-(3-cyano-1-methyl-1H-indol-2-yl)-pyridin-3-yl ester

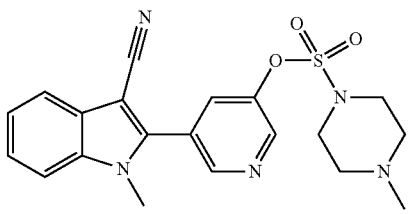 [SMILES: CN1CCN(S(=O)(=O)Oc2cncc(-c3c(C#N)c4ccccc4n3C)c2)CC1]

4-Methyl-piperazine-1-sulfonic acid 5-(1-methyl-1H-indol-2-yl)-pyridin-3-yl ester is processed according to the method described in Example 128 to give 4-methyl-piperazine-1-sulfonic acid 5-(3-cyano-1-methyl-1H-indol-2-yl)-pyridin-3-yl ester. $^1$H NMR (400 MHz, DMSO-d$_6$) δ ppm 2.21 (s, 3H), 2.38-2.43 (m, 4H), 3.38-3.43 (m, 4H), 3.81 (s, 3H), 7.34-7.39 (m, 1H), 7.42-7.48 (m, 1H), 7.73 (d, J=7.8 Hz, 1H), 7.78 (d, J=8.3 Hz, 1H), 8.24 (dd, J=2.5, 1.8 Hz, 1H), 8.84 (d, J=2.5 Hz, 1H), 8.90 (d, J=1.8 Hz, 1H). HRMS (ESI) m/z 412.1443 [(M+H)$^+$ Calcd for C$_{20}$H$_{22}$N$_5$O$_3$S: 412.1443].

Example 162

(a) 6-Chloro-2-[5-(pyrrolidine-1-sulfonyloxy)-pyridin-3-yl]-indole-1-carboxylic acid tert-butyl ester

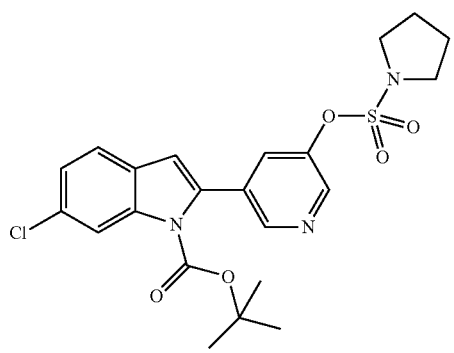 [SMILES: CC(C)(C)OC(=O)n1c(-c2cncc(OS(=O)(=O)N3CCCC3)c2)cc2ccc(Cl)cc21]

1-Pyrrolidine-sulfonyl chloride and 6-chloro-2-(5-hydroxy-pyridin-3-yl)-indole-1-carboxylic acid tert-butyl ester (Example 160a) are processed according to the method described in Example 160b to give 6-chloro-2-[5-(pyrrolidine-1-sulfonyloxy)-pyridin-3-yl]-indole-1-carboxylic acid tert-butyl ester, which is taken onto the next step without further purification. MS (ESI) m/z 478.1 (M+H)$^+$.

(b) Pyrrolidine-1-sulfonic acid 5-(6-chloro-1H-indol-2-yl)-pyridin-3-yl ester

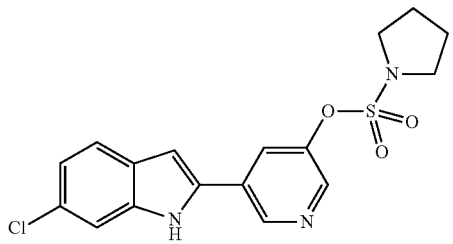 [SMILES: O=S(=O)(Oc1cncc(-c2cc3ccc(Cl)cc3[nH]2)c1)N1CCCC1]

6-Chloro-2-[5-(pyrrolidine-1-sulfonyloxy)-pyridin-3-yl]-indole-1-carboxylic acid tert-butyl ester is dissolved in DCM (2 mL), and the mixture is cooled to 0° C. TFA (2 mL) is added and the mixture is stirred at room temperature for 1 h. Saturated sodium bicarbonate is then added and the mixture is extracted with DCM. The organic layer is dried over sodium sulfate and concentrated in vacuo to afford pyrrolidine-1-sulfonic acid 5-(6-chloro-1H-indol-2-yl)-pyridin-3-yl ester as an oil which is taken onto the next step without further purification. MS (ESI) m/z 376.2 (M+H)$^+$.

(c) Pyrrolidine-1-sulfonic acid 5-(6-chloro-1-methyl-1H-indol-2-yl)-pyridin-3-yl ester

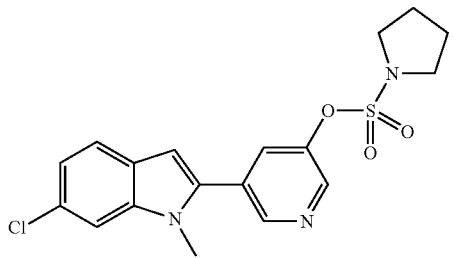 [SMILES: Cn1c(-c2cncc(OS(=O)(=O)N3CCCC3)c2)cc2ccc(Cl)cc21]

Pyrrolidine-1-sulfonic acid 5-(6-chloro-1H-indol-2-yl)-pyridin-3-yl ester is processed according to the method described in Example 109 to give pyrrolidine-1-sulfonic acid 5-(6-chloro-1-methyl-1H-indol-2-yl)-pyridin-3-yl ester. MS (ESI) m/z 392.0 (M+H)$^+$.

(d) Pyrrolidine-1-sulfonic acid 5-(6-chloro-3-cyano-1-methyl-1H-indol-2-yl)-pyridin-3-yl ester

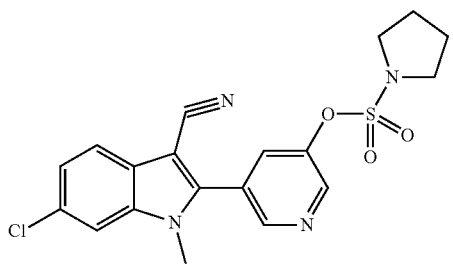 [SMILES: Cn1c(-c2cncc(OS(=O)(=O)N3CCCC3)c2)c(C#N)c2ccc(Cl)cc21]

Pyrrolidine-1-sulfonic acid 5-(6-chloro-1-methyl-1H-indol-2-yl)-pyridin-3-yl ester is processed according to the method described in Example 128 to give pyrrolidine-1-sulfonic acid 5-(6-chloro-3-cyano-1-methyl-H-indol-2-yl)-pyridin-3-yl ester. $^1$H NMR (400 MHz, MeOD) δ ppm 2.01-2.09 (m, 4H), 3.53-3.60 (m, 4H), 3.85 (s, 3H), 7.39 (dd, J=8.3, 1.8 Hz, 1H), 7.74 (d, J=8.6 Hz, 1H), 7.79 (d, J=1.5 Hz, 1H), 8.17 (dd, J=2.5, 1.8 Hz, 1H), 8.81 (d, J=2.5 Hz, 1H), 8.85 (d, J=1.8 Hz, 1H). HRMS (ESI) m/z 417.0788 [(M+H)$^+$ Calcd for C$_{19}$H$_{19}$N$_4$O$_3$SCl: 417.0788].

Example 163

(a)
N-(5-Bromo-pyridin-3-ylmethyl)-methanesulfonamide

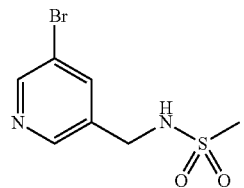

To a solution of 5-bromo-3-pyridine-carboxaldehyde (1.5 g, 7.9 mmol), methanesulfonamide (0.5 g, 5.3 mmol), acetic acid (0.637 g, 10.6 mmol), triethylamine (1.07 g, 10.6 mmol) in DCE (50 mL) at ambient temperature is added NaBH(OAc)$_3$ (3.14 g, 14.84 mmol). The reaction mixture is stirred overnight. Aqueous NaHCO$_3$ (20 mL) is added and the organic phase is separated. The aqueous phase is extracted with dichloromethane and the combined organic phase is dried over Na$_2$SO$_4$. Concentration affords a residue which is purified by silica gel flash chromatography with a methanol in dichloromethane gradient to afford N-(5-bromo-pyridin-3-ylmethyl)-methanesulfonamide as a solid. MS (ESI) m/z 266.9 (M+H)$^+$.

(b) N-[5-(1-Methyl-1H-indol-2-yl)-pyridin-3-ylmethyl]-methanesulfonamide

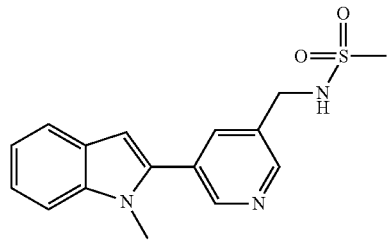 [SMILES: Cn1c(-c2cncc(CNS(C)(=O)=O)c2)cc2ccccc21]

N-(5-Bromo-pyridin-3-ylmethyl)-methanesulfonamide and N-methyl-indoleboronic acid are processed according to the method described in Example 100 to give N-[5-(1-methyl-1H-indol-2-yl)-pyridin-3-ylmethyl]-methanesulfonamide. 1H NMR (400 MHz, MeOD) δ ppm 3.03 (s, 3H), 3.82 (s, 3H), 4.45 (s, 2H), 6.70 (s, 1H), 7.13 (t, J=7.5 Hz, 1 H), 7.23-7.31 (m, 1H), 7.48 (d, J=8.1 Hz, 1H), 7.63 (d, J=7.8 Hz, 1H), 8.10 (t, J=2.0 Hz, 1H), 8.62 (d, J=2.0 Hz, 1H), 8.72 (d, J=2.0 Hz, 1H). HRMS (ESI) m/z 316.1108 [(M+H)+ Calcd for $C_{16}H_{18}N_3O_2S$: 316.1120].

Example 164

N-Methyl-N-[5-(1-methyl-1H-indol-2-yl)-pyridin-3-ylmethyl]-methanesulfonamide

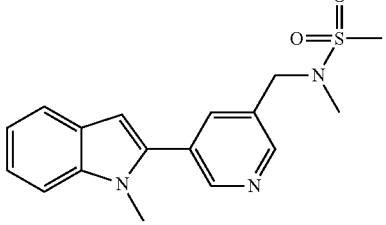

N-[5-(1-Methyl-1H-indol-2-yl)-pyridin-3-ylmethyl]-methanesulfonamide (Example 163) is processed according to the method described in Example 114 to give N-methyl-N-[5-(1-methyl-1H-indol-2-yl)-pyridin-3-ylmethyl]-methanesulfonamide. $^1$H NMR (400 MHz, DMSO-$d_6$) δ ppm 2.77 (s, 3H), 3.02 (s, 3H), 3.78 (s, 3H), 4.41 (s, 2H), 6.72 (s, 1H), 7.07-7.13 (m, 1H), 7.20-7.25 (m, 1H), 7.54 (d, J=8.3 Hz, 1H), 7.61 (d, J=7.8 Hz, 1H), 7.95 (t, J=2.0 Hz, 1H), 8.60 (d, J=2.0 Hz, 1H), 8.78 (d, J=2.0 Hz, 1H). MS (ESI) m/z 330.1 (M+H)+.

Example 165

N-Methyl-N-[5-(1-methyl-3-cyano-1H-indol-2-yl)-pyridin-3-ylmethyl]-methanesulfonamide

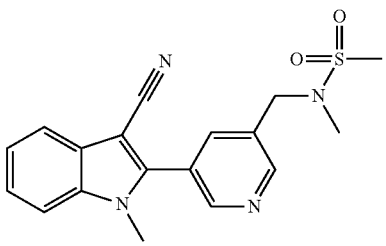 [SMILES: CN(Cc1cncc(-c2c(C#N)c3ccccc3n2C)c1)S(C)(=O)=O]

N-Methyl-N-[5-(1-methyl-1H-indol-2-yl)-pyridin-3-ylmethyl]-methanesulfonamide (Example 164) is processed according to the method described in Example 128 to give N-methyl-N-[5-(1-methyl-3-cyano-1H-indol-2-yl)-pyridin-3-ylmethyl]-methanesulfonamide. $^1$H NMR (400 MHz, DMSO-$d_6$) δ ppm 2.80 (s, 3H), 3.03 (s, 3H), 3.82 (s, 3H), 4.46 (s, 2H), 7.34-7.39 (m, 1H), 7.42-7.47 (m, 1H), 7.72 (d, J=7.8 Hz, 1H), 7.77 (d, J=8.3 Hz, 1H), 8.09 (t, J=2.1 Hz, 1H), 8.77 (d, J=2.0 Hz, 1H), 8.87 (d, J=2.3 Hz, 1H). HRMS (ESI) m/z 355.1229 [(M+H)+ Calcd for $C_{18}H_{19}N_4O_2S$: 355.1229].

Example 166

(a) 6-Chloro-2-[5-(methanesulfonyl-amino-methyl)-pyridin-3-yl]-indole-1-carboxylic acid tert-butyl ester

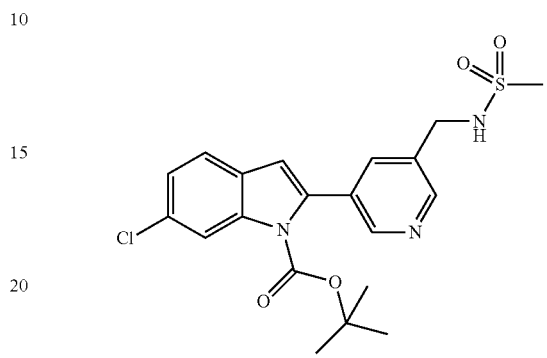

A flask is charged with N-(5-bromo-pyridin-3-ylmethyl)-methanesulfonamide (Example 163a, 530 mg, 2 mmol), N-Boc-6-chloro-indole-2-boronic acid (525 mg, 3.0 mmol), s-Phos (41 mg, 0.10 mmol), finely crushed potassium phosphate (849 mg, 4.0 mmol) and toluene (20 mL), and the mixture is degassed for 15 min. Pd$_2$dba$_3$ (37 mg, 0.04 mmol) is added and the mixture is stirred at 85° C. for 1 h. The mixture is cooled to room temperature, diluted with DCM and silica gel (10 g) is added. The mixture is concentrated in vacuo and the residue is purified by silica gel flash chromatography eluting with a 0 to 90% ethyl acetate-heptane gradient to give 6-chloro-2-[5-(methanesulfonylamino-methyl)-pyridin-3-yl]-indole-1-carboxylic acid tert-butyl ester. MS (ESI) m/z 436.1 and 437.9 (M+H)+.

(b) 6-Chloro-2-[5-(methanesulfonyl-(tert-butoxycarbonyl)-amino-methyl)-pyridin-3-yl]-indole-1-carboxylic acid tert-butyl ester

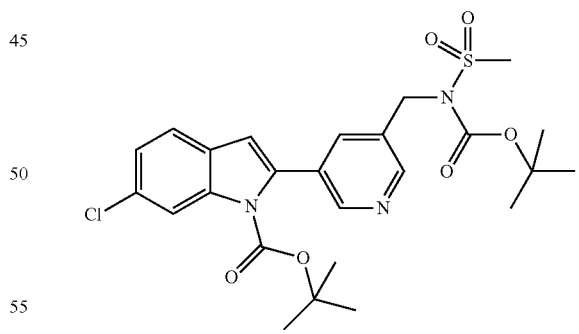

To a solution of 6-chloro-2-[5-(methanesulfonylamino-methyl)-pyridin-3-yl]-indole-1-carboxylic acid tert-butyl ester (530 mg, 1.22 mmol) in acetonitrile (10 mL) are added Boc$_2$O (398 mg, 1.82 mmol) and DMAP (15 mg, 0.12 mmol). The mixture is stirred for 1 h. Silica gel (1 g) is added and the mixture is concentrated in vacuo. The residue is purified by silica gel chromatography to give 6-chloro-2-[5-(methanesulfonyl-(tert-butoxycarbonyl)-amino-methyl)-pyridin-3-yl]-indole-1-carboxylic acid tert-butyl ester. MS (ESI) m/z 536.2 and 538.1 (M+H)+.

(c) N-[5-(6-Chloro-1H-indol-2-yl)-pyridin-3-ylmethyl]-methanesulfonamide

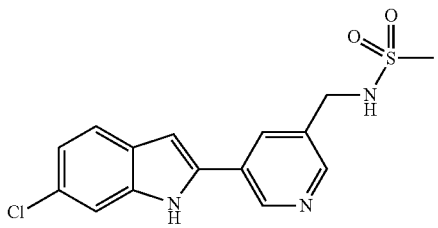 [SMILES: CS(=O)(=O)NCc1cncc(-c2cc3ccc(Cl)cc3[nH]2)c1]

A flask is charged with 6-chloro-2-[5-(methanesulfonyl-(tert-butoxycarbonyl)-amino-methyl)-pyridin-3-yl]-indole-1-carboxylic acid tert-butyl ester (0.52 g, 0.97 mmol) and TFA (5 mL) and the mixture is stirred at room temperature for 1 h. The mixture is concentrated in vacuo to give N-[5-(6-chloro-1H-indol-2-yl)-pyridin-3-ylmethyl]-methanesulfonamide which is used in the next step without further purification. MS (ESI) m/z 336.0 and 337.9 (M+H)$^+$.

(d) N-[5-(6-Chloro-1H-indol-2-yl)-pyridin-3-ylmethyl]-N-methyl-methanesulfonamide

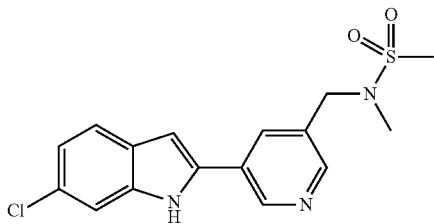 [SMILES: CN(Cc1cncc(-c2cc3ccc(Cl)cc3[nH]2)c1)S(C)(=O)=O]

A flask is charged with N-[5-(6-chloro-1H-indol-2-yl)-pyridin-3-ylmethyl]-methanesulfonamide (670 mg, 1.49 mmol), DMF (10 mL), dimethyl carbonate (403 mg, 4.47 mmol) and potassium carbonate (319 mg, 2.31 mmol), and the mixture is stirred at 150° C. for 5 h. The mixture is cooled to room temperature and purified using Xbridge C18 eluting with a 1:9 to 9:1 acetonitrile-water gradient to give N-[5-(6-chloro-1H-indol-2-yl)-pyridin-3-ylmethyl]-N-methyl-methanesulfonamide. $^1$H NMR (400 MHz, DMSO-d$_6$) δ ppm 2.74 (s, 3H), 3.02 (s, 3H), 4.35 (s, 2H), 7.04 (dd, J=8.5, 1.9 Hz, 1H), 7.09 (d, J=1.5 Hz, 1H), 7.43 (d, J=1.8 Hz, 1H), 7.59 (d, J=8.6 Hz, 1H), 8.14 (t, J=2.1 Hz, 1H), 8.47 (d, J=2.0 Hz, 1H), 9.05 (d, J=2.3 Hz, 1H), 11.92 (s, 1H). HRMS (ESI) m/z 350.0738 [(M+H)$^+$ Calcd for C$_{16}$H$_{17}$ClN$_3$O$_2$S: 350.0730].

Example 167

N-[5-(6-Chloro-1-methyl-1H-indol-2-yl)-pyridin-3-ylmethyl]-N-methyl-methanesulfonamide

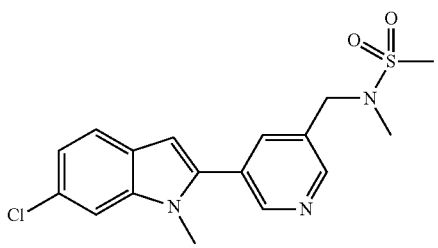 [SMILES: CN(Cc1cncc(-c2cc3ccc(Cl)cc3n2C)c1)S(C)(=O)=O]

The method described in Example 166d also generates N-[5-(6-chloro-1-methyl-1H-indol-2-yl)-pyridin-3-ylmethyl]-N-methyl-methanesulfonamide. $^1$H NMR (400 MHz, DMSO-d$_6$) δ ppm 2.78 (s, 3H), 3.02 (s, 3H), 3.77 (s, 3H), 4.41 (s, 2H), 6.76 (d, J=0.8 Hz, 1H), 7.11 (dd, J=8.5, 1.9 Hz, 1H), 7.62 (d, J=8.5 Hz, 1H), 7.70 (d, J=1.8 Hz, 1H), 7.96 (t, J=2.2 Hz, 1H), 8.62 (d, J=2.2 Hz, 1H), 8.78 (d, J=2.2 Hz, 1H). MS (ESI) m/z 364.1 (M+H)$^+$.

Example 168

N-[5-(6-Chloro-3-cyano-1-methyl-1H-indol-2-yl)-pyridin-3-ylmethyl]-N-methyl-methanesulfonamide

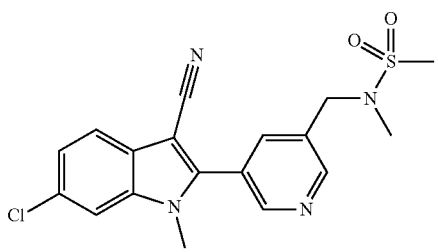 [SMILES: CN(Cc1cncc(-c2c(C#N)c3ccc(Cl)cc3n2C)c1)S(C)(=O)=O]

N-[5-(6-Chloro-1-methyl-1H-indol-2-yl)-pyridin-3-ylmethyl]-N-methyl-methanesulfonamide (Example 167) is processed according to the method described in Example 128 to give N-[5-(6-chloro-3-cyano-1-methyl-1H-indol-2-yl)-pyridin-3-ylmethyl]-N-methyl-methanesulfonamide. $^1$H NMR (400 MHz, DMSO-d$_6$) δ ppm 2.78 (s, 3H), 3.02 (s, 3H), 3.79 (s, 3H), 4.45 (s, 2H), 7.37 (dd, J=8.5, 1.9 Hz, 1H), 7.73 (d, J=8.6 Hz, 1H), 7.97 (d, J=1.5 Hz, 1H), 8.08 (t, J=2.0 Hz, 1H), 8.76 (d, J=2.0 Hz, 1H), 8.85 (d, J=2.0 Hz, 1H). HRMS (ESI) m/z 389.0835 [(M+H)$^+$ Calcd for C$_{18}$H$_{18}$ClN$_4$O$_2$S: 389.0839].

Example 169

(a) 2-[5-(Methanesulfonyl-(tert-butoxycarbonyl)-amino-methyl)-pyridin-3-yl]-1-methyl-indole

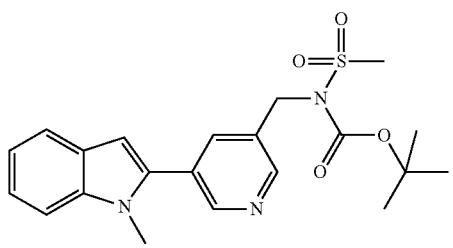 [SMILES: Cn1c(-c2cncc(CN(C(=O)OC(C)(C)C)S(C)(=O)=O)c2)cc2ccccc21]

To a solution of N-[5-(1-Methyl-1H-indol-2-yl)-pyridin-3-ylmethyl]-methanesulfonamide (Example 163b) (337 mg, 0.200 mmol) in acetonitrile (5 mL) are added Boc$_2$O (293 mg, 1.34 mmol) and DMAP (14 mg, 0.11 mmol). The reaction mixture is stirred for 1 h and after removal of the solvent, the residue is purified by silica gel flash chromatography to afford 2-[5-(methanesulfonyl-(tert-butoxycarbonyl)-amino-methyl)-pyridin-3-yl]-1-methyl-indole. MS (ESI) m/z 416.2 (M+H)$^+$.

(b) 2-[5-(Methanesulfonyl-(tert-butoxycarbonyl)-amino-methyl)-pyridin-3-yl]-1-methyl-3-cyano-indole

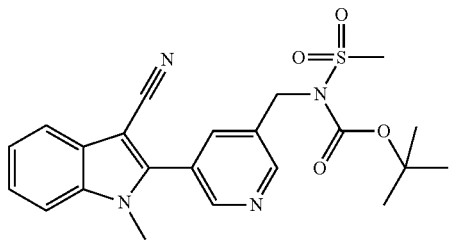 [SMILES: Cn1c(-c2cncc(CN(C(=O)OC(C)(C)C)S(C)(=O)=O)c2)c(C#N)c2ccccc21]

To a solution of 2-[5-(methanesulfonyl-(tert-butoxycarbonyl)-amino-methyl)-pyridin-3-yl]-1-methyl-indole (350 mg, 0.842 mmol) in dichloromethane (10 mL) is added chlorosulfonyl isocyanate (0.358 g, 2.53 mmol). The mixture is stirred at ambient temperature for 20 min, whereupon anhydrous DMF (2 mL) is added. After 1 h, the mixture is concentrated to a volume of 3 mL, and filtered. Purification by RP HPLC affords 2-[5-(methanesulfonyl-(tert-butoxycarbonyl)-amino-methyl)-pyridin-3-yl]-1-methyl-3-cyano-indole. MS (ESI) m/z 441.1 (M+H)$^+$.

(c) N-[5-(3-Cyano-1-methyl-1H-indol-2-yl)-pyridin-3-ylmethyl]-methanesulfonamide

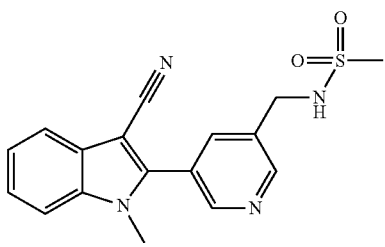 [SMILES: Cn1c(-c2cncc(CNS(C)(=O)=O)c2)c(C#N)c2ccccc21]

2-[5-(Methanesulfonyl-(tert-butoxycarbonyl)-amino-methyl)-pyridin-3-yl]-1-methyl-3-cyano-indole (260 mg, 0.59 mmol) in TFA (3 mL) at ambient temperature is stirred for 30 min. The solvent is then removed in vacuo and the residue is purified by RP HPLC. The fractions containing the product are pooled and concentrated and the residue is further purified by flash silica gel flash chromatography (methanol-dichloromethane gradient) to give N-[5-(3-cyano-1-methyl-1H-indol-2-yl)-pyridin-3-ylmethyl]-methanesulfonamide. $^1$H NMR (400 MHz, DMSO-d$_6$) δ ppm 2.97 (s, 3H), 3.79 (s, 3H), 4.36 (br. s., 2H), 7.33-7.39 (m, 1H), 7.40-7.46 (m, 1H), 7.69-7.79 (m, 3H), 8.10 (t, J=2.1 Hz, 1H), 8.77 (d, J=2.3 Hz, 1H), 8.81 (d, J=2.3 Hz, 1H). HRMS (ESI) m/z 341.1068 [(M+H)$^+$ Calcd for C$_{17}$H$_{17}$N$_4$O$_2$S: 341.1072].

Example 170

N-[5-(6-chloro-3-cyano-1-methyl-1H-indol-2-yl)-pyridin-3-ylmethyl]-methanesulfonamide

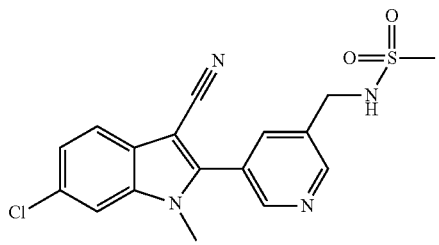 [SMILES: Cn1c(-c2cncc(CNS(C)(=O)=O)c2)c(C#N)c2ccc(Cl)cc21]

6-Chloro-2-(5-formyl-pyridin-3-yl)-1-methyl-1H-indole-3-carbonitrile (Example 126, 50 mg, 0.169 mmol) and methanesulfonamide (24 mg, 0.254 mmol), acetic acid (20 mg, 0.338 mmol), triethylamine (34 mg, 0.338 mmol) in DCE (10 mL) are stirred for 30 min at ambient temperature before adding NaBH(OAc)$_3$ (100 mg, 0.473 mmol). The reaction mixture is stirred overnight. NaHCO$_3$ (1 mL) is added and the solvents are removed in vacuo. The residue is purified using a Sunfire C18 with a gradient of acetonitrile in 0.1% aqueous TFA and further purified with an Xbridge C18 using a gradient of acetonitrile in 0.1% NH$_4$OH to give N-[5-(6-chloro-3-cyano-1-methyl-1H-indol-2-yl)-pyridin-3-ylmethyl]-methanesulfonamide as a solid. $^1$H NMR (400 MHz, DMSO-d$_6$) δ ppm 2.97 (s, 3H), 3.78 (s, 3H), 4.36 (s, 2H), 7.37 (dd, J=8.6, 1.8 Hz, 1H), 7.73 (d, J=8.6 Hz, 1H), 7.75 (br. s., 1H), 7.97 (d, J=1.8 Hz, 1H), 8.10 (t, J=2.1 Hz, 1H), 8.78 (d, J=2.0 Hz, 1H), 8.81 (d, J=2.3 Hz, 1H). HRMS (ESI) m/z 375.0681 [(M+H)$^+$ Calcd for C$_{17}$H$_{16}$ClN$_4$O$_2$S: 375.0682].

Example 171

N-[5-(6-chloro-3-cyano-1-methyl-1H-indol-2-yl)-pyridin-3-ylmethyl]-ethanesulfonamide

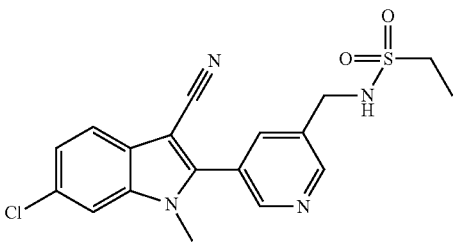 [SMILES: CCS(=O)(=O)NCc1cncc(-c2c(C#N)c3ccc(Cl)cc3n2C)c1]

6-Chloro-2-(5-formyl-pyridin-3-yl)-1-methyl-1H-indole-3-carbonitrile (Example 126b, 2.0 g, 6.09 mmol), ethanesulfonamide (1.33 g, 12.17 mmol) and toluene (250 mL), and titanium(IV) isopropoxide (2.59 g, 9.13 mmol) is added dropwise. The mixture is stirred at 120° C. overnight. The mixture is then concentrated in vacuo. The residue is taken up in DCM (150 mL) and MeOH (150 mL), and NaBH$_4$ (0.461 g, 12.17 mmol) is added at 0° C. The mixture is stirred at 0° C. for 30 min. Water (50 mL) is added and the mixture is stirred for 5 min. The suspension is filtered through a pad of celite. The celite layer is washed with DCM (3×50 mL). The combined organic phase is dried over Na$_2$SO$_4$ and concentrated to give a residue is purified by silica gel flash chromatography (ethyl acetate). The resulting fractions containing the product are concentrated and repurified by silica gel flash chromatography (dichloromethane-methanol, 1:0 to 97:3). The concentrated product is redissolved in MeOH (500 mL) at 60° C. and concentrated in vacuo to give N-[5-(6-chloro-3-cyano-1-methyl-1H-indol-2-yl)-pyridin-3-ylmethyl]-ethanesulfonamide. $^1$H NMR (400 MHz, DMSO-d$_6$) δ ppm 1.20 (t, J=7.3 Hz, 3H), 3.06 (q, J=7.3 Hz, 2H), 3.78 (s, 3H), 4.34 (d, J=6.3 Hz, 2H), 7.37 (dd, J=8.6, 1.8 Hz, 1H), 7.73 (d, J=8.3 Hz, 1H), 7.77 (t, J=6.2 Hz, 1H), 7.97 (d, J=1.8 Hz, 1H), 8.09 (t, J=2.1 Hz, 1H), 8.78 (d, J=1.8 Hz, 1H), 8.80 (d, J=1.8 Hz, 1H). HRMS (ESI) m/z 389.0853 [(M+H)$^+$ Calcd for C$_{18}$H$_{17}$ClN$_4$O$_2$S: 389.0839].

Example 172

N-[5-(6-chloro-3-cyano-1-methyl-1H-indol-2-yl)-pyridin-3-ylmethyl]-C,C,C-trifluoromethanesulfonamide

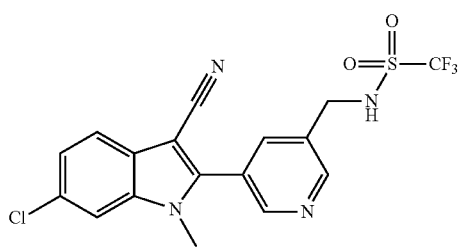 [SMILES: Cn1c(-c2cncc(CNS(=O)(=O)C(F)(F)F)c2)c(C#N)c2ccc(Cl)cc21]

6-Chloro-2-(5-formyl-pyridin-3-yl)-1-methyl-1H-indole-3-carbonitrile (Example 126) and trifluoromethanesulfonamide are processed according to the method described in Example 170 to give N-[5-(6-chloro-3-cyano-1-methyl-1H-indol-2-yl)-pyridin-3-ylmethyl]-C,C,C-trifluoromethanesulfonamide. $^1$H NMR (400 MHz, DMSO-d$_6$) δ ppm 3.78 (s, 3H), 4.56 (s, 2H), 7.37 (dd, J=8.5, 1.9 Hz, 1H), 7.73 (d, J=8.6 Hz, 1H), 7.97 (d, J=1.5 Hz, 1H), 8.09 (t, J=2.1 Hz, 1H), 8.78 (d, J=2.3 Hz, 1H), 8.83 (d, J=2.0 Hz, 1H), 10.16 (br. s., 1H). HRMS (ESI) m/z 429.0412 [(M+H)$^+$ Calcd for C$_{17}$H$_{13}$ClF$_3$N$_4$O$_2$S: 429.0400].

Example 173

2-Methyl-propane-2-sulfonic acid [5-(6-chloro-3-cyano-1-methyl-1H-indol-2-yl)-pyridin-3-ylmethyl]-amide

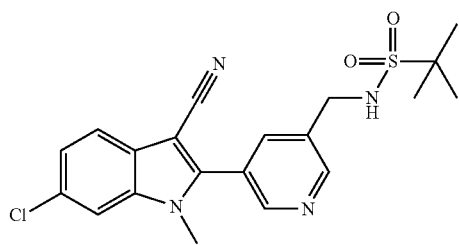 [SMILES: Cn1c(-c2cncc(CNS(=O)(=O)C(C)(C)C)c2)c(C#N)c2ccc(Cl)cc21]

6-Chloro-2-(5-formyl-pyridin-3-yl)-1-methyl-1H-indole-3-carbonitrile (Example 126) and 2-methyl-propane-2-sulfonic acid amide are processed according to the method described in Example 170 to give 2-methyl-propane-2-sulfonic acid [5-(6-chloro-3-cyano-1-methyl-1H-indol-2-yl)-pyridin-3-ylmethyl]-amide. $^1$H NMR (400 MHz, DMSO-d$_6$) δ ppm 1.32 (s, 9H), 3.78 (s, 3H), 4.43 (d, J=6.1 Hz, 2H), 7.37 (dd, J=8.6, 1.8 Hz, 1H), 7.65 (t, J=6.2 Hz, 1H), 7.73 (d, J=8.3 Hz, 1H), 7.97 (d, J=1.5 Hz, 1H), 8.06 (t, J=2.1 Hz, 1H), 8.77 (d, J=1.8 Hz, 1H), 8.80 (d, J=2.0 Hz, 1H). HRMS (ESI) m/z 417.1150 [(M+H)$^+$ Calcd for C$_{20}$H$_{21}$ClN$_4$O$_2$S: 417.1152].

Example 174

N-[5-(6-Chloro-3-cyano-1-methyl-1H-indol-2-yl)-pyridin-3-ylmethyl]-C-phenyl-methanesulfonamide

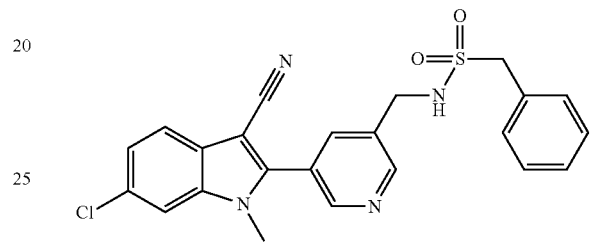

6-Chloro-2-(5-formyl-pyridin-3-yl)-1-methyl-1H-indole-3-carbonitrile (Example 126) and phenyl-methanesulfonamide are processed according to the method described in Example 170 to give N-[5-(6-chloro-3-cyano-1-methyl-1H-indol-2-yl)-pyridin-3-ylmethyl]-C-phenyl-methanesulfonamide. $^1$H NMR (400 MHz, DMSO-d$_6$) δ ppm 3.77 (s, 3H), 4.31 (s, 2H), 4.44 (s, 2H), 7.30-7.41 (m, 6H), 7.73 (d, J=8.3 Hz, 1H), 7.83 (br. s., 1H), 7.97 (d, J=1.5 Hz, 1H), 8.03 (t, J=2.1 Hz, 1H), 8.73 (d, J=2.0 Hz, 1H), 8.79 (d, J=2.0 Hz, 1H). HRMS (ESI) m/z 451.1006 [(M+H)$^+$ Calcd for C$_{23}$H$_{20}$ClN$_4$O$_2$S: 451.0996].

Example 175

N-[5-(6-Chloro-3-cyano-1-methyl-1H-indol-2-yl)-pyridin-3-ylmethyl]-4-fluoro-benzenesulfonamide

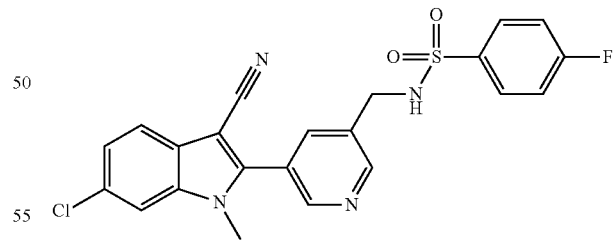

6-Chloro-2-(5-formyl-pyridin-3-yl)-1-methyl-1H-indole-3-carbonitrile (Example 126) and 4-fluoro-benzenesulfonamide are processed according to the method described in Example 170 to give N-[5-(6-chloro-3-cyano-1-methyl-1H-indol-2-yl)-pyridin-3-ylmethyl]-4-fluoro-benzenesulfonamide. $^1$H NMR (400 MHz, DMSO-d$_6$) δ ppm 3.74 (s, 3H), 4.23 (s, 2H), 7.33-7.41 (m, 3H), 7.72 (d, J=8.6 Hz, 1H), 7.82-7.88 (m, 2H), 7.95 (d, J=1.5 Hz, 2H), 8.44 (s, 1H), 8.62 (d, J=2.0 Hz, 1H), 8.73 (d, J=2.0 Hz, 1H). HRMS (ESI) m/z 455.0746 [(M+H)$^+$ Calcd for C$_{22}$H$_{17}$ClFN$_4$O$_2$S: 455.0745].

Example 176

6-Chloro-2-[5-(1,1-dioxo-1 lambda*6*-thiomorpholin-4-ylmethyl)-pyridin-3-yl]-1-methyl-1H-indole-3-carbonitrile

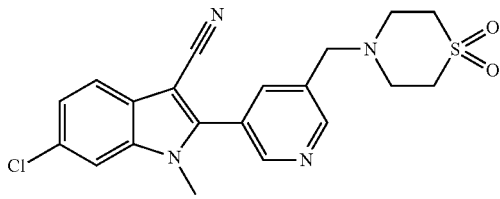 [SMILES: Cn1c(-c2cncc(CN3CCS(=O)(=O)CC3)c2)c(C#N)c2ccc(Cl)cc21]

6-Chloro-2-(5-formyl-pyridin-3-yl)-1-methyl-1H-indole-3-carbonitrile (Example 126) and thiomorpholine-1,1-dioxide are processed according to the method described in Example 170 to give 6-chloro-2-[5-(1,1-dioxo-1lambda*6*-thiomorpholin-4-ylmethyl)-pyridin-3-yl]-1-methyl-1H-indole-3-carbonitrile. $^1$H NMR (400 MHz, DMSO-d$_6$) δ ppm 2.93-2.98 (m, 4H), 3.12-3.18 (m, 4H), 3.81 (s, 3H), 3.87 (s, 2H), 7.37 (dd, J=8.5, 1.9 Hz, 1H), 7.73 (d, J=8.3 Hz, 1H), 7.97 (d, J=1.5 Hz, 1H), 8.13 (t, J=2.0 Hz, 1H), 8.75 (d, J=2.0 Hz, 1H), 8.81 (d, J=2.3 Hz, 1H). HRMS (ESI) m/z 415.1015 [(M+H)$^+$ Calcd for C$_{20}$H$_{20}$ClN$_4$O$_2$S: 415.0996].

Example 177

6-Chloro-2-{5-[(2-hydroxy-ethylamino)-methyl]-pyridin-3-yl}-1-methyl-1H-indole-3-carbonitrile

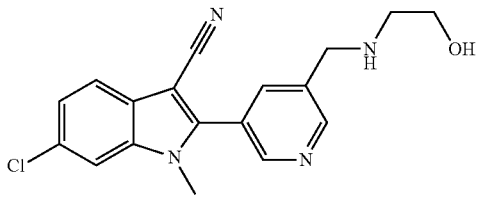 [SMILES: Cn1c(-c2cncc(CNCCO)c2)c(C#N)c2ccc(Cl)cc21]

6-Chloro-2-(5-formyl-pyridin-3-yl)-1-methyl-1H-indole-3-carbonitrile (Example 126) and 2-amino-ethanol are processed according to the method described in Example 170 to give 6-chloro-2-{5-[(2-hydroxy-ethylamino)-methyl]-pyridin-3-yl}-1-methyl-1H-indole-3-carbonitrile. $^1$H NMR (400 MHz, DMSO-d$_6$) δ ppm 2.65-2.72 (m, 2H), 3.49-3.55 (m, 2H), 3.79 (s, 3H), 3.92-3.98 (m, 2H), 4.61 (br. s., 1H), 7.37 (dd, J=8.3, 1.8 Hz, 1H), 7.73 (d, J=8.3 Hz, 1H), 7.97 (d, J=1.8 Hz, 1H), 8.10-8.13 (m, 1H), 8.75-8.79 (m, 2H). HRMS (ESI) m/z 341.1175 [(M+H)$^+$ Calcd for C$_{19}$H$_{18}$ClN$_4$O: 341.1169].

Example 178

(a) {(R)-1-[5-(6-Chloro-3-cyano-1-methyl-1H-indol-2-yl)-pyridin-3-ylmethyl]-pyrrolidin-3-yl}-carbamic acid tert-butyl ester

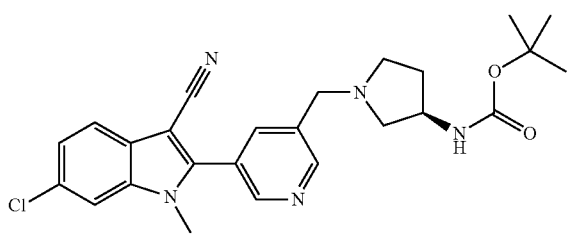 [SMILES: Cn1c(-c2cncc(CN3CC[C@@H](NC(=O)OC(C)(C)C)C3)c2)c(C#N)c2ccc(Cl)cc21]

6-Chloro-2-(5-formyl-pyridin-3-yl)-1-methyl-1H-indole-3-carbonitrile (Example 126) and (R)-pyrrolidin-3-yl-carbamic acid tert-butyl ester are processed according to the method described in Example 170 to give {(R)-1-[5-(6-chloro-3-cyano-1-methyl-1H-indol-2-yl)-pyridin-3-ylmethyl]-pyrrolidin-3-yl}-carbamic acid tert-butyl ester. MS (ESI) m/z 466.17 (M+H)$^+$.

(b) 2-[5-((R)-3-Amino-pyrrolidin-1-ylmethyl)-pyridin-3-yl]-6-chloro-1-methyl-1H-indole-3-carbonitrile

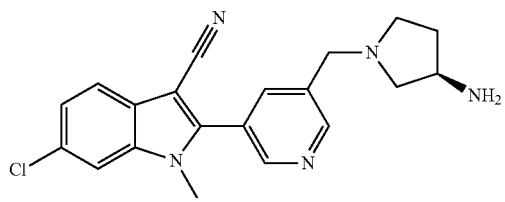 [SMILES: Cn1c(-c2cncc(CN3CC[C@@H](N)C3)c2)c(C#N)c2ccc(Cl)cc21]

To a solution of {(R)-1-[5-(6-chloro-3-cyano-1-methyl-1H-indol-2-yl)-pyridin-3-ylmethyl]-pyrrolidin-3-yl}-carbamic acid tert-butyl ester (140 mg, 0.3 mmol) in dichloromethane (5 mL) is added TFA (2 mL) and the mixture is stirred at room temperature for 2 h. The solvents are then removed in vacuo and the residue is purified by Xbridge C18 with a gradient of acetonitrile in 0.1% NH$_4$OH to give 2-[5-((R)-3-amino-pyrrolidin-1-ylmethyl)-pyridin-3-yl]-6-chloro-1-methyl-1H-indole-3-carbonitrile. $^1$H NMR (400 MHz, DMSO-d$_6$) δ ppm 1.33-1.43 (m, 1H), 1.64 (br. s., 2H), 1.97-2.08 (m, 1H), 2.21 (dd, J=9.0, 4.9 Hz, 1H), 2.59-2.68 (m, 1H), 2.71 (dd, J=9.1, 6.6 Hz, 1H), 3.32-3.39 (m, 1H), 3.72 (q, J=13.6 Hz, 2H), 3.79 (s, 3H), 7.36 (dd, J=8.3, 1.8 Hz, 1H), 7.72 (d, J=8.6 Hz, 1H), 7.96 (d, J=1.5 Hz, 1H), 8.05 (t, J=2.0 Hz, 1H), 8.72 (d, J=2.0 Hz, 1H), 8.77 (d, J=2.3 Hz, 1H). HRMS (ESI) m/z 366.1483 [(M+H)$^+$ Calcd for C$_{20}$H$_{21}$ClN$_5$: 366.1485].

Example 179

6-Chloro-1-methyl-2-{5-[(2-pyrrolidin-1-yl-ethylamino)-methyl]-pyridin-3-yl}-1H-indole-3-carbonitrile

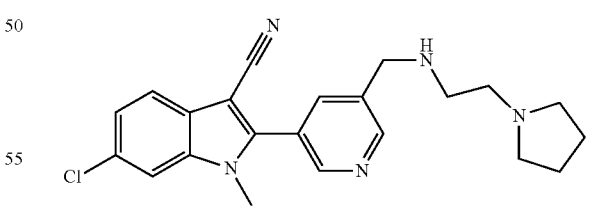

6-Chloro-2-(5-formyl-pyridin-3-yl)-1-methyl-1H-indole-3-carbonitrile (Example 126) and 2-pyrrolidin-1-yl-ethylamine are processed according to the method described in Example 170 to give 6-chloro-1-methyl-2-{5-[(2-pyrrolidin-1-yl-ethylamino)-methyl]-pyridin-3-yl}-1H-indole-3-carbonitrile. The free base is taken up in 4M HCl in dioxane, concentrated in vacuo, dissolved in water and lyophilized to give the HCl salt. $^1$H NMR (400 MHz, DMSO-d$_6$) δ ppm (HCl salt) 1.83-1.93 (m, 2H), 2.04 (br. s., 2H), 3.06 (br. s., 2H), 3.50 (br. s., 2H), 3.54-3.60 (m, 2H), 3.66 (br. s., 2H), 3.84 (s, 3H), 4.43 (br. s., 2H), 7.39 (dd, J=8.6, 1.8 Hz, 1H), 7.75 (d, J=8.3 Hz, 1H), 8.01 (d, J=1.5 Hz, 1H), 8.43 (t, J=2.0 Hz, 1H), 8.94 (d, J=2.0 Hz, 1H), 8.99 (d, J=2.0 Hz, 1H), 9.97 (br. s., 2H), 10.89 (br. s., 1H). HRMS (ESI) m/z 394.1803 [(M+H)$^+$ Calcd for C$_{22}$H$_{25}$ClN$_5$: 394.1798].

Example 180

6-Chloro-2-[5-(4-methanesulfonyl-piperazin-1-ylmethyl)-pyridin-3-yl]-1-methyl-1H-indole-3-carbonitrile

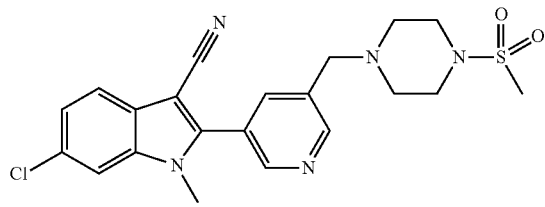 [SMILES: Cn1c(-c2cncc(CN3CCN(S(C)(=O)=O)CC3)c2)c(C#N)c2ccc(Cl)cc21]

6-Chloro-2-(5-formyl-pyridin-3-yl)-1-methyl-1H-indole-3-carbonitrile (Example 126) and 1-methanesulfonyl-piperazine are processed according to the method described in Example 170 to give 6-chloro-2-[5-(4-methanesulfonyl-piperazin-1-ylmethyl)-pyridin-3-yl]-1-methyl-1H-indole-3-carbonitrile. $^1$H NMR (400 MHz, DMSO-d$_6$) δ ppm 2.55 (t, J=4.5 Hz, 4H), 3.14 (t, J=4.5 Hz, 4H), 3.30 (s, 3H), 3.72 (s, 2H), 3.80 (s, 3H), 7.36 (dd, J=8.5, 1.9 Hz, 1H), 7.72 (d, J=8.3 Hz, 1H), 7.96 (d, J=1.5 Hz, 1H), 8.06 (t, J=2.0 Hz, 1H), 8.73 (d, J=2.0 Hz, 1H), 8.80 (d, J=2.0 Hz, 1H). HRMS (ESI) m/z 444.1265 [(M+H)$^+$ Calcd for C$_{22}$H$_{25}$ClN$_5$: 444.1261].

Example 181

(a) {1-[5-(6-Chloro-3-cyano-1-methyl-1H-indol-2-yl)-pyridin-3-ylmethyl]-piperidin-4-yl}-carbamic acid tert-butyl ester

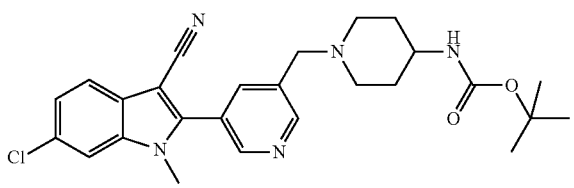 [SMILES: Cn1c(-c2cncc(CN3CCC(NC(=O)OC(C)(C)C)CC3)c2)c(C#N)c2ccc(Cl)cc21]

6-Chloro-2-(5-formyl-pyridin-3-yl)-1-methyl-1H-indole-3-carbonitrile (Example 126) and piperidin-4-yl-carbamic acid tert-butyl ester are processed according to the method described in Example 170 to give {1-[5-(6-chloro-3-cyano-1-methyl-1H-indol-2-yl)-pyridin-3-ylmethyl]-piperidin-4-yl}-carbamic acid tert-butyl ester. MS (ESI) m/z 480.1 (M+H)$^+$.

(b) 2-[5-(4-Amino-piperidin-1-ylmethyl)-pyridin-3-yl]-6-chloro-1-methyl-1H-indole-3-carbonitrile

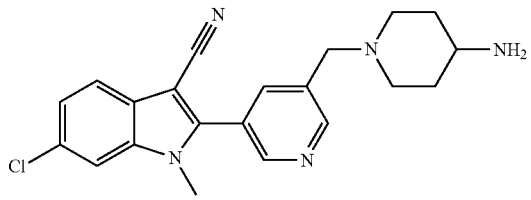 [SMILES: Cn1c(-c2cncc(CN3CCC(N)CC3)c2)c(C#N)c2ccc(Cl)cc21]

{1-[5-(6-Chloro-3-cyano-1-methyl-1H-indol-2-yl)-pyridin-3-ylmethyl]-piperidin-4-yl}-carbamic acid tert-butyl ester is processed according to the method described in Example 178b to give 2-[5-(4-amino-piperidin-1-ylmethyl)-pyridin-3-yl]-6-chloro-1-methyl-1H-indole-3-carbonitrile. $^1$H NMR (400 MHz, DMSO-d$_6$) δ ppm (trifluoroacetate salt) 1.75 (br. s., 2H), 2.07 (s, 3H), 3.08 (br. s., 2H), 3.54 (br. s., 2H), 3.84 (s, 3H), 4.47 (br. s., 2H), 7.39 (dd, J=8.3, 1.8 Hz, 1H), 7.75 (d, J=8.3 Hz, 1H), 8.01 (d, J=1.5 Hz, 1H), 8.09 (br. s., 3H), 8.27 (s, 1H), 8.89 (s, 1H), 9.01 (s, 1H), 10.11 (br. s., 1H). HRMS (ESI) m/z 380.1630 [(M+H)$^+$ Calcd for C$_{21}$H$_{23}$ClN$_5$: 380.1642].

Example 182

(a) (S)-3-{[5-(6-Chloro-3-cyano-1-methyl-1H-indol-2-yl)-pyridin-3-ylmethyl]-amino}-pyrrolidine-1-carboxylic acid tert-butyl ester

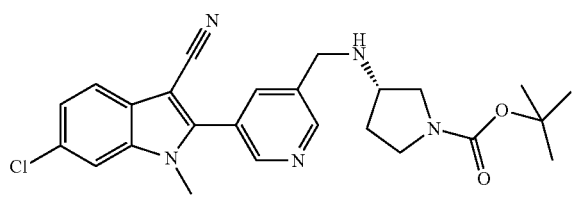 [SMILES: Cn1c(-c2cncc(CN[C@H]3CCN(C(=O)OC(C)(C)C)C3)c2)c(C#N)c2ccc(Cl)cc21]

6-Chloro-2-(5-formyl-pyridin-3-yl)-1-methyl-1H-indole-3-carbonitrile (Example 126) and (S)-3-amino-pyrrolidine-1-carboxylic acid tert-butyl ester are processed according to the method described in Example 170 to give (S)-3-{[5-(6-chloro-3-cyano-1-methyl-1H-indol-2-yl)-pyridin-3-ylmethyl]-amino}-pyrrolidine-1-carboxylic acid tert-butyl ester. MS (ESI) m/z 466.1 (M+H)$^+$.

(b) 6-Chloro-1-methyl-2-[5-((S)-pyrrolidin-3-ylaminomethyl)-pyridin-3-yl]-1H-indole-3-carbonitrile

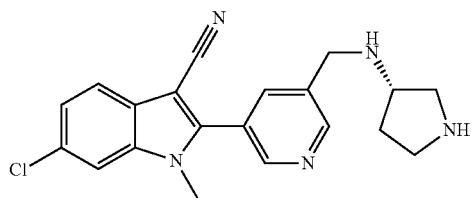 [SMILES: Cn1c(-c2cncc(CN[C@H]3CCNC3)c2)c(C#N)c2ccc(Cl)cc21]

(S)-3-{[5-(6-chloro-3-cyano-1-methyl-1H-indol-2-yl)-pyridin-3-ylmethyl]-amino}-pyrrolidine-1-carboxylic acid tert-butyl ester is processed according to the method described in Example 178b to give 6-chloro-1-methyl-2-[5-((S)-pyrrolidin-3-ylaminomethyl)-pyridin-3-yl]-1H-indole-3-carbonitrile. $^1$H NMR (400 MHz, DMSO-$d_6$) δ ppm 1.50-1.59 (m, 1H), 1.77-1.88 (m, 1H), 2.64-2.69 (m, 1H), 2.72-2.79 (m, 1H), 2.84 (dd, J=11.2, 5.9 Hz, 1H), 2.88-2.96 (m, 1H), 3.13-3.20 (m, 1H), 3.31 (br. s., 2H), 3.79 (s, 3H), 3.82 (s, 2H), 7.37 (dd, J=8.6, 1.8 Hz, 1H), 7.72 (d, J=8.6 Hz, 1H), 7.97 (d, J=1.5 Hz, 1H), 8.09 (t, J=2.1 Hz, 1H), 8.73-8.77 (m, 2H). HRMS (ESI) m/z 366.1495 [(M+H)$^+$ Calcd for $C_{20}H_{21}ClN_5$: 366.1485].

Example 183

6-Chloro-1-methyl-2-[5-(4-methyl-3-oxo-piperazin-1-ylmethyl)-pyridin-3-yl]-1H-indole-3-carbonitrile

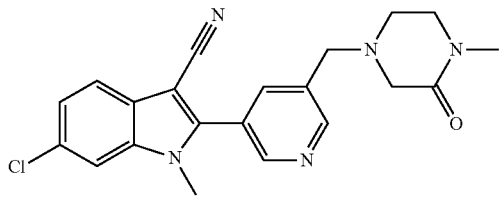 [SMILES: CN1CCN(Cc2cncc(-c3c(C#N)c4ccc(Cl)cc4n3C)c2)CC1=O]

6-Chloro-2-(5-formyl-pyridin-3-yl)-1-methyl-1H-indole-3-carbonitrile (Example 126) and 1-methyl-piperazin-2-one are processed according to the method described in Example 170 to give 6-chloro-1-methyl-2-[5-(4-methyl-3-oxo-piperazin-1-ylmethyl)-pyridin-3-yl]-1H-indole-3-carbonitrile. $^1$H NMR (400 MHz, DMSO-$d_6$) δ ppm 2.70 (br. s., 2H), 2.82 (s, 3H), 3.09 (s, 2H), 3.29 (dd, J=11.0, 5.4 Hz, 2H), 3.73 (s, 2H), 3.80 (s, 3H), 7.36 (dd, J=8.6, 1.8 Hz, 1H), 7.72 (d, J=8.3 Hz, 1H), 7.96 (d, J=1.5 Hz, 1H), 8.09 (s, 1H), 8.74 (d, J=2.0 Hz, 1H), 8.81 (d, J=2.0 Hz, 1H). HRMS (ESI) m/z 394.1437 [(M+H)$^+$ Calcd for $C_{21}H_{21}ClN_5O$: 394.1435].

Example 184

(a) (R)-3-{[5-(6-Chloro-3-cyano-1-methyl-1H-indol-2-yl)-pyridin-3-ylmethyl]-amino}-pyrrolidine-1-carboxylic acid tert-butyl ester

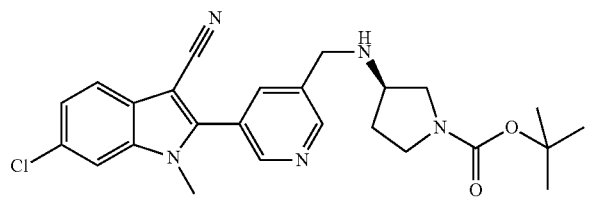 [SMILES: Cn1c(-c2cncc(CN[C@@H]3CCN(C(=O)OC(C)(C)C)C3)c2)c(C#N)c2ccc(Cl)cc21]

6-Chloro-2-(5-formyl-pyridin-3-yl)-1-methyl-1H-indole-3-carbonitrile (Example 126) and (R)-3-amino-pyrrolidine-1-carboxylic acid tert-butyl ester are processed according to the method described in Example 170 to give (R)-3-{[5-(6-chloro-3-cyano-1-methyl-1H-indol-2-yl)-pyridin-3-ylmethyl]-amino}-pyrrolidine-1-carboxylic acid tert-butyl ester. MS (ESI) m/z 466.11 (M+H)$^+$.

(b) 6-Chloro-1-methyl-2-[5-((R)-pyrrolidin-3-ylaminomethyl)-pyridin-3-yl]-1H-indole-3-carbonitrile

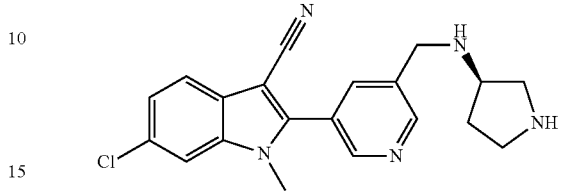

(R)-3-{[5-(6-Chloro-3-cyano-1-methyl-1H-indol-2-yl)-pyridin-3-ylmethyl]-amino}-pyrrolidine-1-carboxylic acid tert-butyl ester is processed according to the method described in Example 178b to give 6-chloro-1-methyl-2-[5-((R)-pyrrolidin-3-ylaminomethyl)-pyridin-3-yl]-1H-indole-3-carbonitrile. $^1$H NMR (400 MHz, DMSO-$d_6$) δ ppm 1.52-1.61 (m, 1H), 1.79-1.88 (m, 1H), 2.70 (dd, J=11.2, 3.9 Hz, 1H), 2.75-2.82 (m, 1H), 2.86 (dd, J=11.1, 5.8 Hz, 1H), 2.90-2.98 (m, 1H), 3.14-3.21 (m, 1H), 3.39 (br. s., 2H), 3.79 (s, 3H), 3.83 (s, 2H), 7.37 (dd, J=8.3, 1.8 Hz, 1H), 7.72 (d, J=8.6 Hz, 1H), 7.96 (d, J=1.5 Hz, 1H), 8.10 (t, J=2.1 Hz, 1H), 8.74-8.77 (m, 2H). HRMS (ESI) m/z 366.1486 [(M+H)$^+$ Calcd for $C_{20}H_{21}ClN_5$ 366.1485].

Example 185

6-Chloro-1-methyl-2-{5-[(1-methyl-piperidin-4-ylamino)-methyl]-pyridin-3-yl}-1H-indole-3-carbonitrile

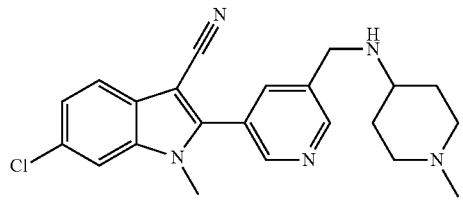 [SMILES: CN1CCC(NCc2cncc(-c3c(C#N)c4ccc(Cl)cc4n3C)c2)CC1]

To a solution of 6-chloro-2-(5-formyl-pyridin-3-yl)-1-methyl-1H-indole-3-carbonitrile (Example 126, 0.150 g, 0.482 mmol) in THF (3 mL) and DMF (1 mL) is added 4-amino-1-methylpiperidine (0.067 g, 0.578 mmol), followed with MP-NaBH$_3$CN (2.42 mmol/g, 0.498 g, 1.205 mmol). After 16 h, MP-NaBH$_3$CN (2.42 mmol/g, 0.200 g, 0.484 mmol) is added. After another 46 h and PL-benzaldehyde (1.8 mmol/g, 0.268 g, 0.482 mmol) is added and after another 8 h, the mixture is filtered and the solids are washed with THF. After evaporation of the solvents, the residue is purified by reverse phase HPLC on a Sunfire C18, eluting with a gradient of 0.1% aqueous TFA-acetonitrile to give 6-chloro-1-methyl-2-{5-[(1-methyl-piperidin-4-ylamino)-methyl]-pyridin-3-yl}-1H-indole-3-carbonitrile as a gum which is triturated with 1M HCl in ether to give the HCl salt. $^1$H NMR (400 MHz, DMSO-$d_6$) δ ppm (HCl salt) 1.46-1.66 (m, 2H), 1.93-2.04 (m, 2H), 2.50-2.57 (m, 4H), 2.66-2.76 (m, 2H), 3.10-3.20 (m, 2H), 3.80 (s, 3H), 3.95 (br. s., 2H), 7.37 (dd, J=8.6, 1.8 Hz, 1H), 7.73 (d, J=8.6 Hz, 1H), 7.98 (d, J=1.8 Hz, 1H), 8.16 (s, 1H), 8.79 (d, J=2.0 Hz, 1H), 8.80 (d, J=2.0 Hz, 1H). HRMS (ESI) m/z 394.1804 [(M+H)$^+$ Calcd for $C_{22}H_{25}ClN_5$: 394.1798].

Example 186

(a) 2-(5-Bromo-pyridin-3-yl)-methanol

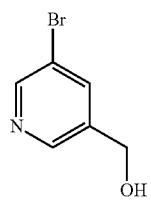

A flask is charged with 5-bromo-pyridine-3-carbaldehyde (5.0 g, 26.1 mmol) and methanol (200 mL) and cooled to 0° C. Sodium borohydride (2.99 g, 78.23 mmol) is added and the reaction is stirred at room temperature for 2 h. The solvent is removed in vacuo. The residue is redissolved in dichloromethane and washed with water twice. The combined aqueous layer is saturated with sodium chloride and extracted with ethyl acetate. The combined organic layer is dried over sodium sulfate and concentrated in vacuo to afford 2-(5-bromo-pyridin-3-yl)-methanol as a solid. MS (ESI) m/z 189.9 (M+H)$^+$

(b) 2-(5-bromo-pyridin-3-ylmethyl)-isoindole-1,3-dione

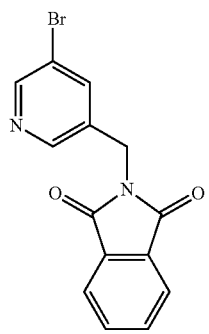 [SMILES: O=C1c2ccccc2C(=O)N1Cc1cncc(Br)c1]

A flask is charged with 2-(5-bromo-pyridin-3-yl)-methanol (4.70 g, 23.75 mmol), phthalimide (3.92 g, 26.12 mmol), tributylphosphine (11.04 mL, 44.527 mmol) and THF (50 mL). 1,1'-(Azodicarbonyl)dipiperidine (11.80 g, 46.31 mmol) is added and the reaction is stirred at room temperature for 6 h, diluted with ethyl acetate and washed with water thrice. The organic layer is dried over sodium sulfate and concentrated in vacuo to give a residue which is purified by silica gel flash chromatography (heptane-ethyl acetate, 1:1) to afford 2-(5-bromo-pyridin-3-ylmethyl)-isoindole-1,3-dione as a solid. MS (ESI) m/z 319.1 (M+H)$^+$.

(c) 2-[5-(6-chloro-1-methyl-1H-indol-2-yl)-pyridin-3-ylmethyl]-isoindole-1,3-dione

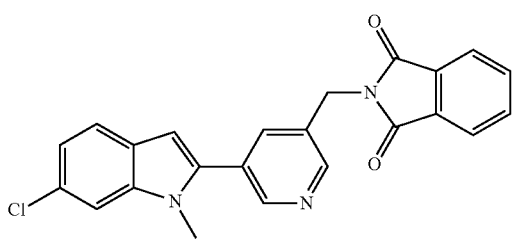 [SMILES: Cn1c(-c2cncc(CN3C(=O)c4ccccc4C3=O)c2)cc2ccc(Cl)cc21]

6-Chloro-1-methyl-indole-2-boronic acid and 2-(5-bromo-pyridin-3-ylmethyl)-isoindole-1,3-dione are processed according to the method described in Example 100 to give 2-[5-(6-chloro-1-methyl-1H-indol-2-yl)-pyridin-3-ylmethyl]-isoindole-1,3-dione. MS (ESI) m/z 402.1 (M+H)$^+$.

(d) 6-chloro-2-[5-(1,3-dioxo-1,3-dihydro-isoindol-2-ylmethyl)-pyridin-3-yl]-1-methyl-1H-indole-3-carbonitrile

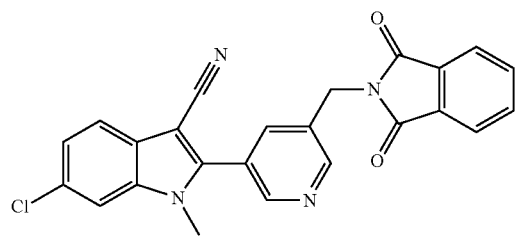 [SMILES: Cn1c(-c2cncc(CN3C(=O)c4ccccc4C3=O)c2)c(C#N)c2ccc(Cl)cc21]

2-[5-(6-Chloro-1-methyl-1H-indol-2-yl)-pyridin-3-ylmethyl]-isoindole-1,3-dione is processed according to the method described in Example 128 to give 6-chloro-2-[5-(1,3-dioxo-1,3-dihydro-isoindol-2-ylmethyl)-pyridin-3-yl]-1-methyl-1H-indole-3-carbonitrile as a solid. MS (ESI) m/z 427.0 (M+H)$^+$.

(e) 2-(5-Aminomethyl-pyridin-3-yl)-6-chloro-1-methyl-1H-indole-3-carbonitrile

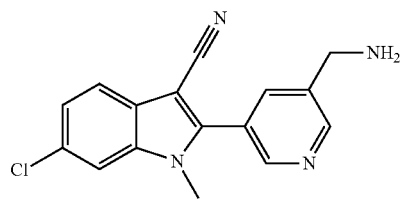

To a solution of 6-chloro-2-[5-(1,3-dioxo-1,3-dihydro-isoindol-2-ylmethyl)-pyridin-3-yl]-1-methyl-1H-indole-3-carbonitrile (8.96 g, 18.89 mmol) in ethanol (200 mL) is added hydrazine (12.10 mL, 378 mmol) and the reaction mixture is stirred overnight. The mixture is then filtered and the solids are washed with ethyl acetate. The filtrate is partially concentrated to remove ethyl acetate. 1M aqueous HCl is added, and the aqueous mixture is washed with EtOAc. The aqueous layer is then basified with 4M aqueous NaOH and extracted with dichloromethane thrice. The dichloromethane extracts are dried over Na$_2$SO$_4$ and concentrated in vacuo to afford 2-(5-aminomethyl-pyridin-3-yl)-6-chloro-1-methyl-1H-indole-3-carbonitrile as a solid. MS (ESI) m/z 297.0 (M+H)$^+$

(f) Propane-2-sulfonic acid [5-(6-chloro-3-cyano-1-methyl-1H-indol-2-yl)-pyridin-3-ylmethyl]-amide

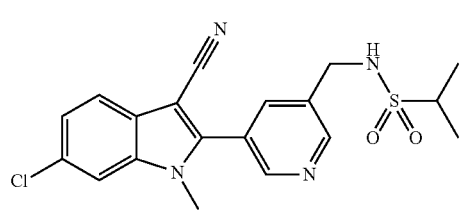 [SMILES: CC(C)S(=O)(=O)NCc1cncc(-c2c(C#N)c3ccc(Cl)cc3n2C)c1]

A flask is charged with 2-(5-aminomethyl-pyridin-3-yl)-6-chloro-1-methyl-1H-indole-3-carbonitrile (0.075 g, 0.253 mmol) and dichloromethane (2 mL). Isopropylsulfonyl chloride (0.031 mL, 0.278 mmol) and triethylamine (0.071 mL, 0.506 mmol) are added and the reaction is stirred at room temperature overnight. The reaction mixture is concentrated in vacuo. The residue is purified by reverse phase HPLC with Xbridge Shield RP18 column and a 0.1% aqueous NH$_4$OH in acetonitrile gradient to afford propane-2-sulfonic acid [5-(6-chloro-3-cyano-1-methyl-1H-indol-2-yl)-pyridin-3-ylmethyl]-amide as a solid. $^1$H NMR (400 MHz, MeOD) δ ppm 1.40 (d, J=6.8 Hz, 6H), 3.25-3.32 (m, 1H), 3.84 (s, 3H), 4.50 (s, 2H), 7.38 (dd, J=8.6, 1.8 Hz, 1H), 7.72 (d, J=8.6 Hz, 1H), 7.77 (d, J=1.5 Hz, 1H), 8.18 (t, J=2.0 Hz, 1H), 8.81 (t, J=1.9 Hz, 2H). HRMS (ESI) m/z 403.0997 [(M+H)$^+$ Calcd for C$_{19}$H$_{20}$ClN$_4$O$_2$S: 403.0996].

Example 187

2,2,2-Trifluoro-ethanesulfonic acid [5-(6-chloro-3-cyano-1-methyl-1H-indol-2-yl)-pyridin-3-ylmethyl]-amide

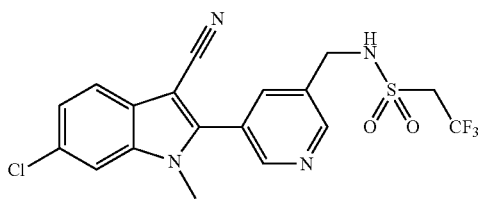 [SMILES: Cn1c(-c2cncc(CNS(=O)(=O)CC(F)(F)F)c2)c(C#N)c2ccc(Cl)cc21]

2-(5-Aminomethyl-pyridin-3-yl)-6-chloro-1-methyl-1H-indole-3-carbonitrile (Example 186e) and 2,2,2-trifluoro-ethanesulfonyl chloride are processed according to the method described in Example 186f to give 2,2,2-trifluoro-ethanesulfonic acid [5-(6-chloro-3-cyano-1-methyl-1H-indol-2-yl)-pyridin-3-ylmethyl]-amide. $^1$H NMR (400 MHz, MeOD) δ ppm 3.84 (s, 3H), 4.29 (q, J=9.6 Hz, 2H), 4.54 (s, 2H), 7.39 (dd, J=8.6, 1.8 Hz, 1H), 7.73 (d, J=8.3 Hz, 1H), 7.78 (d, J=1.8 Hz, 1H), 8.18 (t, J=2.0 Hz, 1H), 8.81 (d, J=2.0 Hz, 1H), 8.83 (d, J=2.0 Hz, 1H). HRMS (ESI) m/z 443.0557 [(M+H)$^+$ Calcd for C$_{18}$H$_{15}$N$_4$O$_2$F$_3$SCl: 443.0556].

Example 188

(a) 2-(1,3-Dioxo-1,3-dihydro-isoindol-2-yl)-ethanesulfonic acid [5-(6-chloro-3-cyano-1-methyl-1H-indol-2-yl)-pyridin-3-ylmethyl]-amide

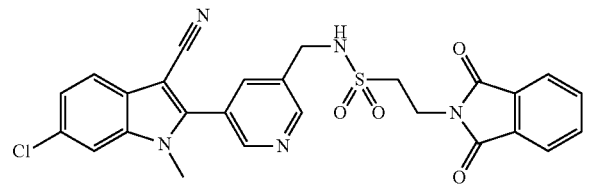 [SMILES: Cn1c(-c2cncc(CNS(=O)(=O)CCN3C(=O)c4ccccc4C3=O)c2)c(C#N)c2ccc(Cl)cc21]

A flask is charged with 2-(5-aminomethyl-pyridin-3-yl)-6-chloro-1-methyl-1H-indole-3-carbonitrile (Example 186e, 0.050 g, 0.160 mmol) and dichloromethane (2 mL). 2-(1,3-Dioxo-1,3-dihydro-isoindol-2-yl)-ethanesulfonyl chloride (0.068 g, 0.239 mmol) and triethylamine (0.045 mL, 0.319 mmol) are added and the reaction is stirred at room temperature for 5 min. The reaction mixture is washed with water and extracted with dichloromethane twice. The combined organic phase is separated, dried over sodium sulfate and concentrated in vacuo to give a residue which is purified by silica gel flash chromatography (dichloromethane-methanol, 19:1) to afford 2-(1,3-dioxo-1,3-dihydro-isoindol-2-yl)-ethane sulfonic acid [5-(6-chloro-3-cyano-1-methyl-1H-indol-2-yl)-pyridin-3-ylmethyl]-amide as a white solid. MS (ESI) m/z 537.3 (M+H)$^+$.

(b) 2-Amino-ethanesulfonic acid [5-(6-chloro-3-cyano-1-methyl-1H-indol-2-yl)-pyridin-3-ylmethyl]-amide

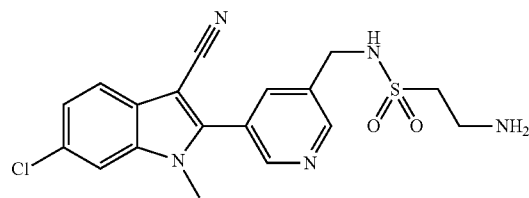 [SMILES: Cn1c(-c2cncc(CNS(=O)(=O)CCN)c2)c(C#N)c2ccc(Cl)cc21]

A flask is charged with 2-(1,3-dioxo-1,3-dihydro-isoindol-2-yl)-ethanesulfonic acid [5-(6-chloro-3-cyano-1-methyl-1H-indol-2-yl)-pyridin-3-ylmethyl]-amide (0.065 g, 0.109 mmol) and MeOH (4 mL). Hydrazine (0.069 mL, 2.183 mmol) is added and the reaction is stirred at room temperature overnight. 2M aqueous HCl is added, followed by concentration in vacuo. Dichloromethane is added and the mixture is filtered through celite. The organic layer is washed with water once and the aqueous layer is basified to using 4M aqueous NaOH and extracted with dichloromethane thrice. The combined dichloromethane fraction is dried over sodium sulfate and concentrated in vacuo to afford a residue which is purified by reverse-phase HPLC to afford 2-amino-ethanesulfonic acid [5-(6-chloro-3-cyano-1-methyl-1H-indol-2-yl)-pyridin-3-ylmethyl]-amide as a solid. $^1$H NMR (400 MHz, MeOD) δ ppm 3.12 (t, J=6.6 Hz, 2H), 3.29 (t, J=6.6 Hz, 2H), 3.84 (s, 3H), 4.49 (s, 2H), 7.38 (dd, J=8.6, 1.8 Hz, 1H), 7.73 (d, J=8.6 Hz, 1H), 7.78 (d, J=1.5 Hz, 1H), 8.19 (t, J=2.1 Hz, 1H), 8.81 (d, J=2.3 Hz, 1H), 8.82 (d, J=2.3 Hz, 1H). HRMS (ESI) m/z 404.0944 [(M+H)$^+$ Calcd for C$_{18}$H$_{19}$ClN$_5$O$_2$S: 404.0948].

Example 189

N,N-diethyl-N'-[5-(6-chloro-3-cyano-1-methyl-1H-indol-2-yl)-pyridin-3-ylmethyl]-sulfamide

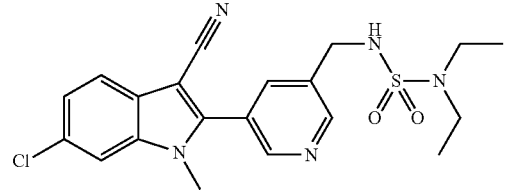 [SMILES: CCN(CC)S(=O)(=O)NCc1cncc(-c2c(C#N)c3ccc(Cl)cc3n2C)c1]

A flask is charged with 2-(5-aminomethyl-pyridin-3-yl)-6-chloro-1-methyl-1H-indole-3-carbonitrile (Example 186e, 0.103 g, 0.349 mmol) and dichloromethane (2 mL). Diethylaminosulfamoyl chloride (0.072 g, 0.419 mmol) and triethylamine (0.100 mL, 0.699 mmol) are added and the reaction is stirred at room temperature overnight. The reaction mixture is concentrated in vacuo and the residue is purified by reverse phase HPLC with Xbridge Shield RP18 column and a 0.1% aqueous NH$_4$OH in acetonitrile gradient to afford N,N-diethyl-N'-[5-(6-chloro-3-cyano-1-methyl-1H-indol-2-yl)-pyridin-3-ylmethyl]-sulfamide as a solid. $^1$H NMR (400 MHz, MeOD) δ ppm 1.20 (t, J=7.1 Hz, 6H), 3.30 (q, J=7.1 Hz, 4H), 3.83 (s, 3H), 4.35 (s, 2H), 7.38 (dd, J=8.6, 1.8 Hz, 1H), 7.71 (d, J=8.6 Hz, 1H), 7.77 (d, J=1.5 Hz, 1H), 8.17 (t, J=2.1 Hz, 1H), 8.79 (dd, J=3.7, 2.1 Hz, 2H). HRMS (ESI) m/z 432.1278 [(M+H)$^+$ Calcd for C$_{20}$H$_{23}$ClN$_5$O$_2$S: 432.1261].

Example 190

5-(6-chloro-3-cyano-1H-indol-2-yl)-pyridin-3-ylmethyl]-carbamic acid ethyl ester

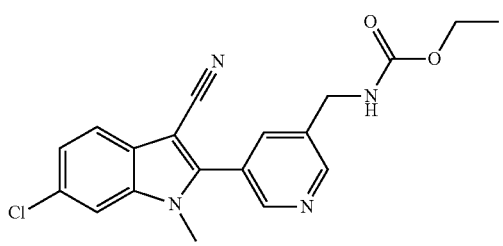 [SMILES: CCOC(=O)NCc1cncc(-c2c(C#N)c3ccc(Cl)cc3n2C)c1]

A flask is charged with 2-(5-aminomethyl-pyridin-3-yl)-6-chloro-1-methyl-1H-indole-3-carbonitrile (Example 186e, 0.100 g, 0.349 mmol) and dichloromethane (4 mL). Ethyl chloroformate (0.055 g, 0.506 mmol) and triethylamine (0.100 mL, 0.675 mmol) are added and the reaction is stirred at room temperature for 10 min. The reaction mixture is concentrated in vacuo and the residue is purified by reverse phase HPLC with Xbridge Shield RP18 column and a 0.1% aqueous NH$_4$OH in acetonitrile gradient to afford 5-(6-chloro-3-cyano-1H-indol-2-yl)-pyridin-3-ylmethyl]-carbamic acid ethyl ester as a solid. $^1$H NMR (400 MHz, MeOD) δ ppm 1.28 (t, J=7.1 Hz, 3H), 3.83 (s, 3H), 4.15 (q, J=7.1 Hz, 2H), 4.48 (s, 2H), 7.37 (dd, J=8.6, 1.8 Hz, 1H), 7.71 (d, J=8.6 Hz, 1H), 7.76 (d, J=1.5 Hz, 1H), 8.09 (t, J=1.9 Hz, 1H), 8.73 (d, J=2.0 Hz, 1H), 8.78 (d, J=2.0 Hz, 1H). HRMS (ESI) m/z 369.1125 [(M+H)$^+$ Calcd for C$_{19}$H$_{18}$ClN$_4$O$_2$: 369.1118].

Example 191

[5-(6-chloro-3-cyano-1H-indol-2-yl)-pyridin-3-ylmethyl]-carbamic acid propyl ester

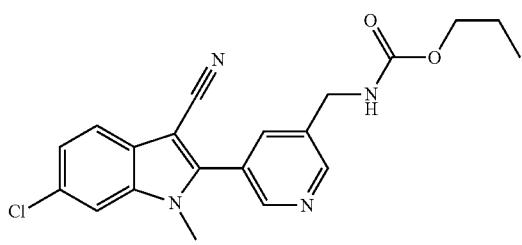 [SMILES: CCCOC(=O)NCc1cncc(-c2c(C#N)c3ccc(Cl)cc3n2C)c1]

2-(5-aminomethyl-pyridin-3-yl)-6-chloro-1-methyl-1H-indole-3-carbonitrile (Example 186e) and N-propyl chloroformate are processed according to the method described in Example 190 to give [5-(6-chloro-3-cyano-1H-indol-2-yl)-pyridin-3-ylmethyl]-carbamic acid propyl ester as a solid. $^1$H NMR (400 MHz, MeOD) δ ppm 0.98 (t, J=7.3 Hz, 3H), 1.58-1.74 (m, 2H), 3.83 (s, 3H), 4.06 (t, J=6.6 Hz, 2H), 4.49 (s, 2H), 7.38 (dd, J=8.6, 1.77 Hz, 1H), 7.72 (d, J=8.6 Hz, 1H), 7.77 (d, J=1.5 Hz, 1H), 8.09 (t, J=2.0 Hz, 1H), 8.74 (d, J=2.0 Hz, 1H), 8.78 (d, J=2.0 Hz, 1H). HRMS (ESI) m/z 383.1260 [(M+H)$^+$ Calcd for C$_{20}$H$_{20}$ClN$_4$O$_2$: 383.1275].

Example 192

5-(6-Chloro-3-cyano-1-methyl-1H-indol-2-yl)-pyridin-3-ylmethyl]-carbamic acid 2-methoxy-ethyl ester

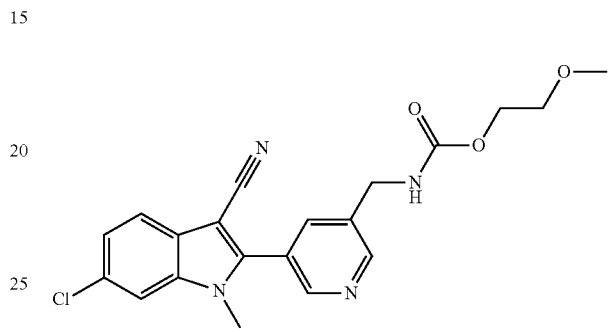

2-(5-aminomethyl-pyridin-3-yl)-6-chloro-1-methyl-1H-indole-3-carbonitrile (Example 186e) and 3-methoxy-ethyl chloroformate are processed according to the method described in Example 190 to give 5-(6-chloro-3-cyano-1-methyl-1H-indol-2-yl)-pyridin-3-ylmethyl]-carbamic acid 2-methoxy-ethyl ester as a solid. $^1$H NMR (400 MHz, MeOD) δ ppm 3.37 (s, 3H), 3.58-3.65 (m, 2H), 3.83 (s, 3H), 4.14-4.27 (m, 2H), 4.50 (s, 2H), 7.38 (dd, J=8.6, 1.8 Hz, 1H), 7.72 (d, J=8.6 Hz, 1H), 7.77 (d, J=1.5 Hz, 1H), 8.10 (s, 1H), 8.74 (d, J=2.0 Hz, 1H), 8.78 (d, J=2.0 Hz, 1H). HRMS (ESI) m/z 399.1221 [(M+H)$^+$ Calcd for C$_{20}$H$_{20}$ClN$_4$O$_3$: 399.1224].

Example 193

5-(6-Chloro-3-cyano-1-methyl-1H-indol-2-yl)-pyridin-3-ylmethyl]-carbamic acid isobutyl ester

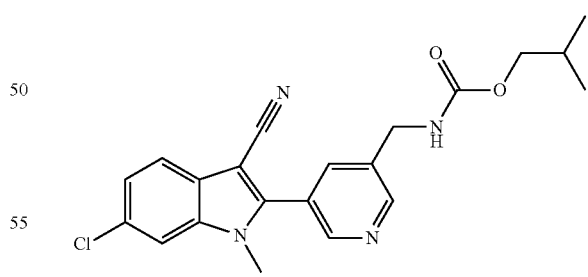

2-(5-Aminomethyl-pyridin-3-yl)-6-chloro-1-methyl-1H-indole-3-carbonitrile (Example 186e) and isobutyl chloroformate are processed according to the method described in Example 190 to give 5-(6-chloro-3-cyano-1-methyl-1H-indol-2-yl)-pyridin-3-ylmethyl]-carbamic acid isobutyl ester. $^1$H NMR (400 MHz, MeOD) δ ppm 0.97 (d, J=6.6 Hz, 6H), 1.85-2.01 (m, 1H), 3.83 (s, 3H), 3.89 (d, J=6.6 Hz, 2H), 4.49 (s, 2H), 7.38 (dd, J=8.6, 1.8 Hz, 1H), 7.72 (d, J=8.3 Hz, 1H), 7.77 (d, J=1.8 Hz, 1H), 8.09 (t, J=2.1 Hz, 1H), 8.74 (d, J=1.8

Hz, 1H), 8.78 (d, J=2.0 Hz, 1H). HRMS (ESI) m/z 397.1424 [(M+H)+ Calcd for $C_{21}H_{22}ClN_4O_2$: 397.1431].

Example 194

5-(6-Chloro-3-cyano-1-methyl-1H-indol-2-yl)-pyridin-3-ylmethyl]-carbamic acid isopropyl ester

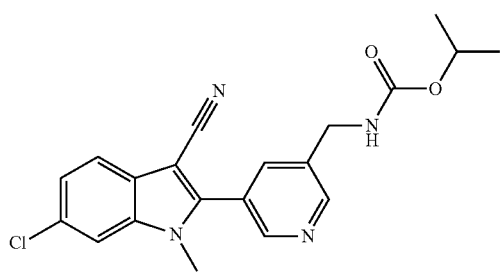 [SMILES: CC(C)OC(=O)NCc1cncc(-c2c(C#N)c3ccc(Cl)cc3n2C)c1]

2-(5-Aminomethyl-pyridin-3-yl)-6-chloro-1-methyl-1H-indole-3-carbonitrile (Example 186e) and isopropyl chloroformate are processed according to the method described in Example 190 to give 5-(6-chloro-3-cyano-1-methyl-1H-indol-2-yl)-pyridin-3-ylmethyl]-carbamic acid isopropyl ester. $^1$H NMR (400 MHz, MeOD) δ ppm 1.27 (d, J=6.3 Hz, 6H), 3.83 (s, 3H), 4.48 (s, 2H), 4.88-4.94 (m, 1H), 7.38 (dd, J=8.6, 1.8 Hz, 1H), 7.72 (d, J=8.6 Hz, 1H), 7.77 (d, J=1.5 Hz, 1H), 8.09 (t, J=1.9 Hz, 1H), 8.73 (d, J=1.8 Hz, 1 H), 8.78 (d, J=2.0 Hz, 1H). HRMS (ESI) m/z 383.1266 [(M+H)+ Calcd for $C_{20}H_{20}ClN_4O_2$: 383.1275].

Example 195

1-[5-(6-Chloro-3-cyano-1-methyl-1H-indol-2-yl)-pyridin-3-ylmethyl]-3-ethyl-urea

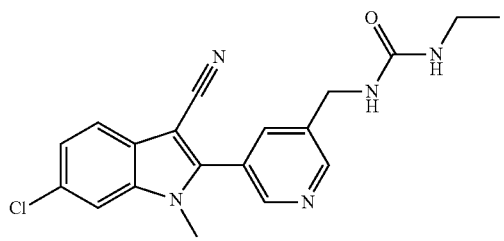 [SMILES: CCNC(=O)NCc1cncc(-c2c(C#N)c3ccc(Cl)cc3n2C)c1]

To a solution of 2-(5-aminomethyl-pyridin-3-yl)-6-chloro-1-methyl-1H-indole-3-carbonitrile (Example 186e, 0.100 g, 0.337 mmol) in dichloromethane (3 mL) is added ethyl isocyanate (0.030 g, 0.422 mmol) and the reaction is stirred at room temperature for 45 min. The mixture is then washed with water and extracted with dichloromethane twice. The organic phase is concentrated in vacuo to give a residue which is purified by reverse phase HPLC with Xbridge Shield RP18 column and a 0.1% aqueous NH$_4$OH in acetonitrile gradient to afford 1-[5-(6-chloro-3-cyano-1-methyl-1H-indol-2-yl)-pyridin-3-ylmethyl]-3-ethyl-urea as a solid. $^1$H NMR (400 MHz, MeOD) δ ppm 1.14 (t, J=7.2 Hz, 3H), 3.20 (q, J=7.3 Hz, 2H), 3.82 (s, 3H), 4.52 (s, 2H), 7.38 (dd, J=8.3, 1.8 Hz, 1H), 7.71 (d, J=8.6 Hz, 1H), 7.76 (d, J=1.5 Hz, 1H), 8.08 (t, J=2.1 Hz, 1H), 8.73 (d, J=2.0 Hz, 1H), 8.76 (d, J=2.3 Hz, 1H). HRMS (ESI) m/z 368.1275 [(M+H)+ Calcd for $C_{19}H_{19}ClN_5O$: 368.1278].

Example 196

1-[5-(6-Chloro-3-cyano-1-methyl-1H-indol-2-yl)-pyridin-3-ylmethyl]-3-isopropyl-urea

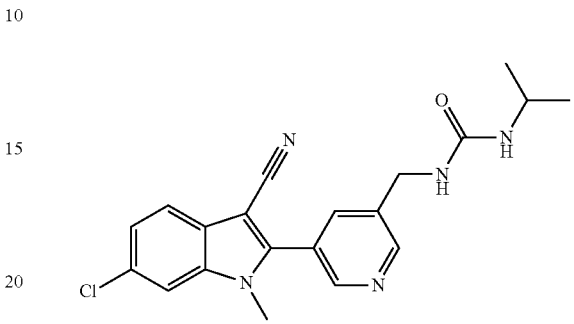

To a solution of 2-(5-aminomethyl-pyridin-3-yl)-6-chloro-1-methyl-1H-indole-3-carbonitrile (Example 186e, 0.060 g, 0.192 mmol) in dichloromethane (3 mL) is added isopropyl isocyanate (0.027 g, 0.240 mmol) and the reaction is stirred at room temperature for 45 min. The mixture is then washed with water and extracted with dichloromethane twice.

The organic phase is concentrated in vacuo to give a residue which is redissolved in methanol. A precipitate crashes out upon standing. The solid is filtered to afford 1-[5-(6-chloro-3-cyano-1-methyl-1H-indol-2-yl)-pyridin-3-ylmethyl]-3-isopropyl-urea as a solid. $^1$H NMR (400 MHz, MeOD) δ ppm 1.17 (d, J=6.6 Hz, 6H), 3.76-3.91 (m, 4H), 4.52 (s, 2H), 7.38 (dd, J=8.5, 1.9 Hz, 1H), 7.72 (d, J=8.3 Hz, 1H), 7.77 (d, J=1.5 Hz, 1H), 8.08 (t, J=2.1 Hz, 1H), 8.73 (d, J=2.0 Hz, 1H), 8.76 (d, J=2.0 Hz, 1H). HRMS (ESI) m/z 382.1431 [(M+H)+ Calcd for $C_{20}H_{21}N_5OCl$: 382.1435].

Example 197

1-[5-(6-Chloro-3-cyano-1-methyl-1H-indol-2-yl)-pyridin-3-ylmethyl]-3-cyclopentyl-urea

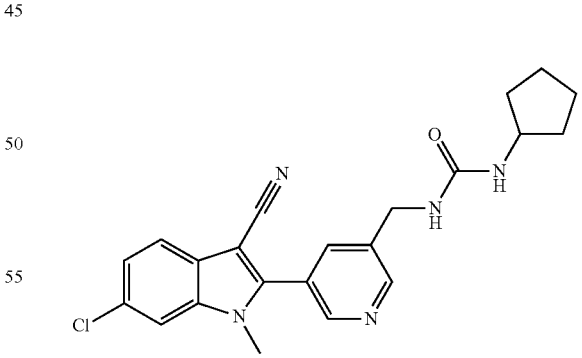

2-(5-Aminomethyl-pyridin-3-yl)-6-chloro-1-methyl-1H-indole-3-carbonitrile (Example 186e) and cyclopentyl isocyanate are processed according to the method described in Example 196 to give 1-[5-(6-chloro-3-cyano-1-methyl-1H-indol-2-yl)-pyridin-3-ylmethyl]-3-cyclopentyl-urea as a solid. $^1$H NMR (400 MHz, MeOD) δ ppm 1.31-1.54 (m, 2H), 1.56-1.68 (m, 2H), 1.68-1.78 (m, 2H), 1.86-2.13 (m, 2H), 3.83 (s, 3H), 3.94-4.09 (m, 1H), 4.52 (s, 2H), 7.38 (dd, J=8.3, 1.8 Hz, 1H), 7.72 (d, J=8.6 Hz, 1H), 7.77 (d, J=1.5 Hz, 1H), 8.08 (t, J=2.0 Hz, 1H), 8.72 (d, J=2.0 Hz, 1H), 8.76 (d, J=2.0 Hz, 1H). HRMS (ESI) m/z 408.1591 [(M+H)$^+$ Calcd for $C_{22}H_{23}N_5OCl$: 408.1591].

Example 198

Morpholine-4-carboxylic acid [5-(6-chloro-3-cyano-1-methyl-1H-indol-2-yl)-pyridin-3-ylmethyl]-amide

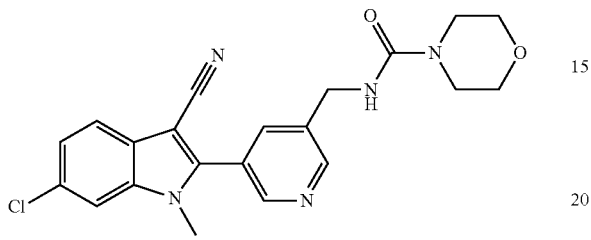

To a solution of 2-(5-aminomethyl-pyridin-3-yl)-6-chloro-1-methyl-1H-indole-3-carbonitrile (Example 186e, 0.060 g, 0.202 mmol) in dichloromethane (2 mL) are added morpholine-4-carbonyl chloride (0.026 g, 0.222 mmol) and triethylamine (0.056 mL, 0.405 mmol) and the reaction is stirred at room temperature overnight. The mixture is then washed with water and extracted with dichloromethane twice. The organic phase is dried over sodium sulfate and concentrated in vacuo. The residue is purified by silica gel flash chromatography (dichloromethane-methanol, 19:1) to afford morpholine-4-carboxylic acid [5-(6-chloro-3-cyano-1-methyl-1H-indol-2-yl)-pyridin-3-ylmethyl]-amide as a solid. $^1$H NMR (400 MHz, MeOD) δ ppm 3.41-3.47 (m, 4H), 3.66-3.72 (m, 4H), 3.84 (s, 3H), 4.55 (s, 2H), 7.38 (dd, J=8.5, 1.9 Hz, 1H), 7.72 (d, J=8.6 Hz, 1H), 7.77 (d, J=1.8 Hz, 1H), 8.11 (t, J=2.1 Hz, 1H), 8.73 (d, J=2.0 Hz, 1H), 8.76 (d, J=2.0 Hz, 1H). MS (ESI) m/z 410.00 (M+H)$^+$.

Example 199

N-[5-(6-Chloro-3-cyano-1-methyl-1H-indol-2-yl)-pyridin-3-ylmethyl]-butyramide

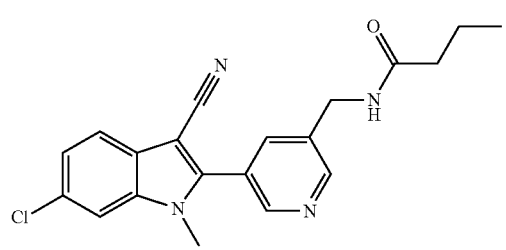

To a solution of 2-(5-aminomethyl-pyridin-3-yl)-6-chloro-1-methyl-1H-indole-3-carbonitrile (Example 186e, 0.060 g, 0.202 mmol) in dichloromethane (2 mL) is added butyryl chloride (0.024 g, 0.222 mmol) and triethylamine (0.056 mL, 0.405 mmol), and the reaction is stirred at room temperature for 30 min. The reaction mixture is diluted with dichloromethane and washed with water. The organic layer is dried over sodium sulfate and concentrated in vacuo. The residue is purified by silica gel flash chromatography (dichloromethane-methanol, 19:1) to afford N-[5-(6-chloro-3-cyano-1-methyl-1H-indol-2-yl)-pyridin-3-ylmethyl]-butyramide as a white solid. $^1$H NMR (400 MHz, MeOD) δ ppm 0.98 (t, J=7.5 Hz, 3H), 1.65-1.77 (m, 2H), 2.29 (t, J=7.5 Hz, 2H), 3.82 (s, 3H), 4.57 (s, 2H), 7.38 (dd, J=8.6, 1.8 Hz, 1H), 7.72 (d, J=8.6 Hz, 1H), 7.77 (d, J=1.5 Hz, 1H), 8.09 (t, J=2.1 Hz, 1H), 8.73 (d, J=2.0 Hz, 1H), 8.78 (d, J=2.0 Hz, 1H). HRMS (ESI) m/z 367.1327 [(M+H)$^+$ Calcd for $C_{20}H_{20}N_4OCl$: 367.1326].

Example 200

(a) 2-[5-(1-Methyl-1H-indol-2-yl)-pyridin-3-ylmethyl]-isoindole-1,3-dione

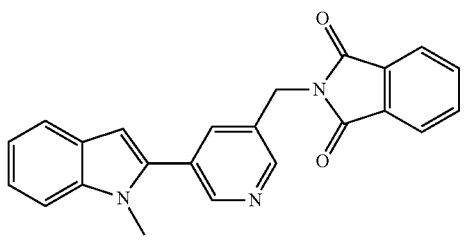 [SMILES: Cn1c(-c2cncc(CN3C(=O)c4ccccc4C3=O)c2)cc2ccccc21]

2-(5-Bromo-pyridin-3-ylmethyl)-isoindole-1,3-dione (Example 186b) and 1-methyl-indole-2-boronic acid are processed according to the method described in Example 100 to give 2-[5-(1-methyl-1H-indol-2-yl)-pyridin-3-ylmethyl]-isoindole-1,3-dione as a solid. MS (ESI) m/z 368.09 (M+H)$^+$.

(b) C-[5-(1-Methyl-1H-indol-2-yl)-pyridin-3-yl]-methylamine

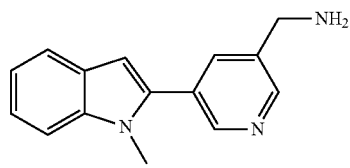 [SMILES: Cn1c(-c2cncc(CN)c2)cc2ccccc21]

2-[5-(1-Methyl-1H-indol-2-yl)-pyridin-3-ylmethyl]-isoindole-1,3-dione is processed according to the method described in Example 186e to give C-[5-(1-methyl-1H-indol-2-yl)-pyridin-3-yl]-methylamine as a solid. MS (ESI) m/z 238.06 (M+H)$^+$.

Example 201

N-[5-(1-Methyl-1H-indol-2-yl)-pyridin-3-ylmethyl]-ethanesulfonamide

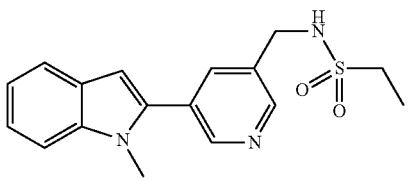 [SMILES: CCS(=O)(=O)NCc1cncc(-c2cc3ccccc3n2C)c1]

C-[5-(1-Methyl-1H-indol-2-yl)-pyridin-3-yl]-methylamine (Example 200b) and ethanesulfonyl chloride are processed according to the method described in Example 186f to give N-[5-(1-methyl-1H-indol-2-yl)-pyridin-3-ylmethyl]-ethanesulfonamide. ¹H NMR (400 MHz, MeOD) δ ppm 1.37 (t, J=7.3 Hz, 3H), 3.13 (q, J=7.4 Hz, 2H), 3.82 (s, 3H), 4.43 (s, 2H), 6.70 (s, 1H), 7.01-7.18 (m, 1H), 7.20-7.36 (m, 1H), 7.48 (d, J=8.3 Hz, 1H), 7.62 (d, J=7.8 Hz, 1H), 8.10 (t, J=2.1 Hz, 1H), 8.61 (d, J=2.0 Hz, 1H), 8.71 (d, J=2.0 Hz, 1H). HRMS (ESI) m/z 330.1288 [(M+H)⁺ Calcd for $C_{17}H_{20}N_3O_2S$: 330.1276].

Example 202

N-[5-(1-Methyl-1H-indol-2-yl)-pyridin-3-ylmethyl]-isopropylsulfonamide

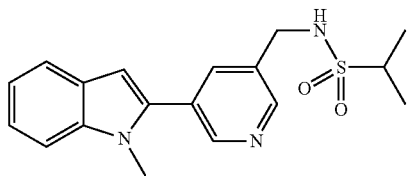 [SMILES: CC(C)S(=O)(=O)NCc1cncc(-c2cc3ccccc3n2C)c1]

C-[5-(1-Methyl-1H-indol-2-yl)-pyridin-3-yl]-methylamine (Example 200b) and isopropylsulfonyl chloride are processed according to the method described in Example 186f to give N-[5-(1-methyl-1H-indol-2-yl)-pyridin-3-ylmethyl]-isopropylsulfonamide. ¹H NMR (400 MHz, MeOD) δ ppm 1.40 (d, J=6.82 Hz, 6H), 3.23-3.32 (m, 1H), 3.83 (s, 3H), 4.45 (s, 2H), 6.70 (s, 1H), 7.09-7.17 (m, 1H), 7.27 (ddd, J=7.6, 1.14 Hz, 1H), 7.48 (d, J=8.3 Hz, 1H), 7.63 (d, J=8.1 Hz, 1H), 8.11 (t, J=2.1 Hz, 1H), 8.61 (d, J=2.0 Hz, 1H), 8.71 (d, J=2.0 Hz, 1H). HRMS (ESI) m/z 344.1431 [(M+H)⁺ Calcd for $C_{18}H_{22}N_3O_2S$: 344.1433].

Example 203

C,C,C-Trifluoro-N-[5-(1-methyl-1H-indol-2-yl)-pyridin-3-ylmethyl]-methanesulfonamide

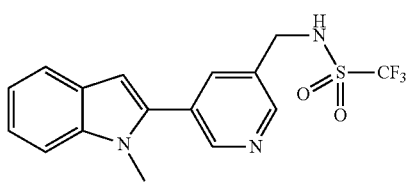 [SMILES: Cn1c(-c2cncc(CNS(=O)(=O)C(F)(F)F)c2)cc2ccccc21]

C-[5-(1-Methyl-1H-indol-2-yl)-pyridin-3-yl]-methylamine (Example 200b) and trifluoromethanesulfonyl chloride are processed according to the method described in Example 186f to give C, C, C-trifluoro-N-[5-(1-methyl-1H-indol-2-yl)-pyridin-3-ylmethyl]-methanesulfonamide. ¹H NMR (400 MHz, MeOD) δ ppm 3.78 (s, 3H), 4.23 (q, J=9.6 Hz, 2H), 6.66 (d, J=0.5 Hz, 1H), 7.04-7.13 (m, 1H), 7.23 (ddd, J=7.7, 1.1 Hz, 1H), 7.44 (d, J=8.2 Hz, 1H), 7.58 (d, J=7.8 Hz, 1H), 8.04 (t, J=2.0 Hz, 1H), 8.56 (d, J=2.0 Hz, 1H), 8.68 (d, J=1.9 Hz, 1H). HRMS (ESI) m/z 370.0835 [(M+H)⁺ Calcd for $C_{16}H_{15}F_3N_3O_2S$: 370.0837].

Example 204

2,2,2-Trifluoro-ethanesulfonic acid [5-(1-methyl-1H-indol-2-yl)-pyridin-3-ylmethyl]-amide

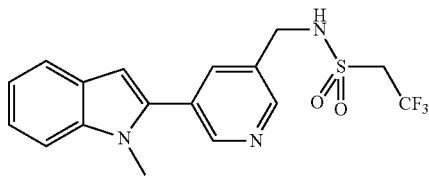 [SMILES: Cn1c(-c2cncc(CNS(=O)(=O)CC(F)(F)F)c2)cc2ccccc21]

C-[5-(1-Methyl-1H-indol-2-yl)-pyridin-3-yl]-methylamine (Example 200b) and 2,2,2-trifluoro-ethanesulfonyl chloride are processed according to the method described in Example 186f to give 2,2,2-trifluoro-ethanesulfonic acid [5-(1-methyl-1H-indol-2-yl)-pyridin-3-ylmethyl]-amide. ¹H NMR (400 MHz, MeOD) δ ppm 3.78 (s, 3H), 4.23 (q, J=9.6 Hz, 2H), 4.44 (s, 2H), 6.66 (d, J=0.5 Hz, 1H), 7.06-7.12 (m, 1H), 7.23 (ddd, J=7.7, 1.1 Hz, 1H), 7.44 (d, J=8.2 Hz, 1H), 7.58 (d, J=7.8 Hz, 1H), 8.04 (t, J=2.0 Hz, 1H), 8.56 (d, J=2.0 Hz, 1H), 8.68 (d, J=1.9 Hz, 1H). HRMS (ESI) m/z 384.0999 [(M+H)⁺ Calcd for $C_{17}H_{17}F_3N_3O_2S$: 384.0994].

Example 205

(a) C-[5-(6-Chloro-1-methyl-1H-indol-2-yl)-pyridin-3-yl]-methylamine

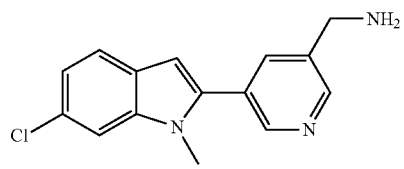 [SMILES: Cn1c(-c2cncc(CN)c2)cc2ccc(Cl)cc21]

2-[5-(6-Chloro-1-methyl-1H-indol-2-yl)-pyridin-3-ylmethyl]-isoindole-1,3-dione (Example 186c) is processed according to the method described in Example 186e to give C-[5-(6-chloro-1-methyl-1H-indol-2-yl)-pyridin-3-yl]-methylamine. MS (ESI) m/z 272.01 (M+H)⁺.

(b) N-[5-(6-Chloro-1-methyl-1H-indol-2-yl)-pyridin-3-ylmethyl]-methanesulfonamide

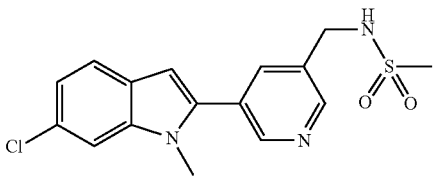 [SMILES: Cn1c(-c2cncc(CNS(C)(=O)=O)c2)cc2ccc(Cl)cc21]

C-[5-(6-Chloro-1-methyl-1H-indol-2-yl)-pyridin-3-yl]-methylamine and methanesulfonyl chloride are processed according to the method described in Example 186f to give N-[5-(6-chloro-1-methyl-1H-indol-2-yl)-pyridin-3-ylmethyl]-methanesulfonamide. ¹H NMR (400 MHz, MeOD) δ ppm 3.03 (s, 3H), 3.80 (s, 3H), 4.45 (s, 2H), 6.71 (s, 1H), 7.12

(dd, J=8.3, 1.8 Hz, 1H), 7.54 (s, 1H), 7.59 (d, J=8.6 Hz, 1H), 8.09 (t, J=2.2 Hz, 1H), 8.63 (d, J=2. Hz, 1H), 8.71 (d, J=2. Hz, 1H). HRMS (ESI) m/z 350.0728 [(M+H)+ Calcd for $C_{16}H_{17}ClN_3O_2S$: 350.0730].

Example 206

N-[5-(6-Chloro-1-methyl-1H-indol-2-yl)-pyridin-3-ylmethyl]-ethanesulfonamide

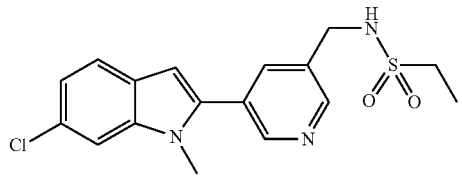

A flask is charged with 6-chloro-2-(5-formyl-pyridin-3-yl)-1-methyl-1H-indole (Example 126a, 1.2 g, 4.43 mmol), ethanesulfonamide (0.726 g, 6.65 mmol), titanium(IV) isopropoxide (2.60 mL, 8.87 mmol) and toluene (50 mL). The reaction mixture is refluxed overnight and then concentrated to dryness. The crude material (1.60 g) is dissolved in MeOH (24 mL) and DCM (24 mL), and sodium borohydride (0.335 g, 8.87 mmol) is added. The reaction mixture is stirred at room temperature for 2 h, then concentrated in vacuo. The residue is taken up in DCM and washed with water twice. The organic layer is dried over sodium sulfate, filtered and concentrated in vacuo. Purification is achieved by silica gel flash chromatography to give N-[5-(6-Chloro-1-methyl-1H-indol-2-yl)-pyridin-3-ylmethyl]-ethanesulfonamide. $^1$H NMR (400 MHz, MeOD) δ ppm 1.38 (t, J=7.3 Hz, 3H), 3.14 (q, J=7.3 Hz, 2H), 3.80 (s, 3H), 4.43 (s, 2H), 6.72 (s, 1H), 7.12 (dd, J=8.5, 1.9 Hz, 1H), 7.54 (d, J=1.8 Hz, 1H), 7.59 (d, J=8.6 Hz, 1H), 8.10 (t, J=2.1 Hz, 1H), 8.63 (d, J=2.0 Hz, 1H), 8.71 (d, J=2.0 Hz, 1H). HRMS (ESI) m/z 364.0869 [(M+H)+ Calcd for $C_{17}H_{19}ClN_3O_2S$: 364.0887].

Example 207

N-[5-(6-Chloro-1-methyl-1H-indol-2-yl)-pyridin-3-ylmethyl]-isopropylsulfonamide

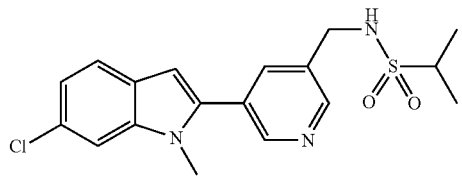 [SMILES: CCS(=O)(=O)NCc1cncc(-c2cc3ccc(Cl)cc3n2C)c1]

C-[5-(6-Chloro-1-methyl-1H-indol-2-yl)-pyridin-3-yl]-methylamine (Example 205a) and isopropylsulfonyl chloride are processed according to the method described in Example 186f to give N-[5-(6-chloro-1-methyl-1H-indol-2-yl)-pyridin-3-ylmethyl]-isopropylsulfonamide. $^1$H NMR (400 MHz, MeOD) δ ppm 1.35 (d, J=6.8 Hz, 6H), 3.19-3.27 (m, 1H), 3.76 (s, 3H), 4.40 (s, 2H), 6.67 (d, J=0.6 Hz, 1H), 7.07 (dd, J=8.4, 1.8 Hz, 1H), 7.49 (d, J=1.6 Hz, 1H), 7.55 (d, J=8.5 Hz, 1H), 8.06 (t, J=2.0 Hz, 1H), 8.58 (d, J=1.9 Hz, 1H), 8.66 (d, J=2.0 Hz, 1H). HRMS (ESI) m/z 378.1036 [(M+H)+ Calcd for $C_{18}H_{21}ClN_3O_2S$: 378.1043].

Example 208

C,C,C-Trifluoro-N-[5-(6-chloro-1-methyl-1H-indol-2-yl)-pyridin-3-ylmethyl]-methanesulfonamide

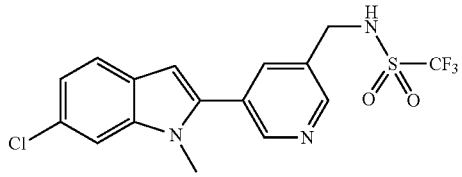

C-[5-(6-Chloro-1-methyl-1H-indol-2-yl)-pyridin-3-yl]-methylamine (Example 205a) and trifluoromethanesulfonyl chloride are processed according to the method described in Example 186f to give C,C,C-trifluoro-N-[5-(6-chloro-1-methyl-1H-indol-2-yl)-pyridin-3-ylmethyl]-methanesulfonamide. $^1$H NMR (400 MHz, MeOD) δ ppm 3.80 (s, 3H), 4.59 (s, 2H), 6.72 (s, 1H), 7.12 (dd, J=8.5, 1.9 Hz, 1H), 7.54 (s, 1H), 7.60 (d, J=8.6 Hz, 1H), 8.05 (t, J=2.1 Hz, 1H), 8.63 (d, J=2.0 Hz, 1H), 8.76 (d, J=2.0 Hz, 1H). HRMS (ESI) m/z 404.0443 [(M+H)+ Calcd for $C_{16}H_{14}ClF_3N_3O_2S$: 404.0447].

Example 209

2,2,2-Trifluoro-ethanesulfonic acid [5-(6-chloro-1-methyl-1H-indol-2-yl)-pyridin-3-ylmethyl]-amide

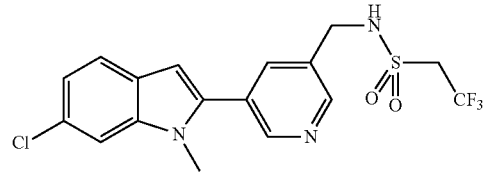 [SMILES: Cn1c(-c2cncc(CNS(=O)(=O)CC(F)(F)F)c2)cc2ccc(Cl)cc21]

C-[5-(6-Chloro-1-methyl-1H-indol-2-yl)-pyridin-3-yl]-methylamine (Example 205a) and 2,2,2-trifluoro-ethanesulfonyl chloride are processed according to the method described in Example 186f to give 2,2,2-trifluoro-ethanesulfonic acid [5-(6-chloro-1-methyl-1H-indol-2-yl)-pyridin-3-ylmethyl]-amide. $^1$H NMR (400 MHz, MeOD) δ ppm 3.75 (d, J=0.6 Hz, 3H), 4.16-4.28 (m, 2H), 4.44 (s, 2H), 6.67 (s, 1H), 7.07 (ddd, J=8.4, 1.8, 0.8 Hz, 1H), 7.50 (s, 1H), 7.55 (d, J=8.3 Hz, 1H), 8.04 (d, J=0.6 Hz, 1H), 8.58 (d, J=1.4 Hz, 1H), 8.68 (d, J=1.6 Hz, 1H). HRMS (ESI) m/z 418.06107 [(M+H)+ Calcd for $C_{17}H_{16}N_3O_2F_3SCl$: 418.06039].

Example 210

(a) Bis-ethanesulfonic acid (5-bromo-pyridin-3-yl)-amide

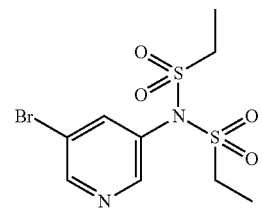 [SMILES: CCS(=O)(=O)N(c1cncc(Br)c1)S(=O)(=O)CC]

To a solution of 3-amino-5-bromo-pyridine (4.300 g, 23.611 mmol) in dichloromethane (100 mL) is added ethanesulfonyl chloride (6.849 g, 70.834 mmol), followed with diisopropylethylamine (16.61 mL, 94.445 mmol). The mixture is stirred at room temperature for 5 h, whereupon it is diluted with ethyl acetate and washed with water twice. The organic layer is dried over sodium sulfate and concentrated in vacuo. The residue is purified by silica gel flash chromatography (heptane-ethyl acetate, 3:2) to afford bis-ethanesulfonic acid (5-bromo-pyridin-3-yl)-amide as a solid. MS (ESI) m/z 359.0 (M+H)$^+$.

(b) Ethanesulfonic acid 3-(6-chloro-1-methyl-1H-indol-2-yl)-benzylamide

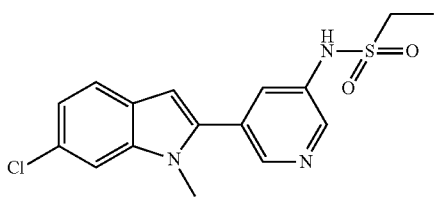

A flask is charged with 6-chloro-1-methyl-indole-2-boronic acid (0.165 g, 0.756 mmol), bis-ethanesulfonic acid (5-bromo-pyridin-3-yl)-amide (0.200 g, 0.504 mmol), potassium phosphate (0.221 g, 1.008 mmol) and DMF (5 mL). The flask is evacuated and back-filled with $N_2$ thrice and Pd(PPh$_3$)$_4$ (0.029 g, 0.025 mmol) is added. The mixture evacuated and back-filled with $N_2$ thrice again, and stirred at 90° C. overnight. It is then cooled to room temperature, diluted with ethyl acetate and washed with water thrice. The organic layer is dried over sodium sulfate and concentrated in vacuo. The residue is purified by silica gel flash chromatography (dichloromethane-methanol, 19:1) and further purified by reverse phase HPLC with Xbridge Shield RP18 column and a 0.1% aqueous NH$_4$OH in acetonitrile gradient to afford ethanesulfonic acid 3-(6-chloro-1-methyl-1H-indol-2-yl)-benzylamide as a solid. $^1$H NMR (400 MHz, MeOD) δ ppm 1.40 (t, J=7.3 Hz, 3H), 3.24 (q, J=7.3 Hz, 2H), 3.80 (s, 3H), 6.71 (s, 1H), 7.12 (dd, J=8.3, 1.8 Hz, 1H), 7.54 (s, 1H), 7.59 (d, J=8.3 Hz, 1H), 7.92 (t, J=2.1 Hz, 1H), 8.47 (d, J=2.5 Hz, 1H), 8.49 (d, J=1.8 Hz, 1H). HRMS (ESI) m/z 350.0731 [(M+H)$^+$ Calcd for $C_{16}H_{17}ClN_3O_2S$: 350.0730].

Example 211

(a) 3-[Bis[[(1,1-dimethylethyl)oxy]carbonyl]amino]-5-bromo-pyridine

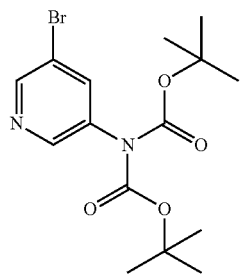 [SMILES: CC(C)(C)OC(=O)N(C(=O)OC(C)(C)C)c1cncc(Br)c1]

To 5-amino-3-bromo-pyridine (1.73 g, 10 mmol) and Boc$_2$O (4.8 g, 22 mmol) in acetonitrile (100 mL) at ambient temperature is added DMAP (212 mg, 1 mmol) and the reaction mixture is heated to 50° C. and stirred overnight. Boc$_2$O (2.2 g, 10 mmol) is added to the reaction mixture, which is stirred at 50° C. for another 4 h. The reaction mixture is then cooled to room temperature. The solvent is removed in vacuo and the residue is purified by silica gel flash chromatography to afford 3-[bis[[(1,1-dimethylethyl)oxy]carbonyl]amino]-5-bromo-pyridine as a white solid. MS (ESI) m/z 374.9 (M+H)$^+$.

(b) 3-[Bis[[(1,1-dimethylethyl)oxy]carbonyl]amino]-5-(6-chloro-1-methyl-1H-indol-2-yl)-pyridine

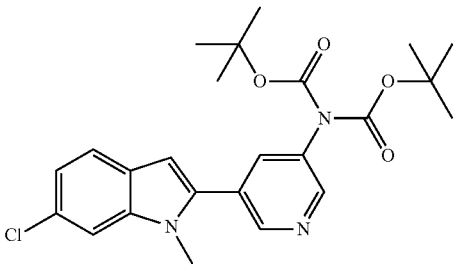 [SMILES: Cn1c(-c2cncc(N(C(=O)OC(C)(C)C)C(=O)OC(C)(C)C)c2)cc2ccc(Cl)cc21]

A flask is charged with 3-[bis[[(1,1-dimethylethyl)oxy]carbonyl]amino]-5-bromo-pyridine (1.12 g, 3.0 mmol), N-methyl-6-chloroindole-2-boronic acid (754 mg, 3.6 mmol), finely crushed potassium phosphate (1.27 g, 6.0 mmol) and DMF (20 mL). After degassing for 15 min, Pd(PPh$_3$)$_4$ (173 mg, 0.15 mmol) is added. The flask is flushed with nitrogen and the mixture is heated to 90° C. and stirred for 5 h. The mixture is then cooled to room temperature and poured into water (100 mL). The mixture is extracted with EtOAc three times and the combined organic phase is washed with water (10 mL) twice. The organic phase is then dried over Na$_2$SO$_4$ and concentrated. The residue is purified by silica gel flash chromatography (ethyl acetate-heptane, 0:1 to 1:9) to give 3-[bis[[(1,1-dimethylethyl)oxy]carbonyl]amino]-5-(6-chloro-1-methyl-1H-indol-2-yl)-pyridine. MS (ESI) m/z 458.1 (M+H)$^+$.

(c) 2-(5-Amino-pyridin-3-yl)-6-chloro-1-methyl-1H-indole-3-carbonitrile

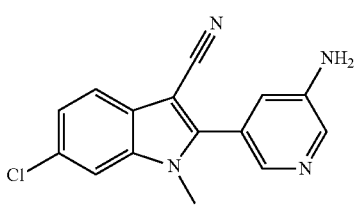 [SMILES: Cn1c(-c2cncc(N)c2)c(C#N)c2ccc(Cl)cc21]

Chlorosulfonyl isocyanate (1.63 g, 11.5 mmol) is added to a solution of 3-[bis[[(1,1-dimethylethyl)oxy]carbonyl]amino]-5-(6-chloro-1-methyl-1H-indol-2-yl)-pyridine (0.91 g, 1.99 mmol) in acetonitrile (200 mL) and the reaction mixture is stirred for 10 min. DMF (3 mL) is added and the reaction mixture is stirred for 3 h. 20 g silica gel is added to the mixture and the solvent is removed in vacuo. The resulting solid is heated to 65° C. under high vacuum for 2 h. The mixture is cooled to room temperature and then purified by silica gel flash chromatography (dichloromethane-methanol-triethylamine, 83:8:9) to afford 2-(5-amino-pyridin-3-yl)-6-chloro-1-methyl-1H-indole-3-carbonitrile. $^1$H NMR (400 MHz, DMSO-d$_6$) δ ppm 3.76 (s, 3H), 5.72 (s, 2H), 7.15 (t, J=2.3 Hz, 1H), 7.35 (dd, J=8.5, 1.9 Hz, 1H), 7.69 (d, J=8.3 Hz, 1H), 7.92 (d, J=1.8 Hz, 1H), 7.97 (d, J=1.8 Hz, 1H), 8.12 (d, J=2.5 Hz, 1H). MS (ESI) m/z 283.0 (M+H)$^+$.

Example 212

Ethanesulfonic acid [5-(6-chloro-3-cyano-1-methyl-1H-indol-2-yl)-pyridin-3-yl]-amide

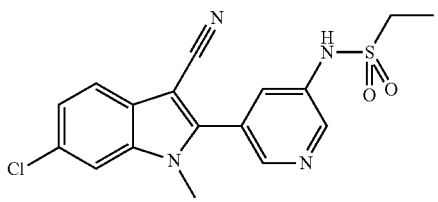 [SMILES: CCS(=O)(=O)Nc1cncc(-c2c(C#N)c3ccc(Cl)cc3n2C)c1]

To a solution of 2-(5-amino-pyridin-3-yl)-6-chloro-1-methyl-1H-indole-3-carbonitrile (Example 211, 85 mg, 0.3 mmol) in DCM (15 mL) is added triethylamine (122 mg, 1.2 mmol) and ethanesulfonyl chloride (77 mg, 0.6 mmol) and the reaction mixture is stirred overnight. The solvent is removed and the residue is redissolved in methanol (15 mL). Aqueous 1M NaOH (1 mL) is added and the reaction mixture is stirred overnight. The solvent is removed in vacuo and the residue is purified by silica gel flash chromatography (methanol in dichloromethane gradient) to give ethanesulfonic acid [5-(6-chloro-3-cyano-1-methyl-1H-indol-2-yl)-pyridin-3-yl]-amide as a solid. $^1$H NMR (400 MHz, DMSO-d$_6$) δ ppm 1.25 (t, J=7.3 Hz, 3H), 3.23-3.33 (m, 2H), 3.79 (s, 3H), 7.36 (dd, J=8.6, 1.8 Hz, 1H), 7.72 (d, J=8.6 Hz, 1H), 7.90 (t, J=2.3 Hz, 1H), 7.95 (d, J=1.5 Hz, 1H), 8.61 (d, J=2.3 Hz, 2H), 10.43 (s, 1H). HRMS (ESI) m/z 375.0692 [(M+H)$^+$ Calcd for C$_{17}$H$_{16}$ClN$_4$O$_2$S: 375.0682].

Example 213

(a) 1-Formyl-cyclobutanecarboxylic acid ethyl ester

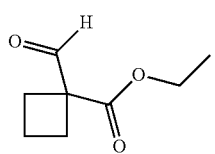

To a solution of diethyl 1,1'-cyclobutanedicarboxylate (9.9 g, 48.4 mmol) in dichloromethane (100 mL) cooled with a dry-ice/acetone bath is added DIBAL-H (20% wt in toluene, 101 mL, 121.1 mmol) by canula over 10 min. The mixture is stirred for another 30 min, whereupon the acetone bath is replaced with an ice water bath and 2M aqueous HCl (250 mL) is added cautiously, with vigorous stirring. Vigorous stirring is continued for 20 min, whereupon two clear phases are obtained. The two phases are separated, the aqueous phase is washed with dichloromethane and the combined organic phase is dried over MgSO$_4$, filtered and concentrated in vacuo. The residue is purified by silica gel flash chromatography (heptane-ethyl acetate, 1:0 to 9:1) to give 1-formyl-cyclobutanecarboxylic acid ethyl ester as a colorless oil. $^1$H NMR (400 MHz, CDCl$_3$) δ ppm 1.29 (t, J=7.1 Hz, 3H), 1.88-2.05 (m, 2H), 2.45-2.49 (m, 4H), 4.24 (t, J=7.1 Hz, 2H), 9.78 (s, 2H).

(b) 1-{[5-(1-methyl-1H-indol-2-yl)-pyridin-3-ylamino]-methyl}-cyclobutanecarboxylic acid ethyl ester

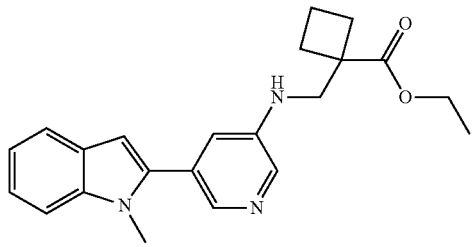 [SMILES: CCOC(=O)C1(CNc2cncc(-c3cc4ccccc4n3C)c2)CCC1]

To a solution of 2-(5-amino-pyridin-3-yl)-1-methyl-1H-indole (Example 100, 0.400 g, 1.756 mmol) and 1-formyl-cyclobutanecarboxylic acid ethyl ester (0.457 g, 2.633 mmol) in dichloromethane (13 mL) is added acetic acid (0.102 g, 1.756 mmol) and the mixture is refluxed. After 2 h, the mixture is cooled with an ice-water bath and sodium triacetoxyborohydride (1.175 g, 5.267 mmol) is added. After 13 h, the mixture is heated to reflux for 1.5 h, cooled to room temperature, diluted with dichloromethane, washed with 1M aqueous NaOH, water and brine. The combined aqueous phase is extracted once with dichloromethane and the combined organic phase is dried over MgSO$_4$, filtered and concentrated in vacuo. The residue is purified by silica gel flash chromatography (heptane-ethyl acetate, 1:1) to give 1-{[5-(1-methyl-1H-indol-2-yl)-pyridin-3-ylamino]-methyl}-cyclobutanecarboxylic acid ethyl ester as an oil. $^1$H NMR (400 MHz, CDCl$_3$) δ ppm 1.28 (t, J=7.1 Hz, 3H), 1.99-2.12 (m, 4H), 2.49-2.59 (m, 2H), 3.53 (d, J=5.8 Hz, 2H), 3.78 (s, 3H), 4.12-4.18 (m, 1H), 4.20 (q, J=7.1 Hz, 2H), 6.61 (d, J=0.8 Hz, 1H), 7.04 (dd, J=2.8, 1.9 Hz, 1H), 7.15-7.19 (m, 1H), 7.26-7.30 (m, 1H), 7.39 (dd, J=8.2, 0.8 Hz, 1H), 7.65 (d, J=7.7 Hz, 1H), 8.09 (d, J=2.8 Hz, 1H), 8.12 (d, J=1.9 Hz, 1H).

(c) 1-{[5-(1-Methyl-1H-indol-2-yl)-pyridin-3-ylamino]-methyl}-cyclobutanecarboxylic acid

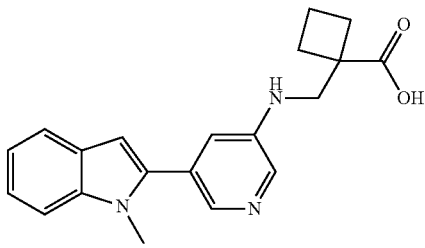 [SMILES: Cn1c(-c2cncc(NCC3(C(=O)O)CCC3)c2)cc2ccccc21]

To a solution of 1-{[5-(1-methyl-1H-indol-2-yl)-pyridin-3-ylamino]-methyl}-cyclobutanecarboxylic acid ethyl ester (0.107 g, 0.288 mmol) in THF (2 mL) and methanol (1 mL) is added aqueous lithium hydroxide (1M, 0.58 mL, 0.58 mmol) and the solution is stirred overnight. The product is isolated by RP HPLC on an Xbridge C18 eluting with an acetonitrile in 0.1% aqueous NH$_4$OH gradient to give 1-{[5-(1-methyl-1H-indol-2-yl)-pyridin-3-ylamino]-methyl}-cyclobutanecarboxylic acid as a white powder. $^1$H NMR (400 MHz, DMSO-d$_6$) δ ppm 1.74-1.86 (m, 1H), 1.87-1.97 (m, 3H), 2.26-2.35 (m, 2H), 3.33 (br. s., 1H), 3.39 (s, 2H), 3.75 (s, 3H), 6.60 (s, 1H), 7.05-7.09 (m, 1H), 7.15 (m, 1H), 7.17-7.21 (m, 1H), 7.50 (d, J=8.3 Hz, 1H), 7.57 (d, J=7.7 Hz, 1H), 7.94 (d, J=1.8 Hz, 1H), 8.06 (d, J=2.7 Hz, 1H). MS (ESI) m/z 336 (M+H)$^+$.

Example 214

2-Methyl-1-(1-{[5-(1-methyl-1H-indol-2-yl)-pyridin-3-ylamino]-methyl}-cyclobutyl)-propan-1-one

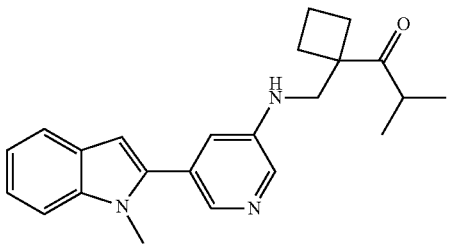 [SMILES: CC(C)C(=O)C1(CNc2cncc(-c3cc4ccccc4n3C)c2)CCC1]

To a solution of 1-{[5-(1-methyl-1H-indol-2-yl)-pyridin-3-ylamino]-methyl}-cyclobutanecarboxylic acid ethyl ester (Example 213b, 0.45 g, 1.21 mmol) in THF (150 mL) cooled with an ice-water bath is added iPrMgCl (2.0M in THF, 2.43 mL, 4.85 mmol) dropwise. After 45 min, the mixture is quenched with 1M aqueous NaHSO$_4$ (5 mL), washed with saturated aqueous sodium bicarbonate and brine, dried over MgSO$_4$, filtered and concentrated in vacuo. The residue is purified by silica gel flash chromatography (heptane-ethyl acetate, 3:2 to 1:1), followed by purification by RP HPLC on an Xbridge RP18 eluting with a gradient of acetonitrile in 0.1% aqueous NH$_4$OH to give 2-methyl-1-(1-{[5-(1-methyl-1H-indol-2-yl)-pyridin-3-ylamino]-methyl}-cyclobutyl)-propan-1-one.

$^1$H NMR (400 MHz, DMSO-d$_6$) δ ppm 0.95 (d, J=6.8 Hz, 6H), 1.68-1.78 (m, 1H), 1.95-2.03 (m, 3H), 2.31-2.41 (m, 2H), 2.97-3.09 (m, 1H), 3.60 (d, J=5.7 Hz, 2H), 3.76 (s, 3H), 5.77 (t, J=5.7 Hz, 1H), 6.61 (s, 1H), 7.06-7.10 (m, 1H), 7.16-7.25 (m, 2H), 7.51 (d, J=8.2 Hz, 1H), 7.58 (d, J=7.8 Hz, 1H), 7.99 (s, 1H), 8.12 (d, J=2.1 Hz, 1H). MS (ESI) m/z 362 (M+H)$^+$.

Example 215

2-[5-(1-Methyl-1H-indol-2-yl)-pyridin-3-yl]-2-aza-spiro[3.3]heptan-1-one

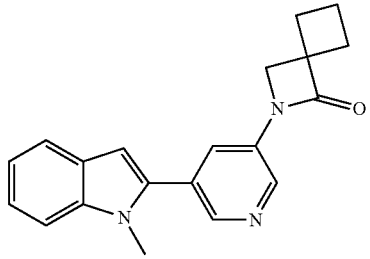 [SMILES: Cn1c(-c2cncc(N3CC4(CCC4)C3=O)c2)cc2ccccc21]

The method described in Example 214 also affords 2-[5-(1-methyl-1H-indol-2-yl)-pyridin-3-yl]-2-aza-spiro[3.3]heptan-1-one. $^1$H NMR (400 MHz, DMSO-d$_6$) δ ppm 1.88-2.03 (m, 2H), 2.32-2.45 (m, 4H), 3.77 (s, 3H), 3.83 (s, 2H), 6.71 (d, J=0.8 Hz, 1H), 7.06-7.14 (m, 1H), 7.19-7.27 (m, 1H), 7.54 (m, 1H), 7.61 (m, 1H), 7.85 (dd, J=2.4, 1.9 Hz, 1H), 8.54 (d, J=1.9 Hz, 1H), 8.68 (d, J=2.4 Hz, 1H). MS (ESI) m/z 318.1 (M+H)$^+$.

Example 216

(a) 1-[5-(6-Chloro-1-methyl-1H-indol-2-yl)-pyridin-3-yl]-ethanone

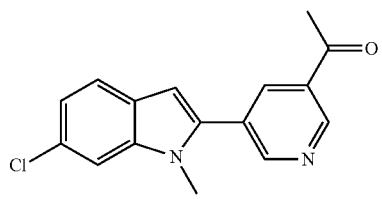 [SMILES: CC(=O)c1cncc(-c2cc3ccc(Cl)cc3n2C)c1]

6-Chloro-1-methyl-indole-2-boronic acid and 5-acetyl-3-bromo-pyridine are processed according to the method described in Example 100 to give 1-[5-(6-chloro-1-methyl-1H-indol-2-yl)-pyridin-3-yl]-ethanone. MS (ESI) m/z 284.98 (M+H)$^+$.

(b) 2-(5-Acetyl-pyridin-3-yl)-6-chloro-1-methyl-1H-indole-3-carbonitrile

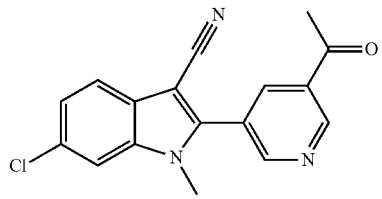 [SMILES: CC(=O)c1cncc(-c2c(C#N)c3ccc(Cl)cc3n2C)c1]

1-[5-(6-Chloro-1-methyl-1H-indol-2-yl)-pyridin-3-yl]-ethanone is processed according to the method described in Example 128 to give 2-(5-acetyl-pyridin-3-yl)-6-chloro-1-methyl-1H-indole-3-carbonitrile. MS (ESI) m/z 310.07 (M+H)$^+$.

(c) 2-[5-(1-Amino-ethyl)-pyridin-3-yl]-6-chloro-1-methyl-1H-indole-3-carbonitrile

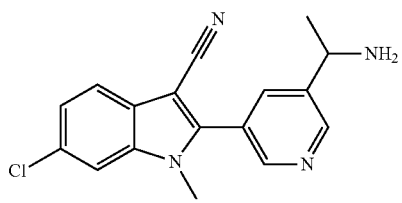 [SMILES: CC(N)c1cncc(-c2c(C#N)c3ccc(Cl)cc3n2C)c1]

Ammonium acetate (0.567 g, 7.207 mmol) is added to a solution of 2-(5-acetyl-pyridin-3-yl)-6-chloro-1-methyl-1H-indole-3-carbonitrile (0.470 g, 1.441 mmol) in MeOH (10 mL), and the reaction is stirred at 50° C. for 48 h. Sodium triacetoxyborohydride (2.251 g, 10.09 mmol) is added and the reaction is stirred for 24 h at 50° C. Additional sodium triacetoxyborohydride (2.251 g, 10.09 mmol) is added and the reaction is stirred for another 24 h at 50° C. It is then diluted with ethyl acetate and washed with water thrice. The organic layer is dried over sodium sulfate and concentrated in vacuo to give 6-chloro-2-[5-(1-hydroxy-ethyl)-pyridin-3-yl]-1-methyl-1H-indole-3-carbonitrile and minor amounts of 2-[5-(1-amino-ethyl)-pyridin-3-yl]-6-chloro-1-methyl-1H-indole-3-carbonitrile. The mixture is redissolved in THF (5 mL) and phthalimide (0.181 g, 1.206 mmol) and triphenylphosphine (0.172 g, 0.804 mmol) are added, followed with di-isopropylazodicarboxylate (0.157 mL, 0.804 mmol). The reaction is stirred at room temperature for 4 h. It is then diluted with ethyl acetate and washed with water thrice. The organic layer is dried over sodium sulfate and concentrated in vacuo, to give a residue which is purified by silica gel flash chromatography (heptane-ethyl acetate, 1:1) to afford a mixture of 6-chloro-2-{5-[1-(1,3-dioxo-1,3-dihydro-isoindol-2-yl)-ethyl]-pyridin-3-yl}-1-methyl-1H-indole-3-carbonitrile and triphehyl phosphine. The mixture is redissolved in ethanol (5 mL). Hydrazine hydrate (65%) (0.411 mL, 8.506 mmol) is added and the reaction is stirred at room temperature overnight. It is then acidified with 2M aqueous HCl and concentrated in vacuo. The residue is redissolved in dichloromethane and filtered through celite to remove the precipitate formed. The organic layer is washed with water. The aqueous layer is separated and basified to with 4M aqueous NaOH, and then extracted with dichloromethane thrice. The organic layer is dried over sodium sulfate and concentrated in vacuo to afford 2-[5-(1-amino-ethyl)-pyridin-3-yl]-6-chloro-1-methyl-1H-indole-3-carbonitrile as a solid. MS (ESI) m/z 311.1 (M+H)$^+$ (d) Ethanesulfonic acid {1-[5-(6-chloro-3-cyano-1-methyl-1H-indol-2-yl)-pyridin-3-yl]-ethyl}-amide

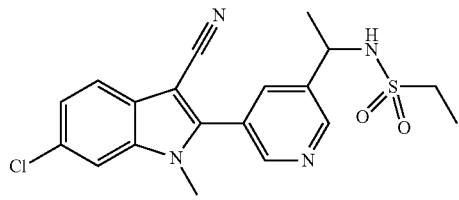 [SMILES: CCS(=O)(=O)NC(C)c1cncc(-c2c(C#N)c3ccc(Cl)cc3n2C)c1]

A flask is charged with 2-[5-(1-amino-ethyl)-pyridin-3-yl]-6-chloro-1-methyl-1H-indole-3-carbonitrile (0.072 g, 0.209 mmol) and dichloromethane (3 mL). Ethanesulfonyl chloride (0.060 g, 0.525 mmol) and triethylamine (0.059 mL, 0.417 mmol) are added and the reaction is stirred at room temperature overnight. The reaction mixture is concentrated in vacuo to give a residue which is purified by silica gel flash chromatography (heptane-ethyl acetate, 1:1) to afford ethanesulfonic acid {1-[5-(6-chloro-3-cyano-1-methyl-1H-indol-2-yl)-pyridin-3-yl]-ethyl}-amide as a white solid. $^1$H NMR (400 MHz, MeOD) δ ppm 1.32 (t, J=7.5 Hz, 3H), 1.65 (d, J=7.1 Hz, 3H), 2.96-3.15 (m, 2H), 3.84 (s, 3H), 4.75-4.86 (m, 1H), 7.39 (dd, J=8.6, 1.8 Hz, 1H), 7.73 (d, J=8.6 Hz, 1H), 7.78 (d, J=1.5 Hz, 1H), 8.20 (t, J=2.0 Hz, 1H), 8.80 (d, J=2.0 Hz, 1H), 8.83 (d, J=2.3 Hz, 1H). HRMS (ESI) m/z 403.1005 [(M+H)$^+$ Calcd for C$_{19}$H$_{20}$N$_4$O$_2$SCl: 403.0996].

(e) (R) and (S)-ethanesulfonic acid {1-[5-(6-chloro-3-cyano-1-methyl-1H-indol-2-yl)-pyridin-3-yl]-ethyl}-amide Racemic ethanesulfonic acid {1-[5-(6-chloro-3-cyano-1-methyl-1H-indol-2-yl)-pyridin-3-yl]-ethyl}-amide is resolved by chiral chromatography using a Chiralpak® AS column, eluting with a 3:2 heptane-ethanol mixture to give (R) and (S)-ethanesulfonic acid {1-[5-(6-chloro-3-cyano-1-methyl-1H-indol-2-yl)-pyridin-3-yl]-ethyl}-amide. The retention times are 6.9 and 9.2 min at 0.8 mL/min on an analytical Chiralpak® AS column.

Example 217

(a) 3-Bromo-5-(2-methoxy-vinyl)-pyridine

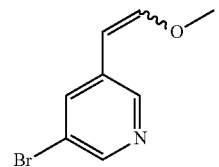

A flask is charged with methoxymethyltriphenylphosphine chloride (3.04 g, 8.87 mmol) and tetrahydrofuran (20 mL). The mixture is cooled to −78° C. and sodium hexamethyldisilazane (1M solution in THF, 9.60 mL, 9.67 mmol) is added dropwise. The reaction mixture is stirred at −78° C. for 30 min, whereupon 5-bromo-pyridine-3-carbaldehyde (1.5 g, 8.06 mmol) is added. The mixture is allowed to warm to room temperature and stirred overnight. Purification by silica gel flash chromatography (heptane-ethyl acetate, 4:1) affords an E/Z mixture of 3-bromo-5-(2-methoxy-vinyl)-pyridine as a colorless oil. MS (ESI) m/z 215.95 (M+H)$^+$.

(b) 2-[5-(2-Methoxy-vinyl)-pyridin-3-yl]-1-methyl-1H-indole

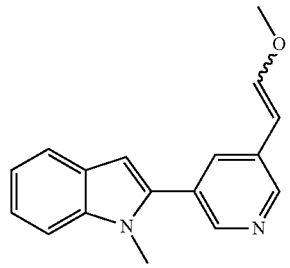 [SMILES: COC=Cc1cncc(-c2cc3ccccc3n2C)c1]

3-Bromo-5-(2-methoxy-vinyl)-pyridine is processed according to the method described in Example 106b to give an E/Z mixture of 2-[5-(2-methoxy-vinyl)-pyridin-3-yl]-1-methyl-1H-indole as an oil. MS (ESI) m/z 265.20 (M+H)$^+$.

(c) 2-[5-(2-Methoxy-ethyl)-pyridin-3-yl]-1-methyl-1H-indole

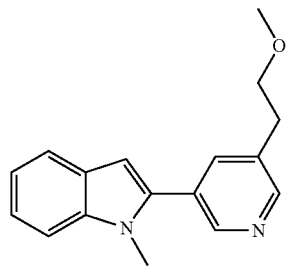 [SMILES: COCCc1cncc(-c2cc3ccccc3n2C)c1]

A flask is charged with 2-[5-(2-methoxy-vinyl)-pyridin-3-yl]-1-methyl-1H-indole (0.550 g, 2.08 mmol) and methanol (5 mL). Palladium on carbon (0.221 g, 0.208 mmol) is added and the reaction mixture is stirred at 50° C. under $H_2$ for 16 h. It is then cooled to room temperature and filtered through celite. The celite layer is thoroughly washed with methanol. The filtrate is concentrated in vacuo, to give a residue which is purified by silica gel flash chromatography (heptane-ethyl acetate, 7:3) to afford 2-[5-(2-methoxy-ethyl)-pyridin-3-yl]-1-methyl-1H-indole as an oil. MS (ESI) m/z 267.36 $(M+H)^+$.

(d) 2-[5-(2-Methoxy-ethyl)-pyridin-3-yl]-1-methyl-1H-indole-3-carbonitrile

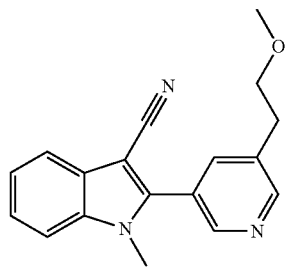 [SMILES: COCCc1cncc(-c2c(C#N)c3ccccc3n2C)c1]

2-[5-(2-Methoxy-ethyl)-pyridin-3-yl]-1-methyl-1H-indole is processed according to the method described in Example 128 to give 2-[5-(2-methoxy-ethyl)-pyridin-3-yl]-1-methyl-1H-indole-3-carbonitrile as a solid. $^1$H NMR (400 MHz, MeOD) δ ppm 3.09 (t, J=6.2 Hz, 2H), 3.41 (s, 3H), 3.76 (t, J=6.3 Hz, 2H), 3.87 (s, 3H), 7.36-7.42 (m, 1H), 7.44-7.51 (m, 1H), 7.68 (d, J=8.3 Hz, 1H), 7.75 (dd, J=7.8, 1.1 Hz, 1H), 8.10 (t, J=2.1 Hz, 1H), 8.68 (d, J=2.0 Hz, 1H), 8.74 (d, J=2.1 Hz, 1H). HRMS (ESI) m/z 292.1458 $[(M+H)^+$ Calcd for $C_{18}H_{18}N_3O$: 292.1450].

Example 218

1-Difluoromethyl-2-pyridin-3-yl-1H-indole-3-carbonitrile

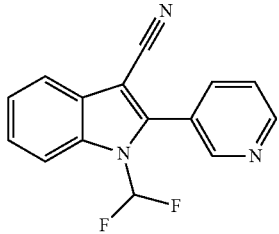 [SMILES: N#Cc1c(-c2cccnc2)n(C(F)F)c2ccccc12]

A flask is charged with 2-pyridin-3-yl-1H-indole-3-carbonitrile (Example 83b, 340 mg, 1.55 mmol) and DMF (10 mL), and 60% NaH in mineral oil (68 mg, 1.71 mmol) is added. The mixture is stirred at room temperature for 20 min. $CClF_2H$ is bubbled into the reaction mixture while the reaction temperature is raised to 100° C. The reaction temperature is raised to 150° C. for 30 min. The mixture is cooled to room temperature and water (1 mL) is added. The mixture is then filtered and the filtrate is purified on Xbridge C18 eluting with a 1:9 to 9:1 acetonitrile-water gradient to give 1-difluoromethyl-2-pyridin-3-yl-1H-indole-3-carbonitrile. $^1$H NMR (400 MHz, DMSO-$d_6$) δ ppm 7.48-7.53 (m, 1H), 7.56 (td, J=7.7, 1.3 Hz, 1H), 7.68-7.73 (m, 1H), 7.86 (t, J=56.6 Hz, 1H), 7.86 (dd, J=37.6, 8.1 Hz, 1H), 7.91 (d, J=8.3 Hz, 1H), 8.13 (dt, J=8.0, 2.0, 1.9 Hz, 1H), 8.85 (dd, J=4.9, 1.6 Hz, 1H), 8.87 (d, J=1.8 Hz, 1H). HRMS (ESI) m/z 270.0841 $[(M+H)^+$ Calcd for $C_{15}H_{10}F_2N_3$: 270.0843].

Example 219

Ethanesulfonic acid [5-(3-cyano-1-methyl-1H-indol-2-yl)-pyridin-3-ylmethyl]-amide

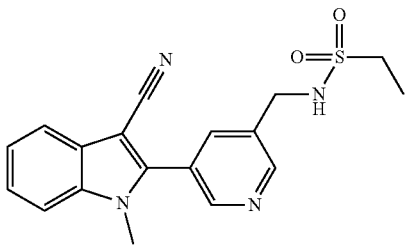 [SMILES: CCS(=O)(=O)NCc1cncc(-c2c(C#N)c3ccccc3n2C)c1]

2-(5-Formyl-pyridin-3-yl)-1-methyl-1H-indole-3-carbonitrile (Example 127) and ethanesulfonamide are processed according to the method described in Example 170 to give ethanesulfonic acid [5-(3-cyano-1-methyl-1H-indol-2-yl)-pyridin-3-ylmethyl]-amide. $^1$H NMR (400 MHz, DMSO-$d_6$) δ ppm 1.20 (t, J=7.3 Hz, 3H), 3.07 (q, J=7.4 Hz, 2H), 3.79 (s, 3H), 4.34 (d, J=6.1 Hz, 2H), 7.34-7.38 (m, 1H), 7.41-7.46 (m, 1H), 7.72 (d, J=7.6 Hz, 1H), 7.75-7.82 (m, 2H), 8.09 (t, J=2.1 Hz, 1H), 8.77 (d, J=2.0 Hz, 1H), 8.81 (d, J=2.1 Hz, 1H). HRMS (ESI) m/z 355.1247 $[(M+H)^+$ Calcd for $C_{18}H_{19}N_4O_2S$: 355.1229].

Example 220

2-(5-Hydroxymethyl-pyridin-3-yl)-1-methyl-1H-indole-3-carbonitrile

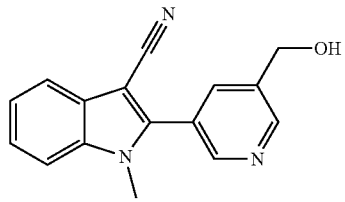 [SMILES: Cn1c(-c2cncc(CO)c2)c(C#N)c2ccccc21]

The method described in Example 219 using 2-(5-formyl-pyridin-3-yl)-1-methyl-1H-indole-3-carbonitrile (Example 127) also affords 2-(5-hydroxymethyl-pyridin-3-yl)-1-methyl-1H-indole-3-carbonitrile as a product of the reaction. MS (ESI) m/z 264.07 $(M+H)^+$.

Example 221

(a) 2-[5-(1,3-Dioxo-1,3-dihydro-isoindol-2-ylmethyl)-pyridin-3-yl]-1-methyl-1H-indole-3-carbonitrile

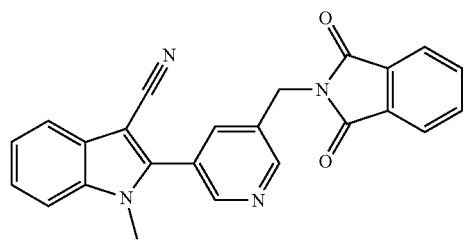 [SMILES: Cn1c(-c2cncc(CN3C(=O)c4ccccc4C3=O)c2)c(C#N)c2ccccc21]

To a solution of 2-(5-hydroxymethyl-pyridin-3-yl)-1-methyl-1H-indole-3-carbonitrile (Example 220, 190 mg, 0.72 mmol) in THF (5 mL) are added sequentially phthalimide (116 mg, 0.79 mmol), 1,1'-(azodicarbonyl)dipiperidine (346 mg, 1.37 mmol) and tributylphosphine (277 mg, 1.37 mmol). The mixture is stirred at room temperature overnight. The mixture is then concentrated in vacuo and the residue is purified by silica gel flash chromatography (heptane-ethyl acetate, 1:0 to 0:1) to give 2-[5-(1,3-dioxo-1,3-dihydro-isoindol-2-ylmethyl)-pyridin-3-yl]-1-methyl-1H-indole-3-carbonitrile. MS (ESI) m/z 393.02 (M+H)+.

(b) 2-(5-Aminomethyl-pyridin-3-yl)-1-methyl-1H-indole-3-carbonitrile

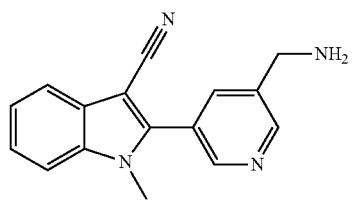 [SMILES: Cn1c(-c2cncc(CN)c2)c(C#N)c2ccccc21]

To a solution of 2-[5-(1,3-dioxo-1,3-dihydro-isoindol-2-ylmethyl)-pyridin-3-yl]-1-methyl-1H-indole-3-carbonitrile (200 mg, 0.51 mmol) in ethanol (15 mL) is added hydrazine hydrate (327 mg, 10.2 mmol). The mixture is stirred at room temperature overnight. The reaction mixture is poured into dichloromethane (100 mL) and extracted with 1M HCl in water. The combined aqueous phase is basified with 5M NaOH in water and extracted with dichloromethane. The combined organic phase is dried over $Na_2SO_4$ and concentrated in vacuo to give 2-(5-aminomethyl-pyridin-3-yl)-1-methyl-1H-indole-3-carbonitrile, which is used in the next step without further purification. MS (ESI) m/z 263.27 (M+H)+.

(c) Propane-2-sulfonic acid [5-(3-cyano-1-methyl-1H-indol-2-yl)-pyridin-3-ylmethyl]-amide

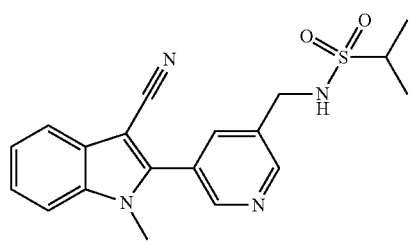 [SMILES: CC(C)S(=O)(=O)NCc1cncc(-c2c(C#N)c3ccccc3n2C)c1]

A flask is charged with 2-(5-aminomethyl-pyridin-3-yl)-1-methyl-1H-indole-3-carbonitrile (130 mg, 0.5 mmol), DBU (304 mg, 2.0 mmol) and DCE (15 mL), and isopropylsulfonyl chloride (142 mg, 1.0 mmol) is added. The mixture is stirred at room temperature for 1 h and concentrated in vacuo. The residue is purified by silica gel flash chromatography (dichloromethane-methanol, 1:0 to 97:3) to give propane-2-sulfonic acid [5-(3-cyano-1-methyl-1H-indol-2-yl)-pyridin-3-ylmethyl]-amide. $^1$H NMR (400 MHz, DMSO-$d_6$) δ ppm 1.24 (d, J=6.8 Hz, 6H), 3.18-3.26 (m, 1H), 3.79 (s, 3H), 4.37 (d, J=6.1 Hz, 2H), 7.34-7.38 (m, 1H), 7.41-7.46 (m, 1H), 7.70-7.79 (m, 3H), 8.08 (t, J=2.0 Hz, 1H), 8.77 (d, J=2.3 Hz, 1H), 8.81 (d, J=2.3 Hz, 1H). HRMS (ESI) m/z 369.1389 [(M+H)+ Calcd for $C_{19}H_{21}N_4O_2S$: 369.1385].

Example 222

Trifluoromethanesulfonic acid [5-(3-cyano-1-methyl-1H-indol-2-yl)-pyridin-3-ylmethyl]-amide

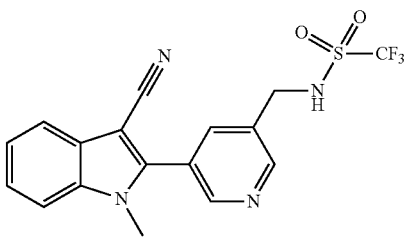 [SMILES: Cn1c(-c2cncc(CNS(=O)(=O)C(F)(F)F)c2)c(C#N)c2ccccc21]

2-(5-Formyl-pyridin-3-yl)-1-methyl-1H-indole-3-carbonitrile (Example 127) and trifluoromethanesulfonamide are processed according to the method described in Example 170 to give trifluoromethanesulfonic acid [5-(3-cyano-1-methyl-1H-indol-2-yl)-pyridin-3-ylmethyl]-amide. $^1$H NMR (400 MHz, DMSO-$d_6$) δ ppm 3.79 (s, 3H), 4.58 (s, 2H), 7.34-7.39 (m, 1H), 7.42-7.47 (m, 1H), 7.72 (d, J=7.7 Hz, 1H), 7.77 (d, J=8.3 Hz, 1H), 8.10 (t, J=2.1 Hz, 1H), 8.78 (d, J=2.1 Hz, 1H), 8.85 (d, J=2.1 Hz, 1H), 10.19 (br. s., 1H). HRMS (ESI) m/z 395.0779 [(M+H)+ Calcd for $C_{17}H_{14}F_3N_4O_2S$: 395.0790].

Example 223

Propane-2-sulfonic acid [5-(6-chloro-3-cyano-1-methyl-1H-indol-2-yl)-pyridin-3-yl]-amide

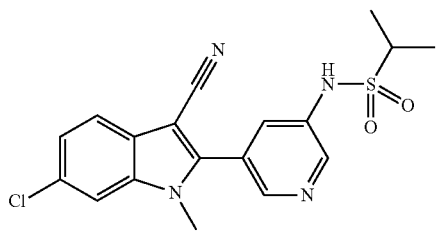 [SMILES: CC(C)S(=O)(=O)Nc1cncc(-c2c(C#N)c3ccc(Cl)cc3n2C)c1]

2-(5-Amino-pyridin-3-yl)-6-chloro-1-methyl-1H-indole-3-carbonitrile (Example 211) is processed according to the method described in Example 221c to give to give propane-2-sulfonic acid [5-(6-chloro-3-cyano-1-methyl-1H-indol-2-yl)-pyridin-3-yl]-amide. $^1$H NMR (400 MHz, DMSO-$d_6$) δ ppm 1.30 (d, J=6.8 Hz, 6H), 3.46 (dq, J=6.8 Hz, 1H), 3.79 (s, 3H), 7.37 (dd, J=8.5, 1.9 Hz, 1H), 7.73 (d, J=8.6 Hz, 1H), 7.93 (t, J=2.1 Hz, 1H), 7.96 (d, J=1.8 Hz, 1H), 8.60 (d, J=1.8 Hz, 1H), 8.63 (d, J=2.5 Hz, 1H), 10.41 (s, 1H). HRMS (ESI) m/z 389.0836 [(M+H)+ Calcd for $C_{18}H_{18}ClN_4O_2S$: 389.0839].

Example 224

N'-[5-(6-Chloro-3-cyano-1-methyl-1H-indol-2-yl)-pyridin-3-yl]-N,N-dimethyl-formamidine

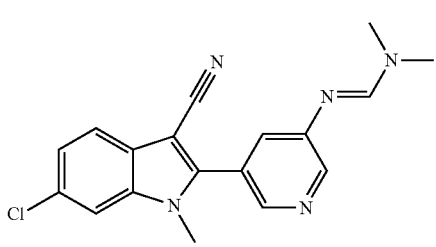 [SMILES: CN(C)/C=N/c1cncc(-c2c(C#N)c3ccc(Cl)cc3n2C)c1]

To a solution of 2-(5-amino-pyridin-3-yl)-6-chloro-1-methyl-1H-indole-3-carbonitrile (Example 211, 85 mg, 0.3 mmol) in DMF (5 mL) is added 60% NaH in mineral oil (48 mg, 1.2 mmol), followed with propane-2-sulfonyl chloride (86 mg, 60.6 mmol). The mixture is stirred at room temperature for 5 h. The mixture is filtered and the filtrate is purified on Xbridge C18 eluting with a 1:9 to 9:1 acetonitrile-water gradient to give N'-[5-(6-chloro-3-cyano-1-methyl-1H-indol-2-yl)-pyridin-3-yl]-N,N-dimethyl-formamidine. $^1$H NMR (400 MHz, DMSO-d$_6$) δ ppm 2.98 (s, 3H), 3.06 (s, 3H), 3.79 (s, 3H), 7.35 (dd, J=8.3, 1.8 Hz, 1H), 7.62 (t, J=2.1 Hz, 1H), 7.70 (d, J=8.3 Hz, 1H), 7.95 (d, J=1.8 Hz, 1H), 7.96 (s, 1H), 8.37-8.39 (m, 2H). HRMS (ESI) m/z 338.1182 [(M+H)$^+$ Calcd for C$_{18}$H$_{17}$ClN$_5$: 338.1173].

Example 225

(a) Ethanesulfonic acid [5-(1-methyl-1H-indol-2-yl)-pyridin-3-yl]-N-ethanesulfonyl-amide

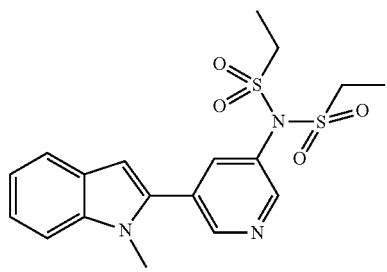 [SMILES: CCS(=O)(=O)N(c1cncc(-c2cc3ccccc3n2C)c1)S(=O)(=O)CC]

To a solution of 2-(5-amino-pyridin-3-yl)-1-methyl-1H-indole (Example 100) (223 mg, 1.0 mmol) in dichloromethane (20 mL) is added ethanesulfonyl chloride (386 mg, 3.0 mmol) and di-isopropylethylamine (517 mg, 4.0 mmol). The mixture is stirred at room temperature for 1 h. Saturated NaHCO$_3$ in water (0.5 mL) and silica gel (10 g) are added and the mixture is concentrated in vacuo. The residue is purified by silica gel chromatography (heptane-ethyl acetate, 1:0 to 1:9) to give ethanesulfonic acid [5-(1-methyl-1H-indol-2-yl)-pyridin-3-yl]-N-ethanesulfonyl-amide. MS (ESI) m/z 408.1 (M+H)$^+$.

(b) Ethanesulfonic acid [5-(3-cyano-1-methyl-1H-indol-2-yl)-pyridin-3-yl]-N-ethanesulfonyl-amide

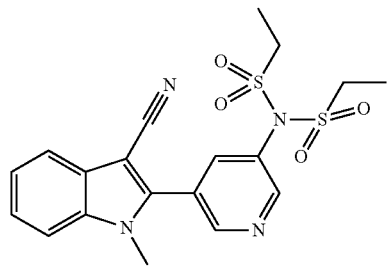 [SMILES: CCS(=O)(=O)N(c1cncc(-c2c(C#N)c3ccccc3n2C)c1)S(=O)(=O)CC]

Ethanesulfonic acid [5-(1-methyl-1H-indol-2-yl)-pyridin-3-yl]-N-ethanesulfonyl-amide is processed according to the method described in Example 128 to give ethanesulfonic acid [5-(3-cyano-1-methyl-1H-indol-2-yl)-pyridin-3-yl]-N-ethanesulfonyl-amide. MS (ESI) m/z 432.96 (M+H)$^+$.

(c) Ethanesulfonic acid [5-(3-cyano-1-methyl-1H-indol-2-yl)-pyridin-3-yl]-amide

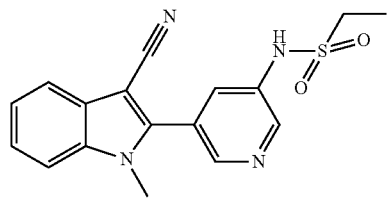 [SMILES: CCS(=O)(=O)Nc1cncc(-c2c(C#N)c3ccccc3n2C)c1]

A solution of ethanesulfonic acid [5-(3-cyano-1-methyl-1H-indol-2-yl)-pyridin-3-yl]-N-ethanesulfonyl-amide in DMF (2 mL), methanol (10 mL) and 5 M NaOH in water (1 mL) is stirred at room temperature for 1 h. The mixture is purified on Xbridge C18 eluting with a 1:9 to 9:1 acetonitrile-water gradient to give ethanesulfonic acid [5-(3-cyano-1-methyl-1H-indol-2-yl)-pyridin-3-yl]-amide. $^1$H NMR (400 MHz, DMSO-d$_6$) δ ppm 1.25 (t, J=7.3 Hz, 3H), 3.24-3.32 (m, 2H), 3.80 (s, 3H), 7.32-7.38 (m, 1H), 7.43 (td, J=7.8, 1.1 Hz, 1H), 7.70 (d, J=7.8 Hz, 1H), 7.75 (d, J=8.3 Hz, 1H), 7.90 (t, J=2.3 Hz, 1H), 8.58-8.62 (m, 2H), 10.42 (s, 1H). HRMS (ESI) m/z 341.1078 [(M+H)$^+$ Calcd for C$_{17}$H$_{17}$N$_4$O$_2$S: 341.1072].

Example 226

Ethanesulfonic acid [5-(1-methyl-1H-indol-2-yl)-pyridin-3-yl]-amide

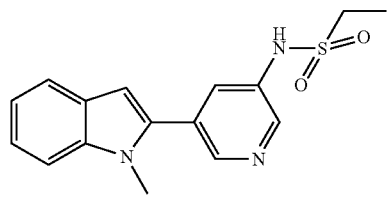 [SMILES: CCS(=O)(=O)Nc1cncc(-c2cc3ccccc3n2C)c1]

Ethanesulfonic acid [5-(1-methyl-1H-indol-2-yl)-pyridin-3-yl]-N-ethanesulfonyl-amide (Example 225a) is processed according to the method described in Example 225c to give ethanesulfonic acid [5-(1-methyl-1H-indol-2-yl)-pyridin-3-yl]-amide. $^1$H NMR (400 MHz, DMSO-$d_6$) δ ppm 1.26 (t, J=7.3 Hz, 3H), 3.26 (q, J=7.3 Hz, 2H), 3.77 (s, 3H), 6.71 (s, 1H), 7.08-7.13 (m, 1H), 7.20-7.27 (m, 1H), 7.54 (d, J=8.1 Hz, 1H), 7.61 (d, J=7.8 Hz, 1H), 7.79 (t, J=2.3 Hz, 1H), 8.48 (d, J=2.5 Hz, 1H), 8.56 (d, J=1.8 Hz, 1H), 10.23 (s, 1H). HRMS (ESI) m/z 316.1125 [(M+H)$^+$ Calcd for $C_{16}H_{18}N_3O_2S$: 316.1120].

Example 227

Methanesulfonic acid [5-(1-methyl-1H-indol-2-yl)-pyridin-3-yl]-amide

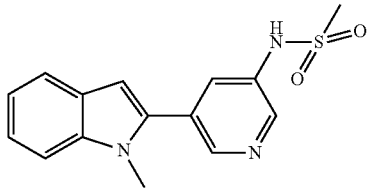 [SMILES: Cn1c(-c2cncc(NS(C)(=O)=O)c2)cc2ccccc21]

2-(5-amino-pyridin-3-yl)-1-methyl-1H-indole (Example 100) and methanesulfonyl chloride are processed according to the methods described in Example 225a and 225c to give methanesulfonic acid [5-(1-methyl-1H-indol-2-yl)-pyridin-3-yl]-amide. $^1$H NMR (400 MHz, DMSO-$d_6$) δ ppm 3.15 (s, 3H), 3.77 (s, 3H), 6.71 (s, 1H), 7.06-7.13 (m, 1H), 7.23 (ddd, J=8.2, 7.1, 1.1 Hz, 1H), 7.53 (d, J=7.6 Hz, 1H), 7.61 (d, J=7.6 Hz, 1H), 7.79 (t, J=2.2 Hz, 1H), 8.48 (d, J=2.3 Hz, 1H), 8.58 (d, J=2.0 Hz, 1H), 10.18 (s, 1H). HRMS: (ESI) m/z 302.0966 [(M+H)$^+$ Calcd for $C_{15}H_{16}N_3O_2S$ 302.0958].

Example 228

Diethyl-sulfamic acid 5-(1-methyl-1H-indol-2-yl)-pyridin-3-yl-amide

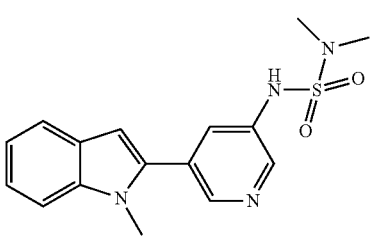 [SMILES: CN(C)S(=O)(=O)Nc1cncc(-c2cc3ccccc3n2C)c1]

To a solution of 2-(5-amino-pyridin-3-yl)-1-methyl-1H-indole (Example 100, 60 mg, 0.269 mmol) and dimethylsulfamoyl chloride (58 mg, 0.403 mmol) in dichloromethane (1 mL) is added triethylamine (54 mg, 0.537 mmol). After overnight stirring, the mixture is concentrated and purified by silica gel flash chromatography (heptane-ethyl acetate, 3:7) to give diethyl-sulfamic acid 5-(1-methyl-1H-indol-2-yl)-pyridin-3-yl-amide. 1H NMR (400 MHz, DMSO-$d_6$) δ ppm 2.77 (s, 6H), 3.76 (s, 3H), 6.89 (s, 1H), 7.07-7.12 (m, 1H), 7.20-7.25 (m, 1H), 7.53 (d, J=8.3 Hz, 1H), 7.61 (d, J=7.8 Hz, 1H), 7.75 (t, J=2.1 Hz, 1H), 8.46 (d, J=2.5 Hz, 1H), 8.52 (d, J=2.0 Hz, 1H). HRMS: (ESI) m/z 331.1226 [(M+H)$^+$ Calcd for $C_{16}H_{18}N_4O_2S$ 331.1223].

Example 229

(a) Ethanesulfonic acid [5-(1-methyl-3-carboxaldehyde-1H-indol-2-yl)-pyridin-3-yl]-N-ethanesulfonyl-amide

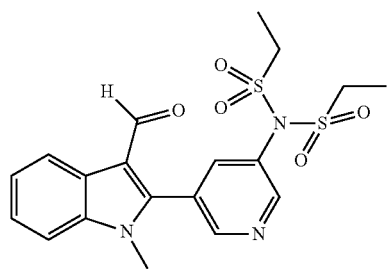 [SMILES: CCS(=O)(=O)N(c1cncc(-c2c(C=O)c3ccccc3n2C)c1)S(=O)(=O)CC]

A flask is charged with DMF (10 mL) and cooled to 0° C. Phosphorus oxychloride (0.297 ml, 3.19 mmol) is added and the reaction mixture is stirred at 0° C. for 20 min followed by the addition of a solution of ethanesulfonic acid [5-(1-methyl-1H-indol-2-yl)-pyridin-3-yl]-N-ethanesulfonyl-amide (Example 225a, 1.00 g, 2.454 mmol) in DMF (10 mL). The reaction mixture is stirred at room temperature for 16 h. The reaction is stopped, washed with saturated NaHCO$_3$ solution and extracted with ethyl acetate. The organic layer is separated and washed with water thrice, then dried over Na$_2$SO$_4$ and concentrated in vacuo to afford ethanesulfonic acid [5-(1-methyl-3-carboxaldehyde-1H-indol-2-yl)-pyridin-3-yl]-N-ethanesulfonyl-amide. MS (ESI) m/z 436.2 (M+H)$^+$ (b) Ethanesulfonic acid [5-(1-methyl-3-vinyl-1H-indol-2-yl)-pyridin-3-yl]-amide

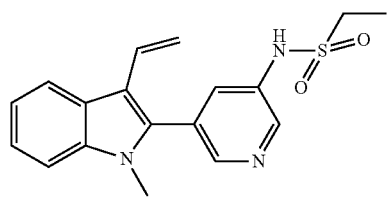 [SMILES: C=Cc1c(-c2cncc(NS(=O)(=O)CC)c2)n(C)c2ccccc12]

A flask is charged with methyl triphenyl phosphine bromide (0.492 g, 1.378 mmol) and THF (20 mL). The reaction mixture is cooled to −78° C. and 1M NaHMDS in THF (1.515 ml, 1.515 mmol) is added. The reaction is stirred at −78° C. for 1 h followed by the addition of ethanesulfonic acid [5-(1-methyl-3-carboxaldehyde-1H-indol-2-yl)-pyridin-3-yl]-N-ethanesulfonyl-amide (0.300 g, 0.689 mmol) at −78° C. The reaction mixture is allowed to warm to room temperature and stirred overnight. The mixture is washed with water and extracted with ethyl acetate. The organic layer is dried over sodium sulfate and concentrated in vacuo. The crude is purified by silica gel flash chromatography (heptane-ethyl acetate, 1:0 to 0-1) to afford ethanesulfonic acid [5-(1-methyl-3-vinyl-1H-indol-2-yl)-pyridin-3-yl]-amide product. MS (ESI) m/z 342.2 (M+H)⁺

(c) Ethanesulfonic acid [5-(1-methyl-3-ethyl-1H-indol-2-yl)-pyridin-3-yl]-amide

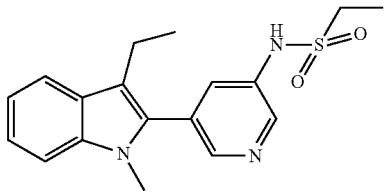 [SMILES: CCc1c(-c2cncc(NS(=O)(=O)CC)c2)n(C)c2ccccc12]

A flask is charged with ethanesulfonic acid [5-(1-methyl-3-vinyl-1H-indol-2-yl)-pyridin-3-yl]-amide (35 mg, 0.082 mmol) and MeOH (5 mL). The flask is evacuated and flushed with $N_2$ thrice. Pd/C (4.36 mg) is added and the reaction stirred under $H_2$ overnight at 50° C. The reaction is filtered over celite and the celite layer is washed thoroughly with MeOH. The filtrate is concentrated in vacuo. The crude is purified by silica gel flash chromatography (dichloromethane-methanol, 19:1) followed by HPLC purification using Xbridge C18 eluting with a 10 to 100% acetonitrile-water gradient to afford the pure product ethanesulfonic acid [5-(3-ethyl-1-methyl-1H-indol-2-yl)-pyridin-3-yl]-amide. ¹H NMR (400 MHz, MeOD) δ ppm 1.27 (t, J=7.6 Hz, 3H), 1.40 (t, J=7.3 Hz, 3H), 2.76 (q, J=7.6 Hz, 2H), 3.25 (q, J=7.3 Hz, 2H), 3.66 (s, 3H), 7.09-7.17 (m, 1H), 7.23-7.31 (m, 1H), 7.43 (d, J=8.3 Hz, 1H), 7.65 (d, J=7.8 Hz, 1H), 7.83 (t, J=2.3 Hz, 1H), 8.36 (d, J=1.8 Hz, 1H), 8.49 (d, J=2.5 Hz, 1H). HRMS: (ESI) m/z 344.1435 [(M+H)⁺ Calcd for $C_{18}H_{21}N_3O_2S$ 344.1427].

Example 230

Ethanesulfonic acid (2-hydroxy-ethyl)-[5-(1-methyl-1H-indol-2-yl)-pyridin-3-yl]-amide

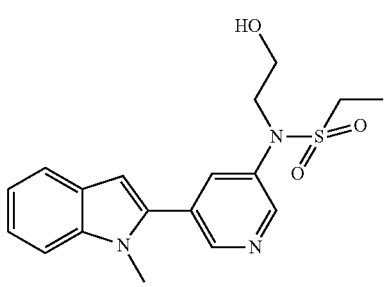 [SMILES: CCS(=O)(=O)N(CCO)c1cncc(-c2cc3ccccc3n2C)c1]

A flask is charged with ethanesulfonic acid [5-(1-methyl-1H-indol-2-yl)-pyridin-3-yl]-amide (example 226, 200 mg, 0.634 mmol) and DMF (3 mL). The reaction is cooled to 0° C. and sodium hydride (38.0 mg, 0.951 mmol) is added. The reaction is stirred at room temperature for 10 min, then 2-chloro-ethoxytrimethylsilane (0.154 mL, 0.951 mmol) is added. The reaction is stirred at 100° C. for 16 h then cooled to room temperature. Aqueous 1M HCl (1 mL) is added and stirring is continued for 30 min. The mixture is purified using an Xbridge C18 eluting with a 10 to 100% acetonitrile-water gradient to afford ethanesulfonic acid (2-hydroxy-ethyl)-[5-(1-methyl-1H-indol-2-yl)-pyridin-3-yl]-amide. MS (ESI) m/z 360.1 (M+H)⁺. ¹H NMR (400 MHz, MeOD) δ ppm 1.42 (t, J=7.3 Hz, 3H), 3.29 (t, 2H), 3.70 (t, J=5.6 Hz, 2H), 3.84 (s, 3H), 3.96 (t, J=5.6 Hz, 2H), 6.75 (s, 1H), 7.14 (td, J=7.5, 0.9 Hz, 1H), 7.28 (td, J=7.7, 1.0 Hz, 1H), 7.49 (d, J=8.3 Hz, 1H), 7.64 (d, J=7.6 Hz, 1H), 8.18 (t, J=2.1 Hz, 1H), 8.71 (d, J=2.3 Hz, 1H), 8.75 (d, J=1.8 Hz, 1H). HRMS (ESI) m/z 360.1383 [(M+H)⁺ Calcd for $C_{18}H_{12}N_3O_3S$ 360.1376].

Example 231

Ethanesulfonic acid methyl-[5-(1-methyl-1H-indol-2-yl)-pyridin-3-yl]-amide

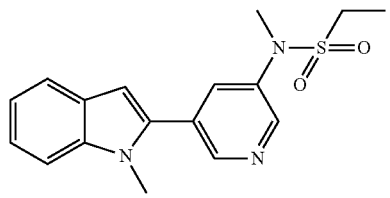 [SMILES: CCS(=O)(=O)N(C)c1cncc(-c2cc3ccccc3n2C)c1]

A flask is charged with ethanesulfonic acid [5-(1-methyl-1H-indol-2-yl)-pyridin-3-yl]-amide (example 226, 100 mg, 0.317 mmol) and DMF (4 mL). The reaction is cooled to 0° C. and sodium hydride (15.85 mg, 0.396 mmol) is added. The reaction is stirred at 0° C. for 10 min, then methyl iodide (56.3 mg, 0.396 mmol) is added. The reaction is stirred for 1 hour at room temperature. The reaction is quenched with water (0.5 mL) and filtered. The filtrate is purified using Xbridge C18 eluting with a 10 to 100% acetonitrile-water gradient to afford ethanesulfonic acid methyl-[5-(1-methyl-1H-indol-2-yl)-pyridin-3-yl]-amide. ¹H NMR (400 MHz, MeOD) δ ppm 1.39 (t, J=7.5 Hz, 3H), 3.28 (q, J=7.5 Hz, 2H), 3.49 (s, 3H), 3.84 (s, 3H), 6.74 (s, 1H), 7.14 (t, J=7.6 Hz, 1H), 7.28 (ddd, J=7.6, 1.1 Hz, 1H), 7.49 (d, J=8.3 Hz, 1H), 7.63 (d, J=7.8 Hz, 1H), 8.13 (t, J=2.1 Hz, 1H), 8.70 (d, J=2.0 Hz, 1H), 8.70 (d, J=2.5 Hz, 1H). HRMS (ESI) m/z 330.1281 [(M+H)⁺ Calcd for $C_{17}H_{19}N_3O_2S$ 330.1270].

Example 232

(a) 2-(5-Bromo-pyridin-3-yl)-isoindole-1,3-dione

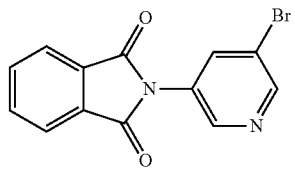 [SMILES: O=C1c2ccccc2C(=O)N1c1cncc(Br)c1]

A flask is charged with 3-amino-5-bromo pyridine (1.00 g, 5.78 mmol), phthalic anhydride (0.856 g, 5.78 mmol) and acetic acid (20 mL). The reaction is refluxed overnight. The reaction is then cooled to room temperature and concentrated in vacuo. The crude is dissolved in ethyl acetate and washed with water once. The organic layer is dried over sodium sulfate and concentrated in vacuo to afford 2-(5-bromo-pyridin-3-yl)-isoindole-1,3-dione. MS (ESI) m/z 305.1 (M+H)+

(b) 2-[5-(6-Methyl-1H-indol-2-yl)-pyridin-3-yl]-isoindole-1,3-dione

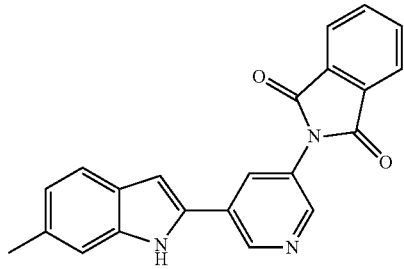 [SMILES: Cc1ccc2cc(-c3cncc(N4C(=O)c5ccccc5C4=O)c3)[nH]c2c1]

2-(5-Bromo-pyridin-3-yl)-isoindole-1,3-dione and N-Boc-6-methyl-indoleboronic acid are processed according to the procedure described in Example 103 to give 2-[5-(6-methyl-1H-indol-2-yl)-pyridin-3-yl]-isoindole-1,3-dione. MS (ESI) m/z 354.1 (M+H)+

(c) 2-[5-(1,6-DiMethyl-1H-indol-2-yl)-pyridin-3-yl]-isoindole-1,3-dione

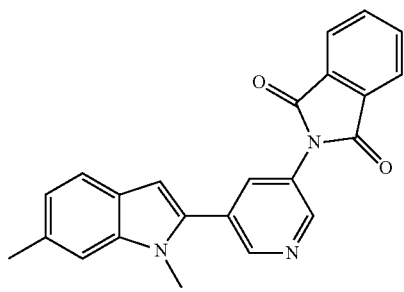 [SMILES: Cc1ccc2cc(-c3cncc(N4C(=O)c5ccccc5C4=O)c3)n(C)c2c1]

2-[5-(6-methyl-1H-indol-2-yl)-pyridin-3-yl]-isoindole-1,3-dione is processed according to the procedure described in Example 114 to give 2-[5-(1,6-dimethyl-1H-indol-2-yl)-pyridin-3-yl]-isoindole-1,3-dione. MS (ESI) m/z 368.3 (M+H)+

(d) 5-(1,6-Dimethyl-1H-indol-2-yl)-pyridin-3-ylamine

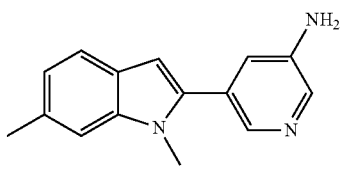 [SMILES: Cc1ccc2cc(-c3cncc(N)c3)n(C)c2c1]

A flask is charged with 2-[5-(1,6-dimethyl-1H-indol-2-yl)-pyridin-3-yl]-isoindole-1,3-dione (1.10 g, 2.096 mmol) and EtOH (30 mL). Hydrazine (1.316 mL, 41.9 mmol) is added and the reaction mixture is refluxed for 1 hour. The reaction mixture is cooled to room temperature, filtered and the precipitate is washed thoroughly with ethyl acetate. The filtrate is concentrated in vacuo. The crude is taken up 1M HCl solution and then extracted with EtOAc. The aqueous layer is separated, basified to pH 14 using 4M aqueous NaOH and extracted with DCM thrice. The organic layer is dried over $Na_2SO_4$ and concentrated in vacuo to afford 5-(1,6-dimethyl-1H-indol-2-yl)-pyridin-3-ylamine. MS (ESI) m/z 238.4 (M+H)+

(e) Ethanesulfonic acid [5-(1,6-dimethyl-1H-indol-2-yl)-pyridin-3-yl]-amide

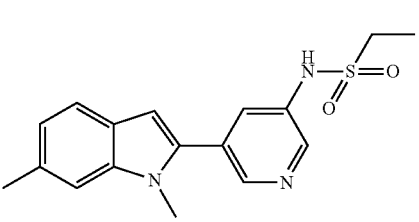 [SMILES: CCS(=O)(=O)Nc1cncc(-c2cc3ccc(C)cc3n2C)c1]

5-(1,6-Dimethyl-1H-indol-2-yl)-pyridin-3-ylamine is processed according to the procedures described in Example 225a and 225c to give ethanesulfonic acid [5-(1,6-dimethyl-1H-indol-2-yl)-pyridin-3-yl]-amide. $^1$H NMR (400 MHz, MeOD) δ ppm 1.40 (t, J=7.3 Hz, 3H), 2.53 (s, 3H), 3.26 (q, J=7.3 Hz, 2H), 3.79 (s, 3H), 6.65 (s, 1H), 6.98 (d, J=8.1 Hz, 1H), 7.28 (s, 1H), 7.50 (d, J=8.1 Hz, 1H), 7.93 (t, J=2.3 Hz, 1H), 8.46 (d, J=2.3 Hz, 1H), 8.53 (d, J=1.8 Hz, 1H). HRMS (ESI) m/z 330.1285 [(M+H)+ Calcd for $C_{17}H_{19}N_3O_2S$ 330.1270].

Example 233

Ethanesulfonic acid [5-(1,6-dimethyl-3-cyano-1H-indol-2-yl)-pyridin-3-yl]-amide

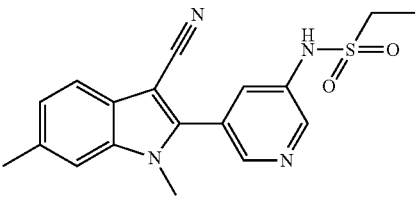 [SMILES: CCS(=O)(=O)Nc1cncc(-c2c(C#N)c3ccc(C)cc3n2C)c1]

5-(1,6-Dimethyl-1H-indol-2-yl)-pyridin-3-ylamine (Example 232d) is processed according to the procedures described in Example 225a, 128 and 225c to give ethanesulfonic acid [5-(1,6-dimethyl-3-cyano-1H-indol-2-yl)-pyridin-3-yl]-amide. $^1$H NMR (400 MHz, MeOD) δ ppm 1.39 (t, J=7.3 Hz, 3H), 2.57 (s, 3H), 3.22 (q, J=7.3 Hz, 2H), 3.84 (s, 3H), 7.22 (d, J=8.1 Hz, 1H), 7.46 (s, 1H), 7.60 (d, J=8.1 Hz, 1H), 7.92-7.94 (m, 1H), 8.39 (d, J=1.8 Hz, 1H), 8.50 (d, J=2.5 Hz, 1H). HRMS: (ESI) m/z 355.1230 [(M+H)+ Calcd for $C_{18}H_{18}N_4O_2S$ 355.1223].

Example 234

Ethanesulfonic acid [5-(1-methyl-6-fluoro-1H-indol-2-yl)-pyridin-3-yl]-amide

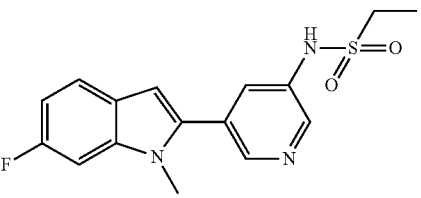 [SMILES: CCS(=O)(=O)Nc1cncc(-c2cc3ccc(F)cc3n2C)c1]

6-Fluoro-1-methyl-indole boronic acid and 3-bromo-5-aminopyridine are processed according to procedures described in examples 100, 225a and 225c to give ethanesulfonic acid [5-(1-methyl-6-fluoro-1H-indol-2-yl)-pyridin-3-yl]-amide. $^1$H NMR (400 MHz, DMSO-$d_6$) δ ppm 1.24 (t, J=7.3 Hz, 3H), 3.17-3.28 (m, 5H), 6.53 (d, J=3.0 Hz, 1H), 7.01 (dd, J=10.2, 8.7 Hz, 1H), 7.29 (d, J=3.3 Hz, 1H), 7.60-7.68 (m, 2H), 8.41 (d, J=1.8 Hz, 1H), 8.53 (d, J=2.5 Hz, 1H), 10.23 (s, 1H). HRMS (ESI) m/z 334.1029 [(M+H)$^+$ Calcd for $C_{16}H_{16}FN_3O_2S$ 334.1020].

Example 235

(a) Bis-ethanesulfonic acid [5-(1-methyl-6-chloro-1H-indol-2-yl)-pyridin-3-yl)-amide

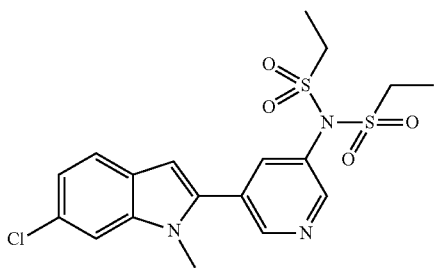 [SMILES: CCS(=O)(=O)N(c1cncc(-c2cc3ccc(Cl)cc3n2C)c1)S(=O)(=O)CC]

Bis-ethanesulfonic acid (5-bromo-pyridin-3-yl)-amide (Example 210a) and 6-chloro-1-methyl-indole-2-boronic acid are processed according to the procedure described in Example 100 to give bis-ethanesulfonic acid [5-(1-methyl-6-chloro-1H-indol-2-yl)-pyridin-3-yl)-amide. MS (ESI) m/z 442.1 (M+H)$^+$ (b) Bis-ethanesulfonic acid [5-(1-methyl-3-carboxaldehyde-6-chloro-1H-indol-2-yl)-pyridin-3-yl)-amide

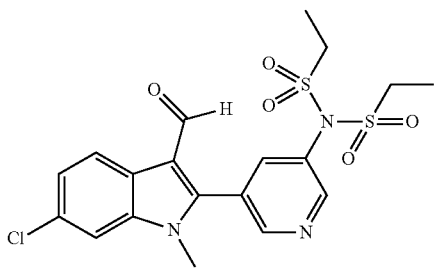 [SMILES: CCS(=O)(=O)N(c1cncc(-c2c(C=O)c3ccc(Cl)cc3n2C)c1)S(=O)(=O)CC]

A flask is charged with DMF (10 mL) and cooled to 0° C. Phosphorus oxychloride (0.205 ml, 2.178 mmol) is added and the reaction mixture is stirred for 20 min. Bis-ethanesulfonic acid [5-(1-methyl-6-chloro-1H-indol-2-yl)-pyridin-3-yl)-amide (0.875 g, 1.980 mmol) is added and reaction mixture is left to stir at room temperature overnight. The reaction is washed with saturated aqueous NaHCO$_3$ and extracted with ethyl acetate. The organic layer is separated and washed with water thrice, then dried over Na$_2$SO$_4$ and concentrated in vacuo to afford bis-ethanesulfonic acid [5-(1-methyl-3-carboxaldehyde-6-chloro-1H-indol-2-yl)-pyridin-3-yl)-amide. MS (ESI) m/z 469.9 (M+H)$^+$.

(c) Bis-ethanesulfonic acid [5-(1,3-dimethyl-6-chloro-1H-indol-2-yl)-pyridin-3-yl)-amide

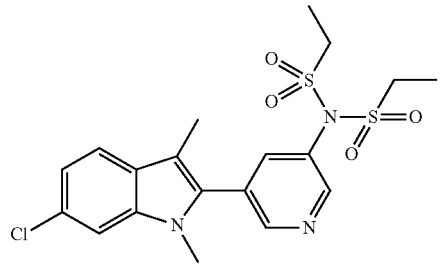 [SMILES: CCS(=O)(=O)N(c1cncc(-c2c(C)c3ccc(Cl)cc3n2C)c1)S(=O)(=O)CC]

A flask is charged with bis-ethanesulfonic acid [5-(1-methyl-3-carboxaldehyde-6-chloro-1H-indol-2-yl)-pyridin-3-yl)-amide (0.225 g, 0.479 mmol), zinc iodide (0.2320 g, 0.718 mmol), NaCN(BH)$_3$ (0.228 g, 3.591 mmol) and dichloroethane (5 mL). The reaction is refluxed for 1.5 hours. The reaction mixture is cooled to room temperature and filtered over celite. The celite layer is washed with DCM. The filtrate is washed with a buffer solution containing 1:1 saturated ammonium hydroxide and saturated ammonium chloride solution. The organic layer is dried over sodium sulfate and concentrated in vacuo to give bis-ethanesulfonic acid [5-(1,3-dimethyl-6-chloro-1H-indol-2-yl)-pyridin-3-yl)-amide. MS (ESI) m/z 455.9 (M+H)$^+$ (d) Ethanesulfonic acid [5-(1,3-dimethyl-6-chloro-1H-indol-2-yl)-pyridin-3-yl)-amide

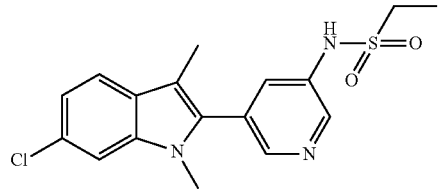 [SMILES: CCS(=O)(=O)Nc1cncc(-c2c(C)c3ccc(Cl)cc3n2C)c1]

Bis-ethanesulfonic acid [5-(1,3-dimethyl-6-chloro-1H-indol-2-yl)-pyridin-3-yl)-amide is processed according to the procedure described in Example 225c to give ethanesulfonic acid [5-(1,3-dimethyl-6-chloro-1H-indol-2-yl)-pyridin-3-yl)-amide. $^1$H NMR (400 MHz, MeOD) δ ppm 1.41 (t, J=7.33 Hz, 3H), 2.31 (s, 3H), 3.26 (q, J=7.33 Hz, 2H), 3.67 (s, 3H), 7.12 (dd, J=8.46, 1.89 Hz, 1H), 7.49 (d, J=1.77 Hz, 1H), 7.57 (d, J=8.34 Hz, 1H), 7.81-7.86 (m, 1H), 8.41 (d, J=1.77 Hz, 1H), 8.51 (d, J=2.27 Hz, 1H). HRMS (ESI) m/z 364.0894 [(M+H)$^+$ Calcd for $C_{17}H_{18}N_3O_2SCl$ 364.0881].

Example 236

Ethanesulfonic acid [5-(1,3-dimethyl-1H-indol-2-yl)-pyridin-3-yl)-amide

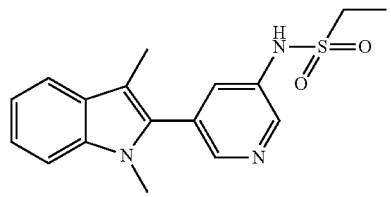 [SMILES: CCS(=O)(=O)Nc1cncc(-c2c(C)c3ccccc3n2C)c1]

Ethanesulfonic acid [5-(1-methyl-1H-indol-2-yl)-pyridin-3-yl]-N-ethanesulfonyl-amide (Example 225a) is processed according to the procedures described in Example 235b, 235c and 225c to give ethanesulfonic acid [5-(1,3-dimethyl-1H-indol-2-yl)-pyridin-3-yl]-amide. $^1$H NMR (400 MHz, MeOD) δ ppm 1.41 (t, J=7.5 Hz, 3H), 2.33 (s, 3H), 3.27 (q, J=7.3 Hz, 2H), 3.69 (s, 3H), 7.14 (t, J=7.5 Hz, 1H), 7.24-7.31 (m, 1H), 7.43 (d, J=8.3 Hz, 1H), 7.61 (d, J=8.1 Hz, 1H), 7.84 (t, J=2.1 Hz, 1H), 8.42 (d, J=1.8 Hz, 1H), 8.50 (d, J=2.5 Hz, 1H). HRMS: (ESI) m/z 330.1276 [(M+H)$^+$ Calcd for C$_{17}$H$_{19}$N$_3$O$_2$S 330.1270].

Example 237

(a)
N-((5-bromopyridin-3-yl)methyl)ethanesulfonamide

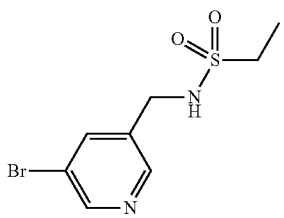

A flask is charged with 5-bromonicotinaldehyde (1.15 g, 6.18 mmol), ethanesulfonamide (1.35 g, 12.37 mmol) and toluene (120 mL), and titanium isopropoxide (2.64 g, 9.27 mmol) is added dropwise. The mixture is stirred at 120° C. overnight. The mixture is concentrated in vacuo. The residue is taken up in DCM (100 mL) and MeOH (100 mL) and NaBH$_4$ (0.468 g, 12.37 mmol) is added at 0° C. The mixture is stirred at 0° C. for 30 min. Water (50 mL) is then added and the mixture is stirred for 5 min. The suspension is filtered through a pad of celite. The celite layer is washed with DCM (50 mL×3). The filtrate is concentrated in vacuo. The resulting aqueous phase is extracted with DCM (500 mL) and the organic phase is dried over Na$_2$SO$_4$, silica gel (20 g) added, and concentrated in vacuo. The residue is purified by silica chromatography eluting with a 0 to 7% MeOH-DCM gradient to give N-((5-bromopyridin-3-yl)methyl)ethanesulfonamide. MS (ESI) m/z 278.9, 280.8, (M+H)$^+$.

(b) N-((5-Bromopyridin-3-yl)methyl)-1-(ethylsulfonyl)ethanesulfonamide

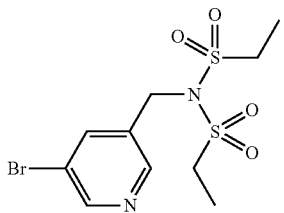 [SMILES: CCS(=O)(=O)N(Cc1cncc(Br)c1)S(=O)(=O)CC]

To a solution of N-((5-bromopyridin-3-yl)methyl)ethanesulfonamide (1.8 g, 5.55 mmol) and triethylamine (1.683 g, 16.64 mmol) in DCM (20 mL) at 0° C. is added ethanesulfonyl chloride (1.426 g, 11.09 mmol), and the mixture is stirred at 0° C. for 1 h. Silica gel (10 g) is added and the mixture is concentrated in vacuo. The residue is purified by silica chromatography eluting with 0 to 2% MeOH-DCM to give N-((5-bromopyridin-3-yl)methyl)-N-(ethylsulfonyl)ethanesulfonamide. $^1$H NMR (400 MHz, DMSO-d$_6$) δ ppm 1.14 (t, J=7.3 Hz, 6H), 3.48 (q, J=7.3 Hz, 4H), 4.92 (s, 2H), 8.0 (t, J=2.1 Hz, 1H), 8.59 (d, J=2.0 Hz, 1H), 8.72 (d, J=2.3 Hz, 1H).

(c) N-(Ethylsulfonyl)-N-((5-(1-methyl-1H-indol-2-yl)pyridin-3-yl)methyl)ethanesulfonamide

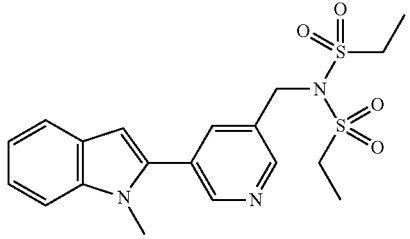 [SMILES: CCS(=O)(=O)N(Cc1cncc(-c2cc3ccccc3n2C)c1)S(=O)(=O)CC]

N-((5-Bromopyridin-3-yl)methyl)-1-(ethylsulfonyl)ethanesulfonamide and N-methyl-indole-2-boronic acid are processed according to the procedure described in Example 100 to give N-(ethylsulfonyl)-N-((5-(1-methyl-1H-indol-2-yl)pyridin-3-yl)methyl)ethanesulfonamide. MS (ESI) m/z 422.0 (M+H)$^+$.

(d) N-(Ethylsulfonyl)-N-((5-(3-formyl-1-methyl-1H-indol-2-yl)pyridin-3-yl)methyl)ethanesulfonamide

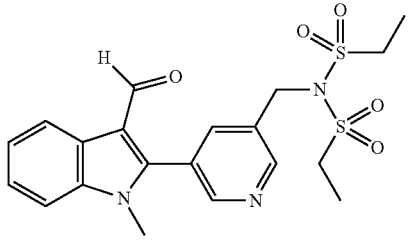 [SMILES: CCS(=O)(=O)N(Cc1cncc(-c2c(C=O)c3ccccc3n2C)c1)S(=O)(=O)CC]

N-(Ethylsulfonyl)-N-((5-(1-methyl-1H-indol-2-yl)pyridin-3-yl)methyl)ethanesulfonamide is processed according to the procedure described in Example 235b to give N-(ethylsulfonyl)-N-((5-(3-formyl-1-methyl-1H-indol-2-yl)pyridin-3-yl)methyl)ethanesulfonamide. MS (ESI) m/z 450.0 (M+H)$^+$.

(e) N-((5-(1,3-Dimethyl-1H-indol-2-yl)pyridin-3-yl)methyl)ethanesulfonamide

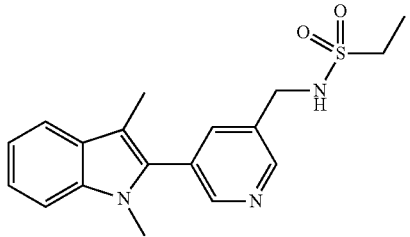 [SMILES: CCS(=O)(=O)NCc1cncc(-c2c(C)c3ccccc3n2C)c1]

N-(Ethylsulfonyl)-N-((5-(3-formyl-1-methyl-1H-indol-2-yl)pyridin-3-yl)methyl)ethanesulfonamide is processed according to the procedure described in Example 235c to give N-(ethylsulfonyl)-N-((5-(1,3-dimethyl-1H-indol-2-yl)pyridin-3-yl)methyl)ethanesulfonamide which is processed according to the procedure described in Example 225c to give N-((5-(1,3-dimethyl-1H-indol-2-yl)pyridin-3-yl)methyl)ethanesulfonamide. $^1$H NMR (400 MHz, DMSO-d$_6$) δ ppm 1.20 (t, J=7.3 Hz, 3H), 2.24 (s, 3H), 3.04 (q, J=7.3 Hz, 2H), 3.62 (s, 3H), 4.31 (s, 2H), 7.10 (t, J=7.5 Hz, 1H), 7.22 (ddd, J=8.2, 7.0, 1.3 Hz, 1H), 7.49 (d, J=8.1 Hz, 1H), 7.58 (d, J=7.8 Hz, 1H), 7.72 (br. s., 1H), 7.87 (t, J=2.0 Hz, 1H), 8.61 (dd, J=7.2, 2.2 Hz, 2H). HRMS: (ESI) m/z 344.1442 [(M+H)$^+$ Calcd for C$_{18}$H$_{22}$N$_3$O$_2$S: 344.1427].

Example 238

(a) Ethanesulfonic acid [5-(1-methyl-3-methoxymethyl-6-chloro-1H-indol-2-yl)-pyridin-3-yl)-amide

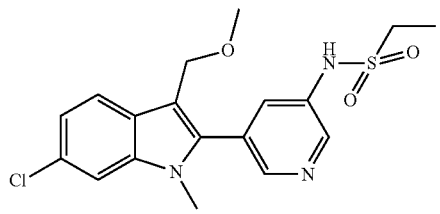 [SMILES: CCS(=O)(=O)Nc1cncc(-c2c(COC)c3ccc(Cl)cc3n2C)c1]

Bis-ethanesulfonic acid [5-(1-methyl-3-carboxaldehyde-6-chloro-1H-indol-2-yl)-pyridin-3-yl)-amide (Example 235b, 0.150 g, 0.319 mmol) is dissolved in methanol (5 mL) and cooled to 0° C. NaBH$_4$ (0.019 g, 0.798 mmol) is added and the reaction mixture is stirred at room temperature for 2 h. 4M aqueous NaOH (1 mL) is added and the reaction is stirred at room temperature for 1 h. The methanol is then removed in vacuo. The crude is taken up in DCM and washed with water twice. The organic layer is dried over Na$_2$SO$_4$ and concentrated in vacuo. The crude is purified by silica gel flash chromatography (dichloromethane-methanol, 9:1) to afford bis-ethanesulfonic acid [5-(1-methyl-3-methoxymethyl-6-chloro-1H-indol-2-yl)-pyridin-3-yl)-amide. $^1$H NMR (400 MHz, MeOD) δ ppm 1.41 (t, J=7.3 Hz, 3H), 3.28 (q, J=7.3 Hz, 2H), 3.39 (s, 3H), 3.72 (s, 3H), 4.54 (s, 2H), 7.18 (dd, J=8.6, 1.8 Hz, 1H), 7.56 (d, J=1.8 Hz, 1H), 7.71 (d, J=8.6 Hz, 1H), 7.93 (t, J=2.3 Hz, 1H), 8.48 (d, J=1.8 Hz, 1H), 8.54 (d, J=2.5 Hz, 1H). HRMS: (ESI) m/z 394.0990 [(M+H)$^+$ Calcd for C$_{18}$H$_{20}$N$_3$O$_3$SCl 394.0986].

Example 239

(a) 2-(Benzyloxy)-N-(5-(1-methyl-1H-indol-2-yl)pyridin-3-yl)ethanesulfonamide

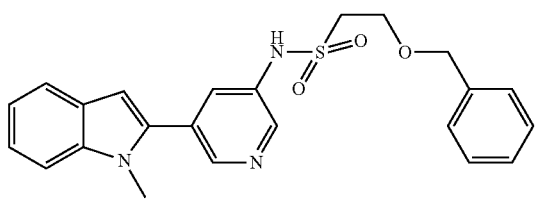 [SMILES: Cn1c(-c2cncc(NS(=O)(=O)CCOCc3ccccc3)c2)cc2ccccc21]

To a solution of 5-(1-methyl-1H-indol-2-yl)pyridin-3-amine (Example 100, 150 mg, 0.672 mmol) and triethylamine (272 mg, 2.69 mmol) in DCM (6 mL) is added 2-chloroethanesulfonyl chloride (274 mg, 1.68 mmol) in DCM (2 mL) dropwise at 0° C. The mixture is stirred at 0° C. for 1 h. Silica gel (5 g) is added and the mixture is concentrated. After elution, the fractions containing the product are concentrated to give a residue, which is redissolved in benzyl alcohol (20 mL). 60% NaH in mineral oil is added. The mixture is stirred at 70° C. for 1 day. The mixture is then filtered and the filtrate is purified on Xbridge C18 eluting with a 1:9 to 9:1 acetonitrile-water gradient to give 2-(benzyloxy)-N-(5-(1-methyl-1H-indol-2-yl)pyridin-3-yl)ethanesulfonamide. MS (ESI) m/z 422.1 (M+H)$^+$.

(b) 2-Hydroxy-N-(5-(1-methyl-1H-indol-2-yl)pyridin-3-yl)ethanesulfonamide

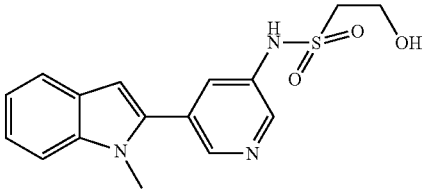 [SMILES: Cn1c(-c2cncc(NS(=O)(=O)CCO)c2)cc2ccccc21]

A flask is charged with 2-(benzyloxy)-N-(5-(1-methyl-1H-indol-2-yl)pyridin-3-yl)ethanesulfonamide (90 mg, 0.214 mmol) and MeOH (5 mL), and the flask is flushed with N$_2$. 10% Pd/C (22.7 mg, 0.021 mmol) is added to the mixture. The flask is flushed with H$_2$ and stirred under H$_2$ atmosphere at 50° C. overnight. The mixture is filtered and the filtrate is purified by silica chromatography eluting with a 0 to 4% methanol-DCM gradient to give 2-hydroxy-N-(5-(1-methyl-1H-indol-2-yl)pyridin-3-yl)ethanesulfonamide. $^1$H NMR (400 MHz, DMSO-d$_6$) δ ppm 3.37 (t, J=6.2 Hz, 2H), 3.77 (s, 3H), 3.80 (t, J=6.3 Hz, 2H), 4.96 (br. s., 1H), 6.70 (s, 1H), 7.10 (t, J=7.1 Hz, 1H), 7.23 (td, J=7.6, 1.1 Hz, 1H), 7.53 (d, J=7.8 Hz, 1H), 7.61 (d, J=7.8 Hz, 1H), 7.79 (t, J=2.3 Hz, 1H), 8.47 (d, J=2.5 Hz, 1H), 8.55 (d, J=1.8 Hz, 1H), 10.12 (br. s., 1H). HRMS: (ESI) m/z 332.1072 [(M+H)$^+$ Calcd for C$_{16}$H$_{18}$N$_3$O$_3$S 332.1063].

Example 240

2-Methoxy-N-(5-(1-methyl-1H-indol-2-yl)pyridin-3-yl) ethanesulfonamide

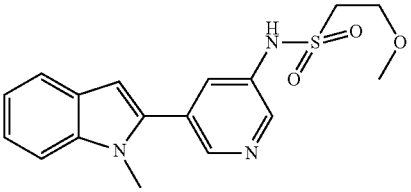 [SMILES: COCCS(=O)(=O)Nc1cncc(-c2cc3ccccc3n2C)c1]

A flask is charged with 5-(1-methyl-1H-indol-2-yl)pyridin-3-amine (Example 100, 22 mg, 0.10 mmol), DCM (2 mL) and TEA (20 mg, 0.20 mmol). 2-Chloroethanesulfonyl chloride (16 mg, 0.10 mmol) in DCM (0.5 mL) is added dropwise at 0° C. The mixture is stirred over weekend at room temperature. The solvent is removed in vacuo and methanol (2 mL)

and 5 M aqueous NaOH (3 mL) are added. The mixture is stirred at 60° C. overnight, concentrated in vacuo and the residue is extracted with DCM. The combined organic phase is dried over $Na_2SO_4$ and concentrated. The residue is purified on silica chromatography eluting with a 0 to 5% methanol-DCM gradient to give 2-methoxy-N-(5-(1-methyl-1H-indol-2-yl)pyridin-3-yl) ethanesulfonamide. $^1$H NMR (400 MHz, DMSO-$d_6$) δ ppm 3.18 (s, 3H), 3.51 (t, J=5.7 Hz, 2H), 3.70 (t, J=5.7 Hz, 2H), 3.77 (s, 3H), 6.70 (d, J=0.5 Hz, 1H), 7.10 (td, J=7.5, 1.0 Hz, 1H), 7.23 (ddd, J=8.2, 7.1, 1.1 Hz, 1H), 7.53 (d, J=8.3 Hz, 1H), 7.61 (d, J=7.8 Hz, 1H), 7.78 (t, J=2.3 Hz, 1H), 8.46 (d, J=2.5 Hz, 1H), 8.55 (d, J=2.0 Hz, 1H). HRMS: (ESI) m/z 346.1251 [(M+H)$^+$ Calcd for $C_{17}H_{20}N_3O_3S$: 346.1225].

Example 241

(a) 5-bromo-N,N-diethylpyridine-3-sulfonamide

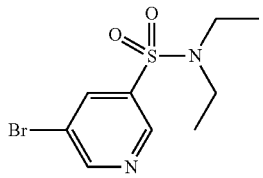

To a suspension of 5-bromopyridine-3-sulfonamide (237 mg, 1 mmol) and $K_2CO_3$ (276 mg, 2 mmol) in DMF (1 mL) is added iodoethane (156 mg, 1 mmol) in DMF (5 mL) via syringe pump over 2 hours. The mixture is then stirred at room temperature overnight. Iodoethane (0.020 mL, 0.2 mmol) in DMF (1 mL) is added dropwise. The mixture is stirred over the weekend and filtered. The filtrate is purified by Xterra RP18 eluting with a 1:9 to 9:1 acetonitrile-water gradient to give 5-bromo-N,N-diethylpyridine-3-sulfonamide. MS (ESI) m/z 293.0, 295.1 (M+H)$^+$.

(b) N-ethyl-5-(1-methyl-1H-indol-2-yl)pyridine-3-sulfonamide

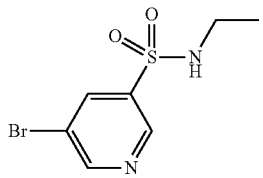

The method described in Example 241a also affords N-ethyl-5-(1-methyl-1H-indol-2-yl)pyridine-3-sulfonamide as a product of the reaction. MS (ESI) m/z 265.0, 267.0 (M+H)$^+$.

(c) N,N-diethyl-5-(1-methyl-1H-indol-2-yl)pyridine-3-sulfonamide

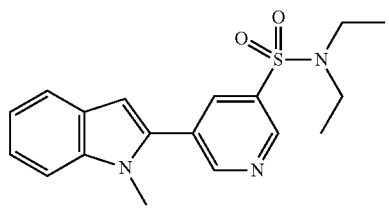 [SMILES: CCN(CC)S(=O)(=O)c1cncc(-c2cc3ccccc3n2C)c1]

A flask is charged with 1-methyl-1H-indol-2-ylboronic acid (90 mg, 0.512 mmol), 5-bromo-N,N-diethylpyridine-3-sulfonamide (100 mg, 0.341 mmol) and polymer supported Pd(PPh$_3$)$_4$ (189 mg, 0.017 mmol), and the flask is flushed with $N_2$ for 5 min. 1,4-Dioxane (10 mL) and 2M $K_2CO_3$ in water (0.512 mL, 1.023 mmol) are added under $N_2$ and the mixture is stirred at 90° C. under $N_2$ for 2 h. The mixture is then cooled to room temperature and DMF (4 mL) is added. The mixture is concentrated in vacuo and the residue is filtered and the filtrate is purified by Xterra RP18 eluting with a 1:9 to 9:1 acetonitrile-water gradient to give N,N-diethyl-5-(1-methyl-1H-indol-2-yl)pyridine-3-sulfonamide. $^1$H NMR (400 MHz, DMSO-$d_6$) δ ppm 1.10 (t, J=7.1 Hz, 6H), 3.29 (d, J=7.1 Hz, 4H), 3.80 (s, 3H), 6.85 (s, 1H), 7.08-7.14 (m, 1H), 7.26 (td, J=7.71, 1.26 Hz, 1H), 7.56 (dd, J=8.3, 0.5 Hz, 1H), 7.63 (d, J=7.8 Hz, 1H), 8.33 (t, J=2.1 Hz, 1H), 9.00 (d, J=2.0 Hz, 1H), 9.10 (d, J=2.2 Hz, 1H). HRMS: (ESI) m/z 344.1428 [(M+H)$^+$ Calcd for $C_{18}H_{22}N_3O_2S$ 344.1427].

Example 242

N-ethyl-5-(1-methyl-1H-indol-2-yl)pyridine-3-sulfonamide

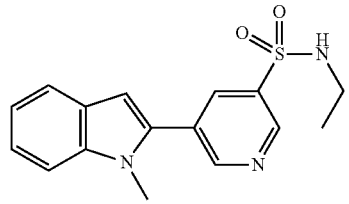 [SMILES: CCNS(=O)(=O)c1cncc(-c2cc3ccccc3n2C)c1]

N-Ethyl-5-(1-methyl-1H-indol-2-yl)pyridine-3-sulfonamide is processed according to the method described in Example 241c to give N-ethyl-5-(1-methyl-1H-indol-2-yl) pyridine-3-sulfonamide. $^1$H NMR (400 MHz, DMSO-$d_6$) δ ppm 1.02 (t, J=7.2 Hz, 3H), 2.92 (q, J=7.2 Hz, 2H), 3.81 (s, 3H), 6.83 (s, 1H), 7.12 (t, J=7.1 Hz, 1H), 7.26 (td, J=7.6, 1.1 Hz, 1H), 7.56 (d, J=8.3 Hz, 1H), 7.63 (d, J=7.8 Hz, 1H), 8.31 (t, J=2.2 Hz, 1H), 8.97 (d, J=2.3 Hz, 1H), 9.08 (d, J=2.2 Hz, 1H). HRMS: (ESI) m/z 316.1126 [(M+H)$^+$ Calcd for $C_{16}H_{18}N_3O_2S$ 316.1114].

Example 243

In-Vitro Assay for Aldosterone Synthase Inhibition

The activities of a compound according to the present invention can be assessed by the following in vitro method well-described in the art. See Fiebeler, A et al. (2005), "Aldosterone Synthase Inhibitor Ameliorates Angiotensin II-Induced Organ Damage," *Circulation*, 111:3087-3094.

In particular, the inhibition of aldosterone and cortisol secretion in vitro can be determined by the following assay.

The cell line NCI-H295R was originally isolated from an adrenocortical carcinoma and has been characterized in the literature through the stimulable secretion of steroid hormones and the presence of the enzymes essential for steroidogenesis. The cells show the physiological property of zonally undifferentiated human foetal adrenocortical cells which, however, have the capacity to produce the steroid hormones which are formed in the three phenotypically distinguishable zones in the adult adrenal cortex. Thus, the NCI-H295R cells have CYP11B2 (aldosterone synthase) and CYP11B1 (steroid 11-hydroxylase).

The human adrenocortical carcinoma NCI-H295R cell line is obtained from American Type Culture Collection (Manassas, Va.). Insulin/transferrin/selenium (ITS)-A supplement (100×), DMEM/F-12, antibiotic/antimycotic (100×), and fetal calf serum (FCS) are purchased from Invitrogen (Carlsbad, Calif.). Anti-mouse PVT scintillation proximity assay (SPA) beads and NBS 96-well plates are obtained from Amersham (Piscataway, N.J.) and Corning (Acton, Mass.), respectively. Clear bottom 96-well flat bottom plates are purchased from Costar (Corning, N.Y.). Aldosterone and angiotensin (Ang II) are purchased from Sigma (St. Louis, Mo.). D-[1,2,6,7-3H(N)]aldosterone and [1,2,6,7-3H(N)]cortisol are acquired from PerkinElmer (Boston, Mass.). Nu-serum is a product of BD Biosciences (Franklin Lakes, N.J.).

For in vitro measurement of aldosterone and cortisol activity, human adrenocortical carcinoma NCI-H295R cells are seeded in NBS 96-well plates at a density of 25,000 cells/well in 100 µL of a growth medium containing DMEM/F12 supplemented with 10% FCS, 2.5% Nu-serum, 1 µg ITS/ml, and 1× antibiotic/antimycotic. The medium is changed after culturing for 3 days at 37° C. under an atmosphere of 5% CO2/95% air. On the following day, cells are rinsed with 100 µL of DMEM/F12 and incubated in quadruplicate wells at 37° C. for 24 hours with 100 µL of treatment medium containing a cell stimulant and a compound at different concentrations. The test substance is added in a concentration range from 0.2 nanomolar to 16 micromolar. Cell stimulants which can be used are angiotensin-II (1 micormolar), potassium ions (16 millimolar), forskolin (10 micromolar) or a combination of two stimulants. At the end of incubation, the excretion of aldosterone and cortisol into the culture medium can be detected and quantified by commercially available, specific monoclonal antibodies in radioimmunoassays in accordance with the manufacturer's instructions.

Measurement of aldosterone can also be performed using a 96-well plate format. Each test sample is incubated with 0.02 µCi of D-[1,2,6,7-3H(N)]aldosterone and 0.3 µg of anti-aldosterone antibody in phosphate-buffered saline (PBS) containing 0.1% Triton X-100, 0.1% bovine serum albumin, and 12% glycerol in a total volume of 200 µL at room temperature for 1 hour. Anti-mouse PVT SPA beads (50 µL) are then added to each well and incubated overnight at room temperature prior to counting in a Microbeta plate counter. The amount of aldosterone in each sample is calculated by comparing with a standard curve generated using known quantities of the hormone. Measurement of cortisol can be performed in a manner similar to that of aldosterone, except that [1,2,6,7-3H(N)]cortisol is used.

Inhibition of the release of a steroid can be used as a measure of the respective enzyme inhibition by the added test compounds. The dose-dependent inhibition of enzymatic activity by a compound is calculated by means of an inhibition plot which is characterized by an $IC_{50}$. The $IC_{50}$ values for active test compounds are ascertained by a simple linear regression analysis in order to construct inhibition plots without data weighting. The inhibition plot is calculated by fitting a 4-parameter logistic function to the raw data points using the least squares method. The equation of the 4-parameter logistic function is calculated as follows: $Y=(d-a)/((1+(x/c)(b)+a)$ where: a=minimum, b=slope, c=$IC_{50}$, d=maximum, x=inhibitor concentrations.

TABLE 1

Inhibitory Activity of Compounds

| Example | Aldosterone cell secretion $IC_{50}$ (nM) | Cortisol cell secretion $IC_{50}$ (nM) |
| --- | --- | --- |
| 6 | 1 | 7 |
| 15 | 27 | 447 |
| 33 | 14 | 662 |
| 42 | 30 | 600 |
| 65 | 10 | 240 |
| 90 | 40 | 400 |
| 101 | 2 | 37 |
| 106 | 85 | 530 |
| 107 | 9 | 220 |
| 123 | 78 | 650 |
| 138 | 43 | 326 |
| 171 | 3 | 168 |
| 180 | 2 | 3 |
| 186 | 21 | 390 |
| 192 | 4 | 20 |
| 196 | 3 | 19 |
| 206 | 2 | 213 |
| 209 | 23 | 788 |
| 214 | 56 | 377 |
| 216 (one enantiomer) | 32 | 600 |
| 216 (other enantiomer) | 35 | 1230 |
| 217 | 4 | 22 |
| 226 | 36 | 345 |
| 228 | 105 | >1000 |
| 229 | 5 | 125 |
| 231 | 2 | 51 |
| 236 | 21 | 1100 |
| 237 | 5 | 1611 |
| 238 | 44 | >1000 |
| 242 | 23 | >1000 |

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The appropriate components, processes, and methods of those patents, applications and other documents may be selected for the present invention and embodiments thereof.

We claim:

1. A compound of Formula I:

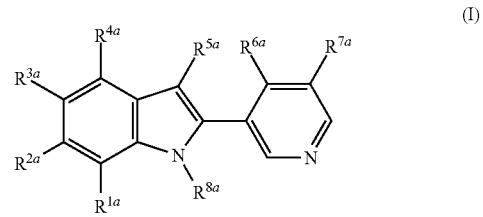

wherein:

$R^{1a}$ is hydrogen;

$R^{2a}$ is hydrogen, halogen, or hydroxy;

$R^{3a}$ is hydrogen, halogen, cyano, or alkoxy;

$R^{4a}$ is hydrogen or halogen;

$R^{5a}$ is hydrogen or alkyl;
$R^{6a}$ and $R^{7a}$ are hydrogen;
$R^{8a}$ is:

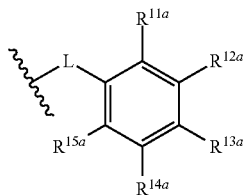

L is carbonyl or sulfonyl; and
$R^{11a}$, $R^{12a}$, $R^{13a}$, $R^{14a}$, and $R^{15a}$ are each independently hydrogen, alkyl, cyano, halogen, alkoxy, alkoxycarbonyl, carboxylate, heteroaryl, or sulfonyl; with the proviso that at least one of $R^{2a}$-$R^{5a}$ is other than hydrogen; or a pharmaceutically acceptable salt thereof.

2. A compound according to claim 1 wherein the compound is selected from:
(3-Methyl-2-pyridin-3-yl-indol-1-yl)-phenyl-methanone;
1-(4-cyano-3-methyl-benzoyl)-2-pyridin-3-yl-1H-indole-5-carbonitrile;
3-(5-Cyano-2-pyridin-3-yl-indole-1-carbonyl)-benzoic acid tert-butyl ester;
1-(3-Methyl-benzoyl)-2-pyridin-3-yl-1H-indole-5-carbonitrile;
1-(3,4-Dimethyl-benzoyl)-2-pyridin-3-yl-1H-indole-5-carbonitrile;
1-(4-Methoxy-benzoyl)-2-pyridin-3-yl-1H-indole-5-carbonitrile
1-(3-Methoxy-benzoyl)-2-pyridin-3-yl-1H-indole-5-carbonitrile;
1-(3,4-Dimethoxy-benzoyl)-2-pyridin-3-yl-1H-indole-5-carbonitrile;
1-(3-Ethyl-benzoyl)-2-pyridin-3-yl-1H-indole-5-carbonitrile;
1-(3,5-Dimethyl-benzoyl)-2-pyridin-3-yl-1H-indole-5-carbonitrile;
5-(5-Cyano-2-pyridin-3-yl-indole-1-carbonyl)-2-methyl-benzoic acid;
3-(5-Cyano-2-pyridin-3-yl-indole-1-carbonyl)-benzoic acid; and
1-(3-Cyano-benzenesulfonyl)-2-pyridin-3-yl-1H-indole-5-carbonitrile;
or a pharmaceutically acceptable salt thereof.

3. A pharmaceutical composition, comprising
an effective amount of a compound according to claim 1, or a pharmaceutically acceptable salt thereof; and a pharmaceutically acceptable carrier or diluent.

4. The pharmaceutical composition of claim 3, further comprising a second agent.

5. The pharmaceutical composition of claim 4, wherein said second agent is an HMG-Co-A reductase inhibitor, an angiotensin II receptor antagonist, angiotensin converting enzyme (ACE) Inhibitor, a calcium channel blocker (CCB), a dual angiotensin converting enzyme/neutral endopeptidase (ACE/NEP) inhibitor, an endothelin antagonist, a renin inhibitor, a diuretic, an ApoA-I mimic, an anti-diabetic agent, an obesity-reducing agent, an aldosterone receptor blocker, an endothelin receptor blocker, or a CETP inhibitor.

6. A pharmaceutical composition, comprising
an effective amount of a compound according to claim 2, or a pharmaceutically acceptable salt thereof; and a pharmaceutically acceptable carrier or diluent.

7. The pharmaceutical composition of claim 6, further comprising a second agent.

8. The pharmaceutical composition of claim 7, wherein said second agent is an HMG-Co-A reductase inhibitor, an angiotensin II receptor antagonist, angiotensin converting enzyme (ACE) Inhibitor, a calcium channel blocker (CCB), a dual angiotensin converting enzyme/neutral endopeptidase (ACE/NEP) inhibitor, an endothelin antagonist, a renin inhibitor, a diuretic, an ApoA-I mimic, an anti-diabetic agent, an obesity-reducing agent, an aldosterone receptor blocker, an endothelin receptor blocker, or a CETP inhibitor.

9. A method of alleviating or ameliorating at least one symptom of an aldosterone synthase associated state in a subject, comprising administering to said subject a therapeutically effective amount of a compound according to claim 1; or a pharmaceutically acceptable salt thereof; wherein the aldosterone synthase associated state is hypertension.

10. A method of alleviating or ameliorating at least one symptom of an aldosterone synthase associated state in a subject, comprising administering to said subject a therapeutically effective amount of a compound of Formula I:

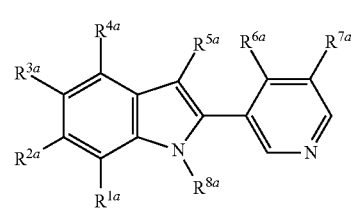

(I)

wherein:
$R^{1a}$ is hydrogen;
$R^{2a}$ is hydrogen, halogen, or hydroxy;
$R^{3a}$ is hydrogen, halogen, cyano, or alkoxy;
$R^{4a}$ is hydrogen or halogen;
$R^{5a}$ is hydrogen or alkyl;
$R^{6a}$ and $R^{7a}$ are hydrogen;
$R^{8a}$ is:

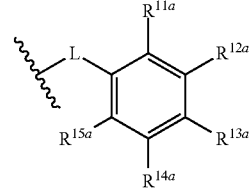

L is alkyl, carbonyl, sulfonyl, or —$(CH_2)_2$—O—; and
$R^{11a}$, $R^{12a}$, $R^{13a}$, $R^{14a}$, and $R^{15a}$ are each independently hydrogen, alkyl, cyano, halogen, alkoxy, or sulfonyl; with the proviso that at least one of $R^{2a}$-$R^{5a}$ is other than hydrogen; or a pharmaceutically acceptable salt thereof; wherein the aldosterone associated state is hypertension.

11. The method according to claim 10 wherein the compound of Formula I is selected from:
1-Benzyl-3-methyl-2-pyridin-3-yl-1H-indole;
3-(5-Chloro-3-methyl-2-pyridin-3-yl-1H-indol-1-ylmethyl)-benzonitrile;

3-(6-Fluoro-3-methyl-2-pyridin-3-yl-1H-indol-1-ylm-ethyl)-benzonitrile hydrochloride;
3-(4-Fluoro-3-methyl-2-pyridin-3-yl-1H-indol-1-ylm-ethyl)-benzonitrile hydrochloride;
4-(4-Fluoro-3-methyl-2-pyridin-3-yl-1H-indol-1-ylm-ethyl)-benzonitrile hydrochloride;
4-(6-Fluoro-3-methyl-2-pyridin-3-yl-1H-indol-1-ylm-ethyl)-benzonitrile;
3-Fluoro-4-(3-methyl-2-pyridin-3-yl-1H-indol-1-ylm-ethyl)-benzonitrile;
3-(3-methyl-2-pyridin-3-yl-1H-indol-1-ylmethyl)-ben-zonitrile;
1-(2-Fluoro-4-methoxy-benzyl)-3-methyl-2-pyridin-3-yl-1H-indole hydrochloride;
3-(3-Methyl-2-pyridin-3-yl-indole-1-carbonyl)-benzoni-trile;
3-Methyl-1-(2-phenoxy-ethyl)-2-pyridin-3-yl-1H-indole-5-carbonitrile;
1-(2-Phenoxy-ethyl)-2-pyridin-3-yl-1H-indole-5-carbo-nitrile;
3-Methyl-1-(2-phenoxy-ethyl)-2-pyridin-3-yl-1H-indole;
4-(3-Methyl-2-pyridin-3-yl-indole-1-carbonyl)-benzoni-trile; and
3-(5-Cyano-3-methyl-2-pyridin-3-yl-indole-1-carbonyl)-benzonitrile; or a pharmaceutically acceptable salt thereof.

\* \* \* \* \*